(12) United States Patent
Takahashi et al.

(10) Patent No.: US 9,359,638 B2
(45) Date of Patent: Jun. 7, 2016

(54) MULTI-NUCLEIC-ACID AMPLIFICATION REACTION TOOL

(71) Applicant: Toshiba Medical Systems Corporation, Otawara-shi (JP)

(72) Inventors: Masayoshi Takahashi, Tokyo (JP); Koji Hashimoto, Atsugi (JP); Masaru Nikaido, Yokohama (JP); Nobuhiro Gemma, Yokohama (JP); Jun Okada, Tokyo (JP); Daiji Hirosawa, Tokyo (JP); Keiichi Yamamoto, Kawasaki (JP); Tetsuya Kuwabara, Fuchu (JP); Madoka Takase, Ageo (JP); Akiko Shimojo, Yokohama (JP); Akiyoshi Nakamura, Tokyo (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 61 days.

(21) Appl. No.: 14/173,442

(22) Filed: Feb. 5, 2014

(65) Prior Publication Data

US 2014/0148359 A1    May 29, 2014

Related U.S. Application Data

(63) Continuation of application No. PCT/JP2012/069918, filed on Aug. 3, 2012.

(30) Foreign Application Priority Data

| Aug. 5, 2011 | (JP) | ................................ | 2011-172396 |
| Mar. 21, 2012 | (JP) | ................................ | 2012-064457 |
| Mar. 23, 2012 | (JP) | ................................ | 2012-067847 |
| Mar. 23, 2012 | (JP) | ................................ | 2012-067946 |
| Mar. 23, 2012 | (JP) | ................................ | 2012-068276 |
| Mar. 26, 2012 | (JP) | ................................ | 2012-069255 |

(51) Int. Cl.
| C12P 19/34 | (2006.01) |
| C12Q 1/68 | (2006.01) |
| B01L 3/00 | (2006.01) |
| B01L 7/00 | (2006.01) |

(52) U.S. Cl.
CPC ......... *C12Q 1/6825* (2013.01); *B01L 3/502761* (2013.01); *B01L 7/525* (2013.01); *B01J 2219/00452* (2013.01); *B01J 2219/00497* (2013.01); *B01J 2219/00596* (2013.01); *B01J 2219/00608* (2013.01); *B01J 2219/00621* (2013.01); *B01J 2219/00657* (2013.01); *B01J 2219/00659* (2013.01); *B01J 2219/00722* (2013.01); *B01L 2200/16* (2013.01); *B01L 2300/0636* (2013.01); *B01L 2300/0645* (2013.01); *B01L 2300/0803* (2013.01); *B01L 2300/0816* (2013.01); *B01L 2300/0819* (2013.01); *B01L 2300/0883* (2013.01); *B01L 2300/163* (2013.01)

(58) Field of Classification Search
CPC ................... B01L 2200/16; B01L 2300/0636; B01L 2300/0645; B01L 2300/0803; B01L 2300/0816; B01L 2300/0819; B01L 2300/0883; B01L 2300/163; B01L 3/502761; B01L 7/525; C12Q 1/6825; G01N 27/3276
USPC ....................................................... 435/91.2
See application file for complete search history.

(56) References Cited

U.S. PATENT DOCUMENTS

| 6,103,463 | A | 8/2000 | Chetverin et al. |
| 6,500,620 | B2 | 12/2002 | Yu et al. |
| 7,642,053 | B2 | 1/2010 | Gumbrecht et al. |
| 2001/0036632 | A1 | 11/2001 | Yu et al. |
| 2002/0058329 | A1 | 5/2002 | Singh et al. |
| 2003/0017467 | A1 | 1/2003 | Hooper et al. |
| 2003/0027352 | A1 | 2/2003 | Hooper et al. |
| 2006/0234236 | A1 | 10/2006 | Gumbrecht et al. |
| 2008/0051295 | A1 | 2/2008 | Okamoto |
| 2008/0070281 | A1 | 3/2008 | White et al. |
| 2008/0241890 | A1 | 10/2008 | Gumbrecht et al. |
| 2010/0173792 | A1 | 7/2010 | Heller et al. |
| 2011/0039720 | A1 | 2/2011 | Vossenaar et al. |

FOREIGN PATENT DOCUMENTS

| DE | 10 2006 010 957 A1 | 10/2007 |
| JP | 2005-261298 A | 9/2005 |
| JP | 2008-263959 A | 11/2008 |
| WO | WO 93/17126 A1 | 9/1993 |
| WO | WO 01/48242 A2 | 7/2001 |

(Continued)

OTHER PUBLICATIONS

English-language Search Report and Written Opinion issued Oct. 20, 2014 in Singaporean Patent Application No. 2014009906.

(Continued)

*Primary Examiner* — Cynthia B Wilder

(74) *Attorney, Agent, or Firm* — Oblon, McClelland, Maier & Neustadt, L.L.P

(57) ABSTRACT

According to one embodiment, a multi-nucleic-acid amplification reaction tool includes a support and a plurality of types of primer sets. The support is configured to be able to support a reaction field of a liquid phase. A plurality of types of primer sets are fixed in a releasable state, for each type, on mutually independent fixing regions of at least a surface of the support, which is in contact with the reaction field, when the liquid phase forms the reaction field. A plurality of types of primer sets are configured to amplify the respectively corresponding target sequences.

17 Claims, 44 Drawing Sheets

(56) References Cited

FOREIGN PATENT DOCUMENTS

| WO | WO 01/61041 A2 | 8/2001 |
| WO | WO 02/072262 A1 | 9/2002 |
| WO | WO 2004/057022 A1 | 7/2004 |
| WO | 2005/054458 A1 | 6/2005 |
| WO | WO 2005/087950 A1 | 9/2005 |
| WO | WO 2009/077982 A1 | 6/2009 |
| WO | WO 2009137415 * | 11/2009 |
| WO | WO 2010/009463 A2 | 1/2010 |

OTHER PUBLICATIONS

Combined Chinese Office Action and Search Report issued Sep. 9, 2014 in Patent Application No. 201280044309.X (with partial English translation).

Extended European Search Report issued on Jul. 20, 2015 in European Patent Application No. 12822401.1.

* cited by examiner

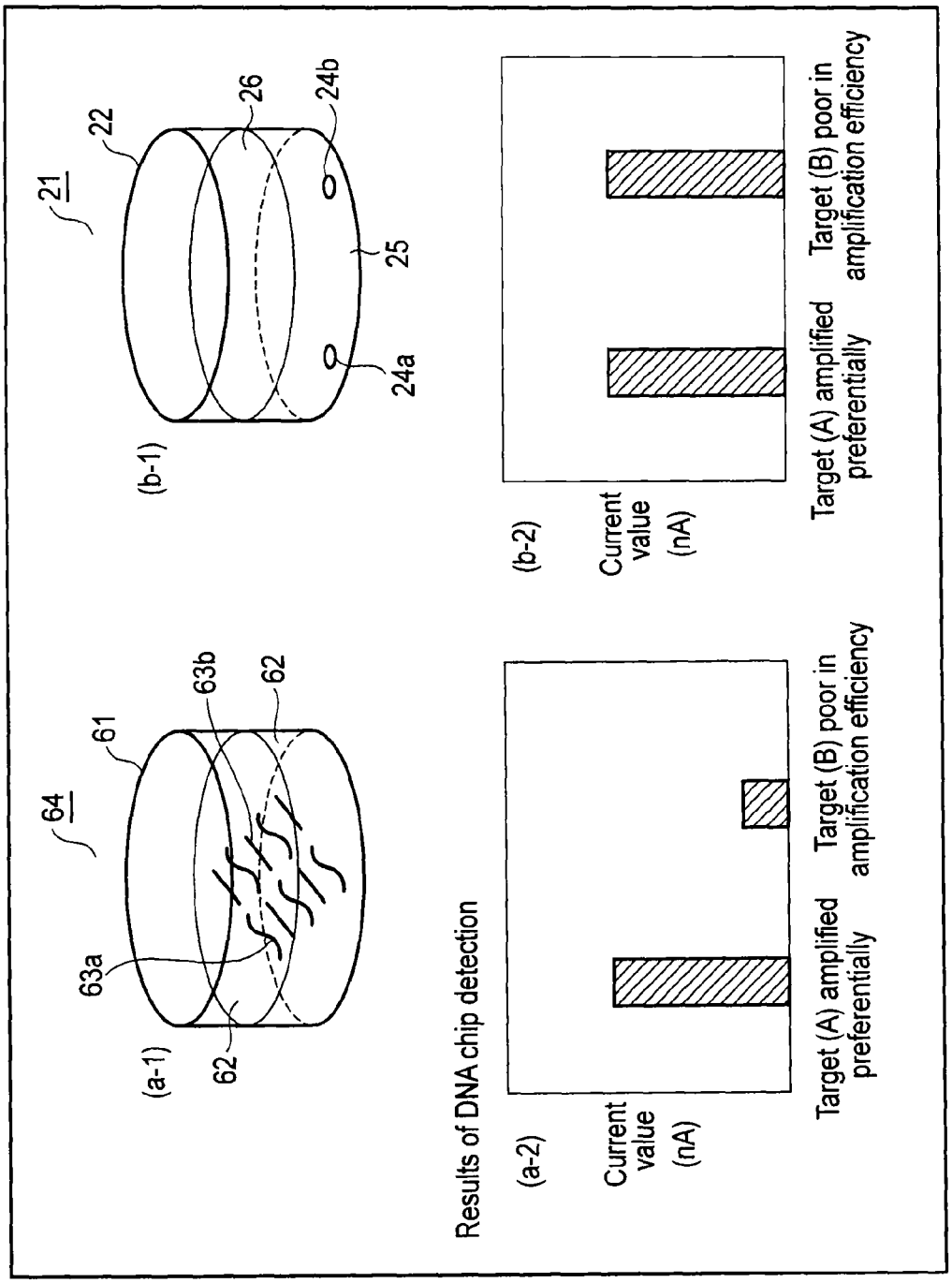
F I G. 6

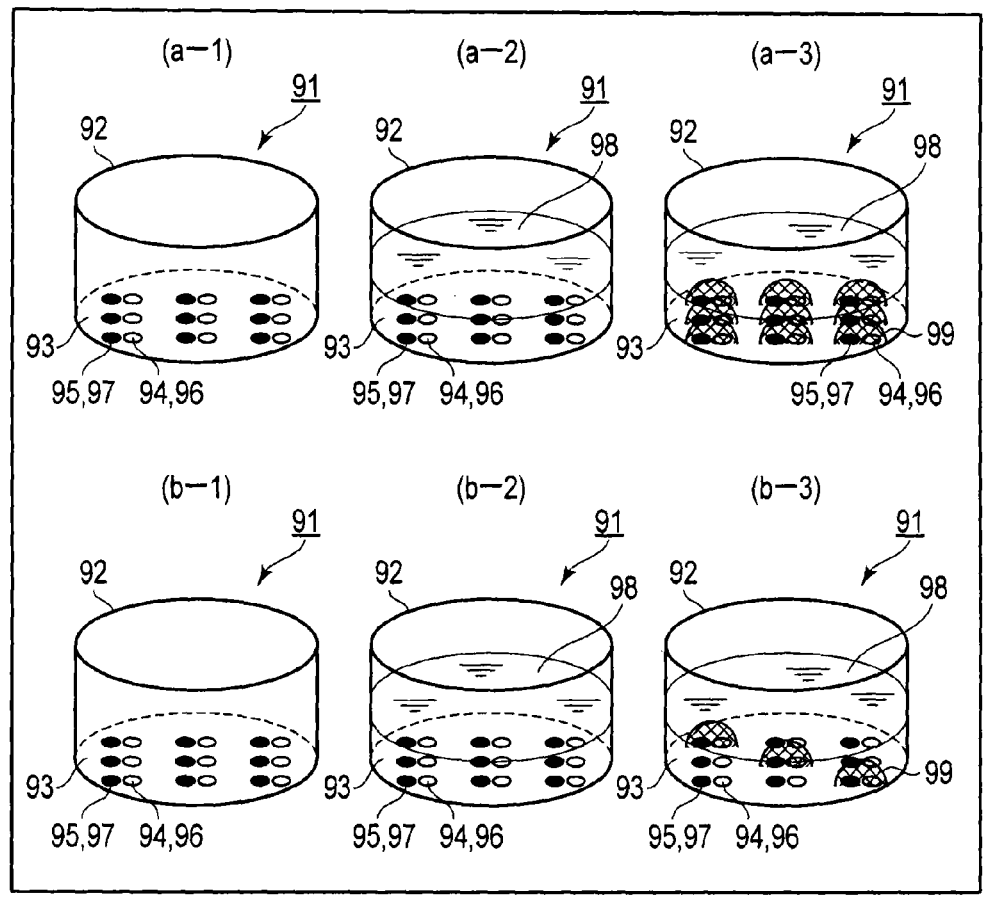
F I G. 10

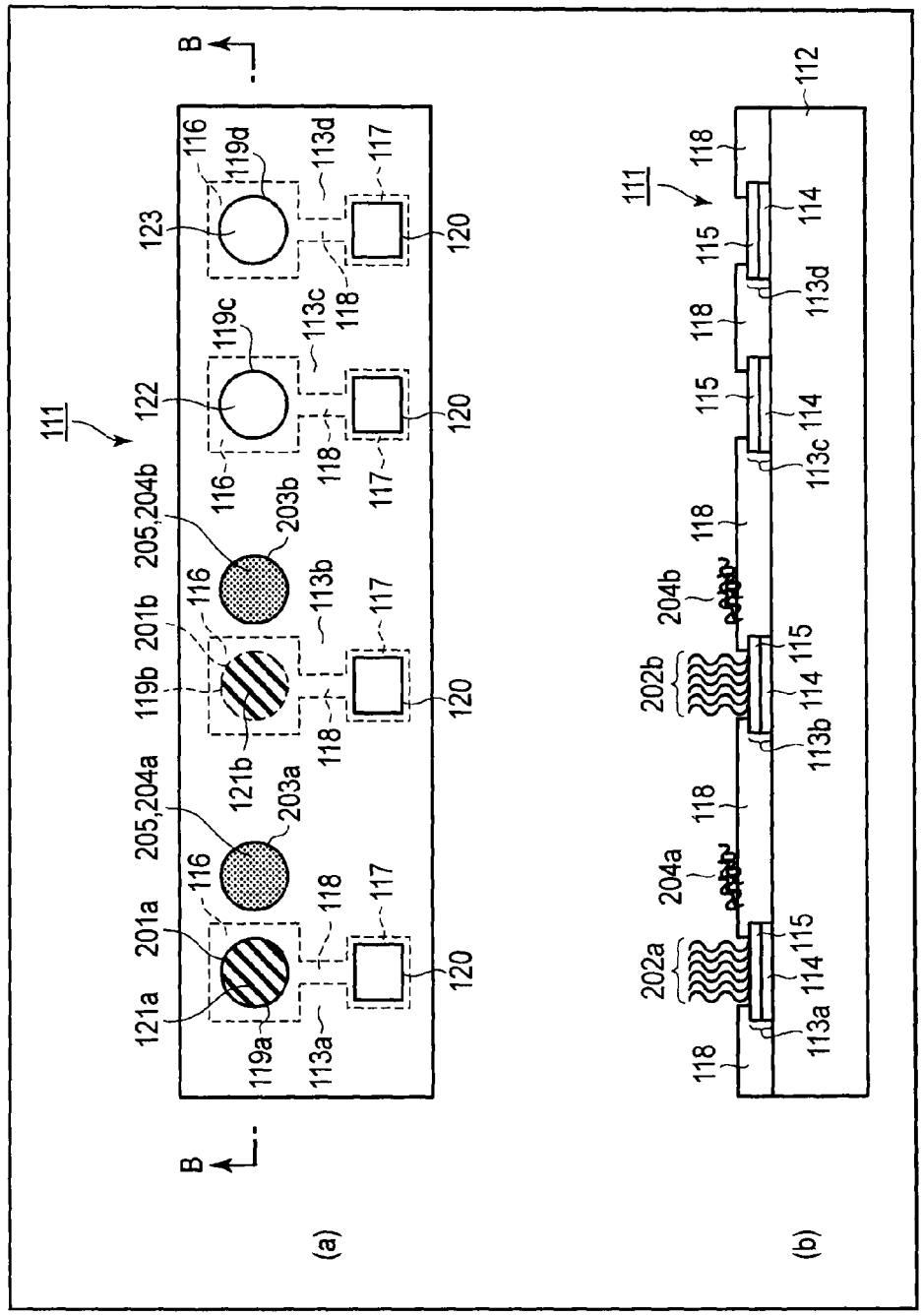
F I G. 12

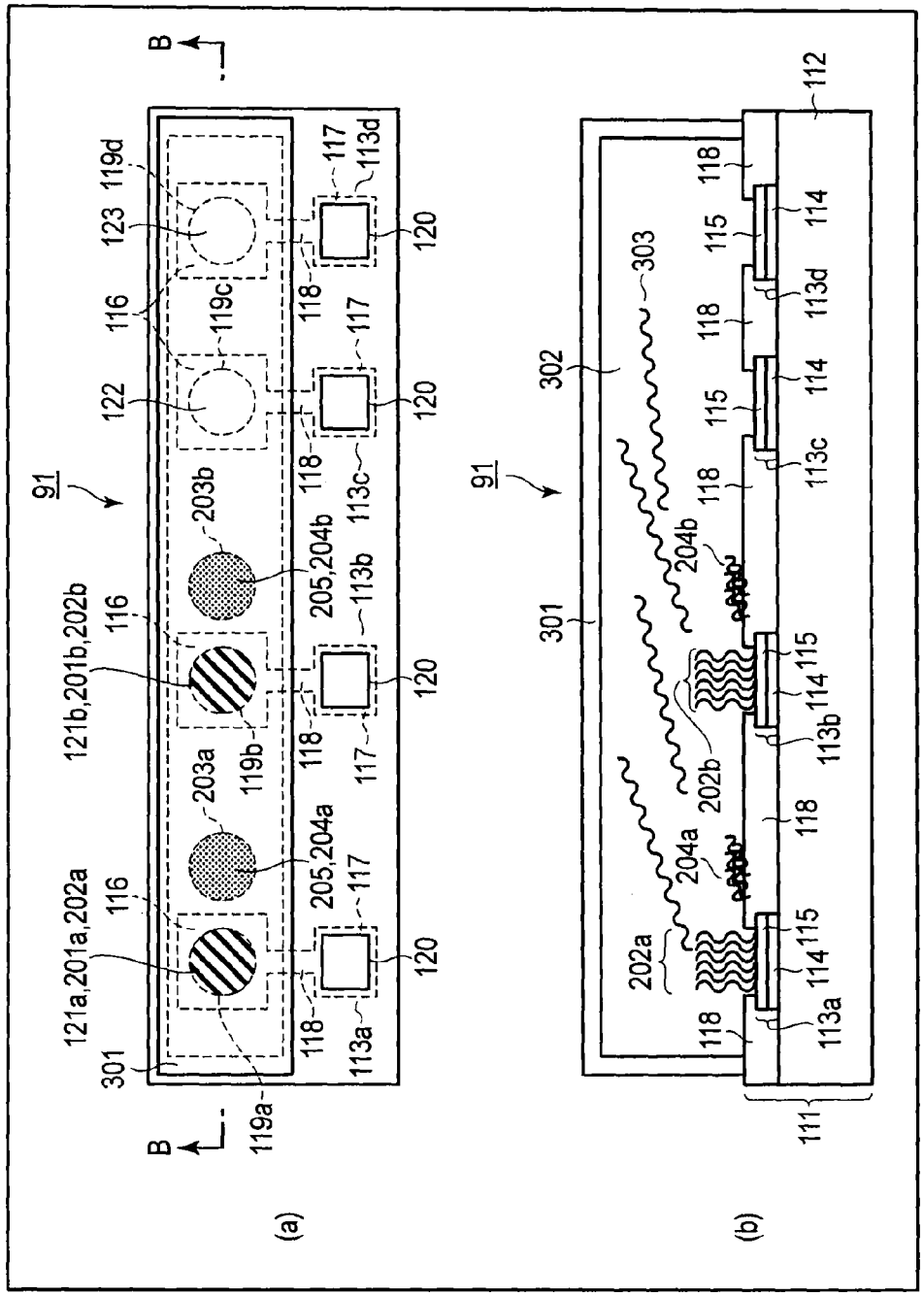
F I G. 13

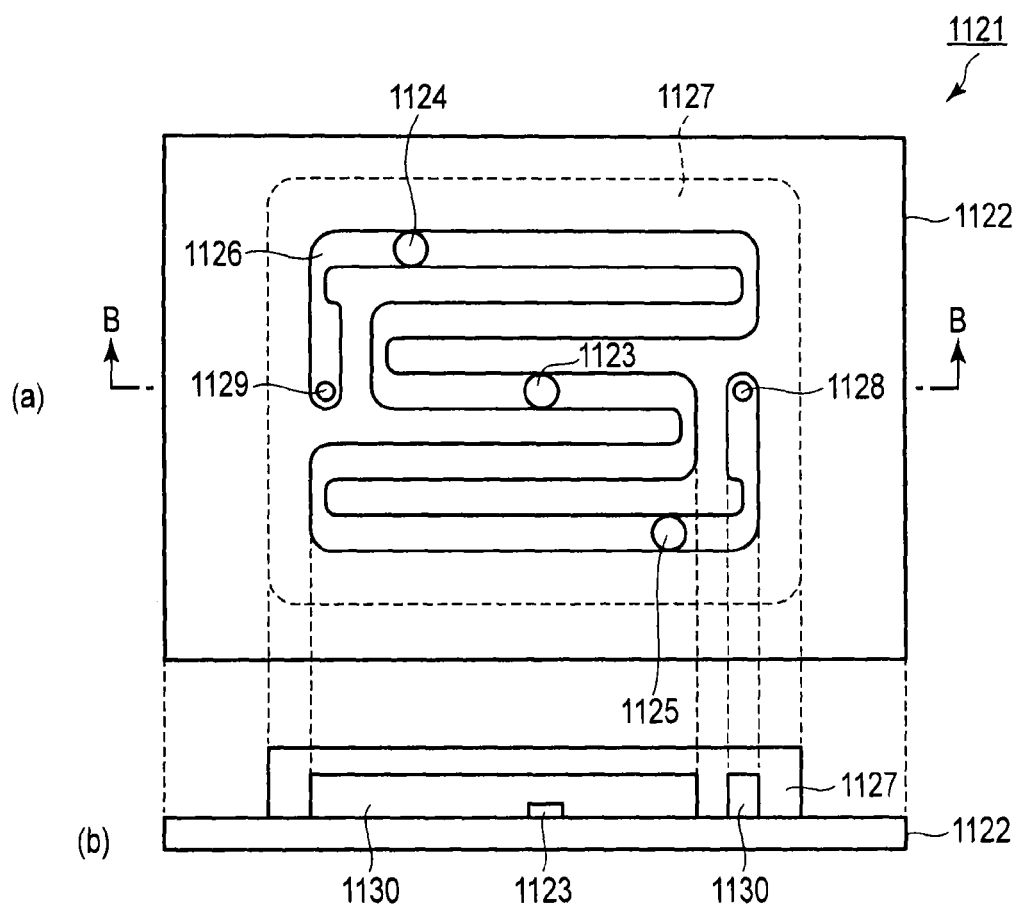
F I G. 15

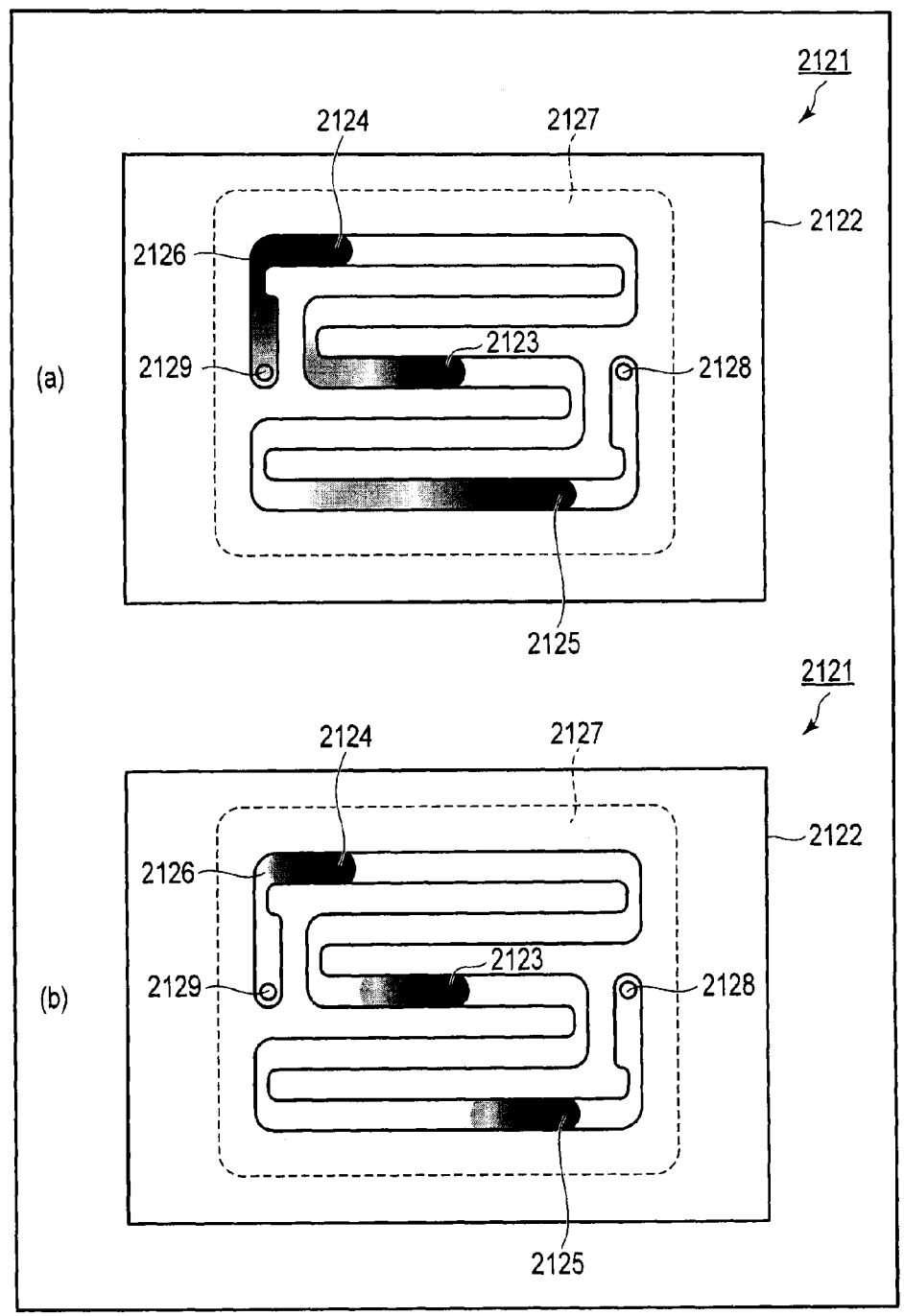
F I G. 16

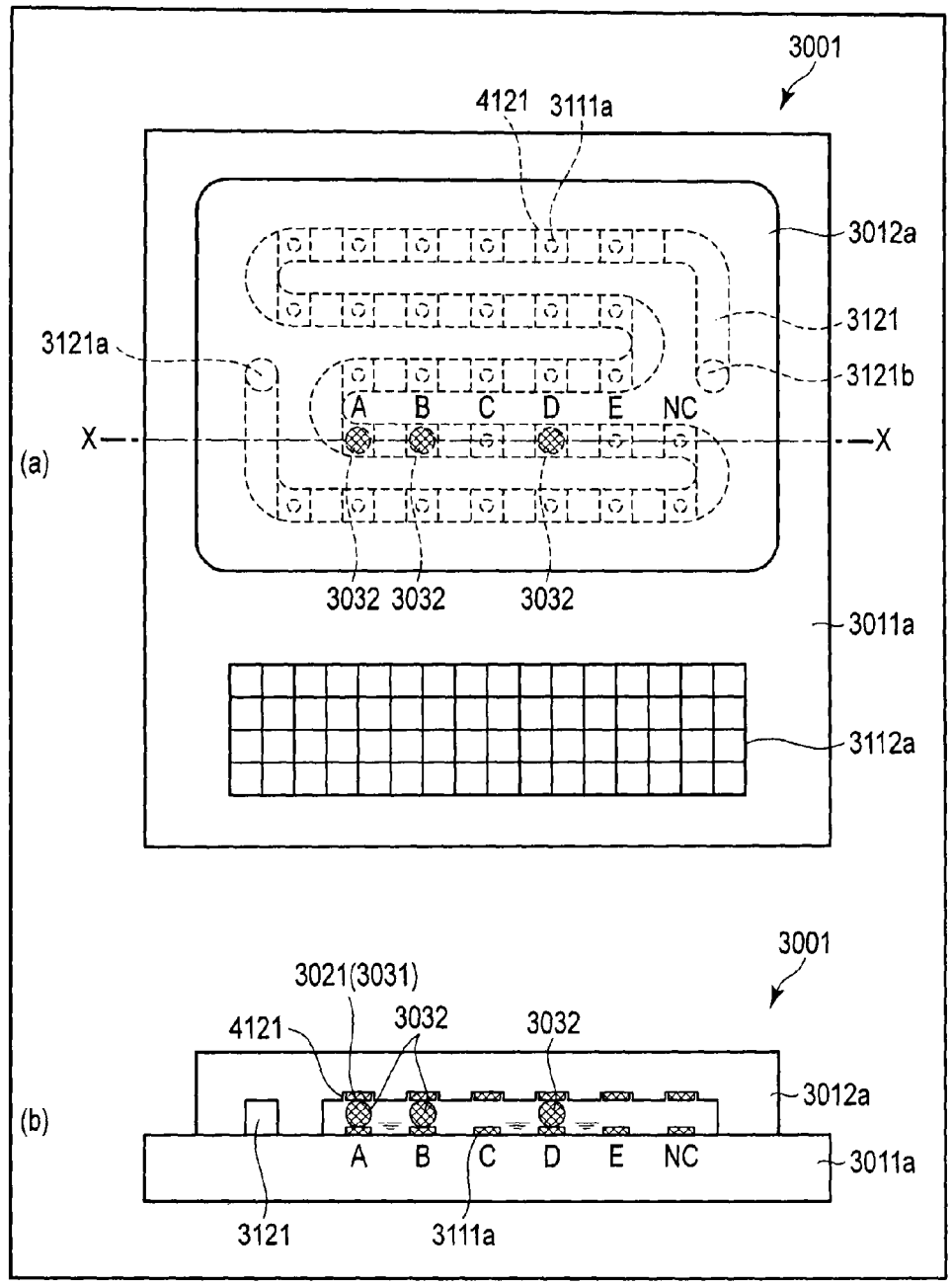
F I G. 23

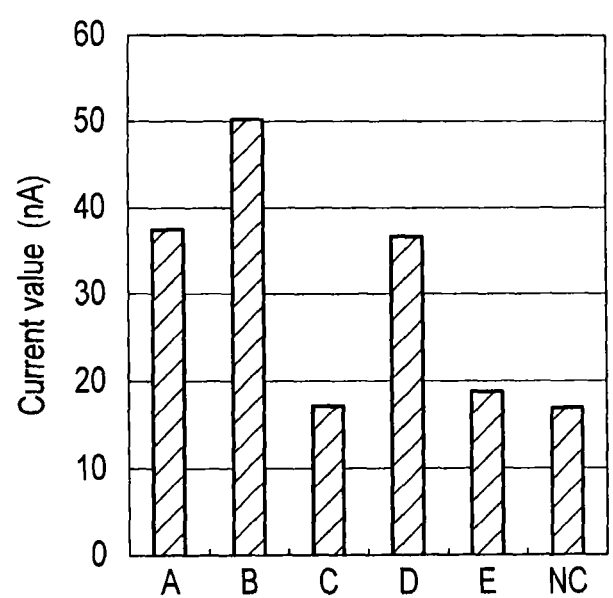
F I G. 24

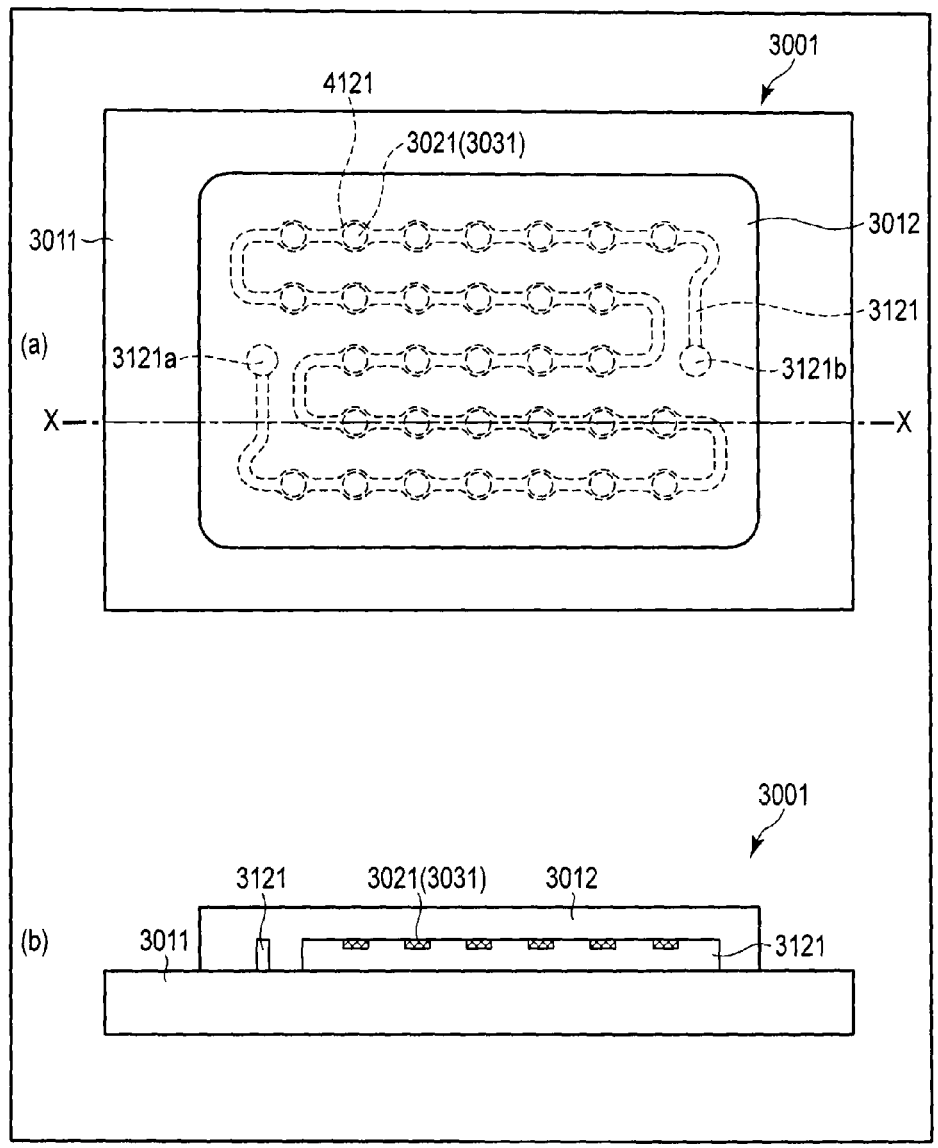
F I G. 25

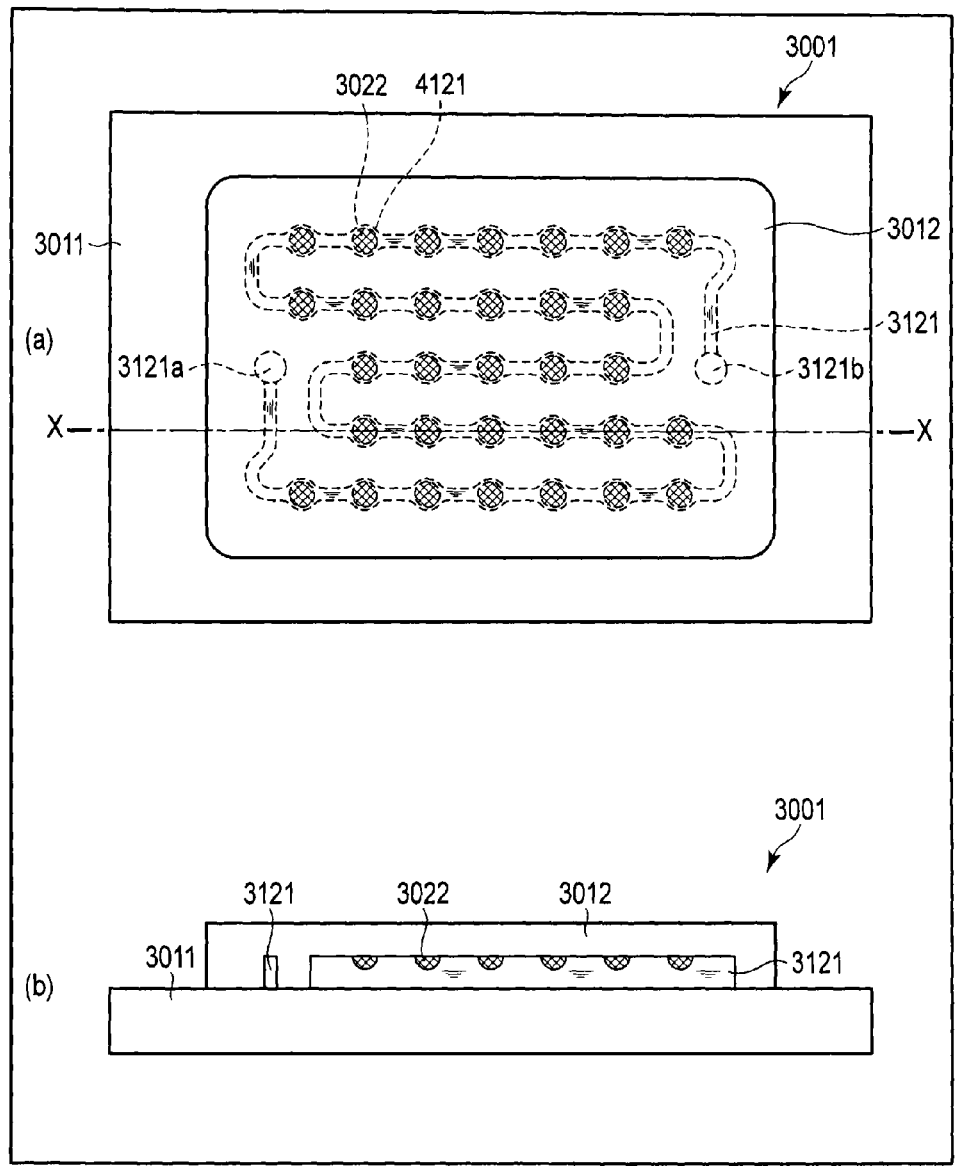
F I G. 26

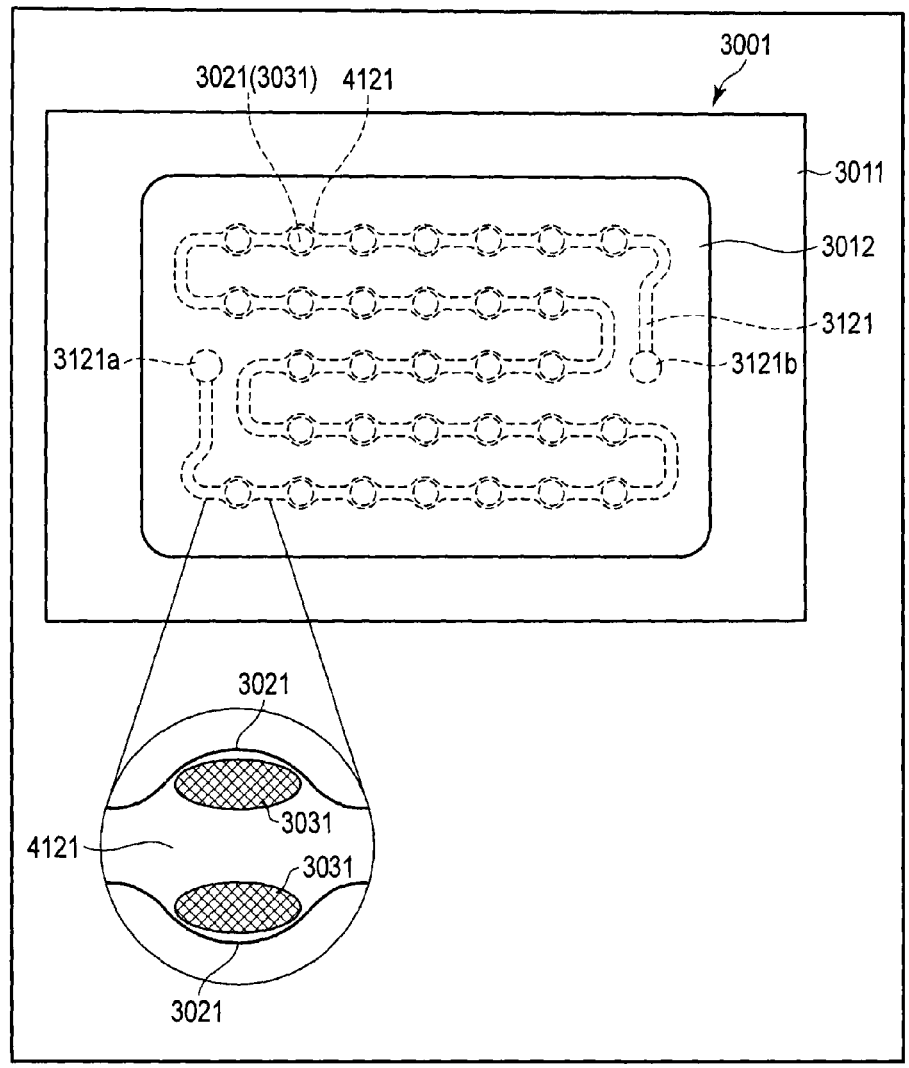
F I G. 27

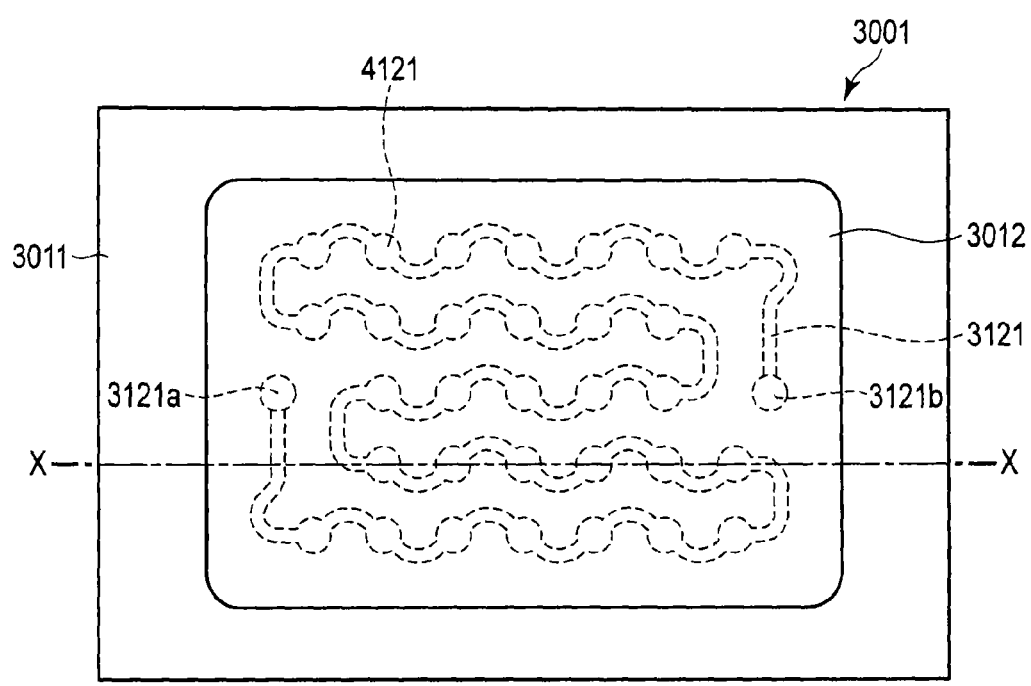
F I G. 28

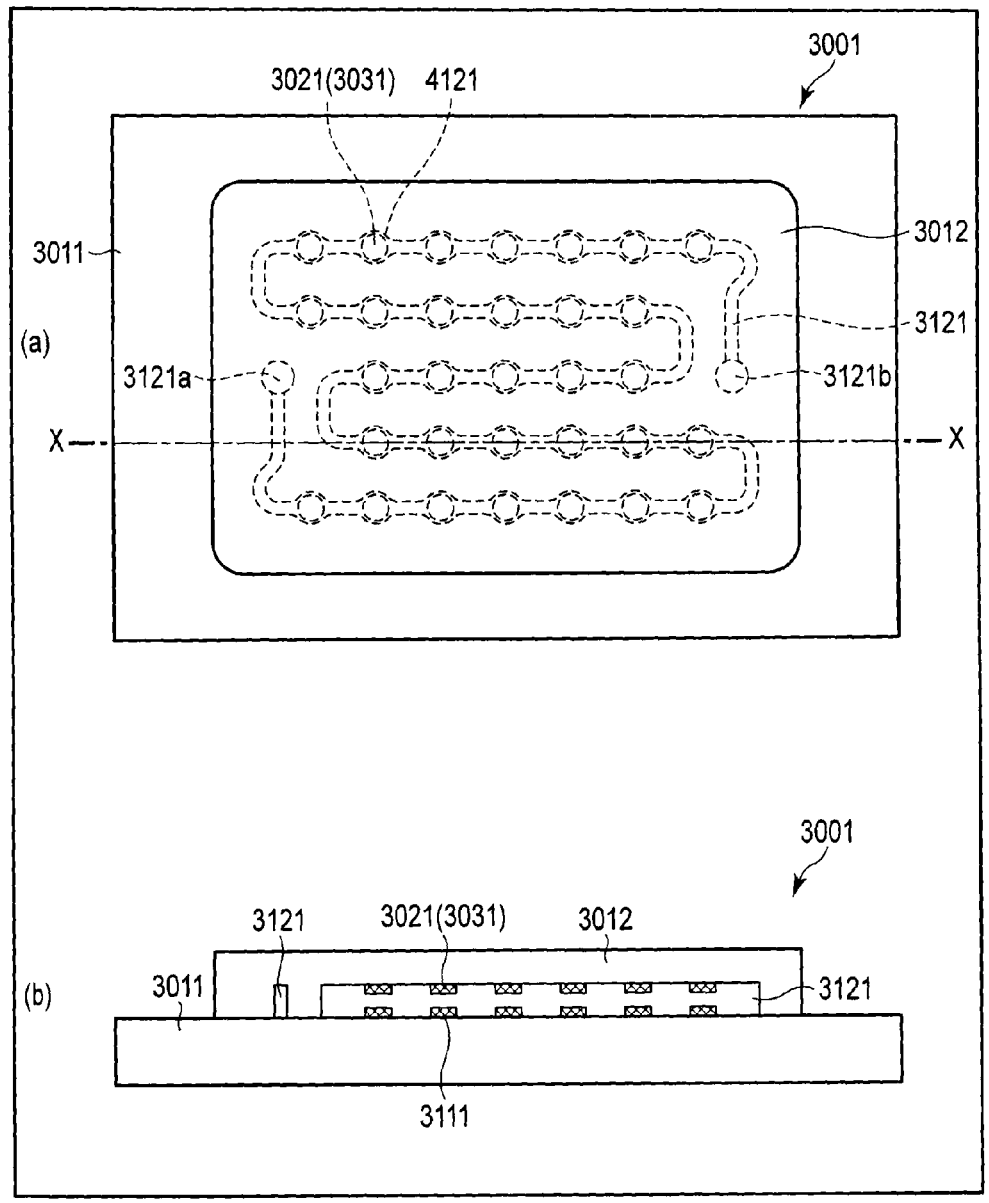
F I G. 29

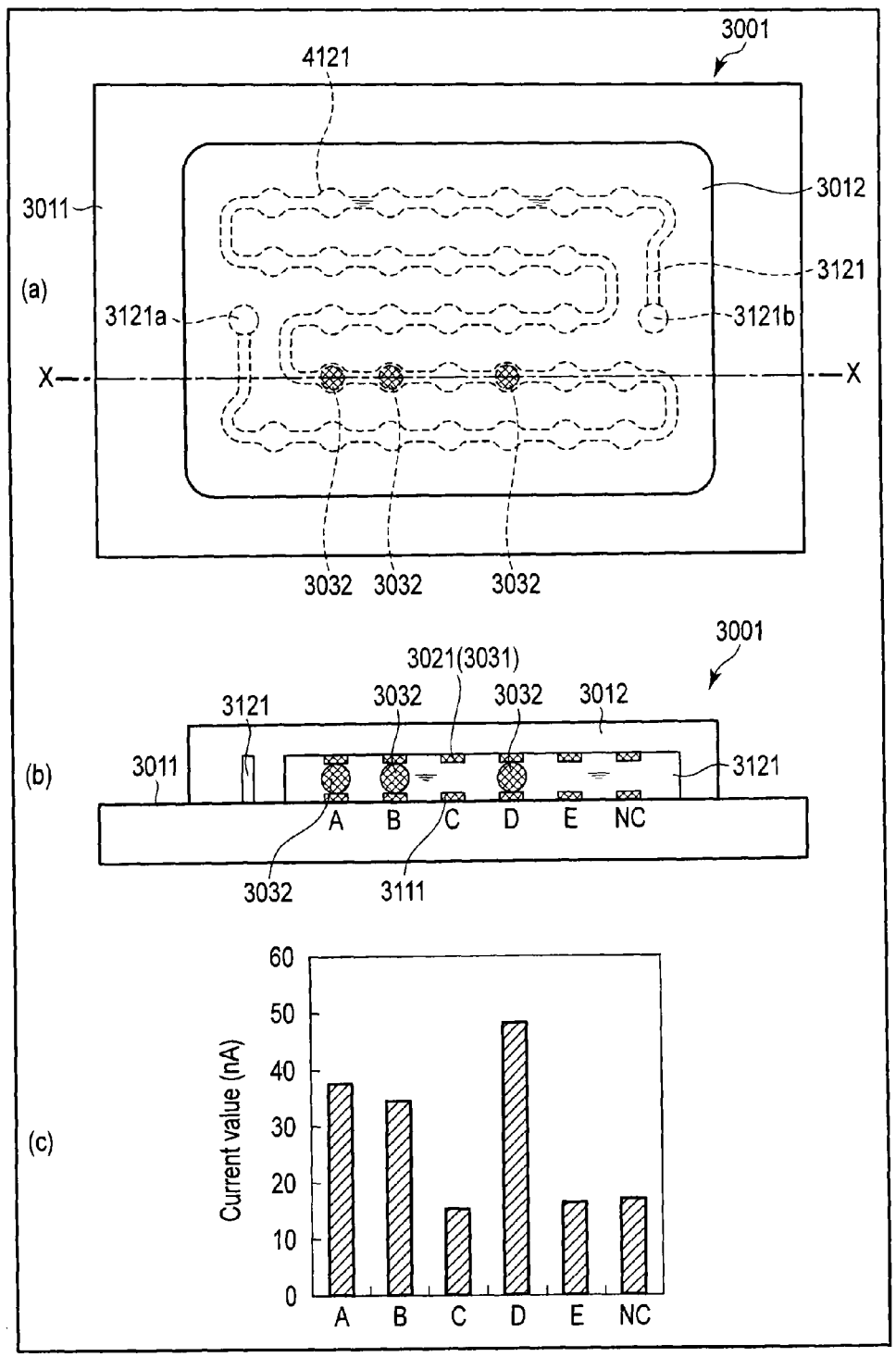
F I G. 30

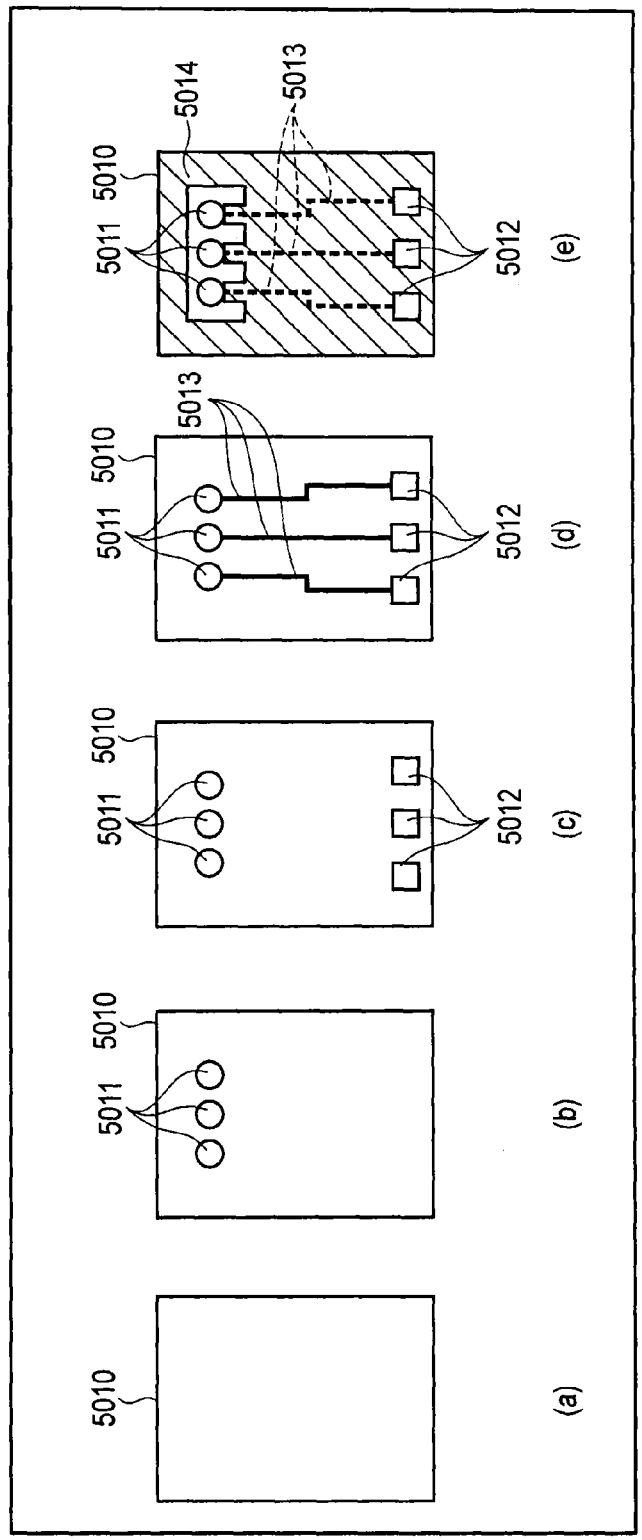
F I G. 31

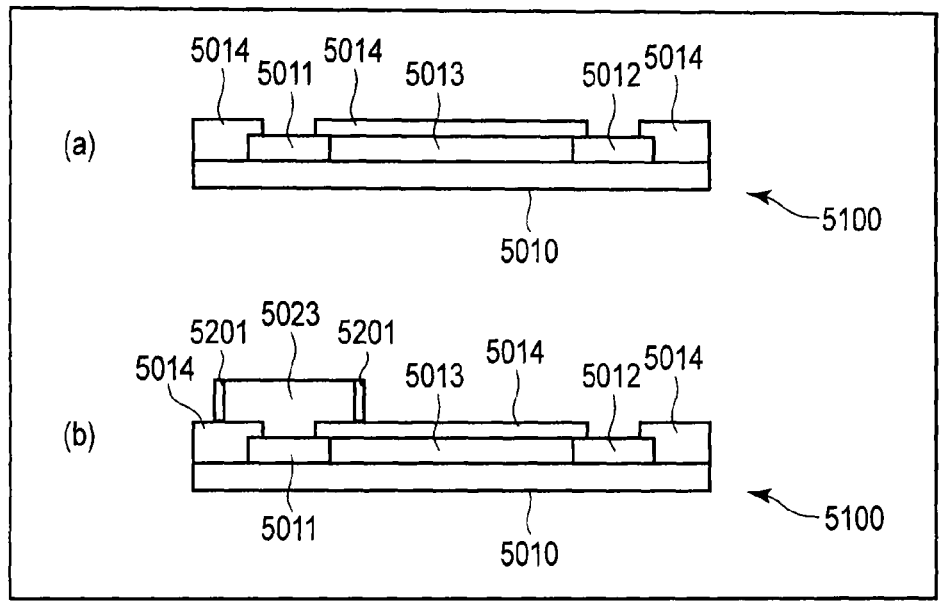
F I G. 32
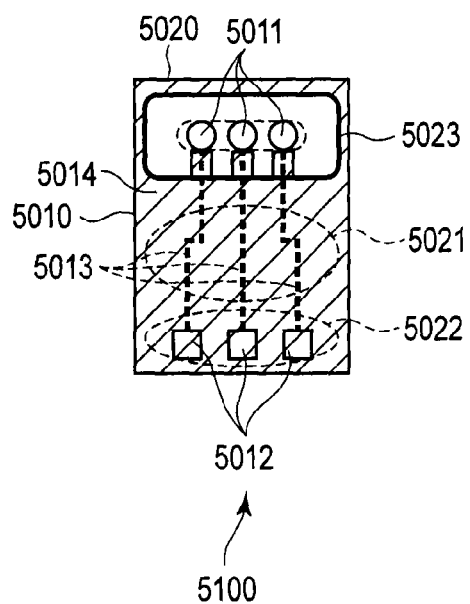
F I G. 33

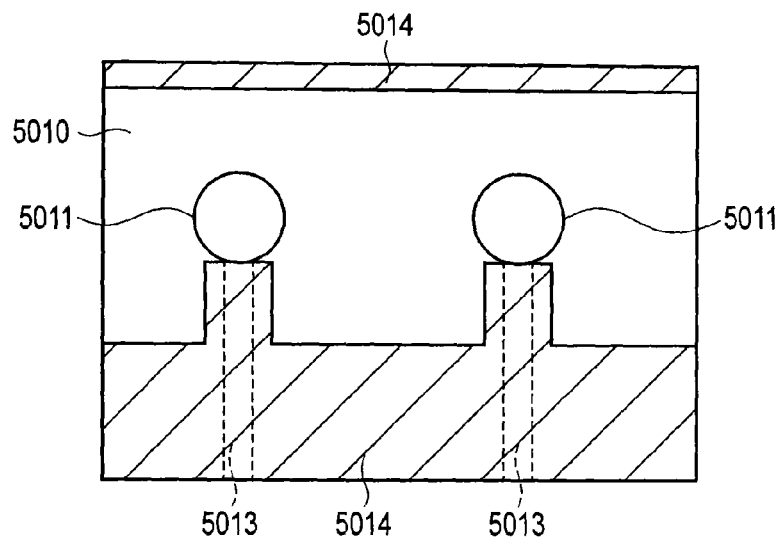
F I G. 34
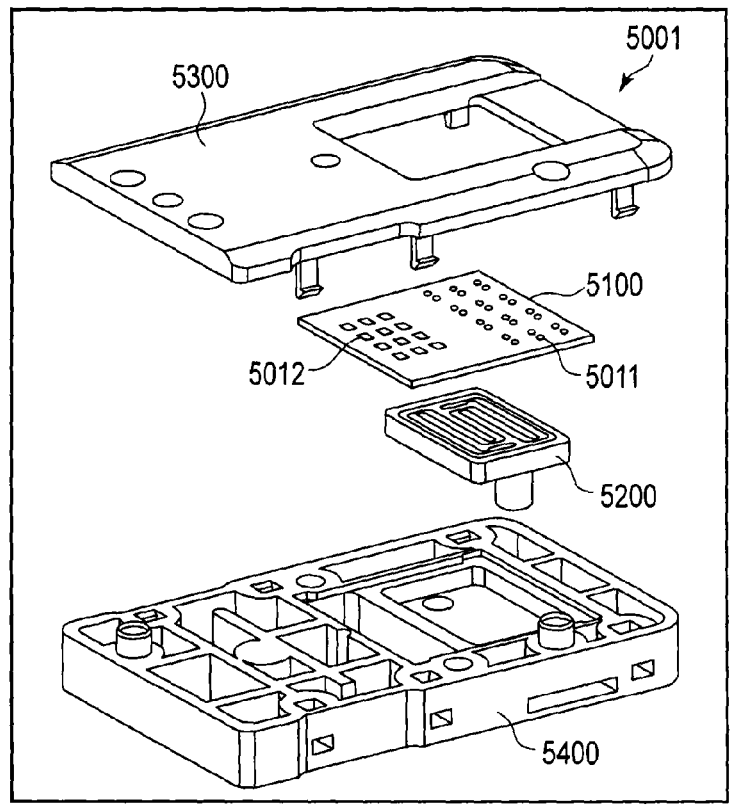
F I G. 35

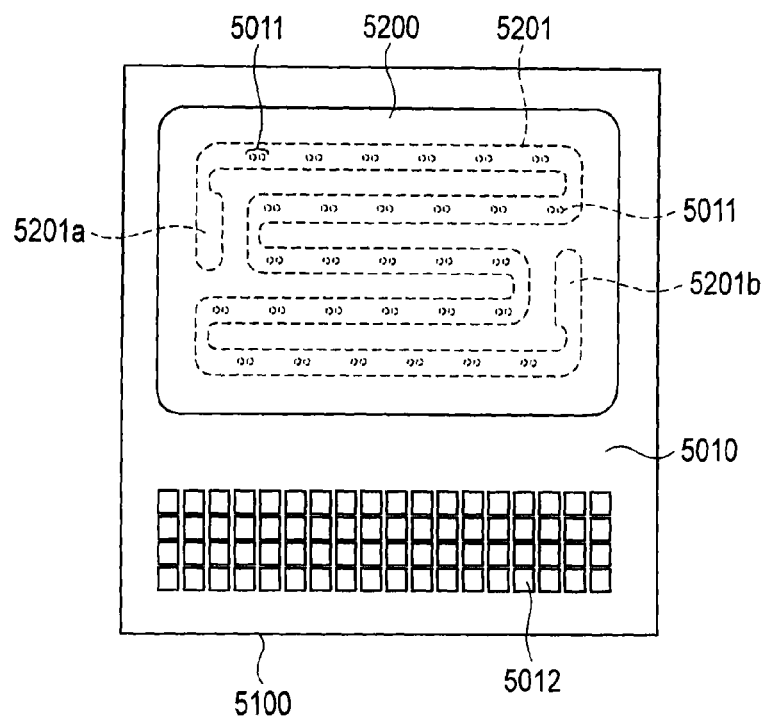
F I G. 36
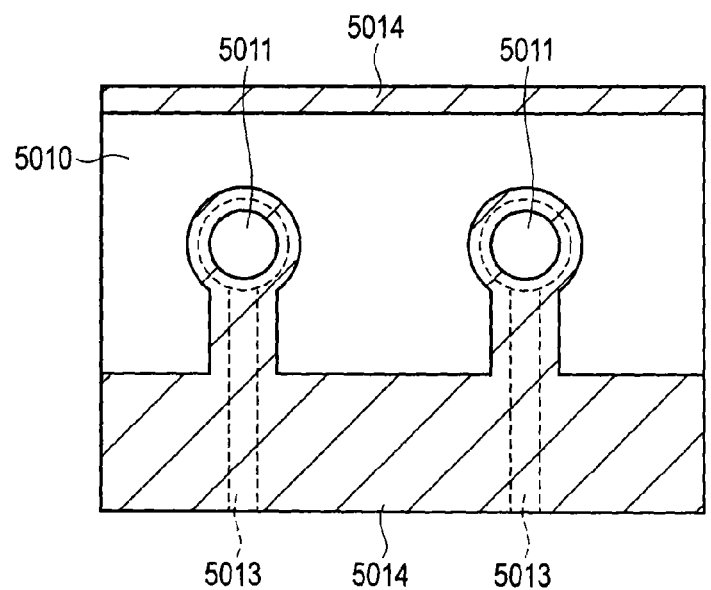
F I G. 37

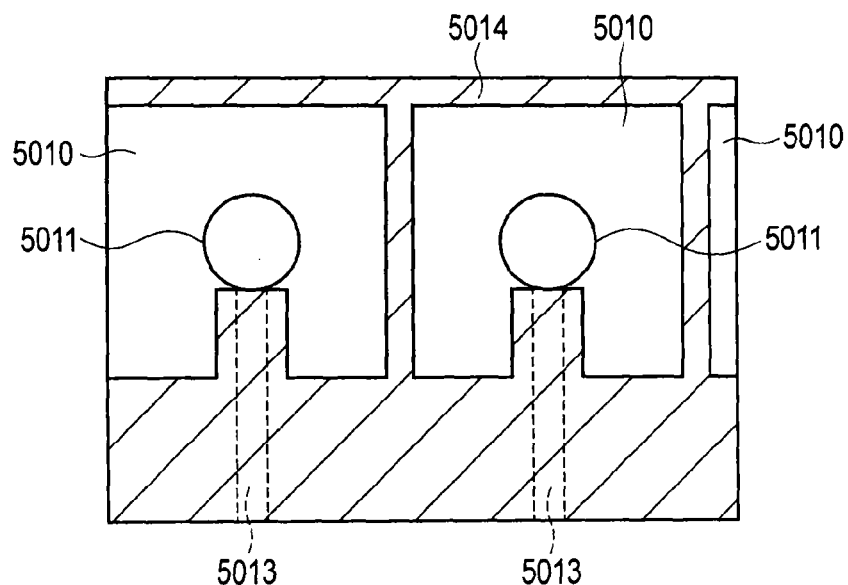
F I G. 38
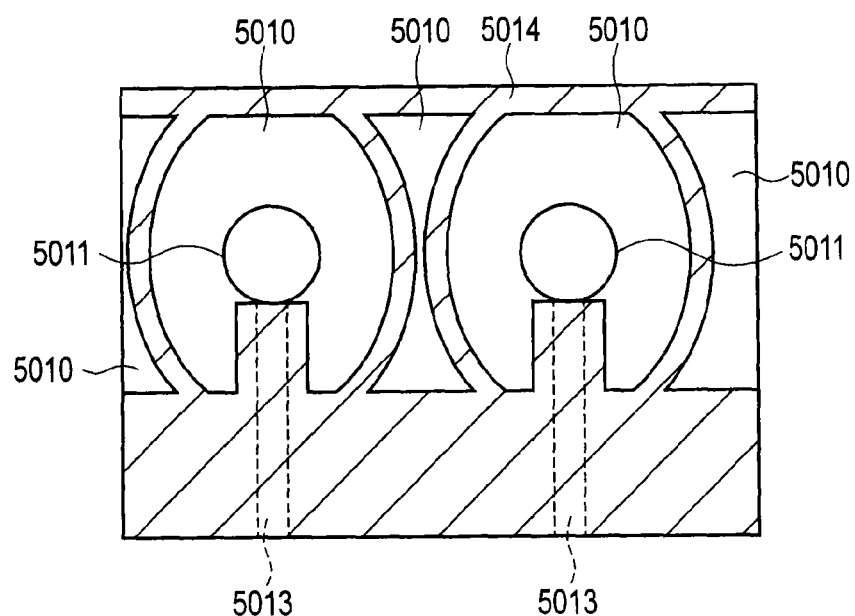
F I G. 39

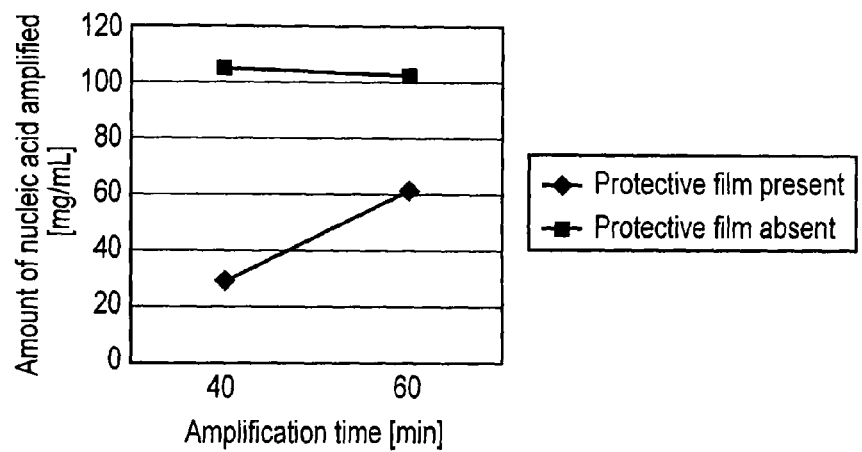
F I G. 40
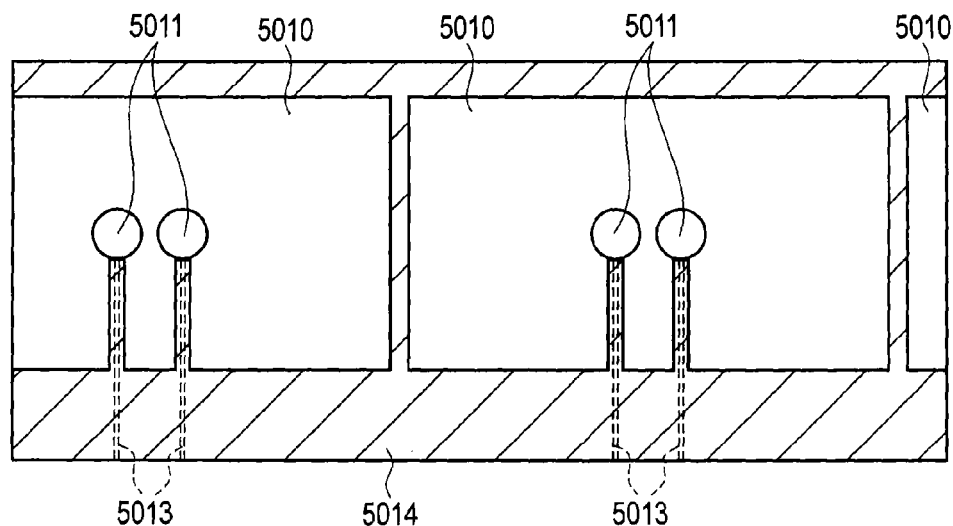
F I G. 41

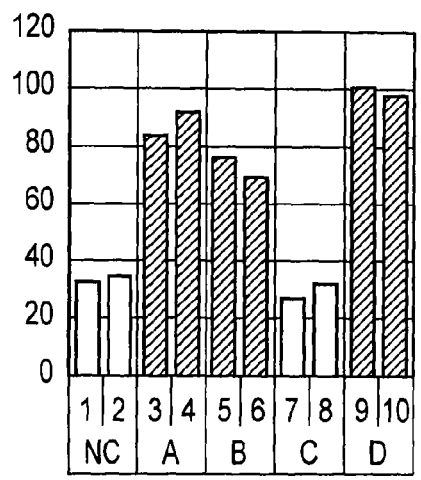
F I G. 42
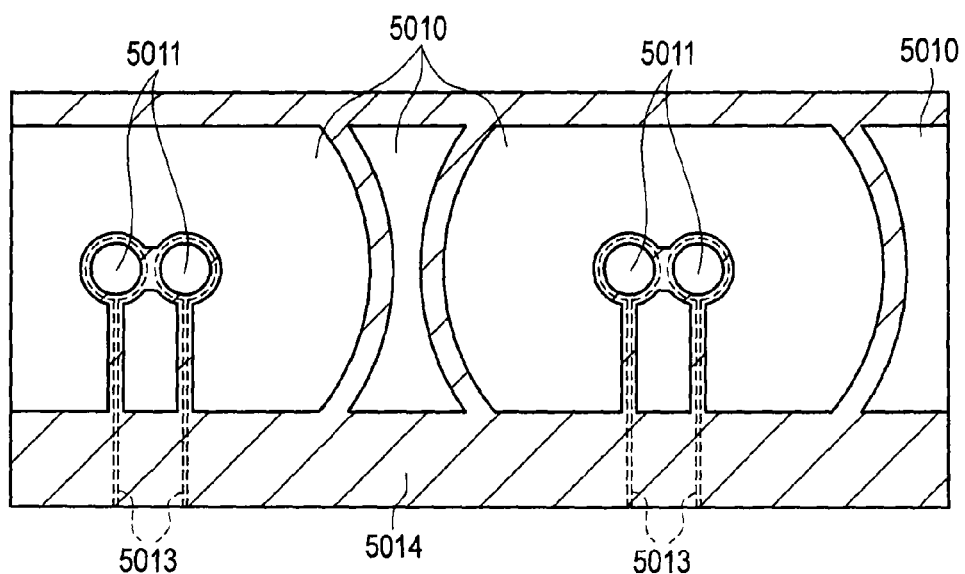
F I G. 43

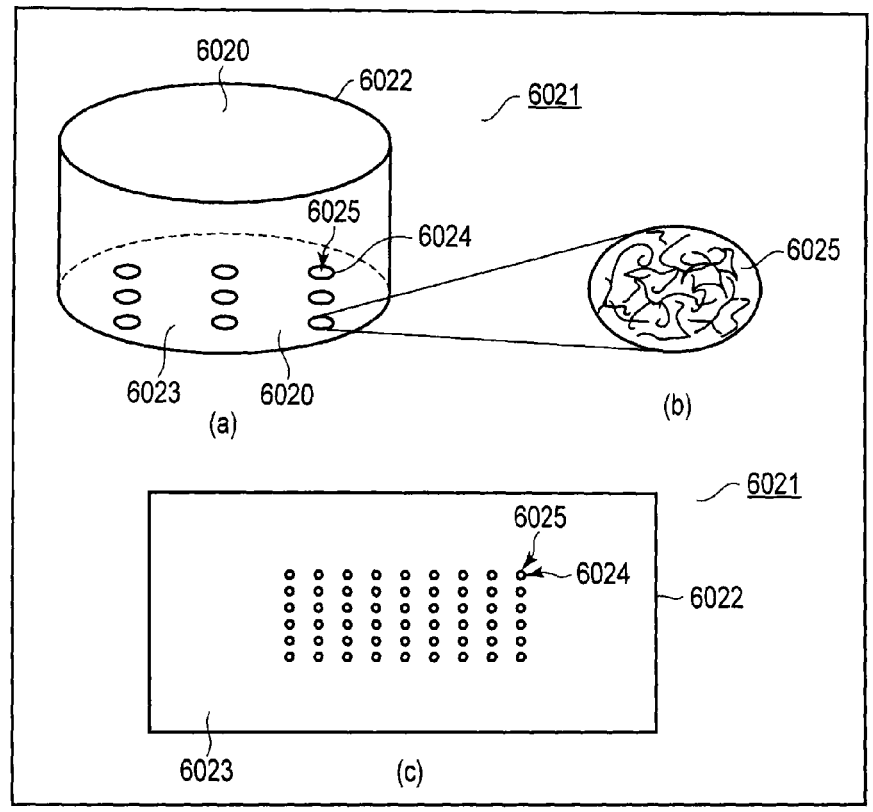
F I G. 46
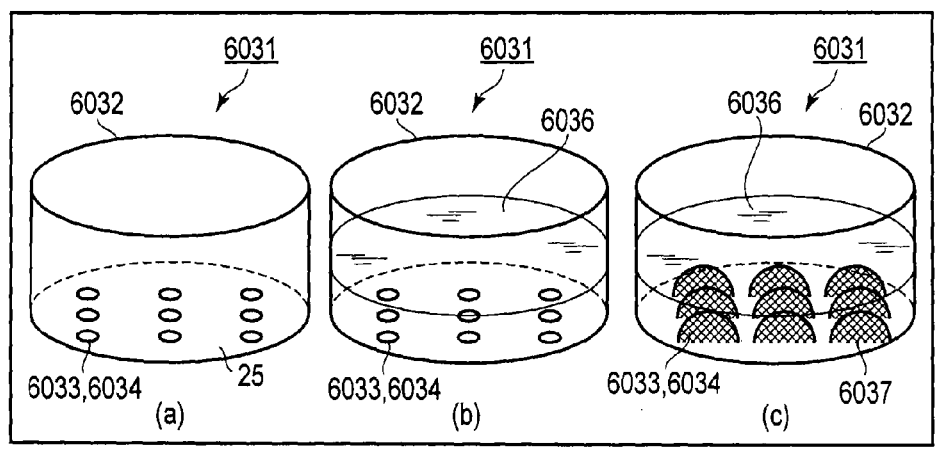
F I G. 47

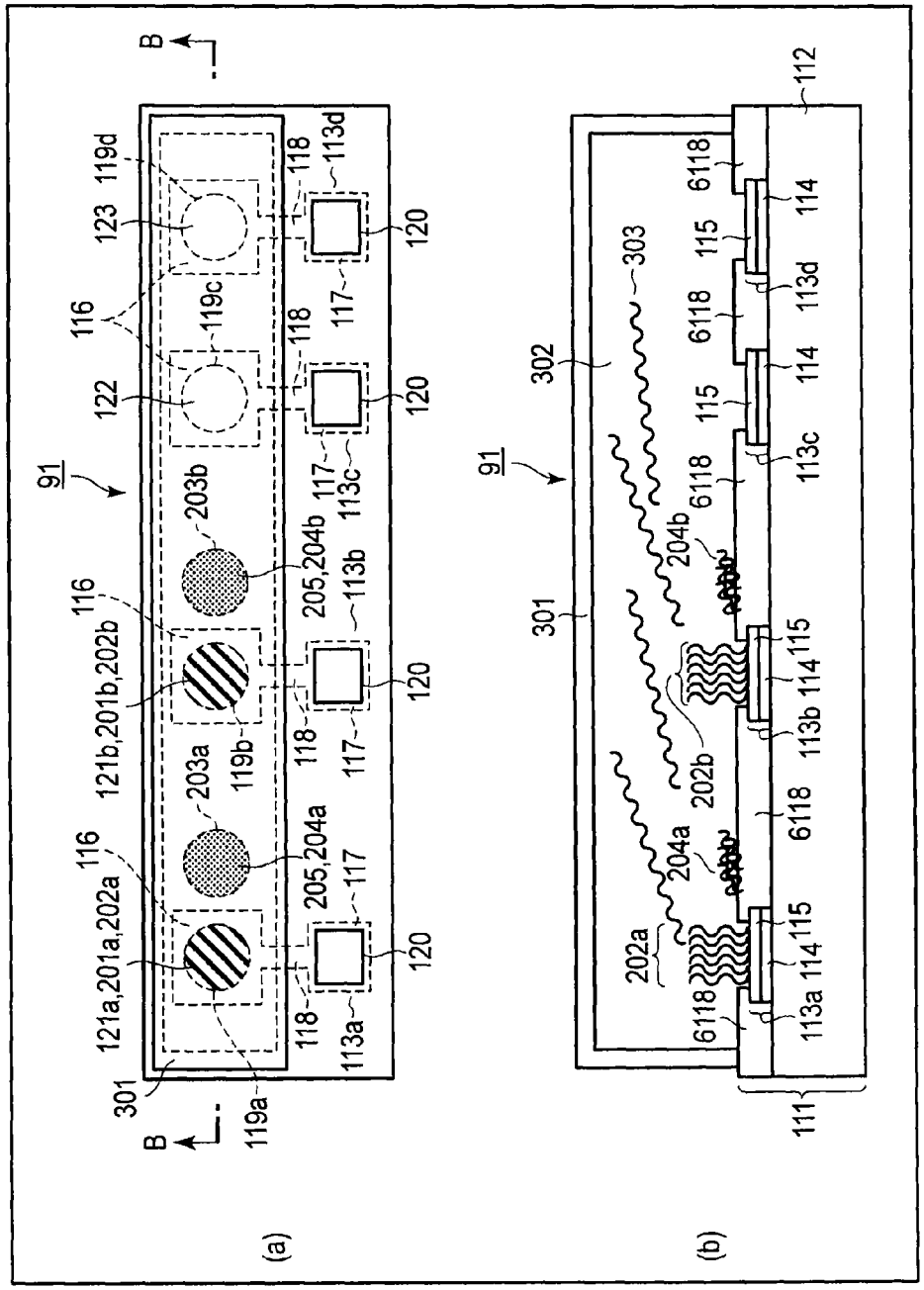
F I G. 52

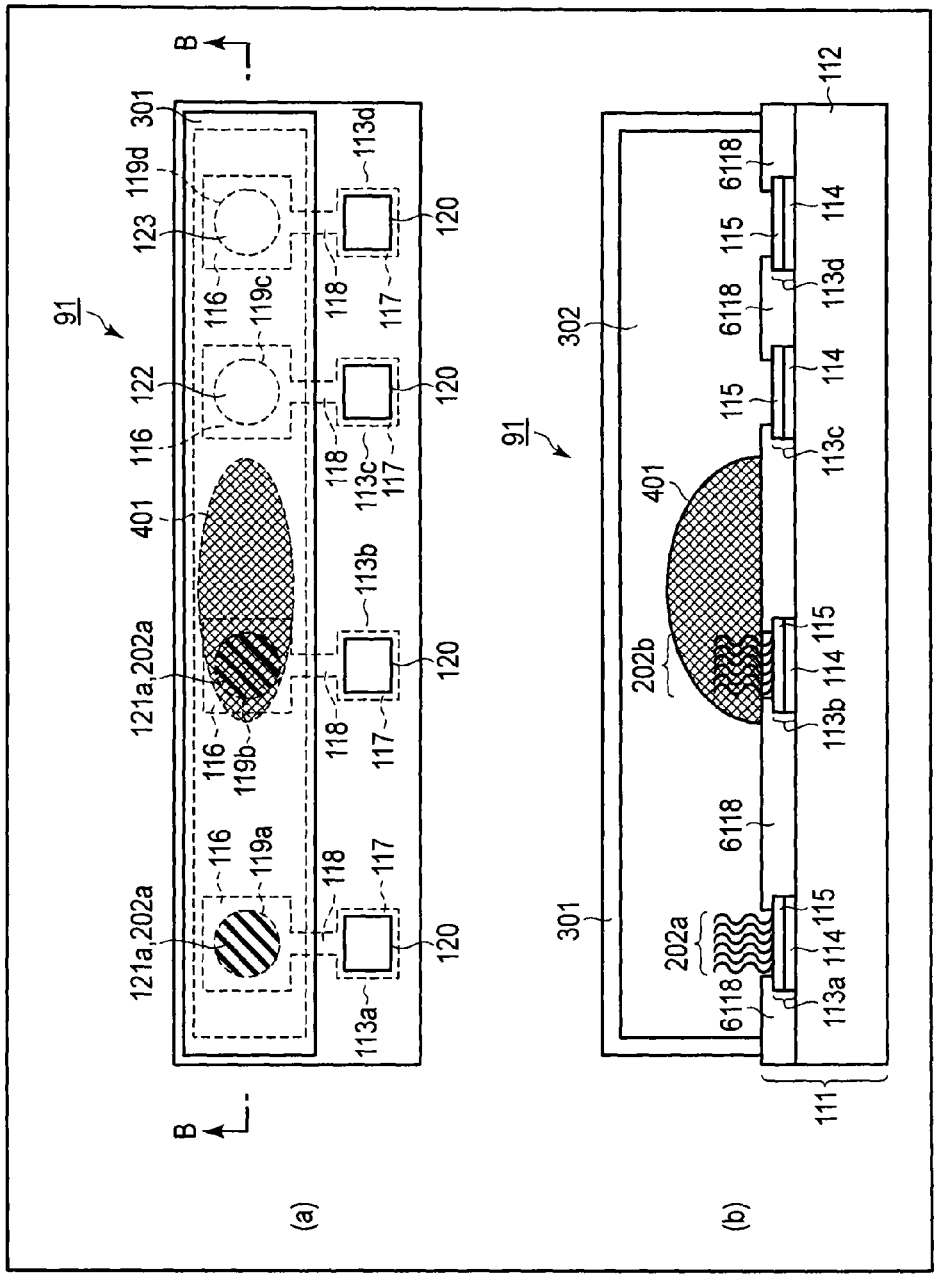
F I G. 53

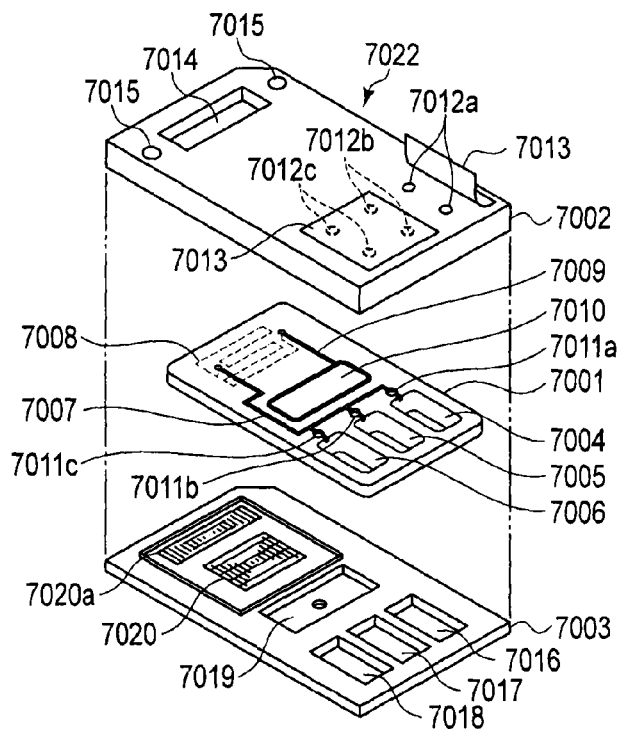
F I G. 54
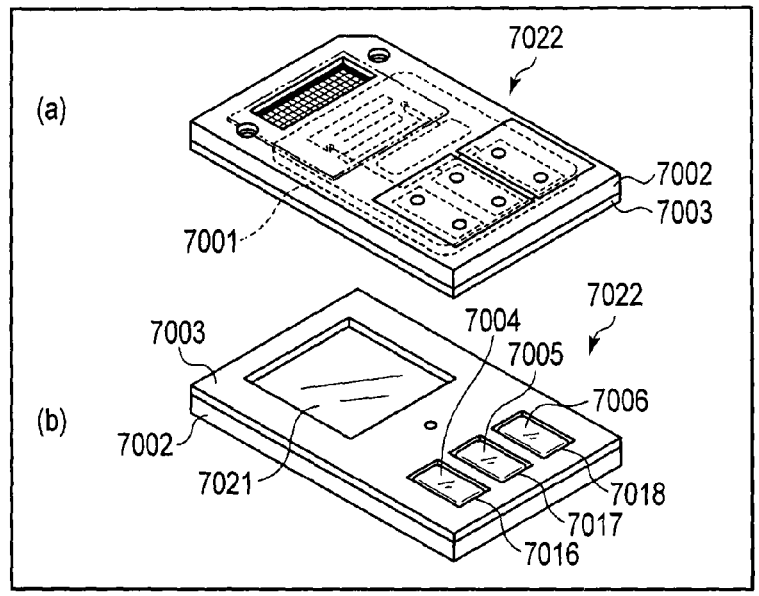
F I G. 55

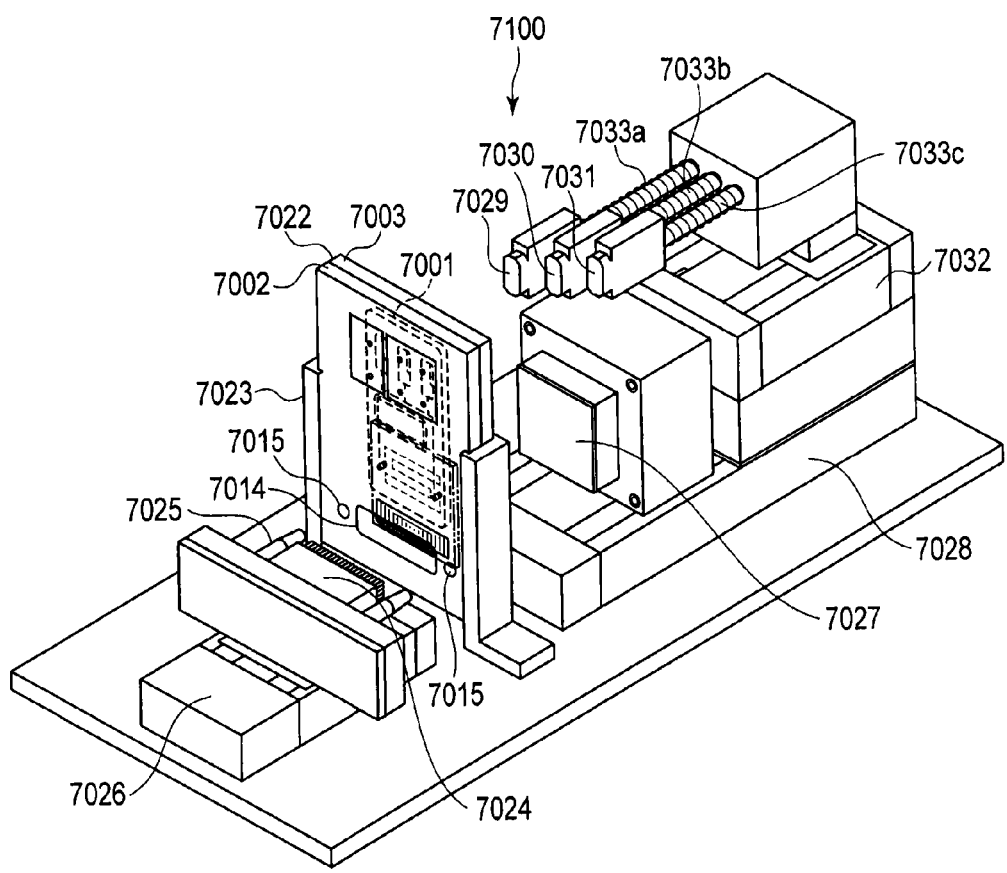
F I G. 56

MULTI-NUCLEIC-ACID AMPLIFICATION REACTION TOOL

CROSS-REFERENCE TO RELATED APPLICATIONS

This application is a Continuation application of PCT Application No. PCT/JP2012/069918, filed Aug. 3, 2012 and based upon and claiming the benefit of priority from Japanese Patent Applications No. 2011-172396, filed Aug. 5, 2011; No. 2012-064457, filed Mar. 21, 2012; No. 2012-067847, filed Mar. 23, 2012; No. 2012-067946, filed Mar. 23, 2012; No. 2012-068276, filed Mar. 23, 2012; and No. 2012-069255, filed Mar. 26, 2012, the entire contents of all of which are incorporated herein by reference.

FIELD

Embodiments described herein relate generally to a multi-nucleic-acid amplification reaction tool.

BACKGROUND

Currently, as a result of the development of genetic testing techniques, genetic tests are conducted in various scenarios including clinical diagnosis, forensics and so on. In many cases, these genetic tests only become effective if a plurality of object genes is detected and the results integrated. When, for example, identification of disease-causing bacteria, etc., is carried out at a clinical facility, a plurality of types of microorganisms suspected to cause infection or a type of each microorganism are identified based on a patient's symptoms. Diagnosis is performed accordingly. And when, for example, identification of individuals, etc., is carried out at a forensic facility, a repeat count is identified for repeated sequences in a plurality of gene loci which are present in every human genome. An individual is identified comprehensively from the identified repeat count in the plurality of gene loci. Consequently, individuals can be identified with high probability. Thus, techniques for detecting a plurality of object genes as described above are of great importance.

Conventionally, first a sample nucleic acid is amplified in a specific reaction container when a plurality of object genes are detected. Thereafter, the resulting amplification product is detected in an additional reaction device for detection.

Amplification is carried out principally in a plurality of reaction containers or one reaction container. When amplification is carried out in a plurality of reaction containers, reaction containers for amplifying object genes, respectively, are provided. When amplification is carried out in one reaction container, reagents for detecting all object genes are stored in one reaction container to carry out a multi-nucleic-acid amplification reaction. Generally, a nucleic acid to be detected is detected by subjecting an amplification product to a DNA chip, electrophoresis or the like.

BRIEF DESCRIPTION OF THE DRAWINGS

FIG. 6 is a graph illustrating in simulation a result obtained when detecting an amplification product obtained from an embodiment.
FIG. 10 is a view illustrating an example of a multi-nucleic-acid amplification detection reaction tool.
FIG. 12 is a view illustrating an example of a multi-nucleic-acid amplification detection reaction tool.
FIG. 13 is a view illustrating an example of a multi-nucleic-acid amplification detection reaction tool.
FIG. 15 is a view illustrating an example of a multi-nucleic-acid reaction tool.
FIG. 16 is a view illustrating an experimental result obtained using a multi-nucleic-acid reaction tool.
FIG. 23 is a schematic view of a nucleic acid detecting device.
FIG. 24 is a graph illustrating a result of a nucleic acid amplification reaction.
FIG. 25 is a schematic view of a nucleic acid detecting device.
FIG. 26 is a schematic view of a nucleic acid detecting device.
FIG. 27 is a schematic view of a nucleic acid detecting device.
FIG. 28 is a schematic view of a nucleic acid detecting device.
FIG. 29 is a schematic view of a nucleic acid detecting device.
FIG. 30 is a schematic view of a nucleic acid detecting device and a graph illustrating a result of a nucleic acid amplification reaction.
FIG. 31 is a view illustrating a process for preparation of a nucleic acid detecting device.
FIG. 32 is a sectional view illustrating an outlined configuration of a nucleic acid detecting device.
FIG. 33 is a sectional view illustrating an outlined configuration of a nucleic acid detecting device.
FIG. 34 is an enlarged view of a vicinity of a reaction region at a surface of a nucleic acid detecting device.
FIG. 35 is a sectional view illustrating an outlined configuration of a nucleic acid detecting device built-in cassette.
FIG. 36 is a view illustrating a nucleic acid detecting device and a reaction portion defining member arranged opposite to each other.
FIG. 37 is an enlarged view of a vicinity of a reaction region at a surface of a nucleic acid detecting device.

FIG. 38 is an enlarged view of a vicinity of a reaction region at a surface of a nucleic acid detecting device.

FIG. 39 is an enlarged view of a vicinity of a reaction region at a surface of a nucleic acid detecting device.

FIG. 40 is a graph illustrating a result of a nucleic acid amplification reaction.

FIG. 41 is an enlarged view of a vicinity of a reaction region at a surface of a nucleic acid detecting device.

FIG. 42 is a graph illustrating a result obtained from each electrode.

FIG. 43 is an enlarged view of a vicinity of a reaction region at a surface of a nucleic acid detecting device.

FIG. 46 is a perspective view illustrating a nucleic acid reaction tool.

FIG. 47 is a perspective view illustrating a nucleic acid reaction tool.

FIG. 52 is a view illustrating an array-type primer probe chip.

FIG. 53 is a view illustrating an array-type primer probe chip.

FIG. 54 is an exploded perspective view illustrating an outlined configuration of a nucleic acid detection cassette.

FIG. 55 is a perspective view illustrating an outlined configuration of a nucleic acid detection cassette.

FIG. 56 is a perspective view illustrating an outlined configuration of a nucleic acid detecting device.

DETAILED DESCRIPTION

Figure 1:
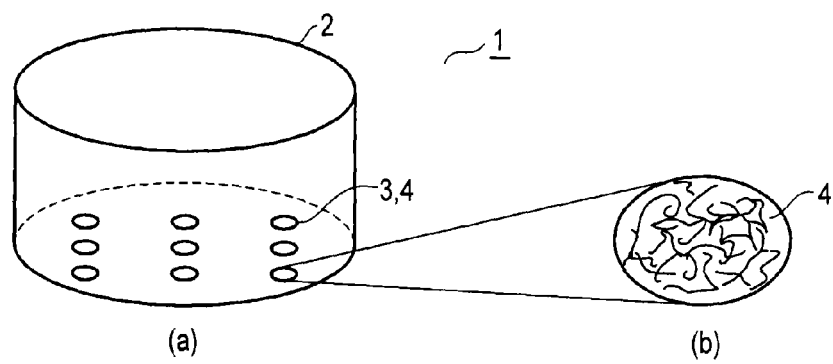
FIG. 1 is a view illustrating an example of a multi-nucleic-acid amplification reaction tool.

In general, according to one embodiment, a multi-nucleic-acid amplification reaction tool includes a support and a plurality of types of primer sets. The support is configured to be able to support a reaction field of a liquid phase. A plurality of types of primer sets are fixed in a releasable state, for each type, on mutually independent fixing regions of at least a surface of the support, which is in contact with the reaction field, when the liquid phase forms the reaction field. A plurality of types of primer sets are configured to amplify the respectively corresponding target sequences.

Various Embodiments will be described hereinafter with reference to the accompanying drawings.

1. DEFINITION

The term "multi-nucleic-acid amplification" means that a plurality of types of target sequences to be amplified are amplified in parallel. The term "amplification" means a process in which a template nucleic acid is continuously replicated using a primer set. The amplification method that can be used should be a method of amplifying a target nucleic acid, and examples thereof include, but are not limited to, PCR amplification, LAMP amplification, RT-LAMP amplification, SMAP amplification and ICAN amplification.

The term "target sequence" means a sequence to be amplified by a primer set, and includes a region with which a primer to be used is bound.

The "target nucleic acid" is a sequence including at least a target sequence, is a nucleic acid to be used as a template by a primer set to be used, and is also referred to as a "template nucleic acid".

The term "primer set" means a set of primers necessary to amplify one target nucleic acid. For example, in the case of a primer set for PCR amplification, one primer set should include one type of forward primer and one type of reverse primer for amplifying one target nucleic acid. For example, in the case of a primer set for LAMP amplification, one primer set should include a FIP primer and a BIP primer for amplifying at least one target nucleic acid, and may include an F3 primer, a B3 primer, an LP primer, that is, an LF primer and/or LB primer as necessary.

The term "object sequence" means a sequence to be detected by the array-type primer probe chip. A object nucleic acid to be detected includes the "object sequence". A nucleic acid including the object sequence is referred to as an "object sequence chain". The object sequence chain is hybridized with a probe nucleic acid including a complementary sequence thereof, and the existence or the amount of the hybridization is detected, so that the existence or the amount of an object nucleic acid is detected or measured.

The term "hybridized signal" means a signal generated by hybridization of a probe nucleic acid with a complementary sequence thereof, and is a generic term for detection signals that are detected as, for example, electric current values, fluorescent intensities and luminescent intensities using the method for detection of a microarray.

The "sample" should be a substance including a nucleic acid to be amplified and/or detected by a nucleic acid reaction tool. Examples of the sample may include, but are not limited to, blood, serum, leukocyte, urine, feces, semen, saliva, tissue, biopsy, oral mucosa, culture cells and sputum, or may be those obtained by extracting any of the aforementioned samples or a mixture thereof into a nucleic acid component using any technique that is publicly known itself.

2. MULTI-NUCLEIC-ACID AMPLIFICATION REACTION TOOL

First Embodiment (1) Multi-Nucleic-Acid Amplification Reaction Tool

An example of a multi-nucleic-acid amplification reaction tool will be described with reference to (a) and (b) of FIG. 1. The multi-nucleic-acid amplification reaction tool is an example of a multi-nucleic-acid amplification reaction tool for multi-amplifying a plurality of types of target nucleic acids.

FIG. 1(a) is a perspective view of an example of the multi-nucleic-acid amplification reaction tool. The multi-nucleic-acid amplification reaction tool 1 described in FIG. 1(a) has a container-shaped support 2. A plurality of mutually independent fixing regions 3 are arranged on the inner bottom surface of the support 2. FIG. 1(b) is a schematic view of the enlarged fixing region 3 part. As illustrated here, one type of primer set 4 is fixed on one fixing region 3. A plurality of primer sets 4 are fixed, for each type, on a plurality of fixing regions 3, respectively. A plurality of primer sets 4 may be different, or may be partially different in sequence, or may be partially the same in sequence as desired.

A plurality of primer sets 4 are provided for amplifying a plurality of intended target nucleic acids, respectively. One type of primer set 4 for amplifying one specific target nucleic acid is fixed on one fixing region 3. For example, in the case of a reaction tool for PCR amplification, one fixing region includes a plurality of forward primers and reverse primers that are necessary to amplify one type of specific target nucleic acid. In the case of a reaction tool for LAMP amplification, one fixing region includes a plurality of FIP primers and BIP primers that are necessary to amplify one type of specific target nucleic acid, and a plurality of F3 primers, B3 primers and LP primers as necessary.

The primer set 4 is fixed on the fixing region 3 in a releasable state so as to release in contact with a liquid phase for providing a reaction field. Fixing of the primer set 4 to the fixing region 3 can be achieved by, for example, adding dropwise to one fixing region 3 a solution including a set of primer sets, followed by drying the solution. Further, for other fixing regions 3, solutions each containing a desired primer set 4 are similarly added dropwise and dried to fix a desired number of primer sets to the support 2. In this way, primer sets 4 are fixed on all fixing regions 3 independently arranged on a surface of the support 2. However, it suffices that the primer set 4 is fixed on the fixing region 3 in a state of being releasable in contact with a liquid phase for providing a reaction field. Therefore, any fixing method that is capable of achieving the above-mentioned fixing and is publicly known itself may be used. In the case of the method of adding dropwise a solution including a primer set, the solution including a primer set may be, for example, water, a buffer solution or an organic solvent.

A plurality of fixing regions 3 to be arranged on the support 2 should be mutually independently arranged. The term "independently arranged" means that fixing regions are arranged at such intervals that amplification made to start and/or proceed for each primer set in a reaction field is not hindered. For example, adjacent fixing regions 3 may be arranged in contact with each other, or may be arranged in the vicinity of each other with a slight distance therebetween, or may be arranged at an interval equivalent to a distance between probes that are fixed in a detector such as so called a DNA chip which is usually used. For example, the distance between adjacent fixing regions 3 may be 0.1 µm to 1 µm, 1 µm to 10 µm, 10 µm to 100 µm, 100 µm to 1 mm, 1 mm to 10 mm or more, or may be preferably 100 µm to 10 mm.

The length of the primer may be, but be not limited to, about five bases or more, about six bases or more, about seven bases or more, about eight bases or more, about nine bases or more, about 10 bases or more, about 15 bases or more, about 20 bases or more, about 25 bases or more, about 30 bases or more, about 35 bases or more, about 40 bases or more, about 45 bases or more or about 55 bases or more, or may be about 80 bases or fewer, about 75 bases or fewer, about 70 bases or fewer, about 65 bases or fewer, about 60 bases or fewer, about 55 bases or fewer, about 50 bases or fewer, about 45 bases or fewer, about 40 bases or fewer, about 35 bases or fewer, about 30 bases or fewer, about 25 bases or fewer, about 20 bases or fewer, about 25 bases or fewer or about 20 bases or fewer, or may be in a range of a combination of any of the above-described upper and lower limits. Examples of the preferred base length may include about 10 bases to about 60 bases, about 13 to 40 bases and about 10 to 30 bases. The lengths of primers that are fixed on one support in parallel may be the same for every primer, or may be different for every primer, or some of the primers may be the same in length, or some of the primers may be different in length. The length may be different for each primer set. Primer sets fixed on one region may be different in length for each type, or all of primer sets fixed on one region may be the same in length.

The liquid phase for providing a reaction field should be a liquid phase such that after fixed primers are separated, an amplification reaction can be caused to proceed using the primers, and the liquid phase may be a reaction solution necessary for desired amplification.

For example, the container-shaped support may be in the form of a tube, a well, a chamber, a channel, a cup and a dish, and a plate having a plurality of these forms, for example a multi-well plate. The material of the support should be a material that is not itself involved in a reaction, and enables an amplification reaction to be carried out therein. The material may be arbitrarily selected from, for example, silicon, glass, a resin and a metal. For the container-shaped support, any container that is commercially available may be used.

In FIG. 1, an example is shown in which the fixing region 3 is arranged on the inner bottom surface of the support 2, but this is not exhaustive, and the fixing region may be arranged on at least a part of the inner side surface of a support 2, or may be arranged on any or all of the inner bottom surface, the inner side surface and the ceiling surface.

Figure 2:
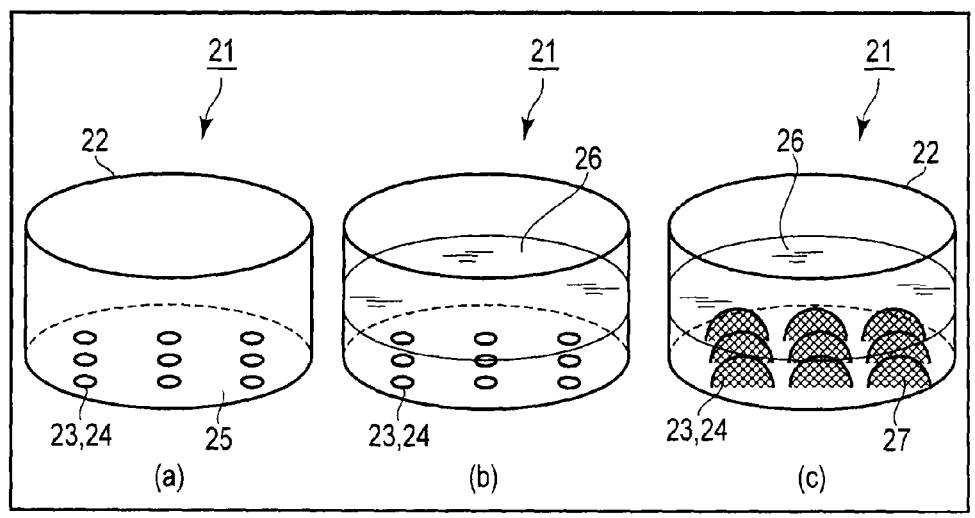
FIG. 2 is a view illustrating an example of a multi-nucleic-acid amplification reaction tool.

(2) Amplification Reaction of Nucleic Acid Using Multi-Nucleic-Acid Amplification Reaction Tool FIG. 2 is a view illustrating a nucleic acid amplification reaction using a multi-nucleic-acid amplification reaction tool 21 similar to that of the first embodiment. FIG. 2(*a*) illustrates the multi-nucleic-acid amplification reaction tool 21 before the reaction. A plurality of primer sets 24 are, respectively, fixed on a plurality of fixing regions 23 arranged on the inner bottom surface of the support 2. FIG. 2(*b*) illustrates a state in which a reaction solution 26 is added and stored in the multi-nucleic-acid amplification reaction tool 21.

The reaction solution 26 should contain components necessary for a desired amplification reaction. Examples of the components may include, but are not limited to, an enzyme such as polymerase, a substrate substance such as deoxynucleoside triphosphate necessary for forming a new polynucleotide chain with a primer as a start point, a reverse transcriptase and a necessary substrate substance, etc., when performing reverse transcription in parallel, and a buffer such as a salt configured to maintain a proper amplification environment.

In the multi-nucleic-acid amplification reaction tool after the reaction solution 26 is added as illustrated in FIG. 2(*b*), primers fixed on the inner bottom surface separate and gradually diffuse as schematically illustrated in FIG. 2(*c*). A region where primers separate and diffuse is schematically shown by a region 27. Primers separating and diffusing encounter other components necessary for amplification which exist in their vicinity, such as a template nucleic acid, polymerase and a substrate substance, so that an amplification reaction is started. A plurality of primer sets independently fixed for each type can cause an amplification reaction to start and proceed for the template nucleic acid independently for each type. In this way, amplification for a plurality of template sequences using a plurality of types of primer sets is achieved independently and in parallel. Here, the term "reaction field" means a region defined by the reaction solution 26 where theoretically the amplification reaction can proceed, that is, a region where the reaction solution exists. Of the reaction field, a region where the amplification reaction actually starts and proceeds is referred to as a "reaction region". If actually the amplification reaction proceeds only in a region 27, the region 27 may be considered as a reaction region.

The reaction solution 26 should be a liquid phase such that after fixed primer sets are separated, an amplification reaction between the primer sets and the target nucleic acid can occur. This reaction solution should be injected mechanically or manually to the reaction field (initially filled with air) on which primers are fixed using any method before the start of the amplification reaction.

In the above-described example, only primer sets are fixed on a support. However, this is not exhaustive, and other components necessary for amplification, for example enzymes such as polymerase and a reverse transcriptase, a substrate substance, a substrate substance and/or a buffer, may be fixed, on the support along with primers under conditions for fixing primer sets, for each type, on each fixing regions. In this case, substances to be fixed should be included in a desired liquid medium along with primers, and added dropwise and dried to be fixed using a method similar to that described above. When the amplification reaction is carried out in such a multi-nucleic-acid amplification reaction tool, a composition of a reaction solution to be added thereto should be selected according to the fixed components.

Second Embodiment

A further example of a multi-nucleic-acid amplification reaction tool will be described with reference to FIG. 3.

Figure 3:
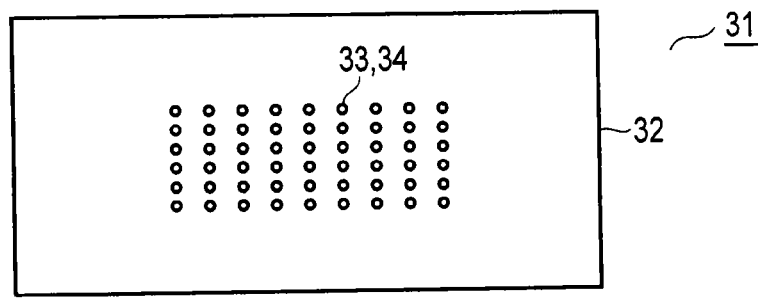
FIG. 3 is a view illustrating an example of a multi-nucleic-acid amplification reaction tool.

FIG. 3 is a plan view illustrating a further example of a multi-nucleic-acid amplification reaction tool. A multi-nucleic-acid amplification reaction tool 31 described in FIG. 3 is an example in which a base plate is used as a support 32. A plurality of mutually independent fixing regions 33 are arranged on a surface of the support 32. In the fixing regions 33, one type of primer set 34 is fixed on one fixing region 33 like FIG. 1. A plurality of primer sets 34 are fixed, for each type, on a plurality of fixing regions 33, respectively. The configuration of the primer set 34 included in one fixing region 33 includes different types of primers necessary to amplify one type of specific target nucleic acid as in the case of the first embodiment.

For amplification using the second embodiment, a reaction field should be formed by placing a reaction solution onto at least a region of the support 32 on which the primer set 34 is fixed.

The fixing region 33 may be arranged on the surface of a recessed portion formed on the surface of the support 32 beforehand, or the inner wall of a channel formed by a recessed portion or a raised portion.

When the base plate is used as a support, the material thereof should be a material that is not itself involved in a reaction, and enables an amplification reaction to be carried out therein. The material may be arbitrarily selected from, for example, silicon, glass, a resin and a metal. Fixing of the primer 34 to the support should be performed in the same manner as in the first embodiment.

Further, a reaction field may be formed by arranging the multi-nucleic-acid amplification reaction tool of the second embodiment in a container which can retain the reaction tool, and adding a reaction solution in the container. In this case, primer sets 34 may be fixed on both surfaces of the support 32. Consequently, more types of primer sets can be fixed to the present multi-nucleic-acid amplification reaction tool, so that a larger number of target sequences can be amplified. In this aspect, the multi-nucleic-acid amplification reaction tool may have a support of any shape as long as it is a support with a plurality of primer sets independently fixed on at least a surface. The material of the support and the method for fixing of primers in this case may be similar to those in the first and second embodiments. The multi-nucleic-acid amplification reaction tool described above may be used as a multi-nucleic-acid amplification reaction carrier including a base body, and a plurality of types of primer sets releasably fixed, for each type, on mutually independent fixing regions of at least a surface of the base body. In this case, a size and a shape of the base body may be arbitrarily selected by a practitioner. For example, the base body may have a plate-like shape, a spherical shape, a rod-like shape and a shape including a part of these shapes.

Third Embodiment

Figure 4:
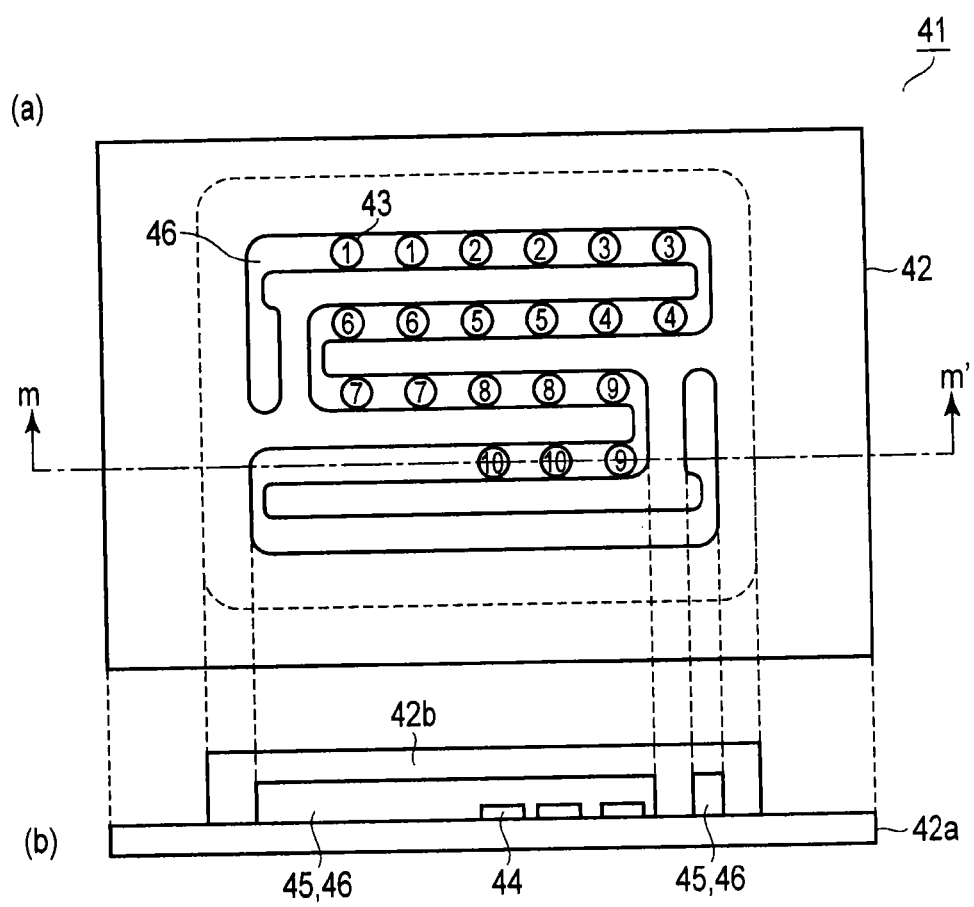
FIG. 4 is a view illustrating an example of a multi-nucleic-acid amplification reaction tool.

A further example of a multi-nucleic-acid amplification reaction tool will be described with reference to FIG. 4. A multi-nucleic-acid amplification reaction tool 41 illustrated in FIG. 4 is an example in which a support having a channel is used. FIG. 4(a) is a plan view, and FIG. 4(b) is a sectional view cut along line m-m'.

The multi-nucleic-acid amplification reaction tool 41 includes a plurality of primers releasably fixed, for each type, on a plurality of mutually independent fixing regions 43 on the inner bottom surface of a channel 46 formed in a support 42.

The support 42 has a base body 42a and a cover 42b. The cover 42b has a recessed portion for defining the channel. Fixing regions 43 are arranged on the surface of the base body 42a which is facing to the interior of the channel 46. The base body 42a and the cover 42b are in close contact with each other so that a liquid stored inside can be retained. The close contact between the base body and the cover may be achieved by a technique that is publicly known itself, such as fixing and/or bonding, or they may be integrated, and the support 42 may be formed in an integrated state.

The multi-nucleic-acid amplification reaction tool 41 is produced using, for example, a first base plate (substrate) 42a and a second base plate 42b. First, a plurality of primer sets 44 are releasably fixed, for each type, on predetermined fixing regions 43 of the first base plate 42a. This fixing can be performed by a method similar to that in the first embodiment. On the other hand, on the second base plate 42b, a recessed portion 45 is formed so as to match the shape of a desired channel. Formation of the recessed portion 45 can be performed by a method, which is publicly known itself, according to a material of a base plate to be used. An arrangement of fixing regions 43 is determined so that they are included in a channel formed by the recessed portion 45 formed on the second base plate 42b. Next, the first base plate 42a and the second base plate 42b are integrated. At this time, they are integrated such that the recessed portion 45 of the second base plate 42b faces the first base plate 42a side. Further, a through-hole (not illustrated) may be provided at a part of the recessed portion 45 of the second base plate 42b. The through-hole may be used as an entrance for a reaction solution or the like to pass into the channel.

The material of the first base plate 42a and the material of the second base plate 42b may be the same or different. The materials of the first base plate 42a and the second base plate 42b should be materials that are not themselves involved in a reaction, and enable an amplification reaction to be carried out therein. The material may be arbitrarily selected from, for example, silicon, glass, a resin and a metal.

In this embodiment, an example is shown in which primer sets are fixed on the inner bottom surface of a channel 46 of the support 42 having the channel, but the arrangement and shape of the channel are not limited thereto. The surface on which primer sets are fixed may be any surface provided with the channel, and primer sets may be fixed on all of surfaces provided with the channel, or may be fixed on two or more of the surfaces.

Alternatively, in the first base plate 42a on which a channel is formed by forming the recessed portion 45 or a groove beforehand, a plurality of primer sets may be independently fixed on the wall surface of a part of the channel, followed by covering the channel with a silicon rubber to produce the multi-nucleic-acid amplification reaction tool of FIG. 4.

Fourth Embodiment

Multi-Nucleic-Acid Amplification and Detection

Figure 5:
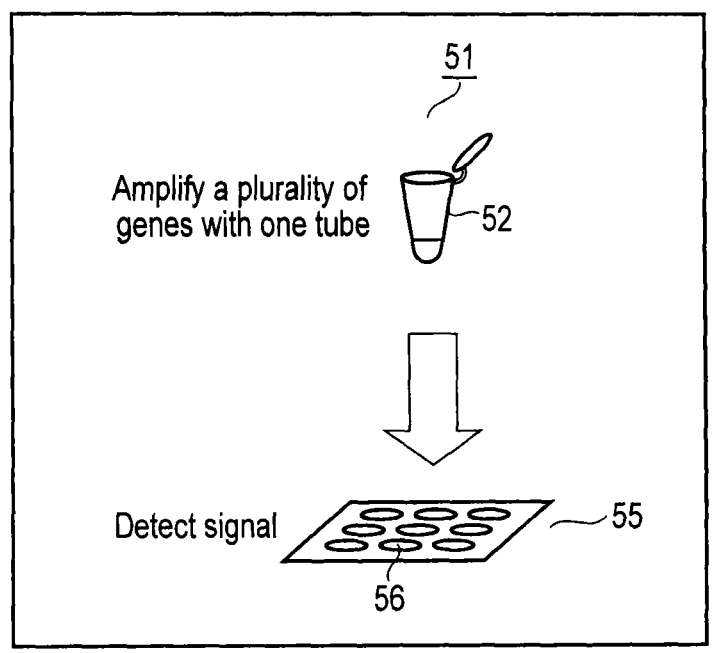
FIG. 5 shows a scheme illustrating a detection method using an embodiment.

As illustrated in FIG. 5, a multi-nucleic-acid amplification reaction tool 51 may include a tube 52 as a support, and a plurality of primer sets (not illustrated) that are independently fixed on the inner surface of the tube 52. A plurality of types of target nucleic acids van also be amplified in this tube-type multi-nucleic-acid amplification reaction tool 51. Thereafter, detection can be performed by adding the obtained amplification products to a device such as a DNA chip 55 on which a plurality of different nucleic acid probes 56 are fixed. The multi-nucleic-acid amplification reaction tool thus illustrated in the embodiment is capable of preparing samples for detection more conveniently than heretofore, and performing a plurality of amplifications independently.

Fifth Embodiment

Multi-Nucleic-Acid Amplification Method

There is also provided as a further embodiment a multi-nucleic-acid amplification reaction method including releasably fixing a plurality of types of primer sets designed to amplify a plurality of types of target nucleic acids, respectively, to at least an inner surface of a support formed of a specific container, a tube, a dish, a base plate provided with a channel, or the like.

The multi-nucleic-acid amplification reaction method may include: releasably fixing a plurality of types of primer sets designed to amplify a plurality of types of target nucleic acids, respectively, to at least a surface of a desired support; adding a reaction solution containing reagents necessary for amplification, for example an enzyme such as polymerase, a substrate substance such as deoxynucleoside triphosphate necessary for forming a new polynucleotide chain with a primer as a start point, a reverse transcriptase and a necessary substrate substance, etc., when performing reverse transcription in parallel, and a buffer such as a salt configured to maintain a proper amplification environment so that a plurality of types of primer sets are included in one reaction field; performing adjustment of a reaction environment suitable for an amplification reaction such as adjustment of temperature by heating or cooling the support on which the primers are fixed; and thereby carrying out a multi-nucleic-acid amplification reaction.

A specific amplification reaction may be carried out using a technique, which is publicly known itself, according to the type of amplification reaction.

There is also provided as a further embodiment a multi-nucleic-acid amplification reaction including releasably fixing a plurality of types of primer sets designed to amplify a plurality of types of target nucleic acids, respectively, to the surface of a base plate such as microbeads, a plate piece or a rod.

The multi-nucleic-acid amplification reaction includes, for example: releasably fixing a plurality of types of primer sets designed to amplify a plurality of types of target nucleic acids, respectively, to at least a surface of a desired base body; placing the base body in a reaction solution containing reagents necessary for amplification, for example an enzyme such as polymerase, a substrate substance such as deoxynucleoside triphosphate necessary for forming a new polynucleotide chain with a primer as a start point, a reverse transcriptase and a necessary substrate substance, etc., when performing reverse transcription in parallel, and a buffer such as a salt configured to maintain a proper amplification environment; performing adjustment of a reaction environment suitable for an amplification reaction such as adjustment of temperature by heating or cooling the reaction solution; and thereby carrying out a multi-nucleic-acid amplification reaction.

Results of amplifying a target nucleic acid by the multi-nucleic-acid amplification described above, followed by performing detection of amplification products using a DNA chip will be described.

FIG. 6(*a*-1) is a view illustrating amplification of target sequences using a plurality of types of primer sets, that is, a first primer set (A) 63a and a second primer set (B) 63b, respectively, in a reaction solution 62 added in a reaction container 61. A reaction system 64 of FIG. 6(*a*-1) is not the multi-nucleic-acid amplification reaction tool disclosed herein, but a conventional general reaction system. That is, any of primer sets is not fixed to any of surfaces of the reaction container 61, and an amplification reaction is carried out with primer sets directly mixed with a reaction solution.

FIG. 6(*b*-1) illustrates a multi-nucleic-acid amplification reaction tool 21 having a configuration similar to that in the second embodiment described above. The multi-nucleic-acid amplification reaction tool 21 includes a container 22, and a first primer fixing region 23a and a second primer fixing region 23b which are arranged on the inner bottom of the container 22. A first primer set (A) 24a is releasably fixed on the first primer fixing region 23a. A second primer set (B) 24b is releasably fixed on the second primer fixing region 23b.

In amplification by the reaction system of FIG. 6(*a*-1), the obtained amplification amount varies due to a difference amplification efficiency, amplification specificity or the like between the primer set (A) 63a and the primer set (B) 63b. An example of a result obtained by such amplification is illustrated in FIG. 6(*a*-2). For example, when a gene expression level is to be detected, a real expression level cannot be reflected by such a general method.

In the case of the multi-nucleic-acid amplification reaction tool 21 as an example of the further embodiment illustrated in FIG. 6(*a*-2), amplifications by the first primer (A) 24a and the second primer (B) 24b that are releasably fixed to the container 22 can be performed independently for the intended target nucleic acid. Therefore, when template nucleic acids of the first primer (A) 24a and the second primer (B) 24b exist in the same amount in the reaction field, detection signals having the same size as illustrated in FIG. 6(*b*-2) can be obtained.

According to the multi-nucleic-acid amplification reaction tool shown in the above-described embodiment as an example, a plurality of types of target sequences can be made in parallel independently without undergoing interferences by different sequences. In the conventional technique, there is the problem that the number of types of primers is limited because deviation occurs in reaction efficiency when multiplex amplification is performed by using a plurality of types of primers in one container. That is, different types of primers may compete for a necessary enzyme and dNTP. There may be difference in reaction specificity and/or reaction efficiency according to a sequence of target sequences or a sequence of primers. In this case, there arises the problem that the amplification reaction start point varies depending on a type of primer, amplification starts and proceeds for only some primer sets, or amplification for some primer sets is not sufficiently achieved. These conventional problems described above are solved by embodiments disclosed in this specification.

That is, when an amplification reaction is carried out using a multi-nucleic-acid amplification reaction tool with the embodiment shown as an example, the amplification reaction proceeds only at or near an amplification reagent, and therefore amplification reactions of various kinds of targets can be made to proceed independently without interfering with one another although the amplification reactions are carried out in the same container and/or the same reaction solution. Different primer sets may be further added after individual reactions proceed to some degree, or the container-shaped multi-nucleic-acid amplification reaction tool shown in the first embodiment and the above-described multi-nucleic-acid amplification reaction carrier may be used in combination.

Example 1

Example of a container for multi-amplification which enables LAMP multi-amplification of 10 types.
 (1) Preparation of Container for Multi-Amplification
  Nucleotide sequences of primers used are shown in Tables 1-1 and 1-2.

TABLE 1-1

List of primer sets

| Set No. | Primer type | Nucleotide sequence (5' → 3') |
|---|---|---|
| 1 | FIP | AACATATACCATTGTTGTGGCCCTTCCATGGTAACCTCTGATTCCC |
|   | BIP | CTACCCGTAGTACCAACTTTACCCACGTGCCTGGTATATTCC |
|   | F3 | GTTCTGTATACTGCCCCTCTC |
|   | B3 | GACATAACATCAGTTGTTAATGTGAC |
|   | LP | CCTTATGTAGCCAATAAGGC |
| 2 | FIP | GCTATGCGTGAATTTTCTGTGCCCTTGGTGTTGGCCTTAG |
|   | BIP | GCACAACAAGATGTTAGAGATAACAATAGGTGGAGCACAGCC |
|   | F3 | GTTGAGGTGGGCAGAGGAC |
|   | B3 | TTGCATGTAGTGCCAATACCC |
|   | LP | CATATTTATTAAATAAGGGATGACCAC |
| 3 | FIP | ATTATTGTGGCCCTGCGCACGTTCTATGGTAACCTCAGAATCCC |
|   | BIP | ACCACTCGTAGCACTAACATGACTCGCCATGACGAAGGTATTCCT |
|   | F3 | GCCACTGTACAAAGCAGTGC |
|   | B3 | TGAATGTATGTCATAACATCAGCTG |
|   | LP | GCTGAGGTTAAAAAGGAAAGCACA |
| 4 | FIP | AGTGTCCCCTACCATGCCCCACGTAGGGAACAGTTATTTGCT |
|   | BIP | TAAGGGCACTGACATACGTGACAGCCATAGACCCACTAGGCGAG |
|   | F3 | CTGCAGATGTATATGGAGACAGTA |
|   | B3 | GTTAAATAACTGGGAGTCTGAGGAT |
|   | LP | CTCTATTCCAAAAATGCCTAGCA |
| 5 | FIP | GTGGCCCTGTGCTCGTTGTCTATGGTTACCTCTGATGCC |
|   | BIP | CACGCAGTACAAATATGTCACCCCATGTCGTAGGTACTCC |
|   | F3 | CAAATTATTTTCCTACACCTAGTGG |
|   | B3 | GTCATAACGTCTGCAGTTAAGG |
|   | LP | GCTGCCATATCTACTTCAGAAACTACA |
| 6 | FIP | GCCAGCAAACACCATTGTTACTCTATTGTTACCTCTGACTCCC |
|   | BIP | ACCACTCGCAGTACCAATTTAACCCTCAACATGTCTGCTATACTGC |
|   | F3 | TGTATTCTCCCTCTCCAAGTG |
|   | B3 | GAATATAGGACATAACATCTGCAG |
|   | LP | ACCCTGTGCCTTATGTAACC |

TABLE 1-2

(Continued from Table 1-1)

| Set No. | Primer type | Nucleotide sequence (5' → 3') |
|---|---|---|
| 7 | FIP | GTTTAGTAACTCCAAAGGAGGACAAAGGCACACCTTGTAATGC |
|   | BIP | GGGACATGGTAGACACAGGACATATATCTAGGGGAACATCAC |
|   | F3 | CCTATAGGTGAACATTGGG |
|   | B3 | GGATATTTGCAAATGGAACTG |
|   | LP | CATTCTCCTGCTTTTACCTGGT |
| 8 | FIP | AATTGATTACCCCAGCAAATGCCGTCTATGATTACGTCTGAGGCAC |
|   | BIP | ATACTACTAGAAGTACTAACATGACCCTCCACATGTCTAAGGTACTG |
|   | F3 | GTATATGTTGCTACGCCTAGTG |
|   | B3 | GCCATAACCTCTGCAGACAAAG |
|   | LP | GCACGTTGCAACCAATAAGG |
| 9 | FIP | GGATAACTGCAGTATTACCGGACCTAGGGCTGGAAAACTTGG |
|   | BIP | TCCAACTCCTAGTGGCTCTATAGCGCTGTAGCCAATAAGGC |
|   | F3 | GACGTGAGCAGATGTTTGT |
|   | B3 | CCATTGTTATGACCTTGTGC |
|   | LP | CCTCAGAATCACAATTATTTAATAAGCC |
| 10 | FIP | TGAGGTCTAAGTGATGACAGCCGCAACTCCTAAGCCAGTGCCAGA |
|   | BIP | CTAGGGTTGGCCAATCTACTCCCAATAGATGGCTCTGCCCTGAC |
|   | F3 | AGGGCTGAGGGTTTGAAGTC |
|   | B3 | TGAACACAGTTGTGTCAGAAGC |

In each primer set, the surface of a glass base plate is spotted with 0.6 μL of a TE solution including FIP: 40 pmol, BIP: 40 pmol, F3: 40 pmol, B3: 5 pmol and LP: 20 pmol, and left standing at room temperature for 10 minutes to dry and fix primers. A silicon rubber provided with a channel beforehand was applied onto the base plate on which primers were dried and fixed, thereby preparing a container for multi-amplification with primers spotted in a channel (FIG. 4).

(2) Preparation of LAMP Reaction Solution for Container for Multi-Amplification and LAMP Reaction The composition of a LAMP reaction solution for container for multi-amplification is shown in Table 2.

TABLE 2

Composition of LAMP solution for multi-amplification container

|  | (μL) |
|---|---|
| Reaction Mixture | 14.0 |
| Bst DNA Polymerase | 4.0 |
| DW | 22.0 |
| Template No. 1 (1.0E+03copies/μL) | 1.0 |
| Template No. 2 (1.0E+03copies/μL) | 1.0 |
| Template No. 3 (1.0E+03copies/μL) | 1.0 |
| Template No. 4 (1.0E+03copies/μL) | 1.0 |
| Template No. 5 (1.0E+03copies/μL) | 1.0 |
| Template No. 6 (1.0E+03copies/μL) | 1.0 |
| Template No. 7 (1.0E+03copies/μL) | 1.0 |
| Template No. 8 (1.0E+03copies/μL) | 1.0 |
| Template No. 9 (1.0E+03copies/μL) | 1.0 |
| Template No. 10 (1.0E+03copies/μL) | 1.0 |
| Total | 50.0 |

Nucleotide sequences of templates Nos. 1 to 10 included in this reaction solution are shown in Tables 3-1, 3-2, 3-3, 3-4, 3-5, 3-6, 3-7, 3-8, 3-9 and 3-10.

TABLE 3-1

| Template No. 1 |
| --- |
| GTTCTGTATACTGCCCCTCTCCCAGCGGTTCCATGGTAACCTCTGATTC |
| CCAGTTATTTAATAAGCCTTATTGGCTACATAAGGCCCAGGGCCACAAC |
| AATGGTATATGTTGGCATAATCAATTATTTCTTACTGTTGTGGACACTA |
| CCCGTAGTACCAACTTTACATTATCTACCTCTATAGAGTCTTCCATACC |
| TTCTACATATGATCCTTCTAAGTTTAAGGAATATACCAGGCACGTGGAG |
| GAGTATGATTTACAATTTATATTTCAACTGTGTACTGTCACATTAACAA |
| CTGATGTTATGTC |

TABLE 3-2

| Template No. 2 |
| --- |
| GTTGAGGTGGGCAGAGGACAGCCCCTTGGTGTTGGCCTTAGTGGTCATC |
| CCTTATTTAATAAATATGATGACACAGAAAATTCACGCATAGCAAATGG |
| CAATGCACAACAAGATGTTAGAGATAACACATCTGTTGACAACAAACAG |
| ACTCAGTTATGTATAATAGGCTGTGCTCCACCTATTGGGAACACTGGG |
| GTATTGGCACTACATGCAA |

TABLE 3-3

| Template No. 3 |
| --- |
| GCCACTGTACAAAGCAGTGCTTTTTTTCCTACTCCTAGTGGTTCTATGGT |
| AACCTCAGAATCCCAATTATTTAATAAACCGTACTGGTTACAACGTGCGC |
| AGGGCCACAATAATGGCATATGTTGGGGCAATCAGTTGTTTGTCACAGTT |
| GTGGATACCACTCGTAGCACTAACATGACTTTATGTGCTGAGGTTAAAAA |
| GGAAAGCACATATAAAAATGAAAATTTTAAGGAATACCTTCGTCATGGCG |
| AGGAATTTGATTTACAATTTATTTTTCAATTGTGCAAAATTACATTAACA |
| GCTGATGTTATGACATACATTCA |

TABLE 3-4

| Template No. 4 |
| --- |
| CTGCAGATGTATATGGAGACAGTATGTTCTTTTGTTTACGTAGGGAACAG |
| TTATTTGCTAGGCATTTTTGGAATAGAGGGGGCATGGTAGGGGACACTAT |
| ACCTACTGAATTGTATATTAAGGGCACTGACATACGTGACAGTCCTAGTA |
| GTTATGTATATGCCCCCTCGCCTAGTGGGTCTATGGTATCCTCAGACTCC |
| CAGTTATTTAAC |

TABLE 3-5

| Template No. 5 |
| --- |
| CAAATTATTTTCCTACACCTAGTGGTTCTATGGTTACCTCTGATGCCCAA |
| ATATTCAATAAACCTTATTGGTTACAACGAGCACAGGGCCACAATAATGG |
| CATTTGTTGGGGTAACCAACTATTTGTTACTGTTGTTGATACTACACGCA |

TABLE 3-5-continued

| Template No. 5 |
| --- |
| GTACAAATATGTCATTATGTGCTGCCATATCTACTTCAGAAACTACATAT |
| AAAAATACTAACTTTAAGGAGTACCTACGACATGGGGAGGAATATGATTT |
| ACAGTTTATTTTTCAACTGTGCAAAATAACCTTAACTGCAGACGTTATGA |
| C |

TABLE 3-6

| Template No. 6 |
| --- |
| TGTATTCTCCCTCTCCAAGTGGCTCTATTGTTACCTCTGACTCCCAGTTG |
| TTTAATAAACCATATTGGTTACATAAGGCACAGGGTCATAACAATGGTGT |
| TTGCTGGCATAATCAATTATTTGTTACTGTGGTAGATACCACTCGCAGTA |
| CCAATTTAACAATATGTGCTTCTACACAGTCTCCTGTACCTGGGCAATAT |
| GATGCTACCAAATTTAAGCAGTATAGCAGACATGTTGAGGAATATGATTT |
| GCAGTTTATTTTTCAGTTGTGTACTATTACTTTAACTGCAGATGTTATGT |
| CCTATATTC |

TABLE 3-7

| Template No. 7 |
| --- |
| CCTATAGGTGAACATTGGGGAAAAGGCACACCTTGTAATGCTAACCAGGT |
| AAAAGCAGGAGAATGTCCTCCTTTGGAGTTACTAAACACTGTACTACAAG |
| ACGGGGACATGGTAGACACAGGATTTGGTGCAATGGATTTTACTACATTA |
| CAAGCTAATAAAAGTGATGTTCCCCTAGATATATGCAGTTCCATTTGCAA |
| ATATCC |

TABLE 3-8

| Template No. 8 |
| --- |
| GTATATGTTGCTACGCCTAGTGGGTCTATGATTACGTCTGAGGCACAGTT |
| ATTTAATAAACCTTATTGGTTGCAACGTGCCCAAGGCCATAATAATGGCA |
| TTTGCTGGGGTAATCAATTATTTGTTACTGTAGTAGATACTACTAGAAGT |
| ACTAACATGACTATTAGTACTGCTACAGAACAGTTAAGTAAATATGATGC |
| ACGAAAATTAATCAGTACCTTAGACATGTGGAGGAATATGAATTACAAT |
| TTGTTTTTCAATTATGCAAAATTACTTTGTCTGCAGAGGTTATGGC |

TABLE 3-9

| Template No. 9 |
| --- |
| GACGTGAGCAGATGTTTGTTAGACACTTTTTTAATAGGGCTGGAAAACTT |
| GGCGAGGCTGTCCCGGATGACCTTTATATTAAAGGGTCCGGTAATACTGC |
| AGTTATCCAAAGTAGTGCATTTTTTCCAACTCCTAGTGGCTCTATAGTTA |

TABLE 3-9-continued

Template No. 9

CCTCAGAATCACAATTATTTAATAAGCCTTATTGGCTACAGCGTGCACAA

GGTCATAACAAT

TABLE 3-10

Template No. 10

A GGGCTGAGGG TTTGAAGTCCAACTCCTAAG CCAGTGCCAG

AAGAGCCAAGGACAGGTACGGCTGTCATCACTTAGACCTCACCCTGTGGA

GCCACACCCTAGGGTTGGCCAATCTACTCCCAGGAGCAGGGAGGGCAGGA

GCCAGGGCTGGGCATAAAAGTCAGGGCAGACAACTGTGTT CA

A LAMP reaction solution for a container for multi-amplification in an amount of 50 μL reaction solution was injected into a channel of a multi-amplification container, the container was placed on a hotplate so that a glass surface came into contact with the hotplate set at 63° C., and a LAMP reaction was carried out for one hour.

(3) Preparation of LAMP Reaction Solution for PCR Tube and LAMP Reaction

The composition of a LAMP reaction solution for PCR tube is shown in Table 4. This reaction solution was set in a thermostat set at 63° C., and a LAMP reaction was carried out for one hour.

TABLE 4

Composition of LAMP solution for PCR tube

| | | (μL) |
|---|---|---|
| Reaction Mixture | | 14.00 |
| Bst DNA Polymerase | | 4.00 |
| DW | | 25.28 |
| Primer set No. 1 | FIP (200 μM) | 0.40 |
| | BIP (200 μM) | 0.40 |
| | F3 (200 μM) | 0.06 |
| | B3 (200 μM) | 0.06 |
| | LP (200 μM) | 0.20 |
| Primer set No. 2 | FIP (200 μM) | 0.40 |
| | BIP (200 μM) | 0.40 |
| | F3 (200 μM) | 0.06 |
| | B3 (200 μM) | 0.06 |
| | LP (200 μM) | 0.20 |
| Primer set No. 3 | FIP (200 μM) | 0.40 |
| | BIP (200 μM) | 0.40 |
| | F3 (200 μM) | 0.06 |
| | B3 (200 μM) | 0.06 |
| | LP (200 μM) | 0.20 |
| Primer set No. 4 | FIP (200 μM) | 0.40 |
| | BIP (200 μM) | 0.40 |
| | F3 (200 μM) | 0.06 |
| | B3 (200 μM) | 0.06 |
| | LP (200 μM) | 0.20 |
| Primer set No. 5 | FIP (200 μM) | 0.40 |
| | BIP (200 μM) | 0.40 |
| | F3 (200 μM) | 0.06 |
| | B3 (200 μM) | 0.06 |
| | LP (200 μM) | 0.20 |
| Primer set No. 6 | FIP (200 μM) | 0.40 |
| | BIP (200 μM) | 0.40 |
| | F3 (200 μM) | 0.06 |
| | B3 (200 μM) | 0.06 |
| | LP (200 μM) | 0.20 |
| Primer set No. 7 | FIP (200 μM) | 0.40 |
| | BIP (200 μM) | 0.40 |
| | F3 (200 μM) | 0.06 |
| | B3 (200 μM) | 0.06 |
| | LP (200 μM) | 0.20 |
| Primer set No. 8 | FIP (200 μM) | 0.40 |
| | BIP (200 μM) | 0.40 |
| | F3 (200 μM) | 0.06 |
| | B3 (200 μM) | 0.06 |
| | LP (200 μM) | 0.20 |
| Primer set No. 9 | FIP (200 μM) | 0.40 |
| | BIP (200 μM) | 0.40 |
| | F3 (200 μM) | 0.06 |
| | B3 (200 μM) | 0.06 |
| | LP (200 μM) | 0.20 |
| Primer set No. 10 | FIP (200 μM) | 0.40 |
| | BIP (200 μM) | 0.40 |
| | F3 (200 μM) | 0.06 |
| | B3 (200 μM) | 0.06 |
| Template No. 1 (1.0E+03copies/μL) | | 1.00 |
| Template No. 2 (1.0E+03copies/μL) | | 1.00 |
| Template No. 3 (1.0E+03copies/μL) | | 1.00 |
| Template No. 4 (1.0E+03copies/μL) | | 1.00 |
| Template No. 5 (1.0E+03copies/μL) | | 1.00 |
| Template No. 6 (1.0E+03copies/μL) | | 1.00 |
| Template No. 7 (1.0E+03copies/μL) | | 1.00 |
| Template No. 8 (1.0E+03copies/μL) | | 1.00 |
| Template No. 9 (1.0E+03copies/μL) | | 1.00 |
| Template No. 10 (1.0E+03copies/μL) | | 1.00 |
| Total | | 50.00 |

(4) Preparation of DNA Chip for Detection of LAMP Amplification Product

Probes (3'-terminal SH-labeled synthetic oligo) shown in Table 5 were synthesized.

TABLE 5

List of probe DNAs

Nucleotide sequence (5' → 3')

Probe No. 1  ATACCTTCTACATATGATCCTTCTAAGTTTAAG

Probe No. 2  GACAACAAACAGACTCAGTTATGTATAATAGGCTGTGC

Probe No. 3  TTGTAACCAGTACGGTTTATTAAATAATTGGGA

Probe No. 4  AGTAGTTATGTATATGCCCCCTCGCCTAGT

Probe No. 5  ACCAATAAGGTTTATTGAATATTTGGGCATCAGA

Probe No. 6  TGCTTCTACACAGTCTCCTGTACCTGGGCA

Probe No. 7  TTTGGTGCAATGGATTTTACTACATTACAAGCTA

Probe No. 8  AGAACAGTTAAGTAAATATGATGCACGAAAAATTAATCAG

Probe No. 9  AGGTCATCCGGGACAGCCTCGCCAAGTTTT

Probe No. 10  CAGGAGCAGGGAGGGCAGGAGCCAGGG

Probe No. 1 is a probe for detecting a LAMP amplification product obtained from primer set No. 1, and similarly probes Nos. 2 to 10 are probes for detecting LAMP amplification products obtained from primer sets Nos. 2 to 10, respectively. 100 mL of a solution including 3 μM of each probe was spotted on an electrode, and dried and fixed to prepare a DNA chip. As a DNA chip and a DNA chip measurement apparatus, those described in SICE Journal of Control, Measurement and System Integration, Vol. 1, No. 3, pp. 266-270, 2008, were used.

(5) Detection of LAMP Amplification Product

LAMP amplification products amplified in containers for multi-amplification and LAMP amplification products amplified in PCR tubes were detected by the DNA chip to identify amplification products amplified in the each amplification containers and tubes.

TABLE 6

Results of DNA chip detection

| | Results of DNA chip detection (current value: nA) | | | |
|---|---|---|---|---|
| | Container for multi-amplification | | PCR tube | |
| | Template present | Template absent | Template present | Template absent |
| Probe No. 1 | 36 | 0 | 0 | 0 |
| Probe No. 2 | 45 | 0 | 0 | 0 |
| Probe No. 3 | 28 | 0 | 0 | 0 |
| Probe No. 4 | 60 | 0 | 50 | 0 |
| Probe No. 5 | 48 | 0 | 0 | 0 |
| Probe No. 6 | 53 | 0 | 30 | 0 |
| Probe No. 7 | 65 | 0 | 72 | 0 |
| Probe No. 8 | 40 | 0 | 0 | 0 |
| Probe No. 9 | 50 | 0 | 0 | 0 |
| Probe No. 10 | 30 | 0 | 0 | 0 |

The results are shown in Table 6. When the PCR tube was used, only three types among 10 types were positive, with other seven types being negative. On the other hand, when the container for multi-amplification was used, 10 types were all positive, showing that 10 types of multi-amplification reactions could be achieved. In the PCR tube, the same solution includes primer sets Nos. 1 to 10 and templates Nos. 1 to 10, and LAMP amplification reactions proceed therein. It was considered that when LAMP amplification reactions of some of 10 types of primer sets were started, an enzyme (Bst DNA polymerase) or the like was consumed for the reactions, so that LAMP amplification reaction efficiency of other types of primer sets was deteriorated. In the container for multi-amplification, the same solution included primer sets Nos. 1 to 10 and templates Nos. 1 to 10, and LAMP amplification reactions proceeded therein, but by spotting primers, a LAMP amplification reaction was started at each spot position in a channel, so that amplification reactions by various kinds of primers could proceed independently.

3. USE OF THICKENER

Sixth Embodiment

A thickener may exist in a reaction solution when a reaction is carried out using a multi-nucleic-acid reaction tool. When a thickener is included in a reaction solution, primers diffuse only locally after fixed primers are separated. The thickener is preferably a substance that does not hinder the amplification reaction. Details of the thickener will be described later.

For achieving the amplification reaction more efficiently, a technique for controlling a rate of addition of a reaction solution to a reaction field is also effective. For example, the flow rate of a reaction solution passing over a primer fixing position is preferably 1 mm/s or more, further preferably 10 mm/s or more. Consequently, separation of fixed primer sets is affected, so that more local diffusion of primer sets becomes possible. However, the flow rate of the reaction solution passing over the primer fixing position can assume any value depending on a shape and size of a reaction portion formed by a support and other members defining a reaction field.

By including a thickener in a reaction solution to be used when the multi-amplification reaction is carried out using the first embodiment described above, the multi-amplification reaction can be achieved more efficiently.

As a method for including a thickener in a reaction solution, a thickener may added to a reaction solution itself, or a thickener may be fixed to a primer fixing region along with a primer set to be used by including the thickener in a solution for fixing the primer set at the time of fixing the primer set to a support. Alternatively, after a primer is fixed, a primer fixing region may be further covered with a thickener to perform fixing. Further, a film-shaped thickener may be applied, etc., and thus the method for including a thickener is not particularly limited.

By including a thickener in a reaction solution, a rate at which a fixed primer set is separated to the reaction solution, that is, the elution rate can be reduced. Consequently, the primer set stays at a local site for a longer period of time. As a result, multi-amplification by a plurality of primer sets is more efficiently achieved independently of reaction efficiency of each of the fixed primer sets.

The thickener is preferably a substance which has a specific viscosity larger than that of a primer and does not hinder a nucleic acid amplification reaction. Examples of the thickener include thickeners derived from saps, for example almond gum, gum elemi resin, dammar gum, gum arabic, karaya gum, tragacanth gum, arabinogalactan, gum ghatti and peach resin; thickeners derived from seeds such as pulses, for example, flax seed gum, guar gum enzymolysis products, tamarind seed gum, *cassia* gum, psyllium seed gum, tara gum, carob bean gum-locust bean gum, *Artemisia sphaerocephala* seed gum, triacanthos gum, guar gum and Sesbania gum; thickeners derived from seaweeds, for example, alginic acid, *Colpomenia sinuosa* extracts, furcellaran and carrageenan; thickeners derived from fruits, leaves, underground stems and the like, for example, aloe vera extracts, Krantz aloe extracts, pectin, okra extracts and sunset hibiscus extracts; thickeners derived from microorganisms, for example, *Aeromonas* gum, *Enterobacter* gum, *bacillus subtilis natto* gum, *Aureobasisium* culture fluids, curdlan, pullulan, *Azotobacter vinelandii* gum, xanthan gum, macrophomopsis gum, welan gum, gellan gum, ramsan gum, Erwinia Mitsuenshisugamu gum, Sclero gum, levan, Enterobacter Simmanas gum and dextran; and other thickening stabilizers, for example, yeast cell membranes, chitin, oligoglucosamine, microfibrous cellulose and glucosamine. Further, the thickener may be one that is generally used as a food and drink additive, for example an agar, a soybean polysaccharide, coconut milk, starch, an *Amorphophallus konjac* extract, gelatin or the like. Preferable are agars such as agarose and/or gelatin, polyethylene glycol and the like, but the thickener is not limited thereto.

When a thickener is added to a reaction solution, the thickener may be added directly to a solvent for preparation of a reaction solution at the time of preparing the reaction solution. Alternatively, first a thickener solution prepared by dissolving a thickener in a solvent is provided. Separately, other components necessary for a reaction are dissolved in a solvent to prepare a reaction solution. The obtained thickener solution and reaction solution may be mixed. The solvent may be water, salt water, a buffer solution or the like.

When a thickener is added to a solution for fixing a primer set, the concentration of the thickener is preferably such that the thickener is liquid at room temperature (25° C.) and can be added dropwise to a reaction field. The concentration of the thickener should be, for example, approximately 30% to 0.01% in terms of final concentration. In the case of agarose, for example, it is mixed in a concentration of preferably 10% to 0.01%, further preferably 5% to 0.05%, more preferably 3% to 0.1% in terms of final concentration. When a thickener is fixed to a primer fixing region, similar concentration may be employed.

When a thickener is added to a reaction solution, the concentration of the thickener is preferably such that the thickener is liquid at room temperature (25° C.). The concentration of the thickener should be, for example, approximately 30% to 0.01% in terms of final concentration. In the case of agarose, for example, it is mixed in a concentration of preferably 10% to 0.01%, more preferably 5% to 0.1% in terms of final concentration.

In conventional method, in the case where reaction containers are provided for amplifying object genes, respectively, the number of necessary reaction containers and the amount of work during inspection are increased the number of object genes increase. In the case where reagents for detecting all object genes are added in one reaction container, the number of object genes is limited due to occurrence of deviation in amplification reaction efficiency. In the case of conventional multi-amplification, when a plurality of types of primer sets are eluted and diffuse, amplification efficiency may be deteriorated by non-specific binding of primers, or only primer sets having good properties may be preferentially amplified, resulting in a reduction in sensitivity of an amplification reaction or a limitation on the type of amplification. These problems are also solved by this embodiment.

Seventh Embodiment

An example is shown above in which a thickener is included in a reaction solution, but a thickener may be fixed to a region on which a primer set is fixed rather than including a thickener in a reaction solution. An example of fixing a thickener will be described below as the seventh embodiment.

When the thickener is fixed on the support, the thickener may be fixed before fixing of the primer set, in parallel with fixing of the primer set, or after fixing of the primer set. Preferably, the thickener is fixed on the support in parallel with fixing of the primer set or after fixing of the primer set.

When the thickener is fixed on the support in parallel with fixing of the primer set, the thickener may be dissolved in a liquid in which the primer set is dissolved. Alternatively, first the thickener may be dissolved in a solvent to provide a thickener solution, followed by mixing the thickener solution with a separately prepared solution for fixing of a primer set. The obtained solution including the primer set and the thickener should be added dropwise and dried to be fixed.

When the thickener solution is fixed before or after fixing of the primer set, the thickener solution should be fixed on a surface of the support including a primer fixing region by drying or the like after a solution including the thickener is added dropwise, sprayed, printed or applied with a brush, or the support is immersed in the thickener solution.

As a method for drying a thickener solution or a solution including the primer set and the thickener, thermal drying may be performed by heating the solution to a temperature greater than or equal to room temperature using a heat block, a hotplate or an incubator. Alternatively, the solution may be left standing at normal temperature to perform natural drying. Alternatively, vacuum drying or freeze drying may be performed. For example, when agarose is used, thermal drying is performed, so that preferably the solution after drying is in the form of a film.

The concentration of the thickener in the thickener solution to be used for fixing should be such that the solution is liquid at room temperature (25° C.) at the time of fixing, and can be added dropwise onto the support. The concentration of the thickener at the time of fixing the thickener should be, for example, approximately 30% to 0.01% in terms of final concentration. In the case of agarose, for example, it is mixed in a concentration of preferably 10% to 0.01%, further preferably 5% to 0.05%, more preferably 3% to 0.1% in terms of final concentration.

Further, the thickener solution to be used for fixing may contain a primer set, or may contain, in addition to the primer set, other substances necessary for the amplification reaction.

Use of the thickener eliminates a reduction in sensitivity in the multi-amplification reaction, a limitation on the type of amplification, and so on.

Eighth Embodiment

A further example of a multi-nucleic-acid amplification reaction tool will be described with reference to FIG. 7.

Figure 7:
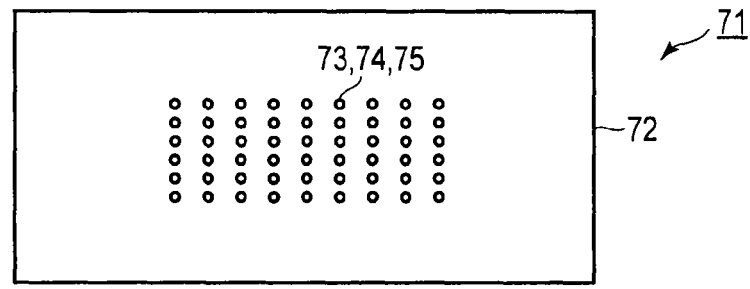
FIG. 7 is a view illustrating an example of a multi-nucleic-acid amplification reaction tool.

FIG. 7 is a plan view illustrating a further example of a multi-nucleic-acid amplification reaction tool. A multi-nucleic-acid amplification reaction tool 71 described in FIG. 7 is an example in which a base plate is used as a support 72. A plurality of mutually independent fixing regions 73 are arranged on a surface of the support 72. In the fixing regions 73, one type of primer set 74 is fixed on one fixing region 73 like FIG. 1. A plurality of primer sets 34 are fixed, for each type, on a plurality of fixing regions 73, respectively. The configuration of the primer set 74 included in one fixing region 73 includes different types of primers necessary to amplify one type of specific target nucleic acid as in the case of the first embodiment. Further, on the fixing region 73, a thickener 75 is fixed by coating so as to cover the primer set 74.

For amplification using the eighth embodiment, a reaction field should be formed by placing a reaction solution onto at least a region of the support 72 on which the primer set 74 is fixed.

The fixing region 73 may be arranged on the surface of a recessed portion formed on the surface of the support 72 beforehand, or the inner wall of a channel formed by a recessed portion.

When the base plate is used as a support, the material thereof should be a material that is not itself involved in a reaction, and enables an amplification reaction to be carried out therein. The material may be arbitrarily selected from, for example, silicon, glass, a resin and a metal. Fixing of the primer to the support should be performed in the same manner as in the first embodiment.

Further, a reaction field may be formed by arranging the multi-nucleic-acid amplification reaction tool of the eighth embodiment in a container which can retain the reaction tool, and adding a reaction solution in the container. In this case, primer sets 74 may be fixed on both surfaces of the support 72. Further, the thickener 75 may be fixed by coating so as to cover the primer set 74. Consequently, more types of primer sets can be fixed to the present multi-nucleic-acid amplification reaction tool, so that a larger number of target sequences can be amplified. In this aspect, the multi-nucleic-acid amplification reaction tool may have a support of any shape as long as it is a support with a plurality of primer sets independently fixed on at least a surface. The material of the support and the method for fixing of primers in this case may be similar to those in the first and second embodiments, etc. The multi-nucleic-acid amplification reaction tool 71 described above may be used as a multi-nucleic-acid amplification reaction carrier including a base body, and a plurality of types of primer sets releasably fixed, for each type, on mutually independent fixing regions of at least a surface of the base body. In this case, a size and a shape of the base body may be arbitrarily selected by a practitioner. For example, the base body may have a plate-like shape, a spherical shape, a rod-like shape and a shape including a part of these shapes.

Fixing of the thickener may be performed in parallel with fixing of the primer set, or before fixing of the primer set. The thickener may be included in a reaction solution rather than performing of fixing of the thickener.

Ninth Embodiment (1) Multi-Nucleic-Acid Amplification Reaction Tool

Figure 8:
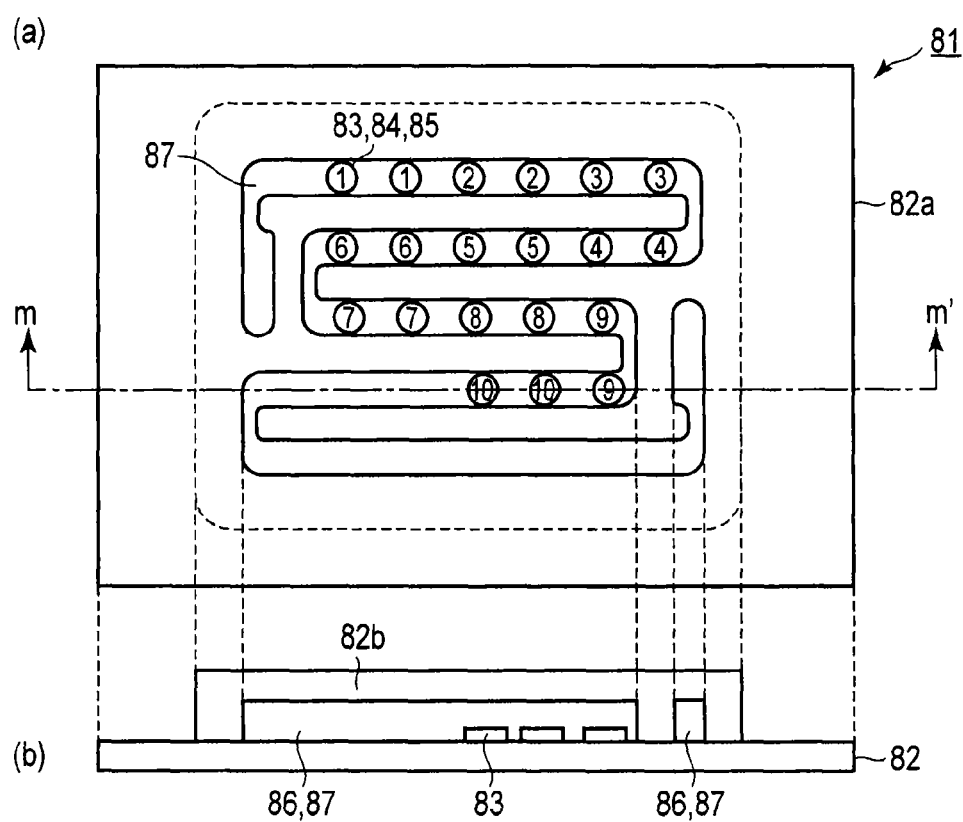
FIG. 8 is a view illustrating an example of a multi-nucleic-acid amplification reaction tool.

A further example of a multi-nucleic-acid amplification reaction tool will be described with reference to FIG. 8. A multi-nucleic-acid amplification reaction tool 81 illustrated in FIG. 8 is an example in which a support having a channel is used. FIG. 8(*a*) is a plan view, and FIG. 8(*b*) is a sectional view cut along line m-m'.

The multi-nucleic-acid amplification reaction tool 81 includes a plurality of primers 84 releasably fixed, for each type, on a plurality of mutually independent fixing regions 83 on the inner bottom surface of a channel 87 formed in a support 82.

The support 82 has a base body 82*a* and a cover 82*b*. The cover 82*b* has a recessed portion 86 defining the channel. The primer fixing region 83 is arranged on a surface of the base body 82*a* which is facing to the interior of the channel 87.

The multi-nucleic-acid amplification reaction tool 81 is produced using, for example, a first base plate and a second base plate. First, a mixture of a plurality of primer sets 84 and a thickener is releasably fixed on the predetermined fixing region 83 of the first base plate. The primer sets 84 are fixed for each type. The fixing can be performed as described above. On the other hand, on the second base plate, a recessed portion 86 is formed so as to match the shape of a desired channel 87. Formation of the recessed portion 86 can be performed by a method, which is publicly known itself, according to a material of a base plate to be used. An arrangement of fixing regions 83 is determined so that they are included in the channel 87 formed by the recessed portion 86 formed on the second base plate. Next, the first base plate and the second base plate are integrated. As a result of integration, a channel-shaped reaction portion is formed by the inner wall of the recessed portion 86 and a surface of the first base plate on the second base plate side. At this time, the base plates are integrated such that the recessed portion 86 of the second base plate faces the first base plate side. Further, a through-hole (not illustrated) may be provided at a part of the recessed portion 86 of the second base plate. The through-hole may be used as an entrance for a reaction solution or the like to pass into the channel 87.

The material of the first base plate and the material of the second base plate may be the same or different. The materials of the first base plate and the second base plate should be a material that are not themselves involved in a reaction, and enable an amplification reaction to be carried out therein. The material may be arbitrarily selected from, for example, silicon, glass, a resin and a metal.

In this embodiment, an example is shown in which primer sets 84 are fixed on the inner bottom surface of the channel 87 of the support 82 having the channel 87, but the arrangement and shape of the channel 87 are not limited thereto. The surface on which primer sets are fixed may be any surface defining the channel 87, and primer sets may be fixed on all of surfaces defining the channel 87, or may be fixed on two or more of the surfaces.

Alternatively, in the first base plate on which the channel 87 is formed by forming a recessed portion or raised portion or a groove beforehand, a plurality of primer sets 84 may be independently fixed to the primer fixing regions 83 arranged on the wall surface of a part of the channel 87. Thereafter, a lid of a silicon rubber or the like may be attached to produce a multi-nucleic-acid amplification reaction tool.

The length of the primer to be used, or the like may be as described above.

Tenth Embodiment (1) Multi-Nucleic-Acid Amplification Detection Reaction Tool

A multi-nucleic-acid reaction tool may be provided as a multi-nucleic-acid amplification detection reaction tool. The multi-nucleic-acid amplification detection reaction tool further includes a probe fixing region and a probe nucleic acid fixed thereon in addition to the components in the first to ninth embodiments described above. An example of the multi-nucleic-acid amplification detection reaction tool will now be described.

An example of the multi-nucleic-acid amplification detection reaction tool will be described with reference to (a), (b) and (c) of FIG. 9.

Figure 9:
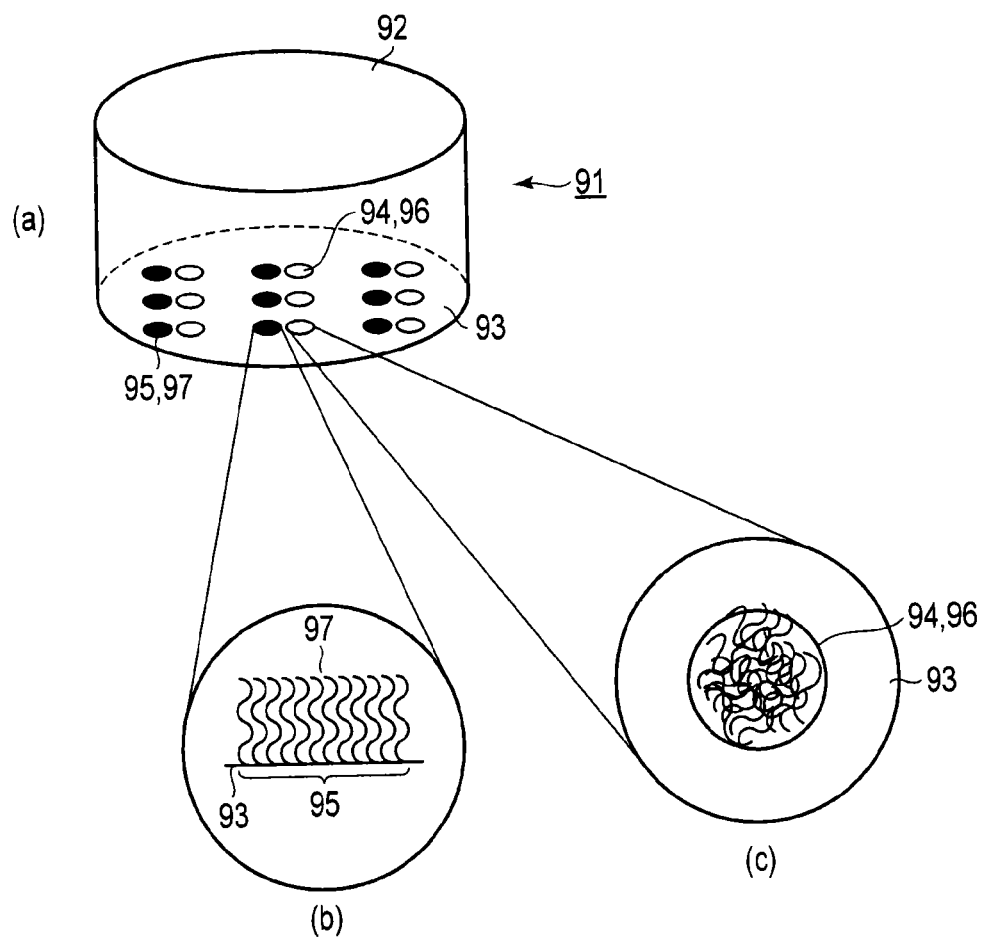
FIG. 9 is a view illustrating an example of a multi-nucleic-acid amplification detection reaction tool.

FIG. 9(*a*) is a perspective view of an example of a multi-nucleic-acid amplification detection reaction tool 91. The multi-nucleic-acid amplification detection reaction tool 91 described in FIG. 9(*a*) has a container-shaped support 92. A plurality of mutually independent fixing regions 94 are arranged on an inner bottom surface 93 of the support 92. A plurality of probe fixing regions 95 are arranged in contiguity with a plurality of primer fixing regions 94 and in correspondence with respective primer regions.

FIG. 9(*c*) is a schematic view of the enlarged primer fixing region 94. As illustrated here, one type of primer set 96 is fixed on one primer fixing region 94. A plurality of primer sets 96 are fixed, for each type, on a plurality of primer fixing regions 94, respectively.

A plurality of primer sets 96 are provided for amplifying a plurality of intended target nucleic acids, respectively. One type of primer set 96 for amplifying one specific target nucleic acid is fixed on one primer fixing region 94. For example, in the case of a reaction tool for PCR amplification, one primer fixing region 94 includes a plurality of forward primers and reverse primers that are necessary to amplify one type of specific target nucleic acid. In the case of a reaction tool for LAMP amplification, one primer fixing region 94 includes a plurality of FIP primers and BIP primers that are necessary to amplify one type of specific target nucleic acid, and a plurality of F3 primers, B3 primers and LP primers as necessary.

The primer set 96 is fixed on the primer fixing region 94 in a releasable state so as to release in contact with a liquid phase for providing a reaction field. Fixing of the primer set 96 to the primer fixing region 94 can be achieved by, for example, adding dropwise to one primer fixing region 94 a solution including a set of primer sets, followed by drying the solution. Further, for other primer fixing regions 94, solutions each containing a desired primer set 96 are similarly added dropwise and dried to fix a desired number of primer sets 96 to the support 92. In this way, primer sets 96 are fixed on all fixing regions 94 independently arranged on a surface of the support 92. However, it suffices that the primer set 96 is fixed on the fixing region 94 in a state of being releasable in contact with a liquid phase for providing a reaction field. Therefore, any fixing method that is capable of achieving the above-mentioned fixing and is publicly known itself may be used. In the case of the method of adding dropwise a solution including a primer set, the solution including a primer set may be, for example, water, a buffer solution or an organic solvent.

A plurality of primer fixing regions 94 to be arranged on the support 92 should be mutually independently arranged. The term "independently arranged" means that fixing regions are arranged at such intervals that amplification made to start and/or proceed for each primer set in a reaction field is not hindered. For example, adjacent primer fixing regions 94 may be arranged in contact with each other, or may be arranged in the vicinity of each other with a slight distance therebetween, or may be arranged at an interval equivalent to a distance between probe nucleic acids that are fixed in a detector such as so called a DNA chip which is usually used.

For example, the distance between adjacent primer fixing regions 94 may be 0.1 µm to 1 µm, 1 µm to 10 µm, 10 µm to 100 µm, 100 µm to 1 mm, 1 mm to 10 mm or more, or may be preferably 100 µm to 10 mm.

The liquid phase for providing a reaction field should be a liquid phase such that after fixed primers are separated, an amplification reaction can be caused to proceed using the primers, and the liquid phase may be a reaction solution necessary for desired amplification.

For example, the container-shaped support 92 may be in the form of a tube, a well, a chamber, a channel, a cup and a dish, and a plate having a plurality of these forms, for example a multi-well plate. The material of the support 92 should be a material that is not itself involved in a reaction, and enables an amplification reaction to be carried out therein. The material may be arbitrarily selected from, for example, silicon, glass, a resin and a metal. For the container-shaped support 92, any container that is commercially available may be used.

In FIG. 9, an example is shown in which the primer fixing region 94 is arranged on the inner bottom surface 93 of the support 92, but this is not exhaustive, and the fixing region may be arranged on at least a part of the inner side surface of a support 92, or may be arranged on any or all of the bottom surface, the inner side surface and the ceiling surface defined by the cover.

FIG. 9(b) is an enlarged view of a probe fixing region 95 arranged in contiguity with the primer fixing region 94. A plurality of probe nucleic acids 97 including a complementary sequence of a desired sequence to be detected are fixed on the probe fixing region 95.

The desired sequence to be detected may be an object sequence. Probe fixing regions 95 are arranged so that hybridization signals of probe nucleic acids 97 and object sequence chains are detected independently among a plurality of probe fixing regions 95.

For fixing of the probe nucleic acid 97 to the probe fixing region 95, any of general techniques for fixing the probe nucleic acid 97 to the surface of a base plate in so called a DNA chip which is publicly known itself can be used. The primer set 96 may be fixed after the probe nucleic acid 97 is fixed, or the probe nucleic acid 97 may be fixed after the primer set 96 is fixed, or fixing of the primer set 96 and fixing of the probe nucleic acid 97 may be performed in parallel.

For example, the distance between adjacent probe fixing regions 95 may be 0.1 µm to 1 µm, 1 µm to 10 µm, 10 µm to 100 µm, 100 µm to 1 mm, 1 mm to 10 mm or more, or may be preferably 100 µm to 10 mm.

For example, the distance between the probe fixing region 95 and the primer fixing region 94 may be 0 to 0.1 µm, 0.1 µm to 1 µm, 1 µm to 10 µm, 10 µm to 100 µm, 100 µm to 1 mm, 1 mm to 10 mm or more, or may be preferably 100 µm to 10 mm.

For example, when the distance between the probe fixing region 95 and the primer fixing region 94 is zero, the probe fixing region 95 and the primer fixing region 94 may be considered to be at the same position on the surface of the support 92. The probe fixing region 95 may be included in the primer fixing region 94, or the primer fixing region 94 may be included in the probe fixing region 95.

(2) Method for Amplification and Detection of Nucleic Acid Using Multi-Nucleic-Acid Amplification Detection Reaction Tool FIG. 10 is a schematic view illustrating a state of a reaction field after a nucleic acid amplification reaction carried out using a multi-nucleic-acid amplification detection reaction tool 91 similar to that in the tenth embodiment. (a-1) and (b-1) of FIG. 10 illustrate the multi-nucleic-acid amplification detection reaction tool 91 before the reaction. A plurality of fixing regions 94 are arranged on an inner bottom surface 93 of the support 92. A plurality of probe fixing regions 95 are arranged in the vicinity of a plurality of primer fixing regions 94. A plurality of primer sets 96 are fixed on a plurality of primer fixing regions 94. A plurality of probe nucleic acids 97 are fixed for each desired type on probe fixing regions 95 arranged in the vicinity of primer fixing regions 94, respectively.

(a-2) and (b-2) of FIG. 10 illustrate a state in which a reaction solution 98 is added and stored in the multi-nucleic-acid amplification detection reaction tool 91.

The reaction solution 98 should contain components necessary for a desired amplification reaction and a thickener. Examples of the components may include, but are not limited to, an enzyme such as polymerase, a substrate substance such as deoxynucleoside triphosphate necessary for forming a new polynucleotide chain with a primer as a start point, a reverse transcriptase and a necessary substrate substance, etc., when performing reverse transcription in parallel, and a buffer such as a salt configured to maintain a proper amplification environment.

The type of substance included as the thickener and the concentration thereof may be similar to those in the sixth embodiment.

Addition of a sample to the reaction field may be performed by adding the sample to the reaction solution 98 before adding the reaction solution 98 to the multi-nucleic-acid amplification detection reaction tool 91, or may be performed after adding the reaction solution 98 to the multi-nucleic-acid amplification detection reaction tool 91, or may be performed by adding the sample to the multi-nucleic-acid amplification detection reaction tool 91 before adding the reaction solution 98 to the multi-nucleic-acid amplification detection reaction tool 91.

In the multi-nucleic-acid amplification detection reaction tool 91 after the reaction solution 98 is added as illustrated in (a-2) and (b-2) of FIG. 10, primer sets 96 fixed on an inner bottom surface 93 of the support 92 separate and gradually diffuse as schematically illustrated in (a-3) and (b-3) of FIG. 10. A region where primer sets separate and diffuse is schematically shown by a region 99. Primer sets 96 separating and diffusing encounter other components necessary for amplification which exist in their vicinity, such as a template nucleic acid, polymerase and a substrate substance, and subsequently an amplification reaction is started. A plurality of primer sets 96 independently fixed for each type can cause an amplification reaction to start and proceed for the template nucleic acid independently for each type. In this way, amplification for a plurality of template sequences using a plurality of types of primer sets 96 is achieved independently and in parallel. Here, the term "reaction field" means a region defined by the reaction solution 98 where theoretically the amplification reaction can proceed, that is, a region where the reaction solution exists. Of the reaction field, a region where the amplification reaction actually starts and proceeds is referred to as a "reaction region". If actually the amplification reaction proceeds only in the region 99, the region 99 may be considered as a reaction region. (a-3) of FIG. 10 is a schematic view where amplification reactions occur by primer sets 96 fixed on all the primer fixing regions 94. (b-3) of FIG. 10 is a schematic view where amplification is caused by fixed primer sets 96 in some of all the primer fixing regions 94 fixed on the bottom surface 93, for example, only three regions in FIG. 10(*b*-3).

When a nucleic acid including an object sequence exists in an amplification product amplified in the region 99, the probe fixing region 95 is hybridized with the nucleic acid. The probe nucleic acid 97 fixed on the probe fixing region 95 is fixed so as to be hybridized with only an amplification product in the corresponding primer fixing region 94. That is, the probe fixing regions 95 and primer fixing regions 94 are arranged with a distance maintained therebetween so that the probe nucleic acid 97 fixed on one probe fixing region 95 is hybridized with only an amplification product in the corresponding primer fixing region 94.

Detection of hybridization of the probe nucleic acid 97 with an object sequence chain may be performed by a technique for detection of a hybridization signal, which is publicly known per se. For example, a fluorescent substance may be given to the primer set 96 beforehand, or a fluorescent substance may be given to a substrate substance such as deoxynucleoside triphosphate. The existence and the amount of hybridization may be determined using as an indicator the fluorescent intensity of the fluorescent substance. Alternatively, a hybridization signal may be detected by an electrochemical technique.

Detection of hybridization may be performed after washing the inside of the multi-nucleic-acid amplification detection reaction tool 91, or may be performed without carrying out washing. When detection is performed by an electrochemical technique, a hybridization signal may be detected using an intercalator. In this case, the intercalator may be included in the reaction solution 98 beforehand, or may be added before the start of hybridization reaction, during hybridization reaction or after hybridization reaction. In any of these cases, detection may be performed after washing the inside of the multi-nucleic-acid amplification detection reaction tool 91, or detection may be performed without carrying out washing. Whether the intercalator is added at the start of hybridization reaction, during hybridization reaction or after hybridization reaction may be determined according to sequences of the primer, the probe nucleic acid and the template nucleic acid, and reaction conditions such as a reaction temperature, or may be determined via a preliminary experiment.

The length of the primer may be as described above.

The length of the probe nucleic acid may be, for example, three bases to 10 bases, 10 bases to 20 bases, 20 bases to 30 bases, 30 bases to 40 bases, 40 bases to 50 bases or 50 bases to 60 bases, preferably 10 bases to 50 bases. The probe nucleic acid includes a complementary sequence of an object sequence to be detected. The probe nucleic acid may include, in addition to a complementary sequence of an object sequence, an additional sequence, for example a spacer sequence.

The length of the target sequence may be, for example, 10 bases to 100 bases, 100 bases to 200 bases, 200 bases to 300 bases or 300 bases to 400 bases, preferably 100 bases to 300 bases.

The length of the object sequence may be, for example, three bases to 10 bases, 10 bases to 20 bases, 20 bases to 30 bases, 30 bases to 40 bases, 40 bases to 50 bases or 50 bases to 60 bases, preferably 10 bases to 50 bases.

The number of types of primer sets 96 fixed on one primer fixing region 94 may be one for amplifying one type of target nucleic acid, or may be two or more for amplifying two or more types of target nucleic acids, respectively.

The number of types of probe nucleic acid 97 groups fixed on one probe fixing region 95 may be one for hybridization with one type of object sequence, or may be two or more for amplifying two or more types of target nucleic acids, respectively. The probe nucleic acids may be those that are the same in object sequence part and further include other sequences different from the object sequence.

The lower limit of the number of primer fixing regions 94 arranged on one array-type multi-nucleic-acid amplification detection reaction tool 91 may be one or more, two or more, three or more, four or more, five or more, 10 or more, 15 or more, 20 or more, 25 or more, 30 or more, 50 or more, 75 or more, 100 or more, 125 or more, 150 or more, 175 or more, 200 or more, 300 or more, 400 or more, 500 or more, 1000 or more, 1500 or more or 2000 or more, and the upper limit thereof may be 10000 or fewer, 5000 or fewer, 2500 or fewer, 2000 or fewer, 1500 or fewer, 1000 or fewer, 500 or fewer, 250 or fewer, 200 or fewer or 150 or fewer, or the number of the primer fixing regions 94 may be in a range of a combination of any of the above-described upper and lower limits.

The numbers of primer fixing regions 94 and probe fixing regions 95 arranged on one multi-nucleic-acid amplification detection reaction tool 91 may be the same or different. That is, probe fixing regions 95 may be arranged with the same number as primer fixing regions 94 so as to correspond to all the primer fixing regions 94, or the number of primer fixing regions 94 may be larger than the number of probe fixing regions 95, or the number of primer fixing regions 94 may be smaller than the number of probe fixing regions 95. A positive control and/or a negative control may be included for checking an amplification reaction state or checking a state of hybridization reaction. The positive control and/or negative control may be provided for the primer set 96 and/or probe nucleic acid.

In the above-described example, only primer sets 96 are fixed on the support 92. However, this is not exhaustive, and other components necessary for amplification, for example enzymes such as polymerase and a reverse transcriptase, a substrate substance, a substrate substance and/or a buffer, may be fixed on the support 92 along with primer sets 96 under conditions for fixing primer sets 96, for each type, on fixing regions. In this case, substances to be fixed should be included in a desired liquid medium along with primer sets 96, and added dropwise and dried to be fixed using a method similar to that described above. When the amplification reaction is carried out the multi-nucleic-acid amplification detection reaction tool 91, a composition of a reaction solution to be added thereto should be selected according to fixed components.

In the above-described example, a thickener is added to a reaction solution, but the thickener may be fixed to the support 92 rather than including the thickener in the reaction solution. Fixing may be performed as described above.

The shape of the support 92 is not limited to a container shape, but may be a plate-like shape, a spherical shape, a rod-like shape and a shape including a part of these shapes as described above, and the size and shape of the base body may be arbitrarily selected by a practitioner. It is preferable to form the support 92 using a base plate having a channel as in the third embodiment.

Eleventh Embodiment

A multi-nucleic-acid amplification detection reaction tool of the eleventh embodiment will be described with reference to FIGS. 11 to 14.

(1) Chip Material

First, an example of the configuration of a chip material of a multi-nucleic-acid amplification detection reaction tool configured to detect a hybridization signal by electrochemical detection and the method for production of the chip material will be described with reference to (a) and (b) of FIG. 11. FIG. 11(a) is a plan view of a chip material 111, and FIG. 11(b) is a sectional view of the chip material 111 taken along line B-B in FIG. 11(a).

The chip material 111 includes, on a rectangular base plate 112, for example four electrodes 113a to 113d arranged longitudinally with respect to the base plate. Electrodes 113a to 113d have a structure in which a first metal thin film pattern 114 and a second metal thin film pattern 115 are stacked in this order. Electrodes 113a to 113d have a shape in which a large rectangular portion 116 and a small rectangular portion 117 are connected by a thin line 117. An insulating film 118 is placed on the base plate 112 including each of electrodes 113a to 113d. A circular window 119 is opened at a part of the insulating film 118 corresponding to the large rectangular portion 116. A rectangular window 120 is opened at a part of the insulating film 118 corresponding to the small rectangular portion 117. The large rectangular portion 116 exposed from the circular window 119 of electrode 113a acts as a first working electrode 121a. The large rectangular portion 116 exposed from the circular window 119 of electrode 113b acts as a second working electrode 121b. The large rectangular portion 116 exposed from the circular window 119 of electrode 113c acts as a counter electrode 122. The large rectangular portion 116 exposed from the circular window 119 of electrode 113d acts as a reference electrode 123. The small rectangular portion 117 exposed from the rectangular window 120 of each of electrodes 113a to 113d acts a prober contact portion.

The chip material 111 can be prepared by the following method.

First, a first metal thin film and a second metal thin film are stacked in this order on the base plate 112 by, for example, a sputtering method or a vacuum deposition method. Subsequently, for example four electrodes 113a to 113d obtained by sequentially selectively etching the metal thin films with, for example, a resist pattern as a mask to stack the first metal thin film pattern 114 and the second metal thin film pattern 115 in this order are formed longitudinally with respect to the base plate 112. Electrodes 113a to 113d have a shape in which a large rectangular portion 116 and a small rectangular portion 117 are connected by a thin line 117.

Then, the insulating film 118 is deposited on the base plate 112 including each of electrodes 113a to 113d by, for example, a sputtering method or a CVD method. Subsequently, a part of the insulating film 118 corresponding to the large rectangular portion 116 of each of electrodes 113a to 113d and a part of the insulating film 118 corresponding to the small rectangular portion 117 of each of electrodes 113a to 113d are selectively etched to open the circular window 119 at the part of the insulating film 118 corresponding to the large rectangular portion 116 and the rectangular window 120 at the part of the insulating film 118 corresponding to the small rectangular portion 117. In this way, the aforementioned chip material 111 is prepared.

The base plate 112 is made from a glass such as Pyrex (registered trademark) glass or a resin.

The first metal thin film acts as a base body metal film for bringing the second metal thin film into close contact with the base plate 112, and is made from, for example, Ti. The second metal thin film is made from, for example, Au.

Examples of etching for patterning the first and second metal thin films include plasma etching or reactive ion etching using an etching gas.

Examples of the insulating film 118 may include metal oxide films such as a silicon oxide film and metal nitride films such as a silicon nitride film.

Examples of etching for patterning the insulating film 118 include plasma etching or reactive ion etching using an etching gas.

(2) Multi-Nucleic-Acid Amplification Detection Reaction Tool

Next, an example of the configuration of a multi-nucleic-acid amplification detection reaction tool with primer sets and probe nucleic acids fixed on the chip material 111 produced in (1) and the method for production of the multi-nucleic-acid amplification detection reaction tool will be described with reference to (a) and (b) of FIG. 12. FIG. 12(a) is a plan view of the multi-nucleic-acid amplification detection reaction tool, and FIG. 12(b) is a sectional view of the multi-nucleic-acid amplification detection reaction tool taken along line B-B in FIG. 12(a).

The first working electrode 121a of electrode 113a formed on the chip material 111 is defined as a first probe fixing region 201a, and first probe nucleic acids 202a including a complementary sequence of a first object sequence are fixed to the first probe fixing region 201a. The first probe nucleic acids 202a to be fixed are fixed with two or more thereof as one probe nucleic acid group. Similarly, the second working electrode 121b of electrode 113b is defined as a second probe fixing region, and second probe nucleic acids 202b including a complementary sequence of a second object sequence different from the first object sequence are fixed to the second probe fixing region.

Examples of the method for fixing probe nucleic acids 202a and 202b include a method in which a thiol group is introduced into the first probe nucleic acid 202a at the 3'-terminal for the chip material 111 including a metal electrode.

Then, the first primer fixing region 203a is arranged in the vicinity of the first working electrode 121a, and the second primer fixing region 203b is arranged in the vicinity of the second working electrode 121b. A first primer set 204a and a thickener 205 are releasably fixed on the first primer fixing region 203a, and a second primer set 204b and a thickener 205 are releasably fixed on the second primer fixing region 203b. In this way, the multi-nucleic-acid amplification detection reaction tool is prepared.

The first primer set 204a has a sequence designed to amplify a first target sequence, and the second primer set 204b has a sequence designed to amplify a second target sequence including a sequence different from the first target sequence.

For fixing the first and second primer sets 204a and 204b to the first and second primer fixing regions 203a and 203b, respectively, the primer set is included in a liquid such as, for example, water, a buffer solution or an organic solvent, and the liquid is added dropwise, and left standing under an appropriate temperature condition such as room temperature for a time until the liquid is dried, for example, 10 minutes at room temperature.

Fixing of the thickener may be performed in a manner similar to that in the seventh embodiment, or the thickener may be made to merely exist in the reaction solution rather than fixing the thickener.

(3) Multi-Nucleic-Acid Amplification Detection Reaction Tool in USE

A method for using the multi-nucleic-acid amplification detection reaction tool prepared in (2) will be described with reference to FIGS. 13 and 14.

FIG. 13(a) is a plan view of the multi-nucleic-acid amplification detection reaction tool in use, and FIG. 13(b) is a sectional view of the multi-nucleic-acid amplification detection reaction tool taken along line B-B in FIG. 13(a).

When the multi-nucleic-acid amplification detection reaction tool 91 of this embodiment is used, the reaction solution is maintained so that the first working electrode 121a, the second working electrode 121b, the counter electrode 122 and the reference electrode 123 formed in electrodes 113a to 113d, respectively, and the first primer fixing region 203a and the second primer fixing region 203b are included in the same single reaction field. Therefore, a cover 301 formed by molding a resin such as, for example, a resin a silicon resin such as a silicon rubber and/or a fluororesin using any resin molding method that is publicly known itself, such as, for example, extrusion molding, injection molding or stamping molding and/or bonding by an adhesive is mounted on the multi-nucleic-acid amplification detection reaction tool 91 before the multi-nucleic-acid amplification detection reaction tool 91 is used. After the cover 301 is mounted, a reaction solution 302 containing a template nucleic acid 303 is added to a space formed by the multi-nucleic-acid amplification detection reaction tool 91 and the cover 301.

In the multi-nucleic-acid amplification detection reaction tool 91 on which the cover 301 is mounted, the small rectangular portion 117 exposed from the rectangular window 120 of each of electrodes 113a to 113d is exposed.

Examples of the method for mounting the cover 301 on the multi-nucleic-acid amplification detection reaction tool 91 include press bonding and bonding by an adhesive.

Then, the reaction solution 302 is added after the cover 301 is mounted on the multi-nucleic-acid amplification detection reaction tool 91.

As a method for adding a liquid to a space formed by the multi-nucleic-acid amplification detection reaction tool 91 and the cover 301, for example, an opening may be provided at a part of the cover 301 beforehand, followed by adding the liquid through the opening, or the liquid may be injected through a part of the cover 301 using a syringe having a sharp tip such as a needle-like tip.

The reaction solution 302 may include a sample, a thickener, an amplification reagent, for example an enzyme such as polymerase, a substrate substance such as deoxynucleoside triphosphate necessary for forming a new polynucleotide chain with a primer as a start point, a reverse transcriptase and a necessary substrate substance, etc., when performing reverse transcription in parallel, and a buffer such as a salt configured to maintain a proper amplification environment and an intercalator that recognizes a double-stranded nucleic acid and generates a signal, such as, for example, Hoechst 33258. When a template nucleic acid including a target sequence to be amplified by a primer set fixed on a specific primer fixing region exists in a sample to be examined, an amplification product is formed in a reaction field including the primer fixing region and a probe fixing region corresponding thereto. This situation is schematically illustrated in FIG. 14.

Figure 14:
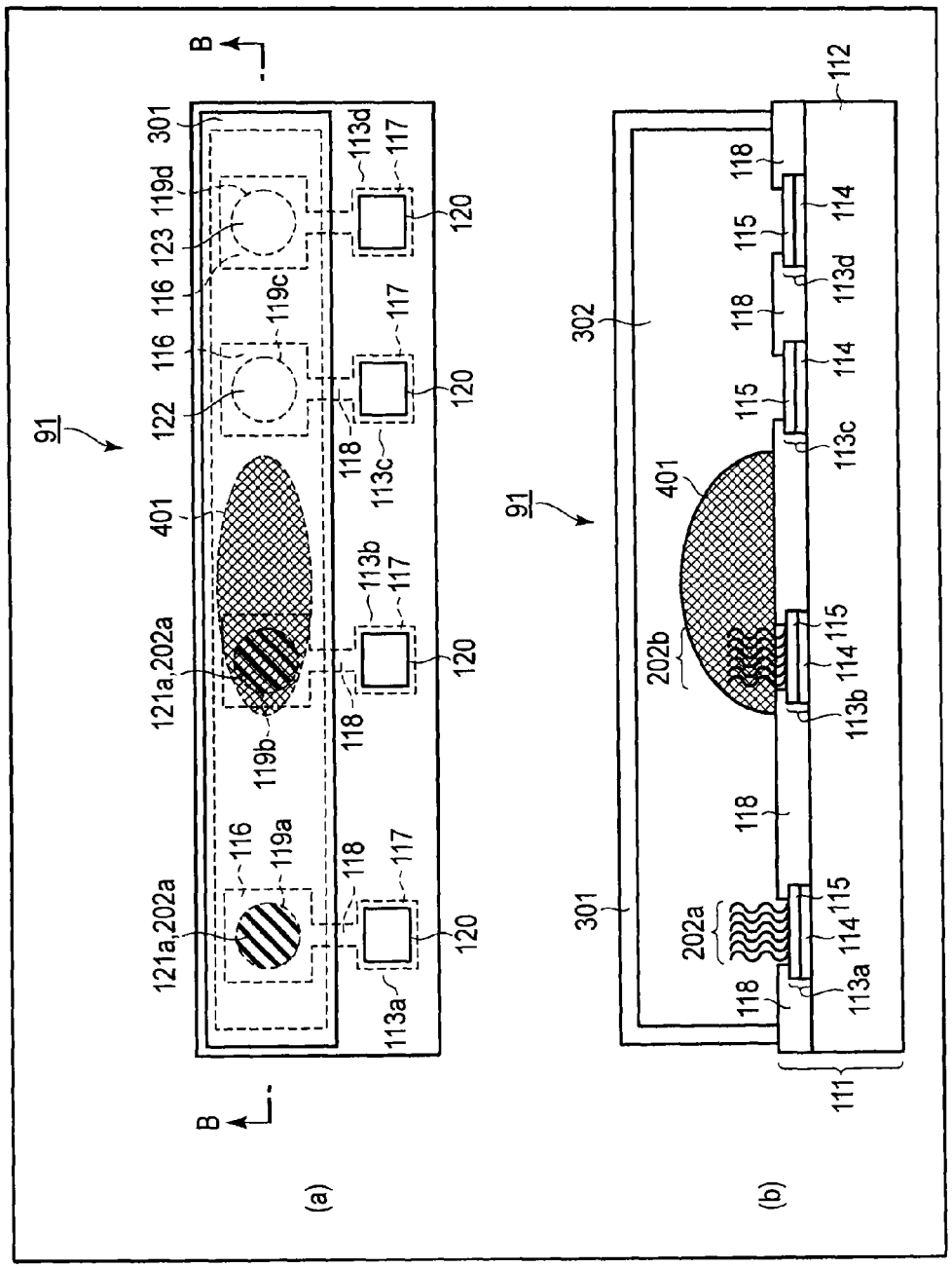
FIG. 14 is a view illustrating an example of a multi-nucleic-acid amplification detection reaction tool.

FIG. 14(a) schematically illustrates a state in which an amplification product is formed in a reaction field 401. FIG. 14(a) is a plan view of the multi-nucleic-acid amplification detection reaction tool in use, and FIG. 14(b) is a sectional view of the multi-nucleic-acid amplification detection reaction tool taken along line B-B in FIG. 14(a). A nucleic acid including a sequence with which the second primer set 204b can be bound is included in the sample added in FIG. 13 as described above, and therefore as illustrated in (a) and (b) of FIG. 14, the second primer set separated and diffuses to the reaction field 401, and encounters a template nucleic acid, followed by causing an amplification reaction to thereby form an amplification product. The amplification product by the second primer set 204b diffuses to the periphery of the second primer fixing region 203b and arrives at the second probe fixing region 201b. When the arriving amplification product includes an object sequence, the second probe nucleic acid 202b and the amplification product are hybridized to form a double-stranded nucleic acid. An intercalator included in the reaction solution 302 is bounded with the double-stranded nucleic acid to generate a hybridization signal.

The hybridization signal is produced by, for example, bringing a prober into contact with the small rectangular portion 117 exposed from the rectangular window 120 of each of electrodes 113a to 113d, and measuring a current response of an intercalator such as Hoechst 33258.

By using an array-type primer probe chip using electrochemical detection, a target nucleic acid included in a sample can be amplified more easily and quickly, followed by detecting an object nucleic acid included in the amplification product.

(4) Method for Detection of Object Nucleic Acid

There is also provided as a further embodiment a method for amplifying a plurality of target nucleic acids and detecting an object nucleic acid with a hybridization signal as an indicator using the multi-nucleic-acid amplification detection reaction tool described above as an example.

There is also provided as a further embodiment a method for detection of an object nucleic acid which includes releasably fixing a plurality of types of primer sets designed to amplify a plurality of types of target nucleic acids, respectively, to at least a surface of a support such as a specific container, a tube, a dish or a base plate provided with a channel, and/or fixing one or more type of probe nucleic acid to a probe fixing region.

The method for detection of an object nucleic acid may include releasably fixing a plurality of types of primer sets designed to amplify a plurality of types of target nucleic acids, respectively, to at least a surface of a desired support; fixing at least one type of probe nucleic acids including a complementary sequence of an object sequence, for each type, to a probe fixing region at or near the position of a plurality of primer fixing regions so that hybridization signals can be detected independently for each probe fixing region; adding a reaction solution containing reagents necessary for amplification, for example an enzyme such as polymerase, a substrate substance such as deoxynucleoside triphosphate necessary for forming a new polynucleotide chain with a primer as a start point, a reverse transcriptase and a necessary substrate substance, etc., when performing reverse transcription in parallel, and a buffer such as a salt configured to maintain a proper amplification environment so that a plurality of types of primer sets are included in one reaction field; bringing a sample to the reaction field by, for example, adding the sample to the reaction solution or an array-type primer probe chip; performing adjustment of a reaction environment suitable for an amplification reaction such as temperature control by heating or cooling the support on which the primer is fixed; thereby carrying out a multi-nucleic-acid amplification reaction; and detecting and/or measuring the existence and/or the amount of hybridization between an amplification product produced by the multi-nucleic-acid amplification reaction and at least one type of probe nucleic acid. The reaction solution may contain a thickener.

A specific amplification reaction may be carried out using a technique, which is publicly known itself, according to a type of amplification reaction.

As a specific detection method, a method of detecting a hybridization signal, which is publicly known itself, for example a method of detecting and/or measuring the fluorescent intensity using a fluorescent label, or a method of detecting and/or measuring a current response using an intercalator, may be used.

Further, there is also provided as a further embodiment a method for detection of an object nucleic acid, which includes releasably fixing a plurality of types of primer sets designed to amplify a plurality of types of target nucleic acids, respectively, to the surface of a base plate such as microbeads, a plate piece or a rod; and fixing at least one type of probe nucleic acids including a complementary sequence of an object sequence, for each type, to a probe fixing region at or near the position of a plurality of primer fixing regions so that hybridization signals can be detected independently for each probe fixing region.

The method for detection of an object nucleic acid may include releasably fixing a plurality of types of primer sets designed to amplify a plurality of types of target nucleic acids, respectively, to at least a surface of a desired base body; fixing at least one type of probe nucleic acids including a complementary sequence of an object sequence, for each type, to a probe fixing region at or near the position of a plurality of primer fixing regions so that hybridization signals can be detected independently for each probe fixing region; placing the base body in a reaction solution containing reagents necessary for amplification, for example an enzyme such as a polymerase, a substrate substance such as deoxynucleoside triphosphate necessary for forming a new polynucleotide chain with a primer as a start point, a reverse transcriptase and a necessary substrate substance, etc., when performing reverse transcription in parallel, and a buffer such as a salt configured to maintain a proper amplification environment; adding a reaction solution configured to maintain a proper amplification environment; bringing a sample to the reaction field by adding the sample to the reaction solution, or the like; performing adjustment of a reaction environment suitable for an amplification reaction such as temperature control by heating or cooling the reaction solution; thereby carrying out a multi-nucleic-acid amplification reaction; and detecting and/or measuring the existence and/or the amount of hybridization between an amplification product produced by the multi-nucleic-acid amplification reaction and at least one type of probe nucleic acid. The reaction solution may contain a thickener.

According to the multi-nucleic-acid amplification detection reaction tool shown in the embodiment as an example, amplification for a plurality of types of target sequences can be performed in parallel independently without undergoing interferences by different sequences. Further, in parallel with or subsequent to the amplification reaction, the existence and/or the amount of an object nucleic acid can be detected and/or measured for the amplification product produced by the amplification reaction in the reaction field where the amplification reaction has been carried out. Owing to application of the thickener, amplification reactions that are carried out in parallel for a plurality of types of target sequences are efficiently achieved.

The thickener may be fixed to the support as described above instead of adding the thickener to the reaction solution. Alternatively, the thickener may merely exist in the reaction solution, or may be merely fixed to the support and provided.

Further, it is preferable to add the reaction solution to the reaction field by injecting the reaction solution at an injection rate of 25 mm/s or more for achieving the amplification reaction more efficiently. Consequently, separation of fixed primer sets is affected, so that more local diffusion of primer sets becomes possible.

In the conventional technique, there is the problem that the number of types of primers is limited because deviation occurs in reaction efficiency when multiplex amplification is performed by using a plurality of types of primers in one container. That is, different types of primers may compete for a necessary enzyme and dNTP. There may be difference in reaction specificity and/or reaction efficiency according to a sequence of target sequences or a sequence of primers. In this case, there arises the problem that the amplification reaction start point varies depending on a type of primer, amplification starts and proceeds for only some primer sets, or amplification for some primer sets is not sufficiently achieved. These conventional problems described above are solved by embodiments disclosed in this specification.

That is, when an amplification reaction is carried out using a multi-nucleic-acid amplification detection reaction tool shown with the embodiment as an example, the amplification reaction proceeds only at or near an amplification reagent, and therefore amplification reactions of various kinds of targets can be made to proceed independently without interfering with one another although the amplification reactions are carried out in the same container and/or the same reaction solution, and in parallel to or subsequent to the amplification reaction, the existence and/or the amount of an object nucleic acid can be detected and/or measured in the reaction container where the amplification reaction has been carried out. After separate amplification reactions proceed to some extent, a different primer set may be further added, or the container-shaped multi-nucleic-acid amplification detection reaction tool shown in the first embodiment and the above-described multi-nucleic-acid amplification detection reaction tool may be used in combination.

When a plurality of object genes are detected, a method of providing reaction containers for amplifying object genes, respectively, or a method of placing reagents for detecting all object genes in one reaction container to carry out a multi-nucleic-acid amplification reaction is used. In the case of the method of providing reaction containers for amplifying object genes, respectively, the number of necessary reaction containers and the amount of work during inspection are increased the number of object genes increase. In the case where reagents for detecting all object genes are added in one reaction container, deviation occurs in amplification reaction efficiency. By using a thickener, occurrence of such deviation in amplification efficiency can be prevented.

Example 2

Example 2-1

A diffusion state of primers was evaluated using the ninth embodiment.

A fluorescence-labeled primer set was provided. A multi-nucleic-acid reaction tool 1121 having a configuration similar to that in FIG. 15 is shown.

The provided primer set was dissolved in a TE buffer (10 mM Tris-HCl, pH 8.0, 1 mM EDTA) so that the final concentration was 200 µM. Agarose was dissolved in this solution so that the final concentration was 0.3%, thereby preparing a fixing solution. A glass base plate was used as a support 1122. The fixing solution was added dropwise to three spots, that is, a center (shown by 1123 in the figure) on the support 1122 and two corners (shown by 1124 and 1125 in the figure) of the support 1122, and left standing to be dried. A silicon rubber plate provided with a groove portion 1126 on one surface was used as a cover 1127. Through-holes 1128 and 1129 were formed, respectively, at two ends of the groove portion 1126 of the cover 1127. The cover 1127 was bonded to the support 1122 such that a region of the support 1122 on which the primer set and agarose were fixed was included in the groove portion 1126 of the cover 1127. In this way, a multi-nucleic-acid reaction tool was obtained. In the multi-nucleic-acid reaction tool, a channel 1130 was formed by the groove portion 1126 of the cover 1127 and a surface of the support 1122.

Two through-holes of the cover 1127 were used as an inlet 1128 and an outlet 1129, respectively. PBS was added through the inlet 1128. Thereafter, a diffusion state of primers was observed with fluorescent intensity as an indicator.

As a control, a control multi-nucleic-acid reaction tool prepared by fixing only a fluorescence-labeled primer set in the same manner as described above without fixing agarose was provided. A TE buffer (10 mM Tris-HCl, pH 8.0, 1 mM EDTA) was similarly added through an inlet A to the control multi-nucleic-acid reaction tool, and a diffusion state of primers was observed with fluorescent intensity as an indicator.

The results are shown in (a) and (b) of FIG. 16. FIG. 16(a) shows a result obtained in the control multi-nucleic-acid reaction tool with only primers fixed therein. FIG. 16(b) shows a result obtained in the multi-nucleic-acid reaction tool with the primer set and agarose fixed therein.

The distance over which primers traveled due to addition of the TE buffer (10 mM Tris-HCl, pH 8.0, 1 mM EDTA) was greater in the control multi-nucleic-acid reaction tool than in the multi-nucleic-acid reaction tool with the primer set and agarose fixed therein. From this result, it has become evident that the multi-nucleic-acid reaction tool with the primer set and agarose fixed therein enables more local diffusion of primers.

Example 2-2

A multi-nucleic-acid amplification detection reaction tool for electrochemical detection, which is similar to that in the eleventh embodiment, was prepared.

(1) Preparation of Chip Material

Figure 11:
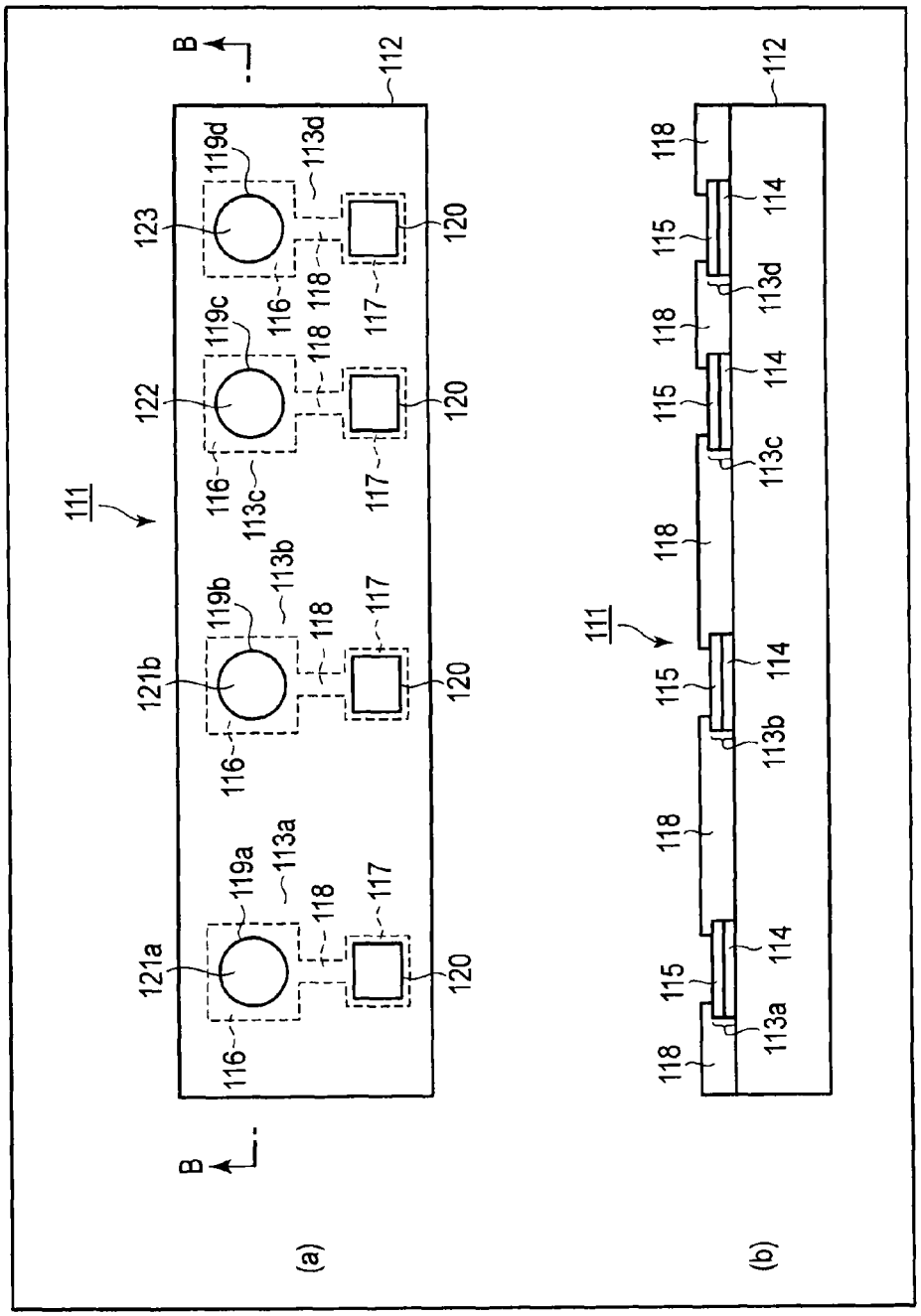
FIG. 11 is a view illustrating an example of a chip material.

A chip material for a multi-nucleic-acid amplification detection reaction tool as illustrated in FIG. 11 was formed. A thin film of titanium and gold was formed on the surface of Pyrex glass by sputtering. Thereafter, an electrode pattern of titanium and gold was formed on the glass surface by an etching treatment. Further an insulating film was applied thereon, and electrodes, that is, a working electrode, a counter electrode, a reference electrode and an electrode for a probe were exposed by an etching treatment. This was set as a chip material for a multi-nucleic-acid amplification detection reaction tool.

(2) Preparation of Multi-Nucleic-Acid Amplification Detection Reaction Tool

A probe DNA was fixed on the working electrode of the chip material prepared as described above. Nucleotide sequences of probe DNAs used are shown in Table 7.

TABLE 7

| Sequence name | Sequence | Number of bases | SEQ ID NO. |
|---|---|---|---|
| A | ACAAGGTCATAATAATGGTATTTGTTGGGGCAATC | 35 | 70 |
| B | TGGTCCTGGCACTGATAATAGGGAATGTATATCAATGGATTATAAACAAACACAA | 55 | 71 |
| C | TTGTAACCAGTACGGTTTATTAAATAATTGGGATTCTGAGG | 41 | 72 |
| D | AGTACTGCTACAGAACAGTTAAGTAAATATGATGCACGAAAAATTAATCAGTACC | 55 | 73 |
| E | GCCCCGACCGATTTCAACACCTACACAGGCCCAGACCAAGCGT | 43 | 74 |
| F | AGCTACAGCTGTTATTACGCAGGATGTTAGGGATAATGTGTCAGTTGATTATAAG | 55 | 75 |
| G | ACCAATAAGGTTTATTGAATATTTGGGCATCAGA | 34 | 76 |
| H | ATTATCTACCTCTATAGAGTCTTCCATACCTTCTACATATGATCCTTCTAAGTTT | 55 | 77 |
| I | CTTTAATATAAAGGTCATCCGGGACAGCCTCGCCAAGTTTT | 41 | 78 |
| J | TCCTAGTAGTTATGTATATGCCCCCTCGCCTAGTGGGT | 38 | 79 |
| K | CTACACAGTCTCCTGTACCTGGGCAATATGATGCTACCAAATTTAAGCAGTATAG | 55 | 80 |
| L | ACATCTGTTGACAACAAACAGACTCAGTTATGTATAATAGGCTGTG | 46 | 81 |
| M | TTTGGTGCAATGGATTTTACTACATTACAAGCTAATAAAAGTGATGTTCCC | 51 | 82 |

Thirteen types of probe DNAs shown with SEQ ID NOS 70 to 82, that is, probe DNAs (A), (B), (C), (D), (E), (F), (G), (H), (I), (J), (K), (L) and (M) were fixed on the chip material prepared as described above. Probe DNA solutions each containing 3 μM of probe DNA were each prepared. The solution of each type of probe DNA in an amount of 100 nL was spotted onto the working electrode. Drying was performed at 40° C., followed by performing washing with ultrapure water. Thereafter, ultrapure water remaining on the surface of the working electrode was removed to prepare a DNA chip with probe DNAs fixed on an electrode of a chip material.

Next, a cover made of a silicon rubber plate was provided as described above. On a surface of the cover, a groove is formed at a position corresponding to a probe fixing region.

A plurality of primer sets were fixed to the inner bottom surface of the cover. The fixing regions of primer sets were adjusted so as to be situated at positions corresponding to the positions of the probe DNAs fixed previously.

First, primer DNAs to be used were provided. The primer DNA to be used is a primer set for amplification by the loop-mediated isothermal amplification (LAMP). Nucleotide sequences of primer DNAs are shown in Tables 8A, 8B and 8C.

TABLE 8A

Nucleotide sequence of DNA primer

| Set name | Sequence name | Sequence | Number of bases | SEQ ID NO. |
|---|---|---|---|---|
| A | A-FIP | GCACTGCTTTGAATAGAGGCACTGTTCCCGATGACCTG | 38 | 83 |
|   | A-BIP | CCATATTGGCTACAACGTGCTACCTGATTGCCCCAACA | 38 | 84 |
|   | A-F3  | AGGGCTGGTACATTAGGAGA | 20 | 85 |
|   | A-B3  | GTCATATTAGTACTGCGAGTGG | 22 | 86 |
|   | A-LPF | CAGTAGTTCCTGAACCTTTAATGTACA | 27 | 87 |
| B | B-FIP | GGATGACCACTAATACCTACACCCTGTGTTGGTTTAGAGGTAGGTC | 46 | 88 |
|   | B-BIP | CACTGAAAACTCTAATAGATATGCCGGTGCAACCAAGTAAACACAGTTGTG | 51 | 89 |
|   | B-F3  | AACTCAACGCTTAGTTTGGGC | 21 | 90 |
|   | B-B3  | CCTTTACCCCAATGCTCTCC | 20 | 91 |
|   | B-LPF | TAATGGCTGCCCGCGA | 16 | 92 |
| C | C-FIP | ATTATTGTGGCCCTGCGCACGTTCTATGGTAACCTCAGAATCCC | 44 | 93 |
|   | C-BIP | ACCACTCGTAGCACTAACATGACTCGCCATGACGAAGGTATTCCT | 45 | 94 |
|   | C-F3  | GCCACTGTACAAAGCAGTGC | 20 | 95 |
|   | C-B3  | TGAATGTATGTCATAACATCAGCTG | 25 | 96 |
|   | C-LPB | GCTGAGGTTAAAAAGGAAAGCACA | 24 | 97 |
| D | D-FIP | AATTGATTACCCCAGCAAATGCCGTCTATGATTACGTCTGAGGCAC | 46 | 98 |
|   | D-BIP | ATACTACTAGAAGTACTAACATGACCCTCCACATGTCTAAGGTACTG | 47 | 99 |
|   | D-F3  | GTATATGTTGCTACGCCTAGTG | 22 | 100 |
|   | D-B3  | GCCATAACCTCTGCAGACAAAG | 22 | 101 |
|   | D-LPF | GCACGTTGCAACCAATAAGG | 20 | 102 |

TABLE 8B (Continued from Table 8A)

| Set name | Sequence name | Sequence | Number of bases | SEQ ID NO. |
|---|---|---|---|---|
| E | E-FIP | CACTGAGTCCTACCCCTAAAGGTTGTCTCAACGCTTGGTCTGG | 43 | 103 |
|   | E-BIP | GATGACACTGAAAACTCTCATGTAGCGCTGAGTTTGTTTATAATCCACAG | 50 | 104 |
|   | E-F3  | CCAGATAACACAGTATATGATCCTAAC | 27 | 105 |
|   | E-B3  | GCAGGTACACAGCCAATAATACAC | 24 | 106 |
|   | E-LPB | GCTGTTGATACCAAAGATACACGTG | 25 | 107 |
| F | F-FIP | TAAAATGGATGGCCACTTAGGCCGGTATGGAAATTGGTCGTGGGC | 45 | 108 |
|   | F-BIP | GGATGATACAGAAAGTGCTCAAAATACACAGCTGTGTTTGC | 41 | 109 |
|   | F-F3  | GAAACACAACGTTTGGTTTGGGC | 23 | 110 |
|   | F-B3  | GTGCTCACCAATAGCAGGTAC | 21 | 111 |
|   | F-LPF | CAATACCTAAAGGCTGCC | 18 | 112 |
| G | G-FIP | GTGGCCCTGTGCTCGTTGTCTATGGTTACCTCTGATGCC | 39 | 113 |
|   | G-BIP | CACGCAGTACAAATATGTCACCCCATGTCGTAGGTACTCC | 40 | 114 |
|   | G-F3  | CAAATTATTTTCCTACACCTAGTGG | 25 | 115 |
|   | G-B3  | GTCATAACGTCTGCAGTTAAGG | 22 | 116 |
|   | G-LPB | GCTGCCATATCTACTTCAGAAACTACA | 27 | 117 |
| H | H-FIP | AACATATACCATTGTTGTGGCCCTTCCATGGTAACCTCTGATTCCC | 46 | 118 |
|   | H-BIP | CTACCCGTAGTACCAACTTTACCCACGTGCCTGGTATATTCC | 42 | 119 |
|   | H-F3  | GTTCTGTATACTGCCCCTCTC | 21 | 120 |
|   | H-B3  | GACATAACATCAGTTGTTAATGTGAC | 26 | 121 |
|   | H-LPF | CCTTATGTAGCCAATAAGGC | 20 | 122 |

TABLE 8C (Continued from Table 8B)

| Set name | Sequence name | Sequence | Number of bases | SEQ ID NO. |
|---|---|---|---|---|
| I | I-FIP | GGATAACTGCAGTATTACCGGACCTAGGGCTGGAAAACTTGG | 42 | 123 |
|   | I-BIP | TCCAACTCCTAGTGGCTCTATAGCGCTGTAGCCAATAAGGC | 41 | 124 |
|   | I-F3  | GACGTGAGCAGATGTTTGT | 19 | 125 |
|   | I-B3  | CCATTGTTATGACCTTGTGC | 20 | 126 |
|   | I-LPB | CCTCAGAATCACAATTATTTAATAAGCC | 28 | 127 |
| J | J-FIP | AGTGTCCCCTACCATGCCCCACGTAGGGAACAGTTATTTGCT | 43 | 128 |
|   | J-BIP | TAAGGGCACTGACATACGTGACAGCCATAGACCCACTAGGCGAG | 45 | 129 |
|   | J-F3  | CTGCAGATGTATATGGAGACAGTA | 25 | 130 |
|   | J-B3  | GTTAAATAACTGGGAGTCTGAGGAT | 26 | 131 |
|   | J-LPF | CTCTATTCCAAAAATGCCTAGCA | 23 | 132 |
| K | K-FIP | GCCAGCAAACACCATTGTTACTCTATTGTTACCTCTGACTCCC | 43 | 133 |
|   | K-BIP | ACCACTCGCAGTACCAATTTAACCCTCAACATGTCTGCTATACTGC | 46 | 134 |
|   | K-F3  | TGTATTCTCCCTCTCCAAGTG | 21 | 135 |
|   | K-B3  | GAATATAGGACATAACATCTGCAG | 24 | 136 |
|   | K-LPF | ACCCTGTGCCTTATGTAACC | 20 | 137 |
| L | L-FIP | GCTATGCGTGAATTTTCTGTGCCCTTGGTGTTGGCCTTAG | 40 | 138 |
|   | L-BIP | GCACAACAAGATGTTAGAGATAACAATAGGTGGAGCACAGCC | 42 | 139 |
|   | L-F3  | GTTGAGGTGGGCAGAGGAC | 19 | 140 |
|   | L-B3  | TTGCATGTAGTGCCAATACCC | 21 | 141 |
|   | L-LPF | CATATTTATTAAATAAGGGATGACCAC | 27 | 142 |
| M | M-FIP | GTTTAGTAACTCCAAAGGAGGACAAAGGCACACCTTGTAATGC | 43 | 143 |
|   | M-BIP | GGGACATGGTAGACACAGGACATATATCTAGGGGAACATCAC | 42 | 144 |
|   | M-F3  | CCTATAGGTGAACATTGGG | 19 | 145 |
|   | M-B3  | GGATATTTGCAAATGGAACTG | 21 | 146 |
|   | M-LPF | CATTCTCCTGCTTTTACCTGGT | 22 | 147 |

For primer DNAs (set A), (set B), (set C), (set D), (set E), (set F), (set G), (set H), (set I), (set J), (set K), (set L) and (set M), FIP, BIP, F3, B3 and LPF each in an amount of 200 μM were provided. 0.100 μL of a 0.6% agarose solution was mixed with 0.100 μL of a solution including FIP, BIP, F3, B3 and LPF in amounts of 0.036 μL, 0.036 μL, 0.005 μL, 0.005 μL and 0.018 μL, respectively. This aqueous solution was fixed to a primer fixing region on the inner bottom surface of a groove portion of a silicon rubber as a cover.

Specifically, 0.200 μL of each of the solutions provided was spotted to the bottom of the groove portion of the cover, and dried at 40° C. for two minutes. The solution was spotted such that each probe DNA was situated at a position facing the corresponding primer set, when the cover was attached to the DNA chip. The cover and the chip material prepared as described above were bonded such that the groove portion of the cover and the surface on which the probe DNA was fixed faced each other. In this way, a multi-nucleic-acid amplification detection reaction tool was obtained. Two through-holes were opened at two ends of the groove portion of the silicon rubber as a cover.

(3) Preparation of LAMP Reaction Solution

The compositions of LAMP reaction solutions are shown in Tables 9 to 12.

TABLE 9

Evaluation of composition of LAMP reaction solution Composition (1)

| Reagent | Template name | Total 50 |
|---|---|---|
| Reaction Mixture |   | 14.00 |
| DNA Polymerase |   | 8.00 |
| Template DNA | A | 2.00 |
|   | C | 2.00 |
|   | E | 2.00 |
|   | G | 2.00 |
|   | I | 2.00 |
|   | K | 2.00 |
|   | M | 2.00 |
| DW |   | 14.00 |
| Total |   | 50.00 |

TABLE 10

Evaluation of composition of LAMP reaction solution Composition (2)

| Reagent | Template name | Total 50 |
|---|---|---|
| Reaction Mixture |   | 14.00 |
| DNA Polymerase |   | 8.00 |
| Template DNA | B | 2.00 |
|   | D | 2.00 |
|   | F | 2.00 |
|   | H | 2.00 |
|   | J | 2.00 |
|   | L | 2.00 |
| DW |   | 16.00 |
| Total |   | 50.00 |

TABLE 11

Evaluation of composition of LAMP reaction solution
Composition (3)

| Reagent | Template name | Total 50 |
|---|---|---|
| Reaction Mixture | | 14.00 |
| DNA Polymerase | | 8.00 |
| Template DNA | A | 2.00 |
| | B | 2.00 |
| | C | 2.00 |
| | D | 2.00 |
| | E | 2.00 |
| | F | 2.00 |
| | G | 2.00 |
| | H | 2.00 |
| | I | 2.00 |
| | J | 2.00 |
| | K | 2.00 |
| | L | 2.00 |
| | M | 2.00 |
| DW | | 2.00 |
| Total | | 50.00 |

TABLE 12

Evaluation of composition
of LAMP reaction solution
Composition (4)

| Reagent | Template name | Total 50 |
|---|---|---|
| Reaction Mixture | | 14.00 |
| DNA Polymerase | | 8.00 |
| DW | | 28.00 |
| Total | | 50.00 |

For compositions (1) to (4), reaction solutions, which included Bst DNA polymerase and a reaction mix in common and to which distilled water (i.e. DW) was added so that the total amount was 50 μL including a later-described template solution, were used.

The composition (1) includes a template A, a template C, a template E, a template G, a template I, a template K and a template M.

The template A is LAMP-amplified by a primer set A. The resulting amplification product is hybridized with a probe DNA (A). The template C is LAMP-amplified by a primer set C. The resulting amplification product is hybridized with a probe DNA (C). The template E is LAMP-amplified by a primer set E. The resulting amplification product is hybridized with a probe DNA (E). The template G is LAMP-amplified by a primer set G. The resulting amplification product is hybridized with a probe DNA (G). The template I is LAMP-amplified by a primer set I. The resulting amplification product is hybridized with a probe DNA (I). The template K is LAMP-amplified by a primer set K. The resulting amplification product is hybridized with a probe DNA (K). The template M is LAMP-amplified by a primer set M. The resulting amplification product is hybridized with a probe DNA (M).

The composition (2) includes a template B, a template D, a template F, a template H, a template J and a template L.

The template B is LAMP-amplified by a primer set B. The resulting amplification product is hybridized with a probe DNA (B). The template D is LAMP-amplified by a primer set D. The resulting amplification product is hybridized with a probe DNA (D). The template F is LAMP-amplified by a primer set F. The resulting amplification product is hybridized with a probe DNA (F). The template H is LAMP-amplified by a primer set H. The resulting amplification product is hybridized with a probe DNA (H). The template J is LAMP-amplified by a primer set J. The resulting amplification product is hybridized with a probe DNA (J). The template L is LAMP-amplified by a primer set L. The resulting amplification product is hybridized with a probe DNA L).

The composition (3) includes all of the template A, the template B, the template C, the template D, the template E, the template F, the template G, the template H, the template I, the template J, the template K, the template L and the template M.

The composition (4) does not include a template. Nucleotide sequences of the template A, template B, template C, template D, template E, template F, template G, template H, template I, template J, template K, template L and template M are shown in Tables 13A, 13B and 13C.

TABLE 13A

Template A (SEQ ID NO: 148)
AGGGCTGGTACATTAGGAGAGGCTGTTCCCGATGACCTGTACATTAAAG
GTTCAGGAACTACTGCCTCTATTCAAAGCAGTGCTTTTTTTCCCACTCC
TAGTGGATCAATGGTTACTTCCGAATCTCAGTTATTTAATAAGCCATATT
GGCTACAACGTGCACAAGGTCATAATAATGGTATTTGTTGGGCAATCA
GGTATTTGTTACTGTGGTAGATACCACTCGCAGTACTAATATGAC Template B (SEQ ID NO: 149)
AACTCAACGCTTAGTTTGGGCCTGTGTTGGTTTAGAGGTAGGTCGCGGG
CAGCCATTAGGTGTAGGTATTAGTGGTCATCCATTATTAAATAAATTTG
ATGACACTGAAAACTCTAATAGATATGCCGGTGGTCCTGGCACTGATAA
TAGGGAATGTATATCAATGGATTATAAACAAACACAACTGTGTTTACTT
GGTTGCAAACCACCTATTGGAGAGCATTGGGGTAAAGG Template C (SEQ ID NO: 150)
GCCACTGTACAAAGCAGTGCTTTTTTTCCTACTCCTAGTGGTTCTATGG
TAACCTCAGAATCCCAATTATTTAATAAACCGTACTGGTTACAACGTGC
GCAGGGCCACAATAATGGCATATGTTGGGGCAATCAGTTGTTTGTCACA
GTTGTGGATACCACTCGTAGCACTAACATGACTTTATGTGCTGAGGTTA
AAAAGGAAAGCACATATAAAAATGAAAATTTTAAGGAATACCTTCGTCA
TGGCGAGGAATTTGATTTACAATTTATTTTTCAATTGTGCAAAATTACAT
TAACAGCTGATGTTATGACATACATTCA Template D (SEQ ID NO: 151)
GTATATGTTGCTACGCCTAGTGGGTCTATGATTACGTCTGAGGCACAGT
TATTTAATAAACCTTATTGGTTGCAACGTGCCCAAGGCCATAATAATGG
CATTTGCTGGGGTAATCAATTATTTGTTACTGTAGTAGATACTACTAGAA
GTACTAACATGACTATTAGTACTGCTACAGAACAGTTAAGTAAATATGA
TGCACGAAAAATTAATCAGTACCTTAGACATGTGGAGGAATATGAATTA
CAATTTGTTTTTCAATTATGCAAAATTACTTTGTCTGCAGAGGTTATGGC

TABLE 13B (Continued from Table 13A)

Template E (SEQ ID NO: 152)
CCAGATAACACAGTATATGATCCTAACTCTCAACGCTTGGTCTGGGCCT
GTGTAGGTGTTGAAATCGGTCGGGGCCAACCTTTAGGGGTAGGACTCA
GTGGTCATCCATTATATAATAAATTGGATGACACTGAAAACTCTCATGT
AGCATCTGCTGTTGATACCAAAGATACACGTGATAATGTATCTGTGGAT
TATAAACAAACTCAGCTGTGTATTATTGGCTGTGTACCTGC Template F (SEQ ID NO: 153)
GAAACACAACGTTTGGTTTGGGCATGTGTAGGTATGGAAATTGGTCGT
GGGCAGCCTTTAGGTATTGGCCTAAGTGGCCATCCATTTTATAATAAA
TTGGATGACACAGAAAGTGCTCATGCAGCTACAGCTGTTATTACGCAG
GATGTTAGGGATAATGTGTCAGTTGATTATAAGCAAACACAGCTGTGT
ATTTTAGGTTGTGTACCTGCTATTGGTGAGCAC Template G (SEQ ID NO: 154)
CAAATTATTTTCCTACACCTAGTGGTTCTATGGTTACCTCTGATG
CCCAAATATTCAATAAACCTTATTGGTTACAACGAGCACAGGGCCACA
ATAATGGCATTTGTTGGGGTAACCAACTATTTGTTACTGTTGTTGATAC
TACACGCAGTACAAATATGTCATTATGTGCTGCCATATCTACTTCAGAA
ACTACATATAAAAATACTAACTTTAAGGAGTACCTACGACATGGGGAG
GAATATGATTTACAGTTTATTTTTCAACTGTGCAAAATAACCTTAACTG
CAGACGTTATGAC

TABLE 13B -continued (Continued from Table 13A)

Template H (SEQ ID NO: 155)
GTTCTGTATACTGCCCCTCTCCCAGCGGTTCCATGGTAACCTCT
GATTCCCAGTTATTTAATAAGCCTTATTGGCTACATAAGGCCCAGGGC
CACAACAATGGTATATGTTGGCATAATCAATTATTTCTTACTGTTGTGG
ACACTACCCGTAGTACCAACTTTACATTATCTACCTCTATAGAGTCTTC
CATACCTTCTACATATGATCCTTCTAAGTTTAAGGAATATACCAGGCAC
GTGGAGGAGTATGATTTACAATTTATATTTCAACTGTGTACTGTCACAT
TAACAACTGATGTTATGTC

TABLE 13C (Continued from Table 13B)

Template I (SEQ ID NO: 156)
GACGTGAGCAGATGTTTGTTAGACACTTTTTTAATAGGGCTGGAAAAC
TTGGCGAGGCTGTCCCGGATGACCTTTATATTAAAGGGTCCGGTAATA
CTGCAGTTATCCAAAGTAGTGCATTTTTTCCAACTCCTAGTGGCTCTAT
AGTTACCTCAGAATCACAATTATTTAATAAGCCTTATTGGCTACAGCGT
GCACAAGGTCATAACAATGG Template J (SEQ ID NO: 157)
CTGCAGATGTATATGGAGACAGTATGTTCTTTTGTTTACGTAGGGAAC
AGTTATTTGCTAGGCATTTTTGGAATAGAGGGGGCATGGTAGGGGACA
CTATACCTACTGAATTGTATATTAAGGGCACTGACATACGTGACAGTC
CTAGTAGTTATGTATATGCCCCCTCGCCTAGTGGGTCTATGGTATCCT
CAGACTCCCAGTTATTTAAC Template K (SEQ ID NO: 158)
TGTATTCTCCCTCTCCAAGTGGCTCTATTGTTACCTCTGACTCCCAG
TTGTTTAATAAACCATATTGGTTACATAAGGCACAGGGTCATAACAA
TGGTGTTTGCTGGCATAATCAATTATTTGTTACTGTGGTAGATACCA
CTCGCAGTTGCTTCTACACAGTCTCCTGTACCTGGGCAATATGATGC

TABLE 13C -continued (Continued from Table 13B)

TACCAAATTTAAGCAGTATAGCAGACATGTTGAGGAATATGATTTGC
AGTTTATTTTTCAGTTGTGTACTATTACTTTAACTGCAGATGTTATGT
CCTATATTC

Template L (SEQ ID NO: 159)
GTTGAGGTGGGCAGAGGACAGCCCCTTGGTGTTGGCCTTAGTGGTC
ATCCCTTATTTAATAAATATGATGACACAGAAAATTCACGCATAGCA
AATGGCAATGCACAACAAGATGTTAGAGATAACACATCTGTTGACAA
CAAACAGACTCAGTTATGTATAATAGGCTGTGCTCCACCTATTGGGG
AACACTGGGGTATTGGCACTACATGCAA Template M (SEQ ID NO: 160)
TCCTATAGGTGAACATTGGGGAAAAGGCACACCTTGTAATGCTAACC
AGGTAAAAGCAGGAGAATGTCCTCCTTTGGAGTTACTAAACACTGTA
CTACAAGACGGGGCATGGTAGACACAGGATTTGGTGCAATGGATT
TTACTACATTACAAGCTAATAAAAGTGATGTTCCCCTAGATATATGC
AGTTCCATTTGCAAATATCC (4) LAMP Amplification Reaction on Multi-Nucleic-Acid Amplification Detection Reaction and Detection of Object Nucleic Acid by Probe DNA One of two through-holes provided in the silicon rubber plate as a cover was set as an inlet. A channel formed by the groove provided on the silicon rubber plate and a surface of the chip material was set as a reaction portion, where a reaction was carried out. A LAMP reaction solution was injected into the reaction portion through the inlet such that the reaction solution passed over the primer fixing position at a flow rate of 25 mm/s. Thereafter, the multi-nucleic-acid amplification detection reaction tool was quickly installed in a DNA automatic examination apparatus. A LAMP reaction was carried out at 64° C. for 60 minutes on a peltier in the DNA automatic examination apparatus.

After the LAMP reaction for 60 minutes, a hybridization reaction was carried out at 55° C. for 10 minutes, and washing was performed at 30° C. for three minutes. Thereafter, the washing solution was removed, and 35.5 μM of a Hoechst 33258 solution was injected through the inlet.

An electrical potential was swept through each probe nucleic acid fixing working electrode to measure an oxidation current of a Hoechst 33258 specifically bound with a double strand formed by the probe DNA and the LAMP product. The series of reactions described above were carried out in the DNA automatic examination apparatus described in SICE Journal of Control, Measurement and System Integration, Vol. 1, No. 3, pp. 266-270, 2008.

(5) Detection Results

Detection results are shown in Table 14.

TABLE 14

Current values (unit: nA) obtained by detecting 13 kinds of templates (A to M)

| Reaction reagent | Probe name | | | | | | | | | | | | |
|---|---|---|---|---|---|---|---|---|---|---|---|---|---|
| | A | B | C | D | E | F | G | H | I | J | K | L | M |
| Composition (1) | 37.52* | 17.26 | 39.55* | 18.50 | 50.45* | 20.08 | 53.93* | 17.29 | 36.76* | 17.34 | 47.73* | 18.86 | 50.31* |
| Composition (2) | 18.20 | 57.34* | 23.10 | 55.59* | 20.72 | 51.53* | 20.53 | 46.82* | 18.96 | 34.02* | 19.81 | 41.07* | 15.29 |
| Composition (3) | 43.67* | 65.60* | 52.46* | 36.45* | 61.80* | 64.96* | 53.40* | 45.91* | 41.27* | 38.45* | 51.35* | 37.79* | 40.84* |
| Composition (4) | 22.50 | 22.91 | 23.80 | 21.43 | 21.94 | 21.67 | 22.67 | 21.68 | 20.01 | 18.55 | 18.06 | 18.17 | 18.41 |

*≥30 nA

[Results of LAMP Reaction Solution Composition (1)]

Results of adding the LAMP reaction solution composition (1) including templates A, C, E, G, I, K and M are as follows.

Probe DNAs with which a current value was obtained were probes DNA (A), DNA (C), DNA (E), DNA (G), DNA (I), DNA (K) and DNA (M). For all of probes DNA (A), DNA (C), DNA (E), DNA (G), DNA (I), DNA (K) and DNA (M), a current value of 30 nA or more was obtained.

Thus, it has become evident that in the case of the LAMP reaction solution of the composition (1), LAMP reactions by primer sets A, C, E, G, I, K and M fixed on the inner bottom surface of the silicon rubber each locally proceeded, and the resulting amplification products were hybridized with the above-described probe DNAs.

On the other hand, when DNAs fixed on the inner bottom surface of the silicon rubber were primer sets B, D, F, H, J and L, a current was not obtained.

From these results, it could be found that by the multi-nucleic-acid amplification detection reaction tool of the embodiment, templates A, C, E, G, I, K and M included in the LAMP reaction solution were amplified by the respectively corresponding primer sets, and hybridized with the respectively corresponding probe nucleic acids.

From the results, it can be determined that the LAMP reaction solution included templates A, C, E, G, I, K and M.

[Results of LAMP Reaction Solution Composition (2)]

Results of adding the LAMP reaction solution composition (2) including templates B, D, F, H, J, and L are as follows.

By adding the reaction solution of the composition (2), a current of 30 nA or more was obtained for all of probes DNA (B), DNA (D), DNA (F), DNA (H), DNA (J) and DNA (L).

Thus, it has been confirmed that templates B, D, F, H, J and L were each locally amplified by primer DNAs fixed on the bottom surface of the silicon rubber, that is, primer sets B, D, F, H, J and L, and the resulting amplification products were hybridized with the corresponding probe DNAs.

On the other hand, when primer DNAs fixed on the bottom surface of the silicon rubber were primer sets A, C, E, G, I, K and M, a current was not obtained.

From the results, it can be determined that the LAMP reaction solution included templates B, D, F, H, J and L.

[Results of LAMP Reaction Solution Composition (3)]

Results of adding the LAMP reaction solution composition (3) including all of 13 types of templates are as follows.

For all the probe DNAs, a current value of 30 nA or more was obtained. As a result, it has become evident that LAMP reactions by 13 types of primer DNAs fixed on the bottom surface of the silicon rubber each locally proceeded, and the resulting LAMP products reacted with 13 types of probe DNAs.

From the results, it can be determined that the LAMP reaction solution included 13 types of templates.

When the LAMP reaction solution composition (4) which did not include a template was added, LAMP amplification reactions by 13 types of primer DNAs fixed on the bottom surface of the silicon rubber did not proceed, and a current value was not obtained.

From the above results, it has been shown that when the array-type primer probe chip described in this Example was used, a plurality of types of templates included in the LAMP reaction solution could be detected, and the sequences thereof could be identified.

Example 2-3

A test was conducted in the same manner as in Example 2-3 except that a primer obtained by mixing water in place of a thickener was fixed. That is, four types of LAMP reaction solutions were identical to the reagents used when the thickener was added, and those including the same types of templates were used.

The results are shown in Table 15.

In the LAMP reaction solution (4) which did not include a template, a current value was not detected for any of the probe DNAs.

On the other hand, even in the results of adding the LAMP reaction solution (1), (2) and (3), a current value derived from a template included in the liquid was not always obtained. This is considered to be because since amplification was not achieved for a part of templates included in the LAMP reaction solutions (1), (2) and (3), an amplification product by LAMP amplification was not produced, and therefore hybridization with a probe DNA did not occur. For the current value for probe DNAs with which a current value was obtained, the obtained current value was low as compared to that obtained when the thickener was fixed along with the primer set.

From these results, it has been indicated that when the thickener was not added at the time of fixing the primer set, the elution range of the primer DNA is expanded, so that there is a high possibility that an amplification reaction supposed to be obtained is not achieved.

The results of Examples 2-2 and 2-3 described above have shown the following. It has been shown that by fixing primer sets and adding a thickener in the multi-nucleic-acid amplification detection reaction tool according to the embodiment as described in this Example, a plurality of types of templates included in a LAMP reaction solution can be more accurately detected, and the sequences thereof can be identified.

Example 2-4

A thickener and a primer set were fixed to the chip material prepared in (1) of Example 2-2 described above.

A method for preparation of a thickener is described. As a thickener, "Agarose-Super LM (melting point≤60° C.)" manufactured by nacalai tesque was used. Agarose has an intrinsic melting temperature, gelation temperature and re-melting temperature according to molecular weight and structure, so that it is necessary to set conditions in accordance with properties.

Agarose in an amount of 0.6 g was added to 100 mL of distilled water, and adequately mixed, and the mixture was then heated at 80° C. to fully dissolve the agarose, thereby preparing a 0.6% agarose solution. When the agarose solution was mixed with a primer solution, the agarose was fully dissolved by heating to 80° C. again, and then mixed with a primer in equal amounts to adjust the agarose concentration to 0.3% in terms of final concentration.

The agarose-mixed primer solution with a final concentration of 0.3%, which was prepared as described above, was added dropwise onto a support. Thereafter, the support was heated for two minutes on a hotplate set at 40° C., thereby drying the solution. After it was confirmed the solution after drying was fully fixed in the form of a film, and it was stored at −20° C. together with the support before being used.

TABLE 15

Current values (unit: nA) obtained by detecting 13 kinds of templates (A to M) (no thickener added)

| Reaction reagent | Probe name | | | | | | | | | | | | |
|---|---|---|---|---|---|---|---|---|---|---|---|---|---|
| | A | B | C | D | E | F | G | H | I | J | K | L | M |
| Composition (1) | 29.08 | 22.58 | 37.10* | 18.47 | 38.62* | 20.65 | 40.71* | 19.08 | 26.37 | 16.63 | 33.33* | 16.27 | 21.36 |
| Composition (2) | 20.00 | 48.04* | 24.71 | 40.00* | 22.87 | 52.06* | 24.24 | 34.69* | 18.29 | 22.41 | 21.04 | 23.37 | 17.67 |
| Composition (3) | 20.34 | 38.05* | 31.24* | 26.46 | 43.55* | 34.43* | 44.45* | 25.22 | 22.50 | 26.98 | 28.88 | 27.10 | 36.64* |
| Composition (4) | 21.20 | 22.83 | 24.94 | 20.70 | 23.94 | 22.47 | 23.77 | 21.65 | 18.70 | 17.50 | 19.26 | 18.35 | 17.81 |

*Yellow cell: ≥30 nA

4. DESIGN OF CHANNEL SHAPE

A multi-nucleic-acid amplification reaction tool described here as a further embodiment may be provided as a reaction device which carries out an amplification reaction of nucleic acid in a fine channel, or a nucleic acid detecting device and a nucleic acid detector which detect an amplification product after the amplification reaction.

With development of genetic engineering in recent years, diagnosis or prevention of diseases with genes is becoming possible in the medical field. This is called a genetic diagnosis, and by detecting a human gene defect or change as a cause of diseases, diseases can be diagnosed or predicted before onset of diseases or in an extremely early stage of diseases. Researches concerned with a relationship between the genotype and the epidemic have been advanced along with decoding of the human genome, and treatments based on genotypes of individuals (personalized medicine) are being realized. Therefore, it is very important to detect a gene and determine a genotype easily and conveniently. Further, in these genetic tests, a plurality of types of genes are often detected to make a comprehensive determination, and therefore it is very important to detect a plurality of types of object genes in parallel in a short time.

As apparatuses for detecting nucleic acids, devices called μ-TAS capable of sequentially carrying out a plurality of reactions involving a plurality of reagents in one device have been extensively researched and developed. They are characterized by including a reagent retention region, a reaction region and a sensor region and having a channel that connects these regions.

When a plurality of types of genes is detected in parallel in one device, a method of providing a plurality of separate containers for amplification for amplifying a plurality of object genes, or a method of carrying out a multi-nucleic-acid amplification reaction with all object genes placed in one a reaction container is conceivable. However, either of these methods has the problem that device integration becomes difficult when the number of object gene types to be detected increases. That is, in the method of providing a plurality of separate amplification containers, the device is complicated because it is necessary to provide a large number of amplification containers, and the method of carrying out a multi-nucleic-acid amplification reaction has the problem that when the number of object genes increases, competition for the gene amplification reaction occurs, so that amplification efficiency is considerably deteriorated.

As one of solutions for the above-described problems, there is a nucleic acid detecting device which subjects a plurality of types of target nucleic acids to amplification reaction independently (in independent regions) in parallel using a plurality of types of primer sets in one reaction field, and measures the amounts the resulting amplification products independently to determine the existence of an object nucleic acid.

However, the nucleic acid detecting device intended to subject a plurality of types of target nucleic acids to amplification reaction independently in parallel using a plurality of types of primer sets in one reaction field as described above has, for example, the following problems.

One of the problems is difficulty of retention of primer sets in amplification regions of the nucleic acid detecting device. For holding primer sets in amplification regions of the nucleic acid detecting device, a solution including the primer set is added dropwise to each amplification region. However, this solution easily moves in the process of holding the primer set. Therefore, the nucleic acid detecting device has the problem that a retention position of the primer set in each amplification region cannot be accurately defined.

Another problem is outflow of a primer set. The primer set held in an amplification region beforehand may flow out from its holding position to an adjacent amplification region when a solution including a target nucleic acid is introduced into the amplification region.

Another problem is hindrance of amplification reaction by movement of a primer set and an amplification product. The primer set and the amplification product diffuse with flow of a solution during amplification reaction. When an unintended primer set and amplification product flow from an adjacent different amplification region, the amplification reaction may be hindered in the amplification region.

Another problem is hindrance of amplification reaction by an eluted substance from a protective film. The amplification reaction is carried out in a region including a detection sensor for an amplification product. However, an eluted substance from the protective film of the sensor may hinder the amplification reaction.

By using this embodiment, the multi-nucleic-acid amplification reaction tool can solve these difficulties and problems, and consequently a multi-nucleic-acid amplification reaction tool which improves efficiency of amplification reaction of an nucleic acid as a further aspect, for example a nucleic acid reacting device, a nucleic acid detecting device and a nucleic acid detector, can be provided.

Various embodiments will be described below with reference to the drawings. Throughout the embodiments, common configurations are given the same symbol, and duplicated explanations are omitted. Each figure is a schematic view for explaining the embodiments and facilitating understandings thereof, and the shape, the dimension, the ratio and the like in the figure may be different from those of the actual apparatus, but they can be appropriately designed and changed by referring to the following descriptions and publicly known techniques.

Twelfth Embodiment

Figure 17:
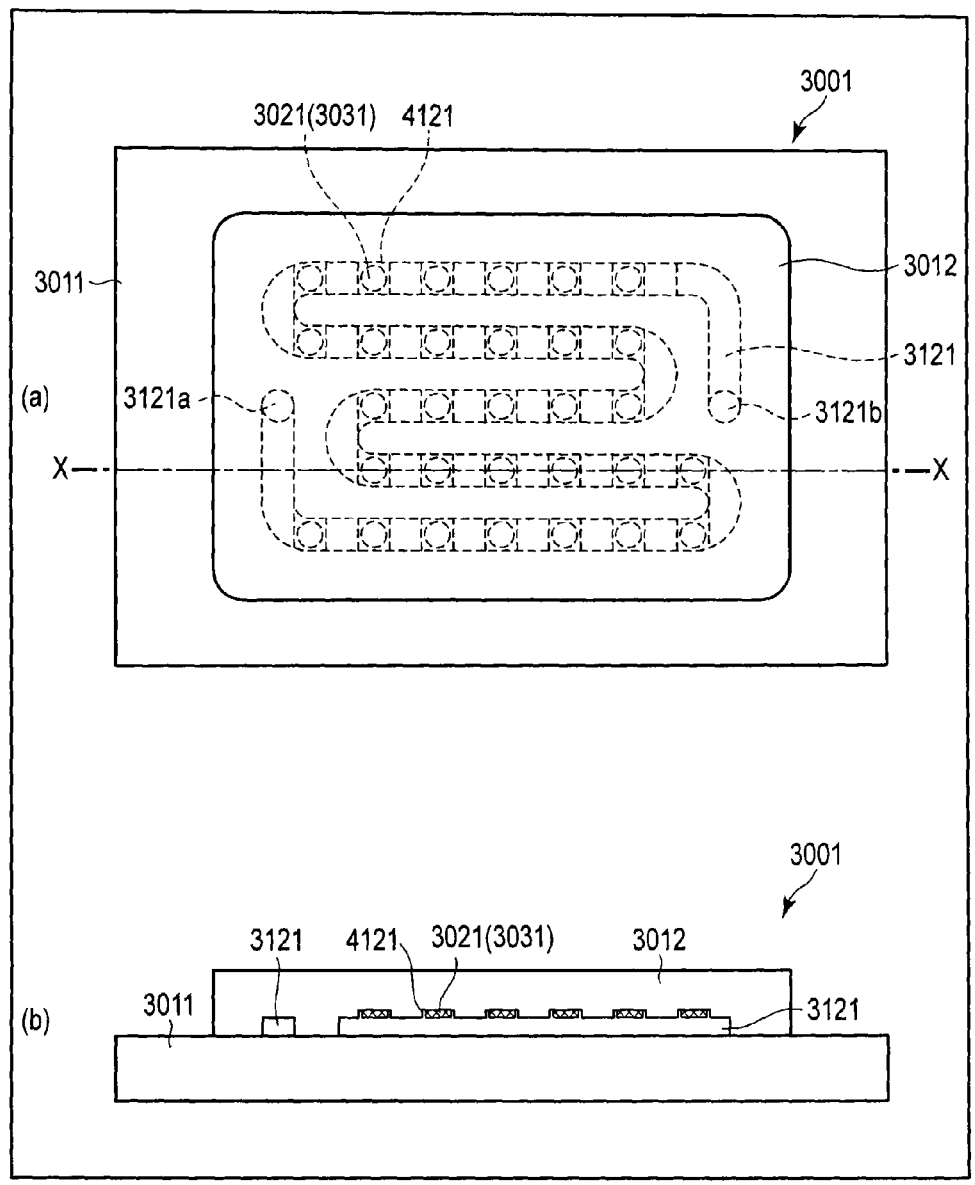
FIG. 17 is a schematic view of a nucleic acid detecting device.

An example of a nucleic acid detecting device 3001 according to the twelfth embodiment will be described with reference to FIG. 17. FIG. 17(*a*) is a plan view of an example of the nucleic acid detecting device 3001. FIG. 17(*b*) is a sectional view of the nucleic acid detecting device 3001 taken along line X-X in FIG. 17(*a*). The nucleic acid detecting device 3001 is used for subjecting a plurality of types of target nucleic acids to amplification reaction independently in parallel using a plurality of types of primer sets 3031 in one reaction field.

The nucleic acid detecting device 3001 includes a support (second member) 3011 and a cover (first member) 3012. The support 3011 has a substantially flat surface as a surface which is in contact with the cover 3012. In the twelfth embodiment, a direction in which the support 3011 and the cover 3012 are arranged in this order is referred to as a stacking direction. The cover 3012 has a groove portion 3121 on a surface (first surface) which is in contact with the support 3011. The groove portion 3121 is provided on a surface which is in contact with the support 3011. The groove portion 3121 is internally sealed by the cover 3012 and the support 3011 which is in contact with the cover. The groove portion 3121 sealed by the cover 3012 and the support 3011 acts as a channel for various types of solutions. As an example, the groove portion 3121 is meandered like a curved line from an entrance 3121*a* to an exit 3121*b* for various kinds of solutions, but its shape is not particularly limited. The groove portion 3121 is formed with substantially the same width from the entrance 3121a to the exit 3121b. In the groove portion 3121, a plurality of chambers (channel-type chambers) 4211 are mutually arranged, for example, at equal intervals. The chamber 4211, where an amplification reaction of nucleic acid is carried out, is used for reacting a later-described electrode (sensor) and a nucleic acid sample. The chamber 4211 is formed in a shape recessed in the stacking direction with respect to regions (areas) other than the chamber 4211 in the groove portion 3121. Namely, the chamber 4211 is formed so as to have a depth greater than that of regions other than the chamber 4211 in the groove portion 3121. Conversely, the depth of regions other than the chamber 4211 in the groove portion 3121 is less than the depth of the chamber 4211. Therefore, the cross section of the chamber 4211 is larger than the cross section of regions other than the chamber 4211 in the groove portion 3121. The cross section of the chamber 4211 and the cross section of regions other than the chamber 4211 in the groove portion 3121 are each a cross section based on a surface orthogonal to a surface provided with the groove portion 3121 in the cover 3012. The cross section of regions other than the chamber 4211 in the groove portion 3121 is preferably, for example, 90% or less of the cross section of the chamber 4211, but is not particularly limited. The chamber 4211 corresponds to the primer fixing region 3021. The primer fixing region 3021 is formed at an upper surface area of the chamber 4211 (area recessed in the stacking direction with respect to regions other than the chamber 4211). A plurality of primer fixing regions 3021 are mutually independently arranged in the groove portion 3121.

The materials of the support 3011 and the cover 3012 may be the same or different. The materials of the support 3011 and the cover 3012 should be such materials that the support 3011 and the cover 3012 are not themselves involved in an amplification reaction or the like. The materials of the support 3011 and the cover 3012 should be materials that enable an amplification to be carried out in the groove portion 3121. The materials of the support 3011 and the cover 3012 may be arbitrarily selected from silicon, glass, a resin, a metal and so on.

Next, fixing (retention) of a primer set 3031 for amplification of nucleic acid in a primer fixing region 3021 will be described. The chamber 4211 holds the primer set 3031 on the channel wall surface. The primer fixing region 3021 corresponds to the position of the chamber 4211, and therefore may be appropriately replaced with the chamber 4211. As illustrated in FIG. 17, the primer set 3031 is fixed in the vicinity of an upper surface area in the stacking direction in the chamber 4211 (primer fixing region 3021) such that the primer set separates when coming into contact with a liquid phase for providing a reaction field. To a plurality of chambers 4211 (primer fixing regions 3021), a plurality of primer sets 3031 are fixed, respectively, for each type of target nucleic acid. That is, a plurality of chambers 4211 (primer fixing regions 3021) hold a plurality of types of primer sets configured to amplify a plurality of target sequences, respectively. Fixing of the primer set 3031 can be performed by, for example, providing only the cover 3012 such that the groove portion 3121 faces upward in the vertical direction, and adding dropwise to one primer fixing region 3021a solution including the primer set 3031, followed by drying the solution. The method for holding the primer set 3031 is not limited to a method by drying, and other methods, such as a method of freeze drying, may be used.

Since the chamber 4211 is formed with a depth greater than that of regions other than 4211 in the groove portion 3121 as described above, a solution including the primer set 3031, which is added dropwise to the primer fixing region 3021, does not easily move to a region other than the chamber 4211. Therefore, adjacent primer fixing regions 3021 can hold different primer sets 3031 independently.

Figure 18:
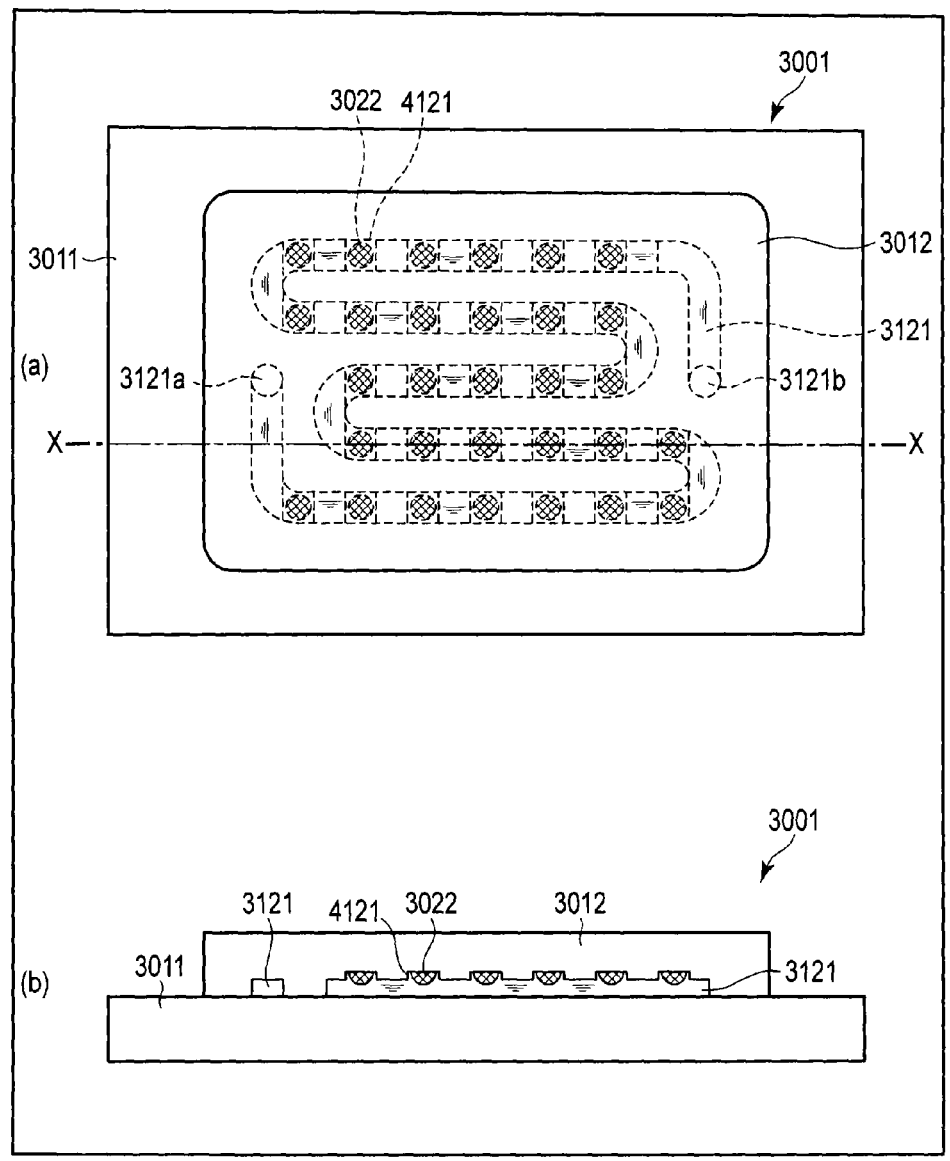
FIG. 18 is a schematic view of a nucleic acid detecting device.

Next, addition of a reaction solution to a nucleic acid detecting device 3001 with a plurality of primer sets 3031 fixed on different primer fixing regions 3021, respectively, will be described. FIG. 18(a) is a plan view of an example of the nucleic acid detecting device 3001. FIG. 18(b) is a sectional view of the nucleic acid detecting device 3001 taken along line X-X in FIG. 18(a). FIG. 18 illustrates a state in which a reaction solution is added to the nucleic acid detecting device 3001. The nucleic acid detecting device 3001 illustrated in FIG. 18 is the same as that in FIG. 1 except that a reaction solution is added to the groove portion 3121.

The reaction solution should include components necessary for nucleic acid amplification reaction. Examples of components included in the reaction solution may include, but are not limited to, an enzyme such as polymerase, a substrate substance such as deoxynucleoside triphosphate necessary for forming a new polynucleotide chain with a primer as a start point, a reverse transcriptase and a necessary substrate substance, etc., when performing reverse transcription in parallel, and a buffer such as a salt configured to maintain a proper amplification environment.

As illustrated in FIG. 18, the primer set 3031 fixed on the primer fixing region 3021 starts to release and diffuse after the reaction solution is added through the entrance 3121a. A region where the primer separates and diffuses is schematically illustrated in FIG. 18 as a primer separation/diffusion region 3022.

It is desired that the primer set 3031 separating and diffusing when the reaction solution is introduced into the nucleic acid detecting device 3001 should not easily flow out to adjacent other primer fixing regions 3021. That is, the primer separation/diffusion region 3022 is desired to correspond to the primer fixing region 3021 (chamber 4211 in other words).

The nucleic acid detecting device 3001 can considerably reduce a flow rate in the vicinity of an area where the primer set 3031 is fixed (area that is recessed in the stacking direction with respect to regions other than the chamber 4211) in the chamber 4211 at the time when the reaction solution is introduced. Accordingly, the nucleic acid detecting device 3001 can prevent the primer set 3031 from flowing out to adjacent other primer fixing regions 3021. Therefore, the nucleic acid detecting device 3001 according to the twelfth embodiment can make primer sets 3031 of adjacent primer fixing regions 3021 mutually independent.

Further, during amplification reaction, the primer set 3031 and the produced amplification in an amplification region (region corresponding to the primer fixing region 3021 (chamber 4211)) are desired to be situated independently within the amplification region without diffusing to other amplification regions. In the nucleic acid detecting device 3001, the depth (channel cross section) of the groove portion 3121 in regions other than the chamber 4211 is shallower (smaller) than the depth (channel cross section) of the chamber 4211. Thus, the nucleic acid detecting device 3001 can inhibit the primer and the produced amplification product in an amplification region from diffusing to other amplification regions during amplification reaction. Therefore, the nucleic acid detecting device 3001 according to the twelfth embodiment can achieve amplification for a plurality of template sequences using a plurality of types of primer sets 3031 independently (locally) and in parallel with high efficiency.

A specific method for detecting an amplification product that is locally obtained is not limited, and a method of detecting a hybridization signal, which is publicly known itself, for example a method of detecting and/or measuring fluorescent intensity using a fluorescent label, or a method of detecting and/or measuring a current response using an intercalator, may be used.

Figure 19:
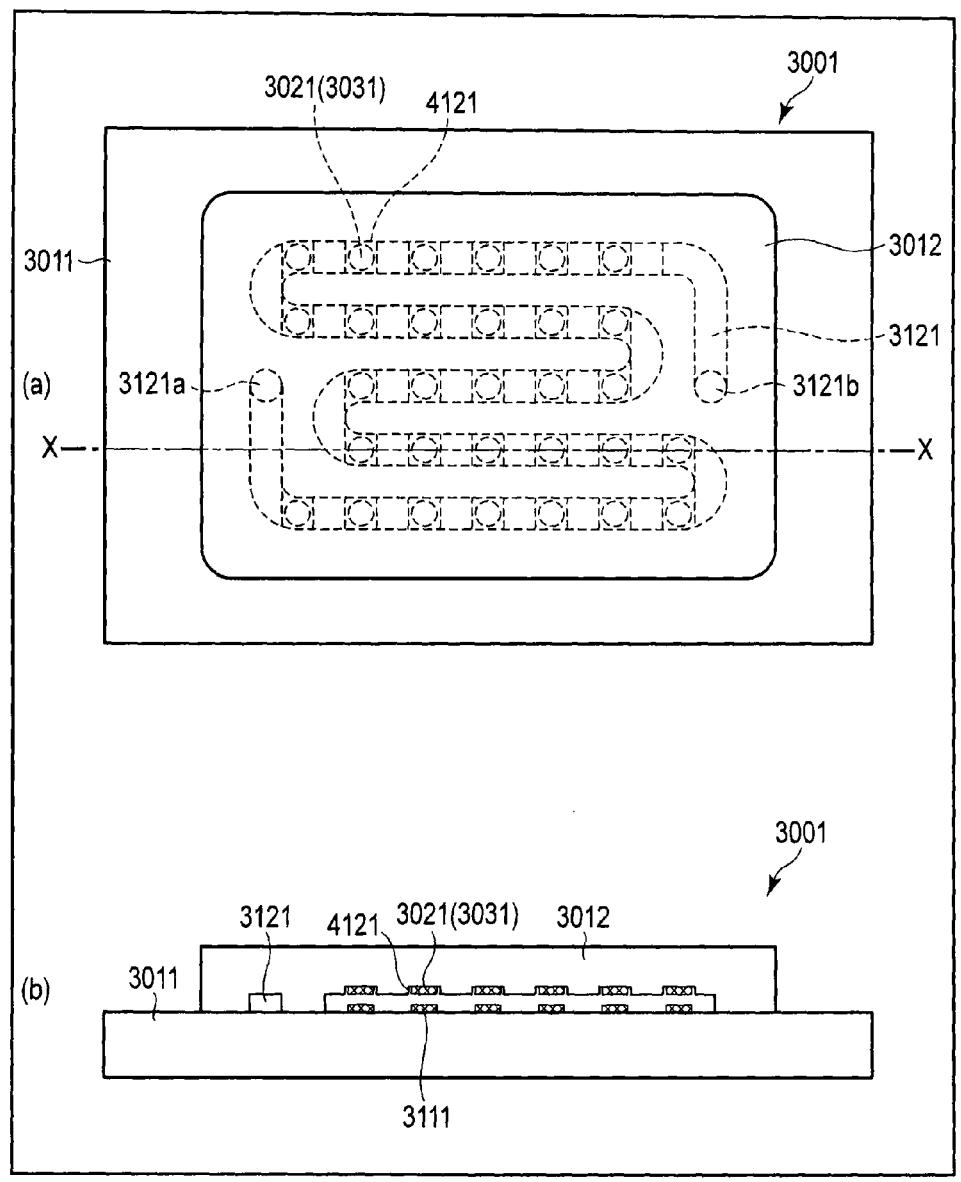
FIG. 19 is a schematic view of a nucleic acid detecting device.

Next, detection of a hybridization signal by the nucleic acid detecting device 3001 will be described. FIG. 19(a) is a plan view of an example of the nucleic acid detecting device 3001. FIG. 19(b) is a sectional view of the nucleic acid detecting device 3001 taken along line X-X in FIG. 19(a). The nucleic acid detecting device 3001 illustrated in FIG. 19 is the same as that in FIG. 1 except that the support 3011 includes the probe fixation region 3111. For example, the probe fixation region 3111 is arranged in the support 3011 at a position facing the primer fixation region 3021 (chamber 4211), but its arrangement is not particularly limited, and may be in any form as long as it is settled inside the chamber 4211. The probe fixation region 3111 is, for example, a region where an electrode to detect a hybridization signal (electrode for detection of nucleic acids) is provided. That is, the electrode for detection of nucleic acids in the probe fixation region 3111 is arranged at a position facing a surface that is in contact with the support 3011 in the cover 3012 and facing the groove portion 3121 (particularly primer fixing region 3021 (chamber 4211)).

A plurality of probe nucleic acids including a complementary sequence of a desired sequence to be detected are fixed on the probe fixing region 3111. The nucleic acid detecting device 3001 can obtain a hybridization signal in the probe fixing region 3111 subsequent to carrying out an amplification reaction in the primer fixing region 3021.

Figure 20:
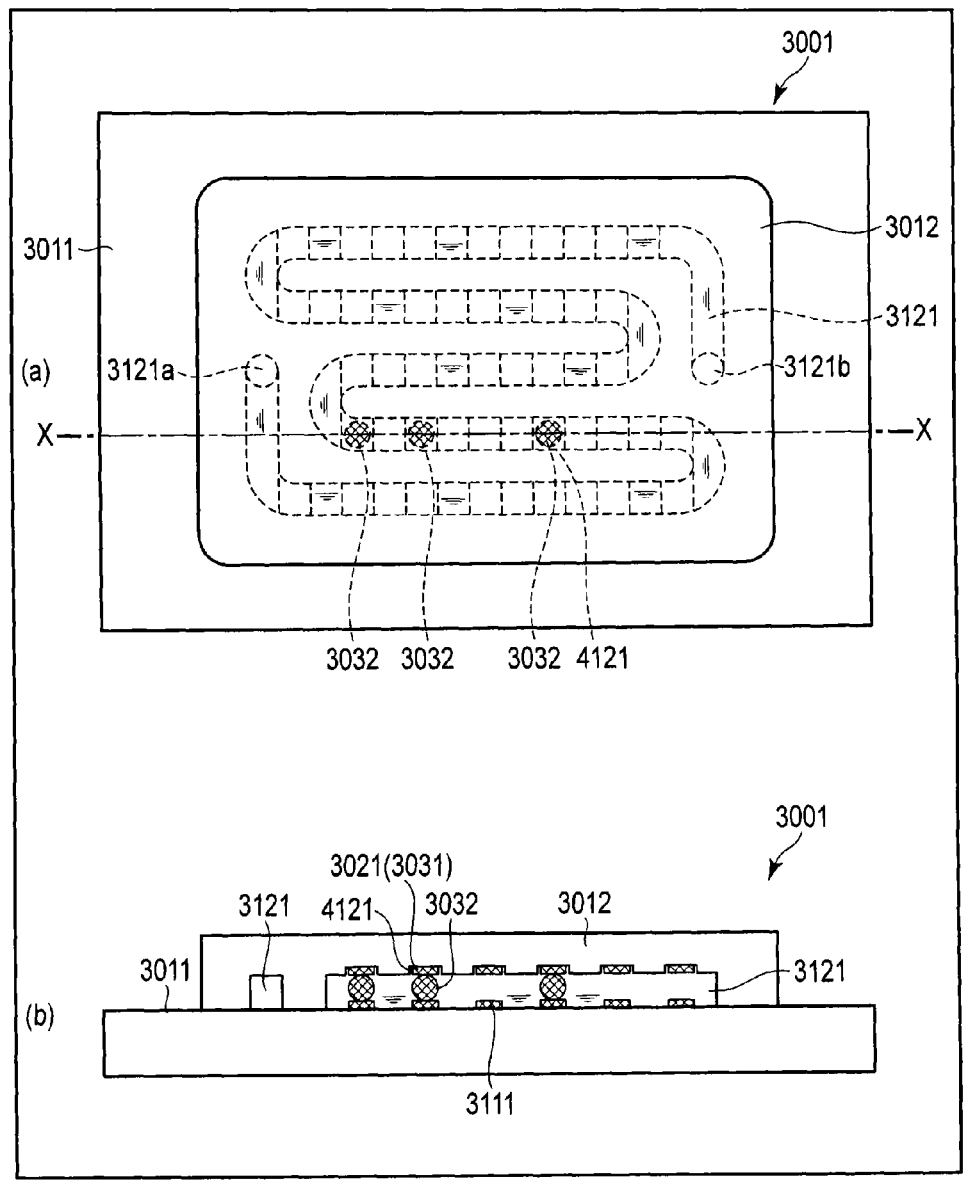
FIG. 20 is a schematic view of a nucleic acid detecting device.

Next, an example will be described in which a reaction solution is introduced into the nucleic acid detecting device 3001 illustrated in FIG. 19 and an amplification reaction is carried out. FIG. 20(a) is a plan view of an example of the nucleic acid detecting device 3001. FIG. 20(b) is a sectional view of the nucleic acid detecting device 3001 taken along line X-X in FIG. 20(a). FIG. 20 illustrates a state in which a reaction solution is added to the nucleic acid detecting device 3001. The nucleic acid detecting device 3001 illustrated in FIG. 20 is the same as that in FIG. 19 except that a reaction solution is added to the groove portion 3121. In the nucleic acid detecting device 3001, if a template nucleic acid exists, introduction of a reaction solution causes the template nucleic acid to be amplified by the corresponding primer set 3031 which separates and diffuses, so that an amplification product 3032 is produced. The amplification product 3032 produced in the amplification reaction is produced locally in the chamber 4211 as illustrated in FIG. 20. The nucleic acid detecting device 3001 can obtain a hybridization signal as the amplification product 3032 reacts with the probe fixed on the probe fixing region 3111.

Example 3

Example 3-1

Figure 21:
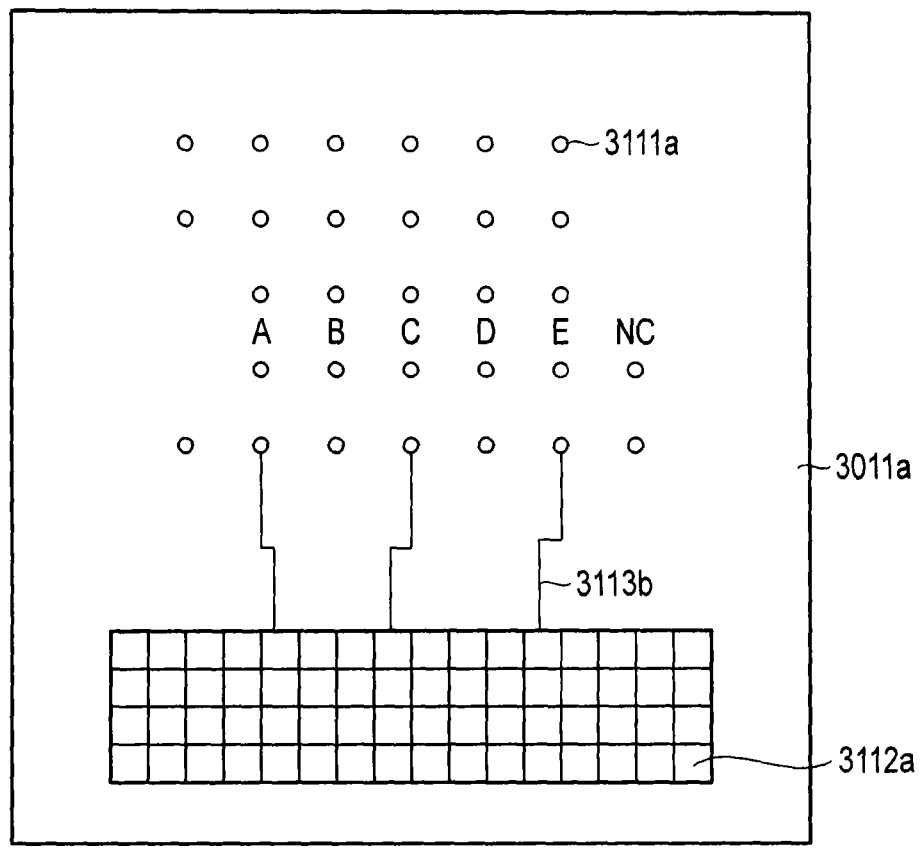
FIG. 21 is a schematic view of a support.

An example of detecting a nucleic acid using the nucleic acid detecting device 3001 according to the twelfth embodiment will be described in detail below. In this Example 3-1, packing 3012a made of silicon rubber was used as the cover 3012, and the primer set 3031 was fixed to the primer fixing region 3021 on a surface of the packing 3012a. FIG. 21 is a schematic view illustrating an example of the support 3011 according to Example 3-1. In Example 3-1, an array-type chip (base plate) for electrochemical detection 3011a with the probe fixing region 3111 as an electrode 3111a was employed as the support, and was used as a sensor that detects a current response generated depending on the existence of hybridization. A pad portion 3112a is configured to transmit a hybridization signal of the electrode 3111a to a nucleic acid detector (not shown) through a wire 3113b. That is, the nucleic acid detector detects a nucleic acid based on the current value from each electrode 3111a.

(1) Provision of Nucleic Acid Detecting Device
1-1. Preparation of Array-Type Chip for Electrochemical Detection For the array-type chip for electrochemical detection 3011a, a thin film of titanium and gold was formed on a Pyrex (registered trademark) glass surface by sputtering. Thereafter, an electrode pattern of titanium and gold was formed on the glass surface by an etching treatment. Further an insulating film was applied thereon, and the electrode 3111a was exposed by an etching treatment.

Next, six types of nucleic probes (sequence A to E and negative control, NC) shown in Table 16 were fixed, respectively, to electrodes 3111a (A to E and NC, negative control, in FIG. 21) on the chip material. A solution including each nucleic acid was added dropwise to each electrode 3111a, and thereafter excessive nucleic probes were washed and removed to perform fixing.

TABLE 16

Nucleotide sequence of DNA probe

| Sequence name | Sequence | Number of bases | SEQ ID NO. |
|---|---|---|---|
| A | ACAAGGTCATAATAATGGTATTTGTTGGGGCAATC | 35 | 161 |
| B | TGGTCCTGGCACTGATAATAGGGAATGTATATCAATGGATTATAAACAAACACAA | 55 | 162 |
| C | TTGTAACCAGTACGGTTTATTAAATAATTGGGATTCTGAGG | 41 | 163 |
| D | AGTACTGCTACAGAACAGTTAAGTAAATATGATGCACGAAAAATTAATCAGTACC | 55 | 164 |
| E | GCCCCGACCGATTTCAACACCTACACAGGCCCAGACCAAGCGT | 43 | 165 |
| NC | AGCTACAGCTGTTATTACGCAGGATGTTAGGGATAATGTGTCAGTTGATTATAAG | 55 | 166 |

Figure 22:
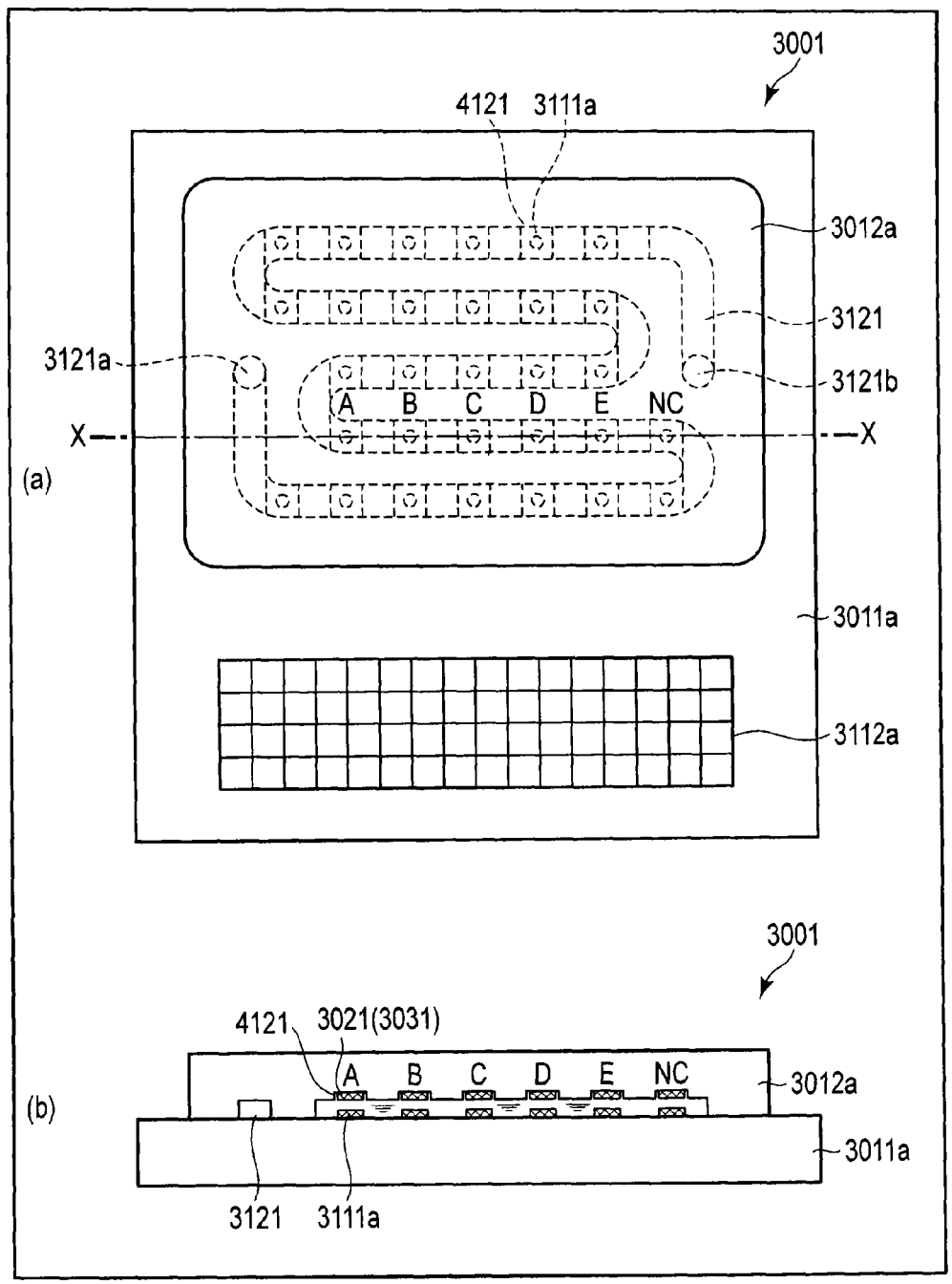
FIG. 22 is a schematic view of a nucleic acid detecting device.

1-2. Preparation of Primer-Fixed Packing 3012a and Assembly of Nucleic Acid Detecting Device First, primer DNAs to be used as the primer set 3031 were provided. The primer DNA to be used is the primer set 3031 for amplification by loop-mediated isothermal amplification (LAMP). Nucleotide sequences of primer DNAs used are shown in Table 17. A solution including a primer DNA was spotted on the bottom surface of the packing 3012a facing a region on which a probe DNA corresponding to each primer DNA was fixed, and drying was performed at 40° C. for two minutes. In this way, the primer-fixed packing 3012a was obtained. This packing 3012a was attached to the array-type chip 3011a to obtain the nucleic acid detecting device 3001 illustrated in FIG. 22. FIG. 22(a) is a plan view of an example of the nucleic acid detecting device 3001 according to Example 3-1. FIG. 22(b) is a sectional view of the nucleic acid detecting device 3001 taken along line X-X in FIG. 22(a).

TABLE 17

Nucleotide sequence of DNA primer

| Set name | Sequence name | Sequence | Number of bases | SEQ ID NO. |
|---|---|---|---|---|
| A | A-FIP | GCACTGCTTTGAATAGAGGCACTGTTCCCGATGACCTG | 38 | 167 |
|   | A-BIP | CCATATTGGCTACAACGTGCTACCTGATTGCCCCAACA | 38 | 168 |
|   | A-F3 | AGGGCTGGTACATTAGGAGA | 20 | 169 |
|   | A-B3 | GTCATATTAGTACTGCGAGTGG | 22 | 170 |
|   | A-LPF | CAGTAGTTCCTGAACCTTTAATGTACA | 27 | 171 |
| B | B-FIP | GGATGACCACTAATACCTACACCCTGTGTTGGTTTAGAGGTAGGTC | 46 | 172 |
|   | B-BIP | CACTGAAAACTCTAATAGATATGCCGGTGCAACCAAGTAAACACAGTTGTG | 51 | 173 |
|   | B-F3 | AACTCAACGCTTAGTTTGGGC | 21 | 174 |
|   | B-B3 | CCTTTACCCCAATGCTCTCC | 20 | 175 |
|   | B-LPF | TAATGGCTGCCCGCGA | 16 | 176 |
| C | C-FIP | ATTATTGTGGCCCTGCGCACGTTCTATGGTAACCTCAGAATCCC | 44 | 177 |
|   | C-BIP | ACCACTCGTAGCACTAACATGACTCGCCATGACGAAGGTATTCCT | 45 | 178 |
|   | C-F3 | GCCACTGTACAAAGCAGTGC | 20 | 179 |
|   | C-B3 | TGAATGTATGTCATAACATCAGCTG | 25 | 180 |
|   | C-LPB | GCTGAGGTTAAAAAGGAAAGCACA | 24 | 181 |
| D | D-FIP | AATTGATTACCCCAGCAAATGCCGTCTATGATTACGTCTGAGGCAC | 46 | 182 |
|   | D-BIP | ATACTACTAGAAGTACTAACATGACCCTCCACATGTCTAAGGTACTG | 47 | 183 |
|   | D-F3 | GTATATGTTGCTACGCCTAGTG | 22 | 184 |
|   | D-B3 | GCCATAACCTCTGCAGACAAAG | 22 | 185 |
|   | D-LPF | GCACGTTGCAACCAATAAGG | 20 | 186 |
| E | E-FIP | CACTGAGTCCTACCCCTAAAGGTTGTCTCAACGCTTGGTCTGG | 43 | 187 |
|   | E-BIP | GATGACACTGAAAACTCTCATGTAGCGCTGAGTTTGTTTATAATCCACAG | 50 | 188 |
|   | E-F3 | CCAGATAACACAGTATATGATCCTAAC | 27 | 189 |
|   | E-B3 | GCAGGTACACAGCCAATAATACAC | 24 | 190 |
|   | E-LPB | GCTGTTGATACCAAAGATACACGTG | 25 | 191 |

(2) Detection of Nucleic Acid 2-1. Provision of Template Solution

As in Table 18, a template solution obtained by mixing three types of templates: genes A, B and D and a reagent for LAMP amplification were provided.

TABLE 18

| Composition | | |
|---|---|---|
| Reagent | Template name | Total 50 |
| Reaction Mixture |  | 14.00 |
| DNA Polymerase |  | 8.00 |

TABLE 18-continued

| Composition | | |
|---|---|---|
| Reagent | Template name | Total 50 |
| Template DNA | A | 2.00 |
|  | B | 2.00 |
|  | D | 2.00 |
| DW |  | 22.00 |
| Total |  | 50.00 |

For the template solution, a solution, which included Bst DNA polymerase and a reaction mix and to which distilled water (i.e. DW) was added so that the total amount was 50 μL, was used. As shown in FIG. 19, the template solution includes a template A which is detected as an amplification reaction by the LAMP method is caused by a primer DNA (set A) and hybridization with a probe DNA (A) occurs, a template B which is detected as an amplification reaction by the LAMP method is caused by a primer DNA (set B) and hybridization with a probe DNA (B) occurs, and a template D which is detected as an amplification reaction by the LAMP method is caused by a primer DNA (set D) and hybridization with a probe DNA (D) occurs.

TABLE 19

DNA template sequence of templates A, B and D

| Sequence name | Sequence (part of sequence excerpted) | Number of bases | SEQ ID NO. |
|---|---|---|---|
| A | AGGGCTGGTACATTAGGAGAGGCTGTTCCCGATGACCTGTACATTAAAGGTTCAGGAACTAC TGCCTCTATTCAAAGCAGTGCTTTTTTTCCCACTCCTAGTGGATCAATGGTTACTTCCGAAT CTCAGTTATTTAATAAGCCATATTGGCTACAACGTGCACAAGGTCATAATAATGGTATTTGT TGGGGCAATCAGGTATTTGTTACTGTGGTAGATACCACTCGCAGTACTAATATGAC | 2.7 kbp | 192 |
| B | AACTCAACGCTTAGTTTGGGCCTGTGTTGGTTTAGAGGTAGGTCGCGGGCAGCCATTAGGTG TAGGTATTAGTGGTCATCCATTATTAAATAAATTTGATGACACTGAAAACTCTAATAGATAT GCCGGTGGTCCTGGCACTGATAATAGGGAATGTATATCAATGGATTATAAACAAACACAACT GTGTTTACTTGGTTGCAAACCACCTATTGGAGAGCATTGGGGTAAAGG | 2.7 kbp | 193 |
| D | GTATATGTTGCTACGCCTAGTGGGTCTATGATTACGTCTGAGGCACAGTTATTTAATAAACC TTATTGGTTGCAACGTGCCCAAGGCCATAATAATGGCATTTGCTGGGGTAATCAATTATTTG TTACTGTAGTAGATACTACTAGAAGTACTAACATGACTATTAGTACTGCTACAGAACAGTTA AGTAAATATGATGCACGAAAAATTAATCAGTACCTTAGACATGTGGAGGAATATGAATTACA ATTTGTTTTTCAATTATGCAAAATTACTTTGTCTGCAGAGGTTATGGC | 2.7 kbp | 194 |

2-2. Addition of Template Solution

The template solution provided in 2-1 was added to the nucleic acid detection device 3001 in an amount of 50 μL.

2-3. Reaction of Nucleic Acid

Various kinds of reactions were carried out under conditions shown below while the channel region of the nucleic acid detecting device 3001 was heated or cooled. FIG. 23(a) is a plan view of an example of the nucleic acid detecting device 3001 according to Example 3-1. FIG. 23(b) is a sectional view of the nucleic acid detecting device 3001 taken along line X-X in FIG. 23(a). As illustrated in FIG. 23, when a template including a target sequence to be amplified is included in a reaction solution for a specific primer, a LAMP reaction locally proceeds at a site where the primer is fixed, and the resulting amplification product 3032 is hybridized with a probe DNA existing in the vicinity thereof.

Nucleic Acid amplification reaction: 64° C., 60 minutes
Hybridization reaction: 50° C., 10 minutes
Washing reaction: 30° C., 5 minutes
Reaction for detection of currents with Reagent (Hoechst 33258): 25° C., three minutes 2-4. Detection of Nucleic Acid An electrical potential was swept through each probe nucleic acid fixing working electrode to measure an oxidation current of a Hoechst 33258 specifically bound with a double strand formed by the probe DNA and the LAMP product. The series of reactions described above were carried out in the DNA automatic examination apparatus described in SICE Journal of Control, Measurement and System Integration, Vol. 1, No. 3, pp. 266-270, 2008.

Results

The obtained results are illustrated in FIG. 24. FIG. 24 is a graph illustrating a result of a nucleic acid amplification reaction according to Example 3-1. In electrodes A, B and D on which probes A, B and D corresponding to genes A, B and D, to which a template was added, were fixed, a current value greater than that of NC was obtained. On the other hand, the current values of electrodes C and E corresponding to genes C and E to which a template was not added were comparable to the current value of NC. From this fact, it has become evident that a template in the template solution could be reliably detected.

Thirteenth Embodiment

The thirteenth embodiment will be described in detail below with reference to the drawings. Configurations identical to those described in the twelfth embodiment are given the same symbols, and descriptions thereof are omitted. An example of a nucleic acid detecting device 3001 according to the thirteenth embodiment will be described with reference to FIG. 25. FIG. 25A is a plan view of an example of the nucleic acid detecting device 3001. FIG. 25(b) is a sectional view of the nucleic acid detecting device 3001 taken along line X-X in FIG. 25(a). The nucleic acid detecting device 3001 is used for subjecting a plurality of types of target nucleic acids to amplification reaction independently in parallel using a plurality of types of primer sets 3031 in one reaction field. The thirteenth embodiment is different from the twelfth embodiment in the shape of a groove portion 3121.

The groove portion 3121 is formed with substantially the same depth in the stacking direction from an entrance 3121a to an exit 3121b. In the groove portion 3121, a plurality of chambers 4211 are arranged at predetermined intervals. The chamber 4211 is formed so as to have a width greater than that of regions other than the chamber 4211 in the groove portion 3121. Conversely, the width of regions other than the chamber 4211 in the groove portion 3121 is narrower than the width of the chamber 4211. The chamber 4211 should have a width greater than that of regions other than the chamber 4211 in the groove portion 3121, and may protrude in a circular-arc form or a rectangular form along a direction orthogonal to the stacking direction. Therefore, the cross section of the chamber 4211 is larger than the cross section of regions other than the chamber 4211 in the groove portion 3121. The cross section of the chamber 4211 and the cross section of regions other than the chamber 4211 in the groove portion 3121 are each a cross section based on a surface orthogonal to a surface provided with the groove portion 3121 in a cover 3012. The cross section of regions other than the chamber 4211 in the groove portion 3121 is preferably, for example, 90% or less of the maximum value of the cross section of the chamber 4211, but is not particularly limited. The chamber 4211 corresponds to a primer fixing region 3021. The primer fixing region 3021 is formed in the vicinity of an upper surface area in the stacking direction in the groove portion 3121. A plurality of primer fixing regions 3021 are mutually independently arranged in the groove portion 3121.

Since the chamber 4211 is formed with a width greater than that of regions other than the chamber 4211 in the groove portion 3121 as described above, a solution including the primer set 3031, which is added dropwise to the primer fixing region 3021, does not easily move to a region other than the chamber 4211.

Therefore, adjacent primer fixing regions 3021 can hold different primer sets 3031 independently.

Next, addition of a reaction solution to a nucleic acid detecting device 3001 with a plurality of primer sets 3031 fixed on different primer fixing regions 3021, respectively, will be described. FIG. 26(a) is a plan view of an example of the nucleic acid detecting device 3001. FIG. 26(b) is a sectional view of the nucleic acid detecting device 3001 taken along line X-X in FIG. 26(a). FIG. 26 illustrates a state in which a reaction solution is added to the nucleic acid detecting device 3001. The nucleic acid detecting device 3001 illustrated in FIG. 26 is the same as that in FIG. 25 except that a reaction solution is added to the groove portion 3121. The reaction solution may have components similar to those in the twelfth embodiment.

As illustrated in FIG. 26, the primer set 3031 fixed on the primer fixing region 3021 starts to release and diffuse after the reaction solution is added through the entrance 3121a. A region where the primer separates and diffuses is schematically illustrated in FIG. 26 as a primer separation/diffusion region 3022. In the nucleic acid detecting device 3001, the width (channel cross section) of the groove portion 3121 in regions other than the chamber 4211 is narrower (smaller) than the width (channel cross section) of the chamber 4211. Thus, the nucleic acid detecting device 3001 can inhibit the primer and the produced amplification product in an amplification region from diffusing to other amplification regions during amplification reaction. Therefore, the nucleic acid detecting device 3001 according to the thirteenth embodiment can achieve amplification for a plurality of template sequences using a plurality of types of primer sets 3031 independently (locally) and in parallel with high efficiency.

FIGS. 25 and 26 illustrates an example in which the primer set 3031 is fixed on the wall surface of the channel in the vicinity of the upper surface area of the chamber 4211, but this is not exhaustive. FIG. 27 is a plan view of an example of the nucleic acid detecting device 3001 which shows another site at which the primer set 3031 is fixed in the chamber 4211 (primer fixing region 3021). The primer set 3031 may be fixed on the wall surface of the channel of the chamber 4211 which is orthogonal to the stacking direction. That is, in the chamber 4211, the primer set 3031 is provided at an area protruding in a direction orthogonal to the stacking direction with respect to regions other than the chamber 4211 in the groove portion 3121.

When the primer set 3031 is fixed to the chamber 4211 as illustrated in FIG. 27, the nucleic acid detecting device 3001 can considerably reduce a flow rate in the vicinity of an area where the primer set 3031 is fixed (area protruding in a direction orthogonal to the stacking direction with respect to regions other than the chamber 4211 in the groove portion 3121) in the chamber 4211 at the time when the reaction solution is introduced. Accordingly, the nucleic acid detecting device 3001 can prevent the primer set 3031 from flowing out to adjacent other primer fixing regions 3021. Therefore, the nucleic acid detecting device 3001 according to the thirteenth embodiment can make primer sets 3031 of adjacent primer fixing regions 3021 mutually independent.

FIGS. 25, 26 and 27 illustrates an example in which a part of the groove portion 3121 connecting the chambers 4211 is formed in a straight line shape to establish connection with the shortest distance, but this is not exhaustive. FIG. 28 is a plan view of an example of the nucleic acid detecting device 3001 which illustrates another shape of the groove portion 3121 connecting the chambers 4211. FIG. 28 illustrates an example in which a part of the groove portion 3121 connecting the chambers 4211 is formed in such a shape that the distance of the channel is longer as compared to the straight line shape (for example, a curved shape). Therefore, the groove portion 3121 illustrated in FIG. 28 can enhance independence between the chambers 4211 as compared to the configuration of the groove portion 3121 connecting the chambers 4211 in a straight line shape as illustrated in FIGS. 25, 26 and 27, so that efficient nucleic acid amplification can be performed. Here, the configuration of the groove portion 3121 connecting the chambers 4211 with regard to the thirteenth embodiment is described, but in the twelfth embodiment, the above-described effect can also be obtained by applying the configuration illustrated in FIG. 28.

A specific method for detecting an amplification product that is locally obtained is not limited, and a method of detecting a hybridization signal, which is publicly known itself, for example a method of detecting and/or measuring fluorescent intensity using a fluorescent label, or a method of detecting and/or measuring a current response using an intercalator, may be used.

Next, detection of a hybridization signal by the nucleic acid detecting device 3001 will be described. FIG. 29(a) is a plan view of an example of the nucleic acid detecting device 3001. FIG. 29(b) is a sectional view of the nucleic acid detecting device 3001 taken along line X-X in FIG. 29(a). The nucleic acid detecting device 3001 illustrated in FIG. 29 is the same as that in FIG. 25 except that the support 3011 includes the probe fixing region 3111. For example, the probe fixing region 3111 is arranged in the support 3011 at a position facing the chamber 4211 (primer fixing region 3021), although its arrangement is not particularly limited. The probe fixing region 3111 is a region where an electrode to detect a hybridization signal is provided.

A plurality of probe nucleic acids including a complementary sequence of a desired sequence to be detected are fixed on the probe fixing region 3111. The nucleic acid detecting device 3001 can obtain a hybridization signal in the probe fixing region 3111 subsequent to carrying out an amplification reaction in the primer fixing region 3021.

When the support 3011 is a current detection type sensor using an intercalator in particular, amplification is hindered by an eluted substance from a sensor protective film due to heating during amplification reaction. However, the nucleic acid detecting device 3001 according to the thirteenth embodiment is configured such that the groove portion 3121 is thinned (the width thereof is narrowed) except the amplification/detection region (chamber 4211), and therefore the liquid contact area with a sensor provided on the probe fixing region 3111 can be reduced, so that elution of an amplification hindering substance can be effectively suppressed.

Example 3-2

For example, detection of nucleic acid in the nucleic acid detecting device 3001 according to the thirteenth embodiment described above is performed as follows. A reaction solution including a nucleic acid to be examined is introduced into a groove portion 31211 formed in the nucleic acid detecting device 3001 using a tool such as a pipette. If a template nucleic acid exists, introduction of a reaction solution causes the template nucleic acid to be amplified by the corresponding primer set 3031 which separates and diffuses, so that an amplification product is produced.

FIG. 30(a) is a plan view of an example of the nucleic acid detecting device 3001 according to Example 3-2. FIG. 30(b) is a sectional view of the nucleic acid detecting device 3001 taken along line X-X in FIG. 30(a). FIG. 30(c) is a graph illustrating a result of a nucleic acid amplification reaction according to Example 3-2. FIG. 30(c) illustrates a result obtained when an amplification reaction occurs in regions A, B and D (chambers 4211) of the nucleic acid detecting device 3001 illustrated in FIGS. 30(a) and 30(b), and an amplification product includes an object sequence complementary to a sequence of the corresponding probe nucleic acid. As illustrated in FIG. 30C, current values obtained for regions A, B and D are greater than the current value of NC. On the other hand, detection signals obtained for regions C and E are comparable to the detection signal of NC. From this fact, it has become evident that a template in the template solution could be reliably detected. Detection signals were obtained particularly for adjacent regions A and B. Therefore, the nucleic acid detecting device 3001 according to the thirteenth embodiment could perform both amplification reaction and detection of nucleic acids independently without causing interference between adjacent regions. Thus, according to Example 3-2, it has been shown that a plurality of types of target nucleic acids can be subjected to amplification reaction in parallel and independently and detected using the nucleic acid detecting device 3001 according to the thirteenth embodiment.

According to the embodiment described above, at least one of the following problems can be solved: difficulty of retention of a primer set in the amplification region of the nucleic acid detecting device; outflow of a primer set; hindrance of amplification reaction due to movement of a primer set and an amplification product; and hindrance of amplification reaction by an eluted substance from a protective film. Therefore, a nucleic acid detecting device which subjecting a plurality of types of target nucleic acids to amplification reaction in parallel and independently using a plurality of types of primer sets, and a nucleic acid detector using the nucleic acid detecting device can achieve efficient amplification reaction and detection in parallel and independently.

The shape of the chamber 4211 according to the twelfth embodiment and the shape of the chamber 4211 according to the thirteenth embodiment can be combined.

5. USE OF PROTECTIVE FILM

As a different embodiment, a multi-nucleic-acid amplification reaction tool may be provided as a nucleic acid detecting device configured to perform both amplification and detection of nucleic acid in the same device.

The multi-nucleic-acid amplification reaction tool may be provided as a nucleic acid detecting device which reduces hindrance of nucleic acid amplification reaction.

One of devices to detect a nucleic acid may be a DNA chip. The DNA chip is a device having a plurality of nucleic acid probes fixed on a base plate, wherein a large number of nucleic acid sequences can be detected.

The fixing region for nucleic acid probes is in a variety of forms, and there is a method in which a nucleic acid probe is fixed on a sensor such as an electrode, and a detection signal from the sensor is drawn through a wire, and detected from the outside.

In this form, regions other than contact areas with the sensor portion and the outside are covered with a film called a protective film (passivation film). This is made by applying a semiconductor technique, and the protective film protects a resulting detection signal against noises, contamination and the like from a wire portion and the like.

On the other hand, devices called μ-TAS capable of sequentially carrying out a plurality of reactions involving a plurality of reagents in one device are extensively researched and developed. Such a device includes a reagent retention region, a reaction region and a sensor region and having a channel that connects these regions. Detectors for detecting nucleic acids are also developed by applying the above-mentioned devices. When nucleic acids are detected, it is necessary to carry out a plurality of reactions using a plurality of reagents. A plurality of reactions include a nucleic acid extraction reaction, a nucleic acid purification reaction, a nucleic acid hybridization reaction, and detection of the existence of hybridization. Among these methods, examples of the nucleic acid amplification reaction include the PCR method, the LAMP method and the ICAN method, but they not only are significantly influenced by an amplification temperature or a reagent composition, but also have the disadvantage that amplification is easily hindered if ingress of impurities occurs, so that the material and cleanliness of the reaction container are very important.

There are a variety of configurations for the nucleic acid detecting device such as the DNA chip, but when a plurality of reactions are carried out in separate reaction containers, losses of reagents and examination time are significant. Accordingly, nucleic acid detecting devices capable of carrying out a nucleic acid amplification reaction and a nucleic hybridization reaction in the same reaction container are developed.

However, in the nucleic acid amplification reaction, amplification is hindered due to ingress of impurities. It has been evident that components eluted from the protective film of the nucleic acid detecting device strongly hinders nucleic acid amplification, leading to a reduction in sensitivity. Therefore, the nucleic acid detecting device is required to reduce the amount of impurities eluted from the protective film, so that the sensitivity is improved.

According to the embodiment, when the multi-nucleic-acid amplification reaction tool is provided as a nucleic acid detecting device, the nucleic acid detecting device includes a base plate, a sensor portion, a wire and a protection portion. The sensor portion is formed on the base plate and configured to detect a nucleic acid. The wire is formed on the base plate and connected to the sensor. The protective film is formed on the base plate. The nucleic acid detecting device detects a nucleic acid amplification product with the sensor portion after a nucleic acid amplification reaction is carried out in a chamber for the sensor portion and a nucleic acid sample to react with each other. The protective film has one or more opening for exposing a lower layer portion including a part of the base plate at a liquid contact region for the nucleic acid sample on the base plate.

Fourteenth Embodiment

FIG. 31 is a view illustrating as an example a process for preparation of a nucleic acid detecting device (DNA chip) 5100 according to the fourteenth embodiment. The nucleic acid detecting device 5100 is formed by stacking components in the order of from (a) to (e) in FIG. 31. FIG. 32 is a sectional view in the stacking direction illustrating as an example an outlined configuration of the nucleic acid detecting device (DNA chip) 5100 according to the fourteenth embodiment. FIG. 33 is a view illustrating as an example an outlined configuration of the nucleic acid detecting device (DNA chip) 5100 according to the fourteenth embodiment.

The nucleic acid detecting device 5100 includes a base plate 5010, a sensor portion 5011, a pad 5012, a wire 5013 and a protective film 5014. The base plate 5010 is a thin plate-shaped member as illustrated in FIG. 32(a). The base plate 5010 is formed of glass, silicon, polycarbonate, polypropylene, polyethylene, polyimide, ABS, a metal or the like, but the material of the base plate is not particularly limited.

The sensor portion 5011 is formed on the surface of the base plate 5010 as illustrated in FIG. 32(b). The sensor portion 5011 is an electrode formed of a conductive member. A plurality of sensor portions 5011 are provided at one end side of the base plate 5010. Various kinds of nucleic acid probes for detecting a nucleic acid as a target are each fixed on the sensor portion 5011 to detect a nucleic acid as a target. One sensor portion 5011 includes one or more sensor.

The pad portion 5012 is formed on the surface of the base plate 5010 as illustrated in FIG. 32(c). The pad portion 5012 is formed of a conductive member. A plurality of pad portions 5012 are provided at the other end side of the base plate 5010. The pad portion 5012 is configured to transmit a detection signal of the sensor portion 5011 to a detector (not illustrated) through a later-described wire 5013.

The wire 5013 is formed on the surface of the base plate 5010 as illustrated in FIG. 32(d). The wire 5013 is formed of a conductive member. The wire 5013 connects the sensor portion 5011 and the pad portion 5012. The wire 5013 may be three-dimensional wire resulting from a multilayer structure using a through-hole. The wire 5013 is configured to take out a detection signal from each sensor portion 5011 and send the detection signal to the pad portion 5012. The protective film 5014 is formed on the surface of the base plate 5010 as illustrated in FIG. 32(e).

The protective film 5014 is a protective film formed of an organic material. The protective film 5014 is of, for example, a material having high hydrophobicity. Generally, the protective films are classified into organic protective films and inorganic protective films. The inorganic protective film is known to have reduced elution of impurities, but is expensive. Therefore, the protective film 5014 used in the fourteenth embodiment is an organic protective film. The shape of the protective film 5014 on the surface of the base plate 5010 will be described later. The protective film 5014 is used for preventing ingress of noises to a detection signal from the wire 5013 and the like, and leakage of the signal to other wires, and protecting the nucleic acid detecting device 5100 against contamination and the like. By the above-described process, the nucleic acid detecting device 5100 is formed by stacking the components as illustrated in FIG. 32. The nucleic acid detecting device 5100 according to the fourteenth embodiment is used for detecting a nucleic acid amplification product with the sensor portion 5011 after a nucleic acid amplification reaction is carried out in a later-described channel-type reaction portion (chamber) 5201 for the sensor portion 5011 and a nucleic acid sample to react with each other. In the fourteenth embodiment, the outermost surface of the nucleic acid detecting device 5100 on the protective film 5014 side in the stacking direction is defined as the surface of the nucleic acid detecting device 5100.

The surface of the nucleic acid detecting device 5100 configured as described above can be classified principally into a sensor region 5020, a wire region 5021, a pad region 5022 and a reaction region 5023 as illustrated in FIG. 31.

The sensor region 5020 is a region provided with the sensor portion 5011. The wire region 5021 is a region provided with the wire 5013. The pad region 5022 is a region provided with the pad portion 5012. The reaction region 5023 is a region where a nucleic acid amplification reaction, a nucleic acid hybridization reaction and the like are carried out.

The reaction region 5023 will now be described. When the nucleic acid detecting device 5100 is used for a nucleic acid amplification reaction, a nucleic acid hybridization reaction and the like as illustrated in FIG. 32(b), a later-described reaction portion defining member 5200 is arranged on the protective film 5014 so as to face the protective film. The sensor portion 5011 and the vicinity of the sensor portion 5011 face a later-described channel-type reaction portion 5201 provided on the reaction portion defining member 5200. In the fourteenth embodiment, the reaction region 5023 refers to a region facing the channel-type reaction portion 5201 on the surface of the nucleic acid detecting device 5100. Therefore, the reaction region 5023 encompasses the sensor region 5020. The reaction region 5023 includes the wire 5013 in the vicinity of the sensor portion 5011. The reaction region 5023 is also a liquid contact region which a reaction solution (nucleic acid sample) for carrying out a nucleic acid amplification reaction contacts on the base plate 5010. The reaction region 5023 at the surface of the nucleic acid detecting device 5100 is defined by the shape of the channel-type reaction portion 5201.

Next, the shape of the protective film 5014 at the surface of the nucleic acid detecting device 5100 will be described. The protective film 5014 covers the wire 5013 so that the wire 5013 is not exposed in the wire region 5021 as illustrated in FIG. 32. The protective film 5014 is provided on the base plate 5010 such that at least a part of each pad portion 5012 is exposed so that each pad portion 5012 is in contact with a detector (not illustrated) in the pad region 5022 as illustrated in FIG. 32. That is, the protective film 5014 covers the surface of the nucleic acid detecting device 5100 except for at least a part of each pad portion 5012 in regions other than the reaction region 5023.

Next, the shape of the protective film 5014 in the reaction region 5023 will be described. FIG. 34 is an enlarged view of the vicinity of the reaction region 5023 at the surface of the nucleic acid detecting device 5100 according to the fourteenth embodiment. The protective film 5014 covers the wire 5013 so that the wire 5013 is not exposed in the reaction region 5023. On the other hand, the protective film 5014 is not provided in the sensor portion 5011 in the reaction region 5023. The protective film 5014 has one or more opening to expose the base plate 5010 or the sensor portion 5011 at least in areas other than the wire 5013 in the reaction region 5023. The protective film 5014 is provided only in minimum necessary areas in the reaction region 5023. The protective film 5014 may be provided on the base plate 5010, or provided in the vicinity of a boundary area between the wire 5013 and the base plate 5010.

As described above, the protective film 5014 according to the fourteenth embodiment has one or more opening to expose a lower layer portion including a part of the base plate 5010 (the base plate 5010 or the sensor portion 5011) in the reaction region 5023. The protective film 5014 may be configured to cover the surface of the nucleic acid detecting device 5100 with a film having one or more opening. The protective film 5014 may be configured to cover the surface of the nucleic acid detecting device 5100 with a plurality of films, the protective film 5014 having one or more opening formed by combination of the films. The configuration of the protective film 5014 in the reaction region 5023 as described above can considerably reduce influences of amplification hindrance caused by impurities eluted from the protective film 5014 when an amplification reaction is carried out in the reaction region 5023. Usually, detection of nucleic acid involves a nucleic acid extraction reaction, a nucleic acid purification reaction, a nucleic acid amplification reaction, a nucleic acid hybridization reaction, detection of the existence of hybridization, and the like, but the nucleic acid detecting device 5100 according to the fourteenth embodiment can carry out not only a nucleic acid hybridization reaction but also a nucleic acid amplification reaction in the same reaction region 5023. The reason why the protective film 5014 covers the wire 5013 even in the reaction region 5023 is that noises enter from the wire 5013 if the wire 5013 is not covered with the protective film 5014 as described above.

FIG. 35 is a view illustrating as an example an outlined configuration of a nucleic acid detecting device built-in cassette (liquid delivery cassette) 1 capable of performing both nucleic acid amplification reaction and detection of nucleic acid in the same reaction container using the nucleic acid detecting device 5100 according to the fourteenth embodiment. In FIG. 35, illustration of the wire 5013 and the protective film 5014 formed on the base plate 5010 are omitted for simplification of the figure. FIG. 36 is a view of the nucleic acid detecting device 5100 with a reaction portion defining member (reaction container) 5200 arranged opposite thereto when viewed from the reaction portion defining member 5200 side. FIG. 36 illustrates an example in which each sensor portion 5011 includes two sensors.

The nucleic acid detecting device built-in cassette 5001 includes the above-described nucleic acid detecting device 5100 and reaction portion defining member 5200, and a first cassette 5300 and a second cassette 5400 as illustrated in FIG. 35.

The reaction portion defining member 5200 includes the channel-type reaction portion 5201 as illustrated in FIG. 36. The channel-type reaction portion 5201 is a groove (channel) provided on a surface that is in contact with the surface of the nucleic acid detecting device 5100. In the channel-type reaction portion 5201, various kinds of solutions for performing both nucleic acid amplification reaction and detection of nucleic acid in the same reaction container are injected through a sample injection port 5201a and discharged through a sample exit 5201b. The channel-type reaction portion 5201 is provided in the shape of a meandered channel, but this is not exhaustive. The channel-type reaction portion 5201 may be provided in a straight line shape, or provided in a circular shape, or provided in a rectangular shape. The reaction portion defining member 5200 may be of a flat plate type or of a tube type.

A nucleic acid amplification primer may be injected into the channel-type reaction portion 5201 after being a nucleic acid sample, or may be held beforehand at any site of the channel-type reaction portion 5201. In the latter case, a plurality of primer sets provided for each amplification object may be held at different locations of the channel-type reaction portion 5201, respectively, or may be all held at one location. The method for holding a plurality of primer sets in the channel-type reaction portion 5201 is not limited. For example, a plurality of primer sets may be dried and held using a method of heating or vacuum-drying, or may be held in a liquid state. A plurality of primer sets may be frozen and held. A plurality of primer sets may be held on holding carrier such as a membrane.

The channel-type reaction portion 5201 is defined as it is formed in the reaction portion defining member 5020, but the form thereof is not particularly limited. The channel-type reaction portion 5201 may be formed by etching the base plate 5010, or the like.

The first cassette 5300 and the second cassette 5400 are outer frames that hold the nucleic acid detecting device 5100 and the reaction portion defining member 5200 therebetween. The first cassette 5300 and the second cassette 5400 are formed of, for example, a hard material. The nucleic acid detecting device built-in cassette 5001 has a cassette structure in which the nucleic acid detecting device 5100 and the reaction portion defining member 5200 that are separate components are sandwiched by the first cassette 5300 and the second cassette 5400, but the structure thereof is not particularly limited. The reaction portion defining member 5200 may be formed integrally with the second cassette 5400. The nucleic acid detecting device built-in cassette 5001 may be of a container type with the reaction portion defining member 5200, the first cassette 5300 and the second cassette 5400 formed integrally, into which the nucleic acid detecting device 5100 is inserted.

Next, as Comparative Example, a nucleic acid detecting device in which areas (including not only a wire but also a base plate) other than a sensor portion are covered with an organic protective film in a reaction region, unlike the fourteenth embodiment, will be described. A nucleic acid hybridization reaction is carried out in the reaction region provided with the sensor portion. Therefore, usually areas other than the sensor portion are covered with the protective film in the reaction region. However, it is known that the protective film has a slight amount of an eluted substance (impurities). Usually, impurities do not affect the nucleic acid hybridization reaction. However, the nucleic acid amplification reaction is a very delicate reaction, so that amplification is easily hindered when impurities exist. Therefore, when the nucleic acid amplification reaction and the nucleic acid hybridization reaction are carried out in the same reaction region, the problem occurs that amplification is hindered as described above by an eluted substance from the protective film existing in the reaction region.

According to the fourteenth embodiment, by reducing the area constituted by the protective film 5014 in the reaction region 5023, the amount of impurities eluted from the protective film 5014 can be significantly decreased, so that hindrance of the nucleic acid amplification reaction can be reduced. As a result, the sensitivity of the nucleic acid detecting device 5100 is improved.

Fifteenth Embodiment

The fifteenth embodiment will be described in detail below with reference to the drawings. Configurations identical to those described in the fourteenth embodiment are given the same symbols, and descriptions thereof are omitted. FIG. 37 is an enlarged view of the vicinity of a reaction region 5023 in a nucleic acid detecting device 5100 according to the fifteenth embodiment. The fifteenth embodiment is different from the first embodiment in the shape of a protective film 5014 in the reaction region 5023.

The protective film 5014 covers the wire 5013 so that the wire 5013 is not exposed in the reaction region 5023 as in the case of the fourteenth embodiment. Further, the protective film 5014 covers the outer peripheral area of a sensor portion 5011 so that the outer peripheral area of the sensor portion 5011 (boundary area between the sensor portion 5011 and a base plate 5010) is not exposed in the reaction region 5023. In other words, the protective film 5014 has an opening at which a substantially central part of the sensor portion 5011 is exposed. That is, the protective film 5014 has one or more opening to expose the base plate 5010 or the sensor portion 5011 at least in areas other than a wire 5013 and the outer peripheral area of the sensor portion 5011 in the reaction region 5023. The protective film 5014 may be provided on the base plate 5010, or provided in the vicinity of a boundary area between the wire 5013 and the base plate 5010.

As described above, the protective film 5014 according to the fifteenth embodiment has one or more opening to expose a lower layer portion including a part of the base plate 5010 (the base plate 5010 or the sensor portion 5011) in the reaction region 5023.

The reason why the protective film 5014 is provided on the outer peripheral area of the sensor portion 5011 is as follows. A detection signal from the sensor portion 5011 is proportional to an exposed area of the sensor portion 5011 (liquid contact area that is not covered with the protective film 5014). Therefore, it is desirable that the exposed area of each sensor portion 5011 be constant. By providing on the base plate 5010 the protective film 5014 provided with an opening at a part facing a substantially central part of each sensor portion 5011, the area of each sensor portion 5011 can be defined strictly constant.

According to the fifteenth embodiment, an effect comparable to that of the fourteenth embodiment is obtained. Further, according to the fifteenth embodiment, the exposed area of each sensor portion 5011 (sum of exposed areas of a plurality of sensors when each sensor portion 5011 includes a plurality of sensors) is defined constant, so that the sensitivity of the nucleic acid detecting device 5100 is further improved.

Sixteenth Embodiment

The sixteenth embodiment will be described in detail below with reference to the drawings. Configurations identical to those described in the fourteenth embodiment are given the same symbols, and descriptions thereof are omitted. FIG. 38 is an enlarged view of the vicinity of a reaction region 5023 in a nucleic acid detecting device 5100 according to the sixteenth embodiment. The sixteenth embodiment is different from the fourteenth embodiment in the shape of a protective film 5014 in the reaction region 5023.

The protective film 5014 covers the wire 5013 so that the wire 5013 is not exposed in the reaction region 5023. The protective film 5014 has a separator shape to cover a base plate 5010 at boundary regions between sensor portions 5011 in the reaction region 5023. Here, the boundary region between the sensor portions 5011 is substantially central part between sensor portions 5011 in the reaction region 5023. The protective film 5014 provided at boundary regions between the sensor portions 5011 covers the base plate 5010 so as to separate (divide) an opening (exposed base plate 5010) provided in the vicinity of the sensor portion 5011 and an opening (exposed base plate 5010) provided in the vicinity of the adjacent different sensor portion 5011 in the reaction region 5023. The shape of the protective film 5010 to cover the base plate 5010 at boundary regions between the sensor portions 5011 is not particularly limited. On the other hand, the protective film 5014 is not provided in the sensor portion 5011 in the reaction region 5023. That is, the protective film 5014 has one or more opening to expose the base plate 5010 or the sensor portion 5011 at least in areas other than a wire 5013 and the boundary region between the sensor portions 5011 in the reaction region 5023. The protective film 5014 may be provided on the base plate 5010, or provided in the vicinity of a boundary area between the wire 5013 and the base plate 5010. The protective film 5014 may be provided so as to cover the outer peripheral area of the sensor portion 5011 as in the case of the fifteenth embodiment.

As described above, the protective film 5014 according to the sixteenth embodiment has one or more opening to expose a lower layer portion including a part of the base plate 5010 (the base plate 5010 or the sensor portion 5011) in the reaction region 5023.

The reason why the protective film 5014 is provided at the boundary region between the sensor portions 5011 is as follows. Various kinds of nucleic acid probes for detecting a nucleic acid as a target are each fixed on each sensor portion 5011. A liquid including each nucleic acid probe is added dropwise onto each sensor portion 5011 during production. However, when the base plate 5010 has high hydrophilicity, a nucleic acid probe solution added dropwise to a sensor portion 5011 comes into contact with a different nucleic acid probe solution added dropwise to the adjacent sensor portion 5011, so that both the solutions are mixed, if the protective film 5014 is not provided at the boundary region between the sensor portions 5011. Generally, organic protective films have low hydrophilicity. Therefore, the protective film 5014 provided at the boundary region between the sensor portions 5011 can prevent a situation in which a nucleic acid probe solution added dropwise to a sensor portion 5011 comes into contact with a different nucleic acid probe solution added dropwise to the adjacent sensor portion 5011.

According to the sixteenth embodiment, an effect comparable to that of the fourteenth embodiment or the fifteenth embodiment is obtained. Further, according to the sixteenth embodiment, fixing of nucleic acid probes to the sensor portions 5014 during production of the nucleic acid detecting device 5100 can be made accurate and easy.

Seventeenth Embodiment

The seventeenth embodiment will be described in detail below with reference to the drawings. Configurations identical to those described in the fourteenth embodiment are given the same symbols, and descriptions thereof are omitted. FIG. 39 is an enlarged view of the vicinity of a reaction region 5023 in a nucleic acid detecting device 5100 according to the seventeenth embodiment. The seventeenth embodiment is different from the sixteenth embodiment in the shape of a protective film 5014 at boundary regions between sensor portions 5011.

The protective film 5014 covers a wire 5013 so that the wire 5013 is not exposed in the reaction region 5023. On the other hand, the protective film 5014 is not provided in the sensor portion 5011 in the reaction region 5023. The protective film 5014 has a separator shape to cover a base plate 5010 at boundary regions between sensor portions 5011 in the reaction region 5023 as in the case of the sixteenth embodiment. The protective film 5014 provided at the boundary region covers the base plate 5010 so as to separate (divide) an opening (exposed base plate 5010) provided in the vicinity of the sensor portion 5011 and an opening (exposed base plate 5010) provided in the vicinity of the adjacent different sensor portion 5011 in the reaction region 5023.

The protective film 5014 is provided so as to surround the circumference of the sensor portions 5011 in the boundary region between the sensor portions 5011. As an example, the protective film 5014 has an opening having a convex arc-like shape for at least one of the adjacent sensor portions 5011 in the vicinity of the sensor portion 5011. Therefore, the base plate 5010 is exposed in the vicinity of the sensor portion 5011, but the circumference thereof is covered with the protective film 5014.

That is, the protective film 5014 has one or more opening to expose the base plate 5010 or the sensor portion 5011 at least in areas other than the wire 5013 and the boundary region in the reaction region 5023. The protective film 5014 may be provided on the base plate 5010, or provided in the vicinity of a boundary area between the wire 5013 and the base plate 5010. The protective film 5014 may be provided so as to cover the outer peripheral area of the sensor portion 5011 as in the case of the fifteenth embodiment.

As described above, the protective film 5014 according to the seventeenth embodiment has one or more opening to expose a lower layer portion including a part of the base plate 5010 (the base plate 5010 or the sensor portion 5011) in the reaction region 5023.

The purpose of providing the protective film 5014 so as to surround the circumference of the sensor portions 5011 in the boundary region between the sensor portions 5011 is to prevent a situation in which a liquid including a nucleic acid probe added dropwise to the sensor portion 5011 is spread more than necessary.

According to the seventeenth embodiment, an effect comparable to that of the fourteenth embodiment or the fifteenth embodiment is obtained. Further, according to the seventeenth embodiment, fixing of nucleic acid probes to the sensor portions during production of the nucleic acid detecting device 5100 can be made accurate and easy.

Example 4

Example 4-1

In Example 4-1, a nucleic acid amplification reaction using the nucleic acid detecting device 5100 according to the sixteenth embodiment described above will be described. FIG. 41 illustrates a result of a nucleic acid amplification reaction using the nucleic acid detecting device 5100 according to the sixteenth embodiment and a result of a nucleic acid amplification reaction using a nucleic acid detecting device of Comparative Example in a comparative manner. The nucleic acid detecting device of Comparative Example has a configuration in which areas including not only a wire but also a base plate) other than a sensor 11 are covered with an organic protective film in a reaction region. FIG. 41 shows amplification time on the abscissa and amplification amount of nucleic acid on the ordinate. In Example 4-1, an amplification reaction reagent was injected into the reaction region of each of the nucleic acid detecting device 5100 according to the sixteenth embodiment and the nucleic acid detecting device of Comparative Example, and the amplification amount of nucleic acid was quantitatively determined just after amplification was performed for 40 minutes and 60 minutes after injection. For the nucleic acid detecting device of Comparative Example, the amplification amount is low at 40 minutes, and was not sufficient even at 60 minutes. On the other hand, for the nucleic acid detecting device 5100 according to the sixteenth embodiment, a sufficient amplification amount is obtained at 40 minutes. Since amplification is saturated at this time, the amplification amount of nucleic acid is not increased at 60 minutes.

From the result illustrated in FIG. 40, it has become evident that hindrance of amplification was considerably reduced in the configuration of the nucleic acid detecting device 5100 according to the sixteenth embodiment. For the nucleic acid detecting devices 5100 according to the fourteenth, fifteenth and seventeenth embodiments, characteristics similar to those described above are obtained because they have configurations similar to the configuration of the nucleic acid detecting device 5100 according to the sixteenth embodiment.

Example 4-2

In Example 4-2, an example of amplification using practically the nucleic acid detecting device built-in cassette 5001 according to the sixteenth embodiment described above will be described in detail. FIG. 41 is an enlarged view of the vicinity of a reaction region 5023 in the nucleic acid detecting device 5100 according to the sixteenth embodiment. In Example 4-2, a sensor portion 5011 includes a pair of sensors as illustrated in FIG. 41. The nucleic acid detecting device 5100 detects different nucleic acids for each sensor portion 5011 (each pair of sensors). A protective film 5014 in the reaction region 5023 is formed only on an area covering a wire 5013 and boundary regions between the sensor portions 5011 as described in the sixteenth embodiment. A base plate 5010 (glass is used in Example 4-2) is exposed at other areas in the reaction region 5023.

(1) Provision of Nucleic Acid Detecting Device Built-in Cassette 5001

1-1. Provision of Nucleic Acid Detecting Device 5100

Five types of nucleic acid probes (sequences A to E) shown in Table 20, below, were fixed to electrodes (hereinafter, corresponding to sensors forming the sensor portions 5011) on the nucleic acid detecting device 5100. A solution including each nucleic acid probes was added dropwise to each electrode pair, and thereafter excessive nucleic probes were washed and removed to thereby perform fixing. A pair of first and second electrodes, a pair of third and fourth electrodes, a pair of fifth and sixth electrodes, a pair of seventh and eighth electrodes and a pair of ninth and tenth electrodes described below form different sensor portions 5011, respectively.

1) Negative control . . . first and second electrodes
2) Detection for gene . . . A third and fourth electrodes
3) Detection for gene . . . B fifth and sixth electrodes
4) Detection for gene . . . C seventh and eighth electrodes
5) Detection for gene . . . D ninth and tenth electrodes

TABLE 20

| Nucleotide sequence of DNA probe | | | |
|---|---|---|---|
| Sequence name | Sequence | Number of bases | SEQ ID NO. |
| NC | TTTGGTGCAATGGATTTTACTACATTACAAGCTAATAAAAGTGATGTTCCC | 51 | 195 |
| A | ACAAGGTCATAATAATGGTATTTGTTGGGGCAATC | 35 | 196 |
| B | TGGTCCTGGCACTGATAATAGGGAATGTATATCAATGGATTATAAACAAACACAA | 55 | 197 |
| C | TTGTAACCAGTACGGTTTATTAAATAATTGGGATTCTGAGG | 41 | 198 |
| D | AGTACTGCTACAGAACAGTTAAGTAAATATGATGCACGAAAAATTAATCAGTACC | 55 | 199 |

1-2. Assembly of Nucleic Acid Detecting Device Built-in Cassette 5001

A reaction portion defining member 5200 capable of forming the reaction region 5023 was mounted on the sensor portion 5011 of the nucleic acid detecting device 5100. The reaction portion defining member 5200 is provided with a sample injection port, and is fixed to the nucleic acid detecting device 5100 so that a reaction solution does not leak out. In the reaction portion defining member 5200, primer sets shown in Table 21 were held in a dried state beforehand. Primers for amplification were designed for amplification by the LAMP method.

TABLE 21

Nucleotide sequence of DNA primer

| Set name | Sequence name | Sequence | Number of bases | SEQ ID NO. |
|---|---|---|---|---|
| A | A-FIP | GCACTGCTTTGAATAGAGGCACTGTTCCCGATGACCTG | 38 | 200 |
|   | A-BIP | CCATATTGGCTACAACGTGCTACCTGATTGCCCCAACA | 38 | 201 |
|   | A-F3 | AGGGCTGGTACATTAGGAGA | 20 | 202 |
|   | A-B3 | GTCATATTAGTACTGCGAGTGG | 22 | 203 |
|   | A-LPF | CAGTAGTTCCTGAACCTTTAATGTACA | 27 | 204 |
| B | B-FIP | GGATGACCACTAATACCTACACCCTGTGTTGGTTTAGAGGTAGGTC | 46 | 205 |
|   | B-BIP | CACTGAAAACTCTAATAGATATGCCGGTGCAACCAAGTAAACACAGTTGTG | 51 | 206 |
|   | B-F3 | AACTCAACGCTTAGTTTGGGC | 21 | 207 |
|   | B-B3 | CCTTTACCCCAATGCTCTCC | 20 | 208 |
|   | B-LPF | TAATGGCTGCCCGCGA | 16 | 209 |
| C | C-FIP | ATTATTGTGGCCCTGCGCACGTTCTATGGTAACCTCAGAATCCC | 44 | 210 |
|   | C-BIP | ACCACTCGTAGCACTAACATGACTCGCCATGACGAAGGTATTCCT | 45 | 211 |
|   | C-F3 | GCCACTGTACAAAGCAGTGC | 20 | 212 |
|   | C-B3 | TGAATGTATGTCATAACATCAGCTG | 25 | 213 |
|   | C-LPB | GCTGAGGTTAAAAAGGAAAGCACA | 24 | 214 |
| D | D-FIP | AATTGATTACCCCAGCAAATGCCGTCTATGATTACGTCTGAGGCAC | 46 | 215 |
|   | D-BIP | ATACTACTAGAAGTACTAACATGACCCTCCACATGTCTAAGGTACTG | 47 | 216 |
|   | D-F3 | GTATATGTTGCTACGCCTAGTG | 22 | 217 |
|   | D-B3 | GCCATAACCTCTGCAGACAAAG | 22 | 218 |
|   | D-LPF | GCACGTTGCAACCAATAAGG | 20 | 219 |

(2) Detection of Nucleic Acid
2-1. Provision of Template Solution

As shown in Table 22, below, a template solution obtained by mixing three types of templates: genes A, B and D and a reagent for amplification was provided.

TABLE 22

Composition

| Reagent | Template name | Total 50 |
|---|---|---|
| Reaction Mixture |  | 14.00 |
| DNA Polymerase |  | 8.00 |

TABLE 22-continued

Composition

| Reagent | Template name | Total 50 |
|---|---|---|
| Template DNA | A | 2.00 |
|  | B | 2.00 |
|  | D | 2.00 |
| DW |  | 22.00 |
| Total |  | 50.00 |

For the template solution, a solution, which included Bst DNA polymerase and a reaction mix and to which distilled water (i.e. DW) was added so that the total amount was 50 μL including a later-described template solution, was used. The template solution includes a template A which is detected as an amplification reaction by the LAMP method is caused by a primer DNA (set A) and hybridization with a probe DNA (A) occurs, a template B which is detected as an amplification reaction by the LAMP method is caused by a primer DNA (set B) and hybridization with a probe DNA (B) occurs, and a template D which is detected as an amplification reaction by the LAMP method is caused by a primer DNA (set D) and hybridization with a probe DNA (D) occurs.

Templates A, B and D are synthetic oligo DNAs having nucleotide sequences shown in Table 23, below.

TABLE 23

DNA template sequence (templates A, B and D)

| Sequence name | Sequence (part of sequence excerpted) | Number of bases | SEQ ID NO. |
|---|---|---|---|
| A | AGGGCTGGTACATTAGGAGAGGCTGTTCCCGATGACCTGTACATTAAAGGTTCAGGAACTAC TGCCTCTATTCAAAGCAGTGCTTTTTTTCCCACTCCTAGTGGATCAATGGTTACTTCCGAAT CTCAGTTATTTAATAAGCCATATTGGCTACAACGTGCACAAGGTCATAATAATGGTATTTGT TGGGGCAATCAGGTATTTGTTACTGTGGTAGATACCACTCGCAGTACTAATATGAC | 2.7 kbp | 220 |
| B | AACTCAACGCTTAGTTTGGGCCTGTGTTGGTTTAGAGGTAGGTCGCGGGCAGCCATTAGGTG TAGGTATTAGTGGTCATCCATTATTAAATAAATTTGATGACACTGAAAACTCTAATAGATAT GCCGGTGGTCCTGGCACTGATAATAGGGAATGTATATCAATGGATTATAAACAAACACAACT GTGTTTACTTGGTTGCAAACCACCTATTGGAGAGCATTGGGGTAAAGG | 2.7 kbp | 221 |
| D | GTATATGTTGCTACGCCTAGTGGGTCTATGATTACGTCTGAGGCACAGTTATTTAATAAACC TTATTGGTTGCAACGTGCCCAAGGCCATAATAATGGCATTTGCTGGGGTAATCAATTATTTG TTACTGTAGTAGATACTACTAGAAGTACTAACATGACTATTAGTACTGCTACAGAACAGTTA AGTAAATATGATGCACGAAAAATTAATCAGTACCTTAGACATGTGGAGGAATATGAATTACA ATTTGTTTTCAATTATGCAAAATTACTTTGTCTGCAGAGGTTATGGC | 2.7 kbp | 222 |

2-2. Addition of Template Solution

The template solution provided in 2-1 was added to the reaction region in an amount of 50 μL.

2-3. Reaction of Nucleic Acid

Various kinds of reactions were carried out under conditions shown below while the reaction region was heated or cooled.

Nucleic acid amplification reaction: 64° C., 60 minutes
Hybridization reaction: 50° C., 10 minutes
Washing reaction: 30° C., five minutes
Reagent for detection of currents (Hoechst 33258): 25° C., three minutes 2-4. Detection of Nucleic Acid An electrical potential was swept through each probe nucleic acid fixing working electrode to measure an oxidation current of a Hoechst 33258 specifically bound with a double strand formed by the probe DNA and the LAMP product. The series of reactions described above were carried out in the DNA automatic examination apparatus described in SICE Journal of Control, Measurement and System Integration, Vol. 1, No. 3, pp. 266-270, 2008.

(3) Results

FIG. 42 is a graph illustrating a result obtained from each electrode. In electrodes 3, 4, 5, 6, 9 and 10 on which probes A, B and D corresponding to genes A, B and D, to which a template was added, were fixed, a current value greater than that of the negative control was obtained. On the other hand, electrodes 7 and 8 on which probe C corresponding to gene C, to which a template was not added, was fixed had current values comparable to the current value of the negative control. From the result illustrated in FIG. 42, it has become evident that a gene, to which a template was added, could be reliably detected by using the nucleic acid detecting device 5100 according to the sixteenth embodiment.

Example 4-3

In Example 4-3, an example of amplification using practically the nucleic acid detecting device built-in cassette 5001 according to the seventeenth embodiment described above will be described in detail. FIG. 43 is an enlarged view of the vicinity of a reaction region 5023 in a nucleic acid detecting device 5100 according to the seventeenth embodiment. In Example 3 a sensor portion 5011 includes a pair of sensors as illustrated in FIG. 43. The nucleic acid detecting device 5100 detects different nucleic acids for each sensor portion 5011 (each pair of sensors). A protective film 5014 in the reaction region 5023 is formed only on an area covering a wire 5013, boundary regions between the sensor portions 5011 and the outer peripheral areas of two sensors forming each sensor portion 5011 as described in the seventeenth embodiment. A base plate 5010 (glass is used in Example 4-1) is exposed at other areas in the reaction region 5023. Materials used for detection and detection conditions are same as those in Example 4-1 except for the nucleic acid detecting device 5100. A pair of first and second electrodes, a pair of third and fourth electrodes, a pair of fifth and sixth electrodes, a pair of seventh and eighth electrodes and a pair of ninth and tenth electrodes described below form different sensor portions 5011, respectively.

Results

Figure 44:
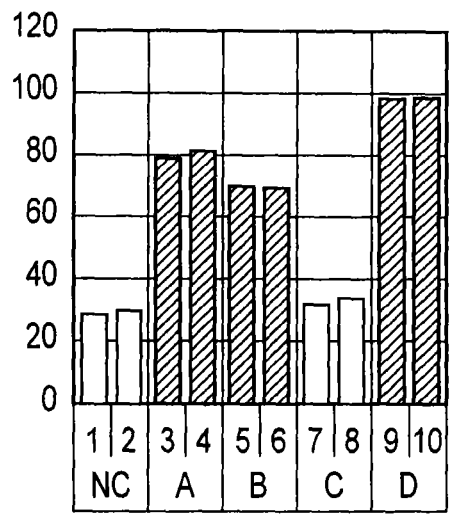
FIG. 44 is a graph illustrating a result obtained from each electrode.

FIG. 44 is a graph illustrating a result obtained from each electrode. In electrodes 3, 4, 5, 6, 9 and 10 on which probes A, B and D corresponding to genes A, B and D, to which a template was added, were fixed, a current value greater than that of the negative control was obtained. On the other hand, electrodes 7 and 8 on which probe C corresponding to gene C, to which a template was not added, was fixed had current values comparable to the current value of the negative control. From the result illustrated in FIG. 44, it has become evident that a gene, to which a template was added, could be reliably detected by using the nucleic acid detecting device 5100 according to the seventeenth embodiment.

6. PREVENTION FROM HINDRANCE OF NUCLEIC ACID REACTION

In a further aspect, the multi-nucleic-acid amplification reaction tool may be provided as a nucleic acid reaction tool that does not hinder a nucleic acid reaction.

As described above, a technique for detecting a plurality of object genes is very important. However, it is becoming evident that some of nucleic acid amplification apparatuses and/or nucleic acid detectors developed in the above-mentioned situations hinder a nucleic acid reaction. A reaction of a primer with a target nucleic acid and a reaction of a probe nucleic acid with a target nucleic acid are nucleic acid reactions that occur between nucleic acids. It is necessary that a reaction supposed to occur be carried out without being hindered in a reaction field.

The multi-nucleic-acid amplification reaction tool may be provided as a nucleic acid reaction tool that does not hinder a nucleic acid reaction by using this embodiment. For example, the nucleic acid reaction tool may be a nucleic acid amplification reaction tool, a nucleic acid detecting reaction tool or a nucleic acid amplification and detecting reaction tool. Specifically, the nucleic acid reaction tool may be an array-type probe chip, an array-type primer chip or an array-type primer probe chip.

The nucleic acid reaction tool has a protective film formed on the surface of a member that forms a reaction field. Here, the "reaction field" refers to a field where a nucleic acid reaction is carried out.

The protective film is formed of at least one selected from the group consisting of polyethylene, ethylene, polypropylene, polyisobutylene, polyethylene terephthalate, unsaturated polyester, a fluorine-containing resin, polyvinyl chloride, polyvinyliden chloride, polyvinyl acetate, polyvinyl alcohol, polyvinyl acetal, an acrylic resin, polyacrylonitrile, polystyrene, an acetal resin, polycarbonate, polyamide, a phenol resin, a urea resin, an epoxy resin, a melamine resin, a styrene-acrylonitrile copolymer, an acrylonitrile-butadiene-styrene copolymer, a silicon resin, polyphenylene oxide and polysulfone, and glass, quartz glass, alumina, sapphire, forsterite, silicon carbide and a metal oxide.

Examples of the preferred material of the protective film include a novolak resin, an epoxy resin, a polyolefin resin and a silicon resin, or may include resin compositions containing these resins. Preferably a photosensitive material is not included when a novolak resin is used.

The protective film should be formed so as to be in contact with a reaction field of a member that forms the reaction field of the nucleic acid reaction tool. Formation of the protective film should be performed using a technique that is publicly known itself according to a type of the protection film material. Alternatively, the protective film should be applied for preventing separation of problematic substances from a member which may hinder the reaction. In this case, at least a part of the member that is in contact with the reaction field should be covered with the protective film.

The term "primer set" means a set of primers necessary to amplify one target nucleic acid. For example, in the case of a primer set for PCR amplification, one primer set should include one type of forward primer and one type of reverse primer for amplifying one target nucleic acid. For example, in the case of a primer set for LAMP amplification, one primer set should include a FIP primer and a BIP primer for amplifying at least one target nucleic acid, and may include an F3 primer, a B3 primer, an LP primer, that is, an LF primer and/or an LB primer as necessary. When an amplification reaction is carried out in one reaction tool, amplification that is performed therein is generally one specific amplification. Therefore, in the case of a reaction tool for LAMP amplification reaction, a plurality of types of primer sets included in one reaction tool may be mutually different primer sets for amplifying target sequences including mutually different nucleotide sequences. Alternatively, a plurality of types of primer sets included in one reaction tool may be primer sets having combinations of mutually different primers for amplifying a specific target sequence.

Examples of the nucleic acid reaction tool will be described below. As examples that are individually shown, an array-type probe chip, an array-type primer chip and an array-type primer probe chip as nucleic acid reaction tools are described.

Eighteenth Embodiment

Array-Type Probe Chip

Figure 45:
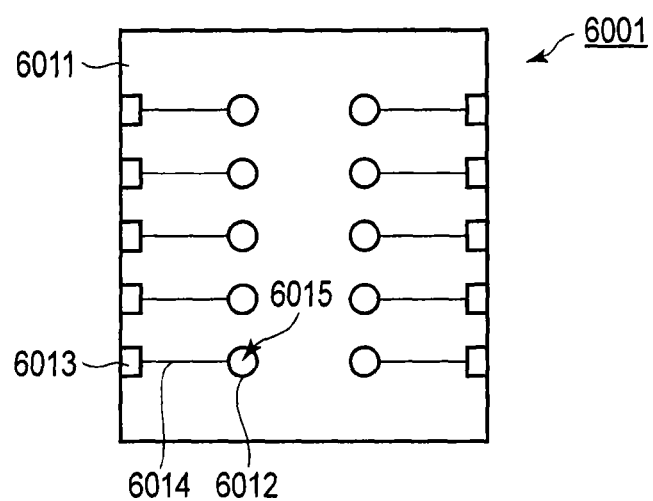
FIG. 45 is a plan view illustrating a nucleic acid reaction tool.

A schematic view of an embodiment of an array-type probe chip 6001 is illustrated in FIG. 45. The array-type probe chip 6001 includes an electrode 6012 on a base body 6011. A signal extraction portion 6013 for extracting electrical information of the electrode 6012 is arranged at a position corresponding to each electrode 6012. The electrode 6012 and the signal extraction portion 6013 are connected by a lead 6014. A probe nucleic acid 6015 is fixed on the surface of the electrode 6012. The surface of the base body 6011 except the surface of the electrode 6012 and the surface of the lead 6014 are covered with the protective film 6013.

The protective film 6013 may be formed at desired sites by coating, or by using a technique such as patterning, masking, etching and the like, a protective film having a desired size and shape may be formed at desired sites after forming the protective film over the entire surface. At least the lead 6014 may be covered to prevent contact between the lead 6014 and a reaction solution. Alternatively, the protective film may be formed at least on a region that is in contact with a reaction solution.

Examples of the material from which the base body 6011 can be produced include, but are not limited to, glass, sapphire, ceramic, resin, rubber, elastomer, $SiO_2$, SiN and $Al_2O_3$. Preferably, the base body 6011 is formed of any of materials which are themselves electrically and chemically inactive and which are publicly known themselves.

Production of the electrode 6012 may be performed using a publicly known technique. Examples of the material with which the electrode can be produced include, but are not particularly limited to, single metals such as gold, a gold alloy, platinum, mercury, nickel, palladium, silicon, germanium, gallium and tungsten, and alloys thereof, carbon such as graphite and glassy carbon, and oxides or compounds thereof.

Fixing of the probe nucleic acid 6015 to the electrode 6012 may be performed by chemical bonding or may be performed by spotting and drying a probe nucleic acid solution.

A hybridization signal generated by hybridization of the probe nucleic acid 6015 and a sample nucleic acid (not illustrated) is transmitted by the electrode 6012 and extracted from the signal extraction portion 6013.

The array-type probe chip base body illustrated in FIG. 45 has 10 electrodes 6012, but the number of electrodes arranged on a base body is not limited thereto, and can be arbitrarily changed. The arrangement pattern of electrodes is not limited to that illustrated in the figure, and can be appropriately changed as necessary by a person skilled in the art. The base body 6011 may be provided with a reference electrode and a counter electrode as necessary.

The base body 6022 may be in the form of a tube, a well, a chamber, a channel, a cup and a dish, and a plate having a plurality of these forms, for example a multi-well plate, or have a plate-like shape, a spherical shape, a rod-like shape and a shape including a part of these shapes.

When the base body 6022 is in the form of a container shape, for example a tube, a well, a chamber, a channel, a cup and a dish, and a plate having a plurality of these forms, for example a multi-well plate, a reaction solution may be stored in the container to form a reaction field. Further, the array-type probe chip may be provided with a lid. The lid should be configured to cover at least a region of the container-shaped or plate-shaped base body 6022 where the probe nucleic acid 6015 is fixed. The lid may have a plate-like shape. A recessed portion such as a groove may be formed on a part of the plate-shaped lid. A reaction field may be formed in a space between the recessed portion of the lid and the base body 6022.

When the base body 6022 has a plate-like shape, a spherical shape, a rod-like shape and a shape including a part of these shapes, a reaction field may be formed by immersing the base body in an additional container including a reaction solution, or a reaction field may be formed by placing a reaction solution on a region where the probe nucleic acid arranged on the base body 6022 is fixed.

Nineteenth Embodiment

Array-Type Primer Chip

An example of an array-type primer chip will be described with reference to (a) (b) and (c) in FIG. 46.

FIG. 46(*a*) is a perspective view of an example of the array-type primer chip. An array-type primer chip 6021 described in FIG. 46(*a*) includes a container 6022 with a protective film 6020 formed on the inner wall. A plurality of mutually independent fixing regions 6024 are arranged on an inner bottom surface 6023 of the base body 6022 on which the protective film 6020 is formed. FIG. 46B is a schematic view of the enlarged fixing region 6024 part. As illustrated here, one type of primer set 6025 is fixed on one fixing region 6024. A plurality of primer sets 6025 are fixed, for each set, on a plurality of fixing regions 6024, respectively.

A plurality of types of primer sets 6025 are provided according to types of target nucleic acids to be amplified. One primer set 6025 for amplifying one specific target nucleic acid is fixed on one fixing region 6024. For example, for PCR amplification, one primer set includes a forward primer and a reverse primer that are necessary to amplify one type of specific target nucleic acid. For LAMP amplification, one primer set includes a FIP primer and a BIP primer that are necessary to amplify one type of specific target nucleic acid, and an F3 primer, a B3 primer and an LP primer as necessary.

The primer set 6025 is fixed on the fixing region 6024 in a releasable state so as to release in contact with a liquid phase for providing a reaction field. Fixing of the primer set 6025 to the fixing region 6024 can be achieved by, for example, adding dropwise to one fixing region 6024 a solution including a set of primer sets, followed by drying the solution. Further, for other fixing regions 6024, solutions each containing a desired primer set 6025 are similarly added dropwise and dried to fix a desired number of primer sets to the base body 6022. In this way, primer sets 6025 are fixed on all fixing regions 6024 independently arranged on a surface of the base body 6022. However, it suffices that the primer set 6025 is fixed on the fixing region 6024 in a state of being releasable in contact with a liquid phase for providing a reaction field. Therefore, any fixing method that is capable of achieving the above-mentioned fixing and is publicly known itself may be used. In the case of the method of adding dropwise a solution including a primer set, the solution including a primer set may be, for example, water, a buffer solution or an organic solvent.

A plurality of fixing regions 6024 to be arranged on the base body 6022 should be mutually independently arranged. The term "independently arranged" means that fixing regions are arranged at such intervals that amplification made to start and/or proceed for each primer set in a reaction field is not hindered. For example, adjacent fixing regions 6024 may be arranged in contact with each other, or may be arranged in the vicinity of each other with a slight distance therebetween, or may be arranged at an interval equivalent to a distance between primer sets that are fixed in a detector such as so called a DNA chip which is usually used.

For example, the distance between adjacent fixing regions 6024 may be 0.1 μm to 1 μm, 1 μm to 10 μm, 10 μm to 100 μm, 100 μm to 1 mm, 1 mm to 10 mm or more, or may be preferably 100 μm to 10 mm.

The liquid phase for providing a reaction field should be a liquid phase such that after fixed primer sets are separated, an amplification reaction can be caused to proceed using the primers, and the liquid phase may be a reaction solution necessary for desired amplification.

The nucleic acid reaction tool illustrated in FIGS. 46A and 46B is an example in which the base body 6022 has a container-like shape. Examples of the container-shaped base body 6022 may include a tube, a well, a chamber, a channel, a cup and a dish, and a plate having a plurality of these forms, for example a multi-well plate. The material of the base body may be any material. For the base body 6022, a material of the base body similar to that of the array-type probe chip described above may be used. The base body 6022 may have a plate-like shape. Further, the array-type primer chip may be provided with a lid. The lid should be configured to cover at least a region of the container-shaped or plate-shaped base body 6022 where the primer 6025 is fixed. The lid may have a plate-like shape. A recessed portion such as a groove may be formed on a part of the plate-shaped lid. A reaction field may be formed in a space between the recessed portion of the lid and the base body 6022.

The nucleic acid reaction tool may have the primer set 6025 fixed on the primer fixing region 6024 arranged on at least a surface 6023 of the base body 6022 as illustrated in FIG. 46(*c*). In this case, the reaction field should be formed by placing a reaction solution onto at least a region of the base body 6022 where the primer set 6025 is fixed. In this case, a recessed portion and/or a raised portion may be formed on the surface 6023 of the base body 6022, or a channel may be formed by the recessed portion and/or raised portion. The primer fixing region 6024 and the primer set 6025 may be arranged in the recessed portion of the base body 6022, or may be arranged on a region surrounded by a plurality of recessed portions. A reaction field may be formed by arranging the base body 6022 in a container including a reaction container. In this case, the base body 6022 may have a plate-like shape, a spherical shape, a rod-like shape and a shape including a part of these shapes.

For formation of the protective film, any technique that is publicly known itself may be used.

In (a) and (b) in FIG. 46, an example is illustrated in which the fixing region 6024 is arranged only on the inner bottom surface of the base body 6022, but this is not exhaustive. The fixing region 6024 should be arranged on at least a part of the inside of the base body 6022, and may be arranged on any or all of the inner bottom surface, the inner side surface and the ceiling surface formed by the lid.

(a) to (c) in FIG. 47 illustrate a nucleic acid amplification reaction using the above-described array-type primer chip 6031. FIG. 47(*a*) illustrates the array-type primer chip 6031 before the reaction. A plurality of primer sets 6034 are, respectively, fixed on a plurality of fixing regions 6033 arranged on the inner bottom surface of a base body 6032 with the protective film formed on the inner surface. FIG. 47(*b*) illustrates a state in which a reaction solution 6036 is added and stored in the array-type primer chip 6031.

The reaction solution 6036 should contain components necessary for a desired amplification reaction. Examples of the components may include, but are not limited to, an enzyme such as polymerase, a substrate substance such as deoxynucleoside triphosphate necessary for forming a new polynucleotide chain with a primer as a start point, a reverse transcriptase and a necessary substrate substance, etc., when performing reverse transcription in parallel, and a buffer such as a salt configured to maintain a proper amplification environment.

In the array-type primer chip 6031 after the reaction solution 6036 is added therein as illustrated in FIG. 47B, primer sets fixed on the inner bottom surface provided with the protective film separate and gradually diffuse as schematically illustrated in FIG. 47C. A region where primers separate and diffuse is schematically shown by a region 6035. Primer sets separating and diffusing encounter other components necessary for amplification which exist in their vicinity, such as a template nucleic acid, polymerase and a substrate substance, and an amplification reaction is started. A plurality of primer sets independently fixed for each type can cause an amplification reaction to start and proceed for the template nucleic acid independently for each type. In this way, amplification for a plurality of template sequences using a plurality of types of primer sets is achieved independently and in parallel. Here, the term "reaction field" means a region defined by the reaction solution 6036 where theoretically the amplification reaction can proceed, that is, a region where the reaction solution exists. Of the reaction field, a region where the amplification reaction actually starts and proceeds is referred to as a "reaction region". If actually the amplification reaction proceeds only in the region 6035, the region 6035 may be considered as a reaction region.

In the above-described example, only primer sets are fixed on a base body. However, this is not exhaustive, and other components necessary for amplification, for example enzymes such as polymerase and a reverse transcriptase, a substrate substance, a substrate and/or a buffer, may be fixed, for each type, on the base body along with primers under conditions for fixing primer sets on fixing regions. In this case, substances to be fixed should be included in a desired liquid medium along with primers, and added dropwise and dried to be fixed using a method similar to that described above. When the amplification reaction is carried out in such an array-type primer chip, a composition of a reaction solution to be added thereto should be selected according to fixed components.

Twentieth Embodiment

Array-Type Primer Probe Chip.

Figure 48:
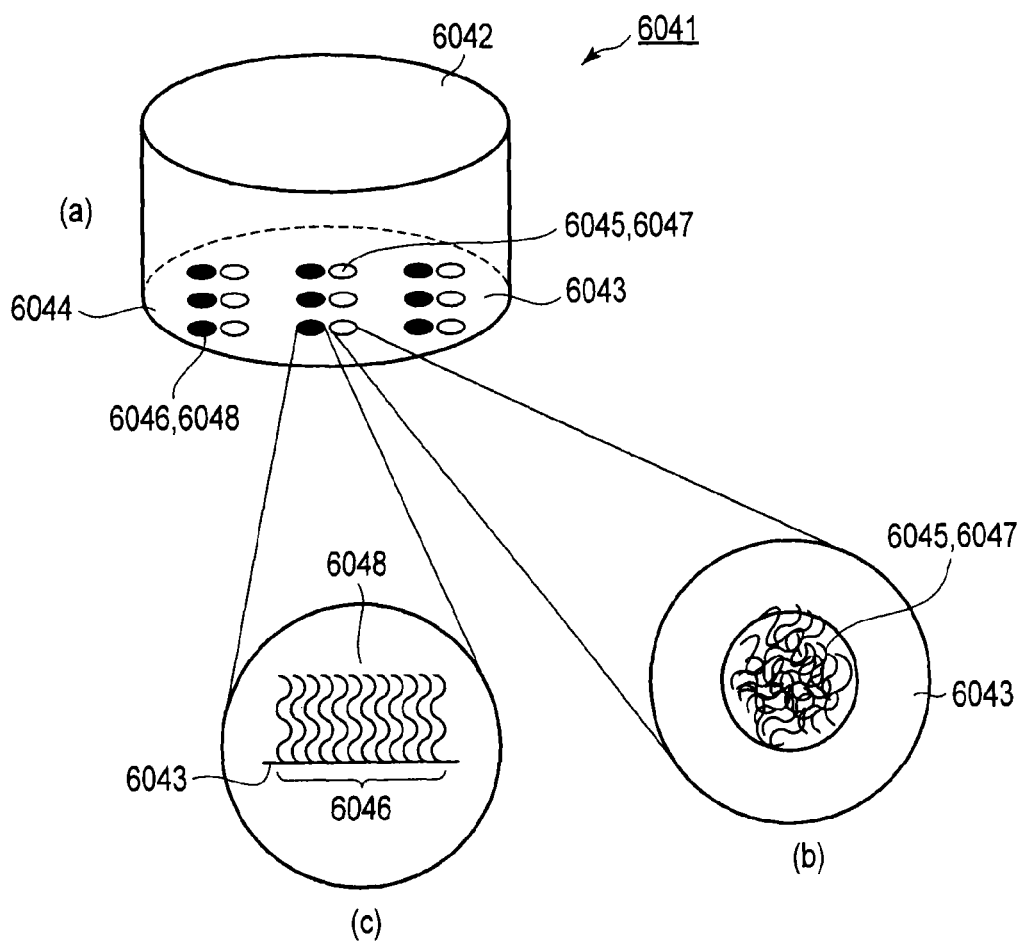
FIG. 48 is a perspective views illustrating a nucleic acid reaction tool.

An example of a further embodiment is illustrated in FIG. 48. This embodiment includes the above-described base body, probe nucleic acids fixed on at least a surface of the base body, and releasably fixed primers. This embodiment may be referred to as an array-type primer probe chip. The array-type primer probe chip is a nucleic acid reaction tool including probe nucleic acids and primers in one base body. The configuration of the base body may be similar to the configurations of the array-type probe chip and array-type primer chip described above.

FIG. 48(a) is a perspective view of an example of an array-type primer probe chip. An array-type primer probe chip 6041 described in FIG. 48A includes a container-shaped base body 6042. A protective film 6043 is formed on the inner wall of the base body 6042. A plurality of mutually independent fixing regions 6045 are arranged on the protective film 6043 at an inner bottom surface 6044 of the base body 6042. A plurality of probe fixing regions 6046 are arranged in contiguity with a plurality of primer fixing regions 6045 and in correspondence with respective primer fixing regions.

FIG. 48(b) is a schematic view of the enlarged primer fixing region 6045. As illustrated here, one type of primer set 6047 is fixed on one primer fixing region 6045. A plurality of primer sets 6047 are fixed, for each set, on a plurality of primer fixing regions 6045, respectively.

Primer sets 6047 should be fixed in the same manner as in the array-type primer chip described above.

FIG. 48(c) is an enlarged view of a probe fixing region 6046 arranged in contiguity with the primer fixing region 6045. A plurality of probe nucleic acids 6048 including a complementary sequence of a desired sequence to be detected are fixed on the probe fixing region 6046.

A desired sequence to be detected may be a complementary sequence of a probe nucleic acid. Probe fixing regions 6046 are arranged so that hybridization signals of probe nucleic acids 6048 and object sequences are detected independently among a plurality of probe fixing regions 6046.

For fixing of the probe nucleic acid 6048 to the probe fixing region 6046, any of general techniques for fixing the probe nucleic acid to the surface of a base plate in so called a DNA chip which is publicly known itself. The primer set 6047 may be fixed after fixing of the probe nucleic acid 6048, or the probe nucleic acid 6048 may be fixed after fixing of the primer set 6047. Fixing of the primer set 6047 and fixing of the probe nucleic acid 6048 may be performed in parallel.

For example, the distance between adjacent probe fixing regions 6046 may be 0.1 μm to 1 μm, 1 μm to 10 μm, 10 μm to 100 μm, 100 μm to 1 mm, 1 mm to 10 mm or more, or may be preferably 100 μm to 10 mm.

For example, the distance between the probe fixing region 6046 and the primer fixing region 6045 may be 0 μm to 0.1 μm, 0.1 μm to 1 μm, 1 μm to 10 μm, 10 μm to 100 μm, 100 μm to 1 mm, 1 mm to 10 mm or more, or may be preferably 100 μm to 10 mm.

For example, when the distance between the probe fixing region 6046 and the primer fixing region 6045 is zero μm, the probe fixing region 6046 and the primer fixing region 6045 may be considered to be at the same position on the surface of the base body. The probe fixing region 6046 may be included in the primer fixing region 6045, or the primer fixing region 6045 may be included in the probe fixing region 6046.

Figure 49:
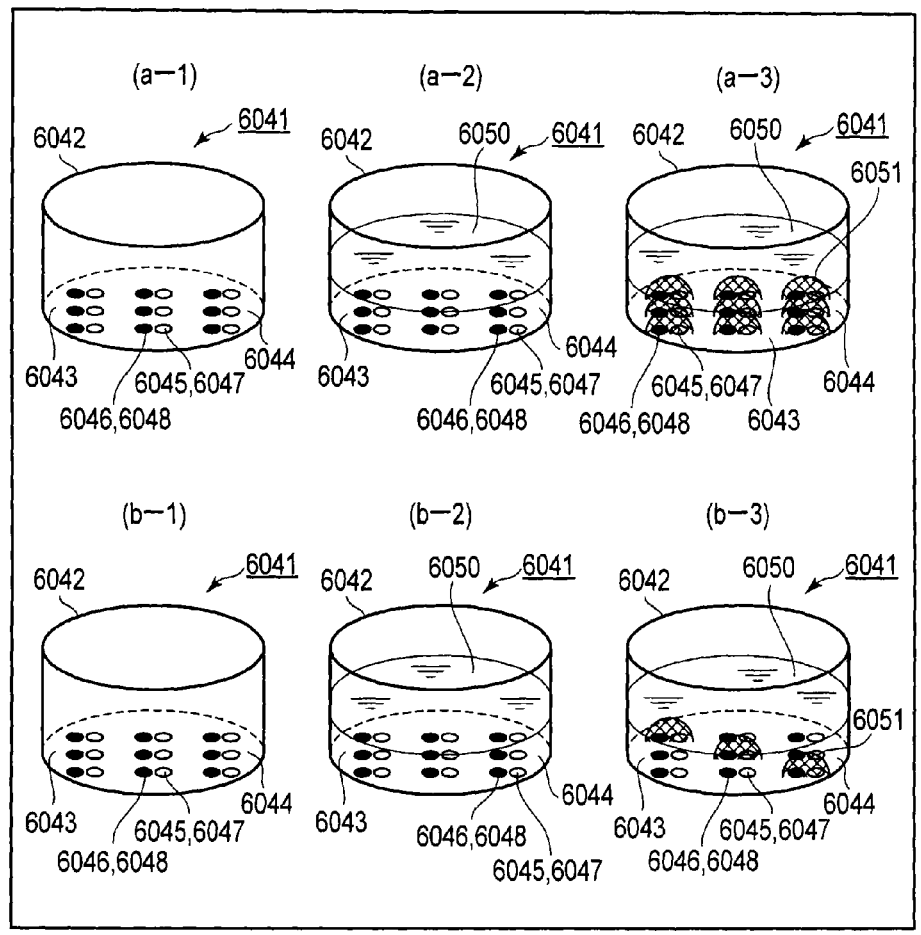
FIG. 49 is a perspective view illustrating a nucleic acid reaction tool.

FIG. 49 is a schematic view illustrating a state of the reaction field after the nucleic acid amplification reaction is carried out using the array-type primer probe chip 6041. (a-1) and (b-2) in FIG. 49 illustrate the array-type primer probe chip 6041 before the reaction. A protective film 6043 is formed on the inner wall of the base body 6042. A plurality of primer sets 6047 are fixed, respectively, on a plurality of primer fixing regions 6045 arranged on the protective film 6043 at the inner bottom surface 6044 of the base body 6042. Probe fixing regions 6046 are arranged in the vicinities of primer fixing regions 6045 in correspondence with primer fixing regions 6045, respectively. A plurality of probe nucleic acids 6048 are fixed, for each type, on probe fixing regions 6046.

(a-2) and (b-2) in FIG. 49 illustrate a state in which a reaction solution 6050 is added and stored in the array-type primer probe chip 6041.

The reaction solution 6050 should contain components necessary for a desired amplification reaction. Examples of the components may include, but are not limited to, an enzyme such as polymerase, a substrate substance such as deoxynucleoside triphosphate necessary for forming a new polynucleotide chain with a primer as a start point, a reverse transcriptase and a necessary substrate substance, etc., when performing reverse transcription in parallel, and a buffer such as a salt configured to maintain a proper amplification environment.

Addition of a sample to the reaction field may be performed by adding the sample to the reaction solution 6050 before adding the reaction solution 6050 to the array-type primer probe chip 6041, or may be performed by adding after adding the reaction solution 6050 to the array-type primer probe chip 6041, or may be performed by adding the sample to the array-type primer probe chip 6041 before adding the reaction solution 6050 to the array-type primer probe chip 6041.

In the array-type primer probe chip 6041 after the reaction solution 6050 is added as illustrated in FIGS. 49A-2 and 49B-2, primer sets 6047 fixed on the protective film 6043 at the bottom surface 6044 separate and gradually diffuse as schematically illustrated in FIGS. 49A-3 and 49B-3. A region where primers separate and diffuse is schematically shown by a region 6051. Primers separating and diffusing encounter other components necessary for amplification which exist in their vicinity, such as a template nucleic acid, polymerase and a substrate substance, so that an amplification reaction is started. A plurality of primer sets independently fixed for each type can cause an amplification reaction to start and proceed for the template nucleic acid independently for each type. In this way, amplification for a plurality of template sequences using a plurality of types of primer sets is achieved independently and in parallel. Here, the term "reaction field" means a region defined by the reaction solution 6050 where theoretically the amplification reaction can proceed, that is, a region where the reaction solution exists. Of the reaction field, a region where the amplification reaction actually starts and proceeds is referred to as a "reaction region". If actually the amplification reaction proceeds only in the region 6051, the region 6051 may be considered as a reaction region. FIG. 49(a-3) is a schematic view where amplification reactions occur by primer sets fixed on all the primer fixing regions 6045. FIG. 49(b-3) is a schematic view where amplification is caused by fixed primer sets in some of all the primer fixing regions 6045 formed on the protective film 6043 at the bottom 6044, for example, only three regions in FIG. 49(b-3).

When a nucleic acid including an object sequence exists in an amplification product amplified in the region 6051, the probe fixing region 6046 is hybridized with the nucleic acid. The probe nucleic acid 6048 fixed on the probe fixing region 6046 is fixed so as to be hybridized with only an amplification product in the corresponding primer fixing region 6045. That is, the probe fixing regions 6046 and primer fixing regions 6045 are arranged with a distance maintained therebetween so that the probe nucleic acid 6048 fixed on one probe fixing region 6046 is hybridized with only an amplification product in the corresponding primer fixing region 6045.

Detection of hybridization of the probe nucleic acid 6048 with its object sequence may be performed by a technique for detection of a hybridization signal, which is publicly known itself. For example, a fluorescent substance may be given to the primer beforehand, or a fluorescent substance may be given to a substrate substance such as oxynucleoside triphosphate. The existence and the amount of hybridization may be determined using as an indicator the fluorescent intensity of a fluorescent substance. Alternatively, a hybridization signal may be detected by an electrochemical technique.

Detection of hybridization may be performed after washing the inside of the array-type primer probe chip 6041, or may be performed without carrying out washing. When detection is performed by an electrochemical technique, a hybridization signal may be detected using an intercalator. In this case, the intercalator may be included in the reaction solution 6050 beforehand, or may be added before the start of hybridization reaction, during hybridization reaction or after hybridization reaction. In any of these cases, detection may be performed after washing the inside of the array-type primer probe chip 6041, or detection may be performed without carrying out washing. Whether the intercalator is added at the start of hybridization reaction, during hybridization reaction or after hybridization reaction may be determined according to sequences of the primer, the probe nucleic acid and the template nucleic acid, and reaction conditions such as a reaction temperature, or may be determined via a preliminary experiment.

The length of the primer may be, but be not limited to, about five bases or more, about six bases or more, about seven bases or more, about eight bases or more, about nine bases or more, about 10 bases or more, about 15 bases or more, about 20 bases or more, about 25 bases or more, about 30 bases or more, about 35 bases or more, about 40 bases or more, about 45 bases or more or about 55 bases or more, or may be about 80 bases or fewer, about 75 bases or fewer, about 70 bases or fewer, about 65 bases or fewer, about 60 bases or fewer, about 55 bases or fewer, about 50 bases or fewer, about 45 bases or fewer, about 40 bases or fewer, about 35 bases or fewer, about 30 bases or fewer, about 25 bases or fewer, or about 20 bases or fewer, or may be in a range of a combination of any of the above-described upper and lower limits. Examples of the preferred base length may include about 10 bases to about 60 bases, about 13 to 40 bases and about 10 to 30 bases. The lengths of primers that are fixed on one fixing region in parallel may be the same for every primer, or may be different for every primer, or some of the primers may be the same in length, or some of the primers may be different in length. The length may be different for each primer set. Primer sets fixed on one fixing region may be different in length for each type, or all of primer sets fixed on one fixing region may be the same in length.

The length of the probe nucleic acid may be, for example, three bases to 10 bases, 10 bases to 20 bases, 20 bases to 30 bases, 30 bases to 40 bases, 40 bases to 50 bases or 50 bases to 60 bases, preferably 10 bases to 50 bases. The probe nucleic acid includes a complementary sequence of an object sequence to be detected. The probe nucleic acid may include, in addition to a complementary sequence of an object sequence, an additional sequence, for example a spacer sequence.

The length of the target sequence may be, for example, 10 bases to 100 bases, 100 bases to 200 bases, 200 bases to 300 bases or 300 bases to 400 bases, preferably 100 bases to 300 bases.

The length of the object sequence may be, for example, 3 bases to 10 bases, 10 bases to 20 bases, 20 bases to 30 bases, 30 bases to 40 bases, 40 bases to 50 bases or 50 bases to 60 bases, preferably 10 bases to 50 bases.

The number of types of primer sets fixed on one primer fixing region may be one for amplifying one type of target nucleic acid, or may be two or more for amplifying two or more types of target nucleic acids, respectively.

The number of types of probe nucleic acid groups fixed on one probe fixing region may be one for hybridization with one type of object sequence, or may be two or more for amplifying two or more types of target nucleic acids, respectively. The probe nucleic acids may be those that are the same in object sequence part and further include other sequences different from the object sequence.

The lower limit of the number of primer fixing regions arranged on one array-type primer probe chip may be one or more, two or more, three or more, four or more, five or more, 10 or more, 15 or more, 20 or more, 25 or more, 30 or more, 50 or more, 75 or more, 100 or more, 125 or more, 150 or more, 175 or more, 200 or more, 300 or more, 400 or more, 500 or more, 1000 or more, 1500 or more or 2000 or more, and the upper limit thereof may be 10000 or fewer, 5000 or fewer, 2500 or fewer, 2000 or fewer, 1500 or fewer, 1000 or fewer, 500 or fewer, 250 or fewer, 200 or fewer or 150 or fewer, or the number of primer fixing regions may be in a range of a combination of any of the above-described upper and lower limits.

The numbers of primer fixing regions and probe fixing regions 95 arranged on one array-type primer probe chip may be the same or different. That is, probe fixing regions may be arranged with the same number as primer fixing regions so as to correspond to all the primer fixing regions, or the number of primer fixing regions may be larger than the number of probe fixing regions, or the number of primer fixing regions may be smaller than the number of probe fixing regions. A positive control and/or a negative control may be included for checking an amplification reaction state or checking a state of hybridization reaction. The positive control and/or negative control may be provided for each of the primer sets and/or probe nucleic acids.

In the above-described example, only primer sets are fixed on a base body. However, this is not exhaustive, and other components necessary for amplification, for example enzymes such as polymerase and a reverse transcriptase, a substrate substance, a substrate substance and/or a buffer, may be fixed, for each type, on the base body along with primers under conditions for fixing primer sets on fixing regions. In this case, substances to be fixed should be included in a desired liquid medium along with primers, and added dropwise and dried to be fixed using a method similar to that described above. When the amplification reaction is carried out in such an array-type primer probe chip, a composition of a reaction solution to be added thereto should be selected according to fixed components.

Twenty-First Embodiment

An array-type primer probe chip of the twenty-first embodiment will be described with reference to FIGS. 50 to 53.

(1) Chip Material

First, an example of the configuration of a chip material of an array-type primer probe chip configured to detect a hybridization signal by electrochemical detection and the method for production of the chip material will be described with reference to (a) and (b) in FIG. 50. FIG. 50(a) is a plan view of a chip material, and FIG. 50(b) is a sectional view of the chip material taken along line B-B in FIG. 50(a).

A chip material 111 includes, on a rectangular base plate 112, for example four electrodes 113a to 113d arranged longitudinally with respect to the base plate. Electrodes 113a to 113d have a structure in which first metal thin film pattern 114 and a second metal thin film pattern 115 are stacked in this order. Electrodes 113a to 113d have a shape in which a large rectangular portion 116 and a small rectangular portion 117 are connected by a thin line 117. An insulating protective film 6118 is placed on the base plate 112 including each of electrodes 113a to 113d. A circular window 119 is opened at a part of the insulating protective film 6118 corresponding to the large rectangular portion 116. A rectangular window 120 is opened at a part of the insulating protective film 6118 corresponding to the small rectangular portion 117. The large rectangular portion 116 exposed from the circular window 119 of electrode 113a acts as a first working electrode 121a. The large rectangular portion 116 exposed from the circular window 119 of electrode 113b acts as a second working electrode 121b. The large rectangular portion exposed from the circular window 119 of electrode 113c acts as a counter electrode 122. The large rectangular portion exposed from the circular window 119 of electrode 113d acts as a reference electrode 123. The small rectangular portion 117 exposed from the rectangular window 120 of each of electrodes 113a to 113d acts a prober contact portion.

The chip material can be prepared by the following method.

First, a first metal thin film and a second metal thin film are stacked in this order on the base plate 112 by, for example, a sputtering method or a vacuum deposition method. Subsequently, for example four electrodes 113a to 113d obtained by sequentially selectively etching the metal thin films with, for example, a resist pattern as a mask to stack the first metal thin film pattern 114 and the second metal thin film pattern 115 in this order are formed longitudinally with respect to the base plate 112. Electrodes 113a to 113d have a shape in which a large rectangular portion 116 and a small rectangular portion 117 are connected by a thin line 118.

Then, the protective film 6118 is deposited on the base plate 112 including each of electrodes 113a to 113d by, for example, a sputtering method or a CVD method. Subsequently, a part of the protective film 6118 corresponding to the large rectangular portion 116 of each of electrodes 113a to 113d and a part of the protective film 6118 corresponding to the small rectangular portion 117 of each of electrodes 113a to 113d are selectively etched to open the circular window 119 at the part of the insulating protective film 6118 corresponding to the large rectangular portion 116 and the rectangular window 120 at the part of the insulating protective film 6118 corresponding to the small rectangular portion 117. In this way, the aforementioned chip material 111 is prepared.

The base plate 112 is made from a glass such as Pyrex (registered trademark) glass or a resin.

The first metal thin film acts as a base body metal film for bringing the second metal thin film into close contact with the base plate 112, and is made from, for example, Ti. The second metal thin film is made from, for example, Au.

Examples of etching for patterning the first and second metal thin films include plasma etching or reactive ion etching using an etching gas.

The material of insulating protective film 6118 should be selected from the group consisting of polyethylene, ethylene, polypropylene, polyisobutylene, polyethylene terephthalate, unsaturated polyester, a fluorine-containing resin, polyvinyl chloride, polyvinyliden chloride, polyvinyl acetate, polyvinyl alcohol, polyvinyl acetal, an acrylic resin, polyacrylonitrile, polystyrene, an acetal resin, polycarbonate, polyamide, a phenol resin, a urea resin, an epoxy resin, a melamine resin, a styrene-acrylonitrile copolymer, an acrylonitrile-butadiene-styrene copolymer, a silicon resin, polyphenylene oxide and polysulfone, and glass, quartz glass, alumina, sapphire, forsterite, silicon carbide and a metal oxide. The insulating protective film 6118 may include metal oxide films such as a silicon oxide film and metal nitride films such as a silicon nitride film.

Examples of etching for patterning the insulating protective film 6118 include plasma etching or reactive ion etching using an etching gas.

(2) Array-Type Primer Probe Chip.

Figure 51:
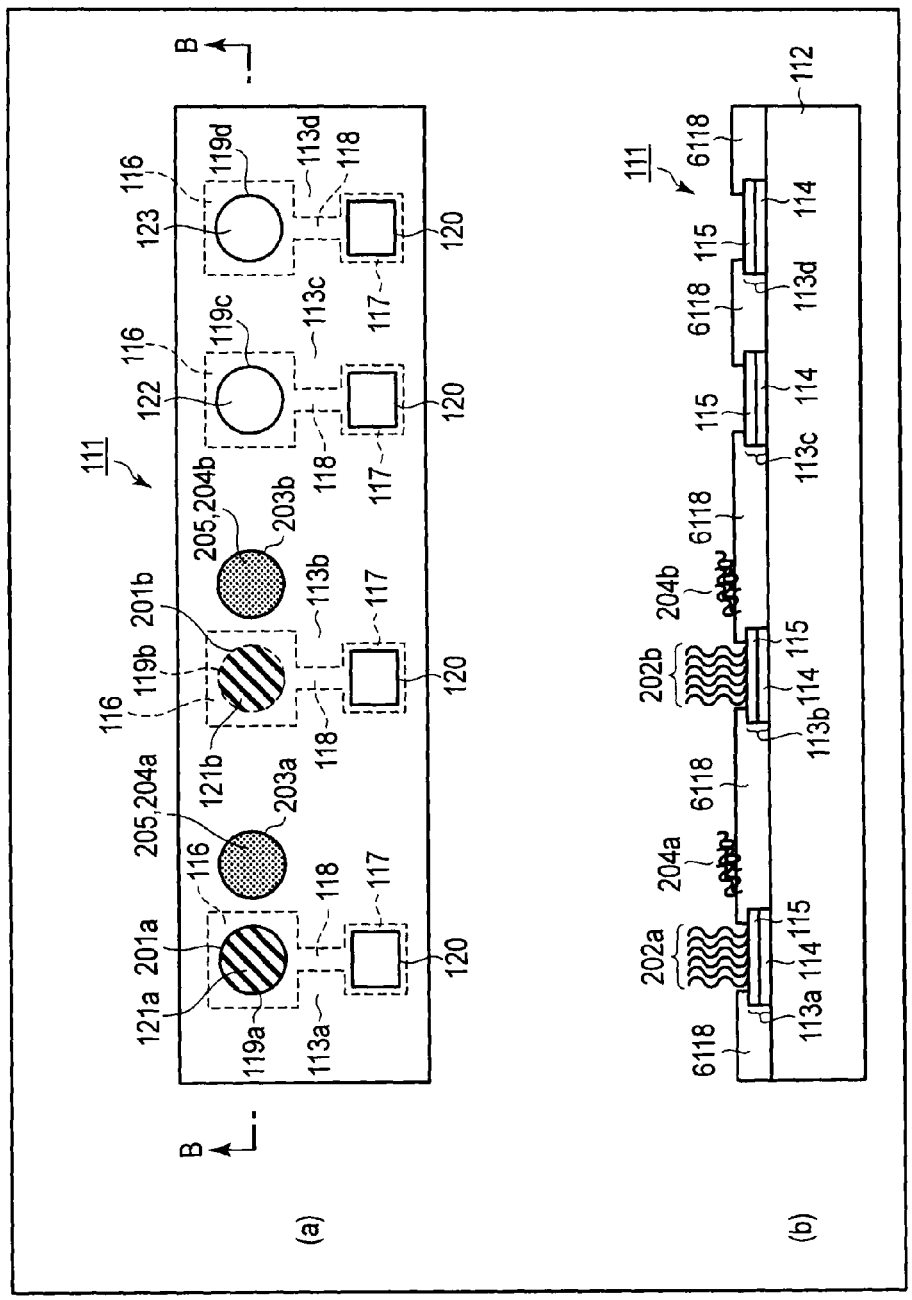
FIG. 51 is a view illustrating an array-type primer probe chip.

Next, an example of the configuration of an array-type primer probe chip with primer sets and probe nucleic acids fixed on the chip material 111 produced in (1) and the method for production of the multi-nucleic-nucleic-acid amplification detection reaction tool will be described with reference to (a) and (b) in FIG. 51. FIG. 51(a) is a plan view of the array-type primer probe chip, and FIG. 51(b) is a sectional view of the array-type primer probe chip taken along line B-B in FIG. 51(a).

The first working electrode 121a of electrode 113a formed on the chip material 111 is defined as a first probe fixing region 201a, and first probe nucleic acids 202a including a complementary sequence of a first object sequence are fixed to the first probe fixing region 201a. The first probe nucleic acids 202a to be fixed are fixed with two or more thereof as one probe nucleic acid group. Similarly, the second working electrode 121b of electrode 113b is defined as a second probe fixing region, and second probe nucleic acids 202b including a complementary sequence of a second object sequence different from the first object sequence are fixed to the second probe fixing region.

Examples of the method for fixing probe nucleic acids 202a and 202b include a method in which a thiol group is introduced into the first probe nucleic acid 202a at the 3'-terminal for the chip material 111 including a metal electrode.

Then, the first primer fixing region 203a is arranged in the vicinity of the first working electrode 121a, and the second primer fixing region 203 b is arranged in the vicinity of the second working electrode 121b. A first primer set 204a is fixed on the first primer fixing region 203a, and a second primer set 204b is fixed on the second primer fixing region 203b. In this way, the array-type primer probe chip is prepared.

The first primer set 204a has a sequence designed to amplify a first target sequence, and the second primer set 204b has a sequence designed to amplify a second target sequence including a sequence different from the first target sequence.

For fixing the first and second primer sets 204a and 204b to the first and second primer fixing regions 203a and 203b, respectively, the primer set is included in a liquid such as, for example, water, a buffer solution or an organic solvent, and the liquid is added dropwise, and left standing under an appropriate temperature condition such as room temperature for a time until the liquid is dried, for example, 10 minutes at room temperature.

(3) Array-Type Primer Probe Chip in Use.

A method for using the array-type primer probe chip prepared in (2) will be described with reference to FIGS. 52 and 53.

FIG. 52(a) is a plan view of the array-type primer probe chip in use, and FIG. 52(b) is a sectional view of the array-type primer probe chip taken along line B-B in FIG. 52(a).

When a array-type primer probe chip 91 of this embodiment is used, the reaction solution is maintained so that the first working electrode 121a, the second working electrode 121b, the counter electrode 122 and the reference electrode 123 formed in electrodes 113a to 113d, respectively, and the first primer fixing region 203a and the second primer fixing region 203b are included in the same single reaction field. Therefore, a cover 301 formed by molding a resin such as, for example, a silicon resin such as a silicon rubber and/or a fluororesin using any resin molding method that is publicly known itself, such as, for example, extrusion molding, injection molding or stamping molding and/or bonding by an adhesive is mounted on the array-type primer probe chip 91 before the array-type primer probe chip 91 is used. After the cover 301 is mounted, a reaction solution 302 containing a template nucleic acid 303 is added to a space formed by array-type primer probe chip 91 and the cover 301.

In the array-type primer probe chip 91 on which the cover 301 is mounted, the small rectangular portion 117 exposed from the rectangular window 120 of each of electrodes 113a to 113d is exposed.

Examples of the method for mounting the cover 301 on the array-type primer probe chip 91 include press bonding and bonding by an adhesive.

Then, the reaction solution 302 is added after the cover 301 is mounted on the array-type primer probe chip 91.

As a method for adding a liquid to a space formed by array-type primer probe chip 91 and the cover 301, for example, an opening may be provided at a part of the cover 301 beforehand, followed by adding the liquid through the opening, or the liquid may be injected through a part of the cover 301 using a syringe having a sharp tip such as a needle-like tip.

The reaction solution 302 includes a sample, an amplification reagent, for example an enzyme such as polymerase, a substrate substance such as deoxynucleoside triphosphate necessary for forming a new polynucleotide chain with a primer as a start point, a reverse transcriptase and a necessary substrate substance, etc., when performing reverse transcription in parallel, and a buffer such as a salt configured to maintain a proper amplification environment and an intercalator that recognizes a double-stranded nucleic acid and generates a signal, such as, for example, Hoechst 33258. When a template nucleic acid including a target sequence to be amplified by a primer set fixed on a specific primer fixing region exists in a sample to be examined, an amplification product is formed in a reaction field including the primer fixing region and a probe fixing region corresponding thereto. This situation is schematically illustrated in FIG. 53.

FIG. 53(a) schematically illustrates a state in which an amplification product is formed in a reaction field 302. FIG. 53(a) is a plan view of the array-type primer probe chip in use, and FIG. 53(b) is a sectional view of the array-type primer probe chip taken along line B-B in FIG. 53(a). A nucleic acid including a sequence with which the second primer set 204b can be bound is included in the sample added in (a) and (b) in FIG. 52 as described above, and therefore as illustrated in (a) and (b) in FIG. 53, the second primer set separated and diffuses to the reaction field 302, and encounters a template nucleic acid, followed by causing an amplification reaction to thereby form an amplification product. The amplification product by the second primer set 204b diffuses to the periphery of the second primer fixing region 203b and arrives at the second probe fixing region 201b. When the arriving amplification product includes an object sequence, the second probe nucleic acid 202b and the amplification product are hybridized to form a double-stranded nucleic acid. An intercalator included in the reaction solution 302 is bounded with the double-stranded nucleic acid to generate a hybridization signal.

The hybridization signal is produced by, for example, bringing a prober into contact with the small rectangular portion 117 exposed from the rectangular window 120 of each of electrodes 113a to 113d, and measuring a current response of an intercalator such as Hoechst 33258.

By using an array-type primer probe chip using electrochemical detection, a target nucleic acid included in a sample can be amplified more easily and quickly, followed by detecting an object nucleic acid included in the amplification product.

Twenty-Second Embodiment

Detection Method

When detection of nucleic acid is performed using an array-type probe chip and an array-type primer probe chip, it may be performed as follows.

(a) Current Detecting Method

A method for electrochemically detecting a double-stranded nucleic acid will be described. In this method, a double strand recognizer which specifically recognizes a double-stranded nucleic acid is used.

Examples of the double strand recognizer include, but are not limited to, Hoechst 33258, acridine orange, quinacrine, daunomycin, metallointercalators, bisintercalators such as bisacridine, trisintercalators and polyintercalators. Further, these materials can be modified with an electrochemically active metal complex, for example ferrocene, viologen or the like.

The concentration of the double strand recognizer varies depending on its type, but is generally in a range of 1 ng/mL to 1 mg/mL. At this time, a buffer solution with an ion intensity of 0.001 to 5 and a pH of 5 to 10 should be used.

A double strand recognizer is added in a reaction solution during or after hybridization reaction. When a double-stranded nucleic acid is produced by hybridization, the double strand recognizer is bounded with the double-stranded nucleic acid. Then, a reaction current value derived from the double strand recognizer can be measured by, for example, applying an electrical potential higher than the electrical potential at which the double strand recognizer is electrochemically reacted. At this time, an electrical potential may be applied at a constant rate, or applied in pulses, or a constant electrical potential may be applied. At the time of the measurement, a current and a voltage may be controlled using a device such as, for example, a potentiostat, a digital multimeter or a function generator. A publicly known electrochemical detection unit as described in, for example, Jpn. Pat. Appln. KOKAI Publication No. 10-146183 is suitably used.

(b) Fluorimetric Detection Method

A method for fluorimetrically detecting a double-stranded nucleic acid will be described. At least one primer included in a primer set is labeled with a fluorimetrically active substance beforehand. Alternatively, a double-stranded nucleic acid is detected using a secondary probe nucleic acid labeled with a fluorimetrically active substance. Alternatively, a plurality of labels may be used. Examples of the fluorimetrically active substance include, but are not limited to, fluorescent dyes such as FITC, Cy3, Cy5 and rhodamine. A fluorescent substance is detected using, for example, a fluorescence detector. A labeled detection sequence or secondary probe nucleic acid is detected using an appropriate detector corresponding to a type of label.

Example 5

Example 5-1

For examining an effect of a protective film on nucleic acid reaction, an amplification reaction was carried out in a chip for amplification, which has a channel as reaction field, without fixing a primer. Thereafter, detection was performed using an array-type probe chip.

(1) Preparation of Chip Material

A wafer-size Pyrex glass was used as a plate-shaped base body (i.e., base plate). A protective film material was applied to the surface by a spin coater. As the protective film material, a negative resist (epoxy), a positive resist (novolak, polyolefin) and a material (novolak) free from a photosensitizer were used.

After each material was applied, the base plate was placed in a drying oven, and prebaking was performed at 150° C. to dry the film.

Subsequently, in the case of the negative photoresist material, exposure was performed at 400 mJ using a close-contact type exposure machine, followed by performing a development treatment. In the case of the positive resist material, an exposure treatment was not performed, but only a development treatment was performed. For materials other than photoresists, either exposure or a development treatment was not performed.

Post baking was performed at 160° C. in a drying oven to fully cure the film. After curing, a chemical dry etching (CDE) treatment was performed for two minutes to form a chip material.

(2) Chip for Amplification

A silicon rubber provided with a channel beforehand was attached to the chip material. This was set as a chip for amplification.

(3) Preparation of LAMP Reaction Solution and LAMP Reaction

Nucleotide sequences of primers used are shown in Table 24.

TABLE 24

LAMP primer sequence

| Primer name | Sequence (5' → 3') | SEQ ID NO. |
|---|---|---|
| 35-13 FIP | GTTTAGTAACTCCAAAGGAGGACAAAGGCAC ACCTTGTAATGC | 223 |
| 35-13 BIP | GGGACATGGTAGACACAGGACATATATCTAG GGGAACATCAC | 224 |
| 35-13 F3 | CCTATAGGTGAACATTGGG | 225 |
| 35-13 B3 | GGATATTTGCAAATGGAACTG | 226 |
| 35-13 Lfc-2 | CATTCTCCTGCTTTTACCTGGT | 227 |

The composition of a LAMP reaction solution is shown in Table 25.

TABLE 25

Composition of LAMP reaction solution

| Reagent name | Volume (μl) |
|---|---|
| Reaction Mixture | 14 |
| 80 μM FIP | 1 |
| 80 μM BIP | 1 |
| 10 μM F3 | 1 |
| 10 μM B3 | 1 |
| 40 μM loop primer* | 1 |
| Bst DMA polymerase | 2 |
| Template (1 × $10^6$ copies/μl) | 2 |
| DW | 27 |
| Total | 50 |

The composition of a reaction mixture to be used for the reaction solution is shown in Table 26.

TABLE 26

Reaction mixture composition table

| | Concentration | Maker |
|---|---|---|
| Tris-HCl (pH 8.8) | 56 mM | Bio Vision Inc |
| KCl | 28 mM | Ambion Co., Ltd |
| $MgSO_4$ | 22 mM | SIGMA Corporation |

TABLE 26-continued

Reaction mixture composition table

| | Concentration | Maker |
|---|---|---|
| $(NH_4)SO_4$ | 28 mM | HAMPTON RESEARCH Corp. |
| Tween20 | 0.20% | Wako Pure Chemical Industries, Ltd. |
| Betaine | 2.2M | S Company |
| dNTPs | 3.9 mM each | Promega K.K. |

The nucleotide sequence of a template included in the LAMP reaction solution is shown in Table 27.

TABLE 27

Nucleotide sequence of template

| Template name | Sequence (5' → 3') | SEQ ID NO. |
|---|---|---|
| HPV35 | TCCTATAGGTGAACATTGGGG AAAAGGCACACCTTGTAATGC TAACCAGGTAAAAGCAGGAGA ATGTCCTCCTTTGGAGTTACTA AACACTGTACTACAAGACGGG GACATGGTAGACACAGGATTTG GTGCAATGGATTTTACTACATT ACAAGCTAATAAAAGTGATGTT CCCCTAGATATATGCAGTTCCA TTTGCAAATATCC | 228 |

The LAMP reaction solution was injected into a channel of the chip for amplification in an amount of 50 μL, the chip for amplification was set in a genelyzer set at a Peltier temperature of 63° C., and a LAMP reaction was carried out for one hour.

<Preparation of DNA Chip for Detection of LAMP Amplification Product>

Figure 50:
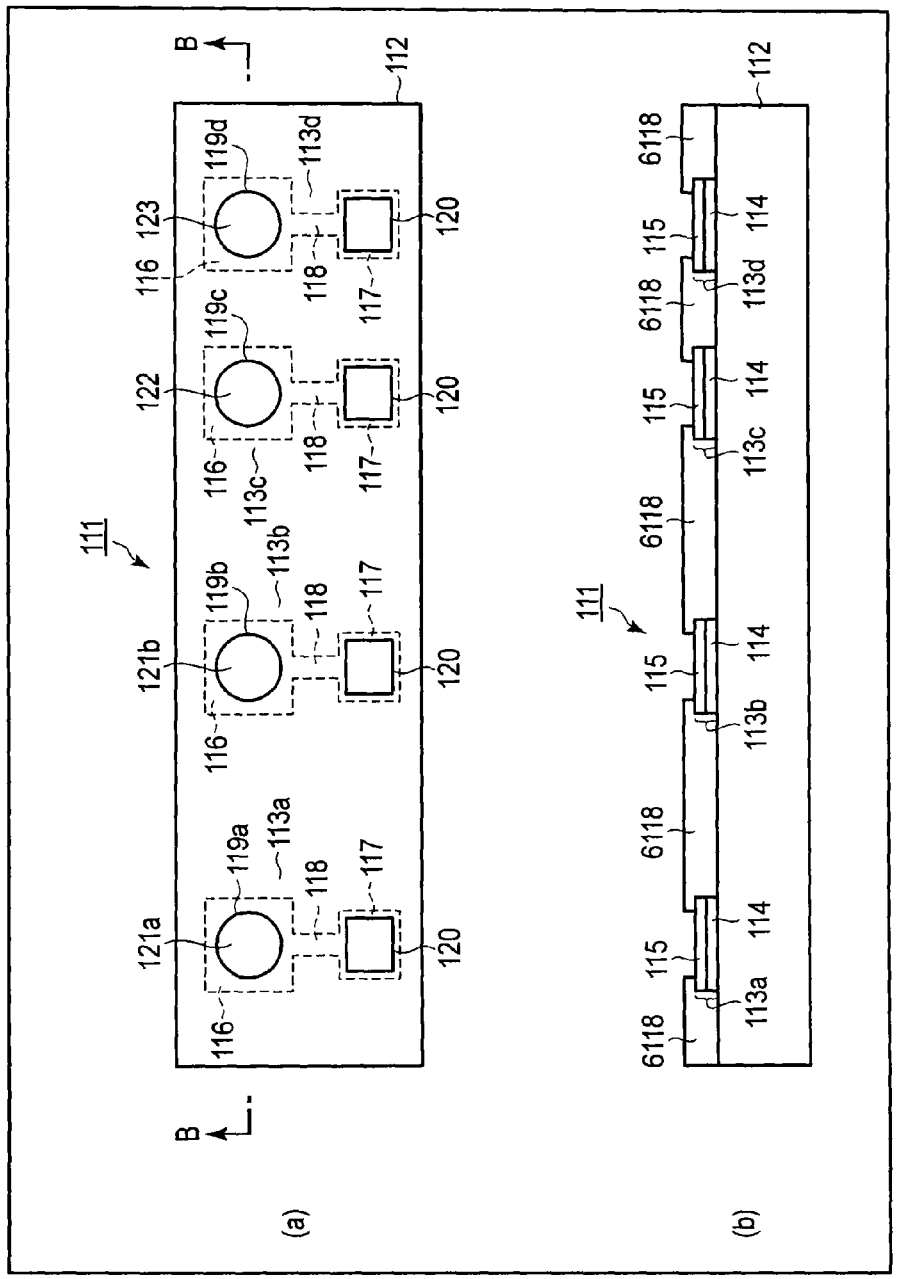
FIG. 50 is a view illustrating a chip material.

(4) Array-Type Probe Chip (a) and (b) in FIG. 50 illustrate outlined views of a chip material for an array-type primer probe chip. A thin film of titanium and gold was formed on the surface of Pyrex glass by sputtering. Thereafter, an electrode of titanium and gold was formed on the glass surface by an etching treatment. Further an insulating film was applied thereon, and a circular window and a rectangular window was opened in the insulating film by an etching treatment to expose a working electrode, a counter electrode, a reference electrode and a prober contact area. This was set as a chip material for an array-type primer probe chip.

(5) Preparation of Array-Type Probe Chip

A probes nucleic acid (3'-terminal SH-labeled synthetic oligo) shown in Table 28 was synthesized.

TABLE 28

| Probe name | Sequence (5' → 3') | SEQ ID NO. |
|---|---|---|
| 35-1-34 | TTTGGTGCAATGGATTTTACTACATTACAAGCTA | 229 |

A probe DNA solution including 3 μM of each of probe DNAs was prepared, and 100 nL of the solution was spotted onto the working electrode. The working electrode was dried at 40° C., and washed with ultrapure water, and ultrapure water remaining on the surface of the working electrode was then removed to fix the probe DNA to the working electrode of the chip material.

For details of the DNA chip and the DNA chip measurement apparatus, see the document (SICE Journal of Control, Measurement and System Integration, Vol. 1, No. 3, pp. 266-270, 2008).

<Detection of LAMP Amplification Product>

For testing influences of each protective film on an amplification reaction, a LAMP amplification product amplified in the chip for amplification was detected using an array-type probe chip.

The results are shown in Table 29.

TABLE 29

| Protective film material | Results of detection of LAMP amplification product |
|---|---|
| Novolak resin (containing a naphthoquinone-based photosensitizer) | Negative |
| Novolak resin | Positive |
| Epoxy resin | Positive |
| Polyolefin resin | Positive |
| Silicon resin | Positive |

As shown in Table 29, the hybridization signal was negative when a novolak resin (containing a naphthoquinone-based photosensitizer) was used for the protective film. The hybridization signal was positive when a novolak resin, an epoxy resin, a polyolefin resin and a silicon resin were used for the protective film.

Therefore, it has become evident that a novolak resin (containing a naphthoquinone-based photosensitizer) influences a nucleic acid reaction such as an amplification reaction. On the other hand, it has become evident that a novolak resin, an epoxy resin, a polyolefin resin and a silicon resin have a low possibility of influencing a nucleic acid reaction such as an amplification reaction.

The novolak resin (containing a naphthoquinone-based photosensitizer) is an example which is used as a positive resist in production of a device intended to carry out a nucleic acid reaction in general. It has become evident in this test that such a material influences a nucleic acid reaction. In a device intended to carry out a nucleic acid reaction, it is necessary to avoid a material that influences a nucleic acid reaction.

From the results described above, it has been shown that a novolak resin, an epoxy resin, a polyolefin resin and a silicon resin are materials which are preferably used in a device intended to carry out a nucleic acid reaction.

Example 5-2

An example will be described below in which an array-type primer probe chip for electrochemical detection including a primer set fixed on a primer fixing region and a probe DNA as a probe nucleic acid fixed on a probe fixing region in the vicinity of the primer fixing region was prepared and used. The probe fixing region included an electrode, and was used as a sensor for detecting a current response generated depending on the existence of hybridization.

(1) Preparation of Chip Material

FIG. 50 illustrates an outlined view of a chip material for an array-type primer probe chip. A thin film of titanium and gold was formed on the surface of Pyrex glass by sputtering. Thereafter, an electrode of titanium and gold was formed on the glass surface by an etching treatment. Further an insulating film was applied thereon, and a circular window and a rectangular window was opened in the insulating film by an etching treatment to expose a working electrode, a counter electrode, a reference electrode and a prober contact area. This was set as a chip material for an array-type primer probe chip.

(2) Preparation of Array-Type Primer Probe Chip

First, a probe DNA was fixed on a working electrode. Nucleotide sequences of probe DNAs used are shown in Table 30.

TABLE 30

List of probe DNAs

| | Nucleotide sequence (5' → 3') | SEQ ID NO. |
|---|---|---|
| Probe DNA (A) | ACCAATAAGGTTTATTGAATATTTGGGCATCAGA-SH | 230 |
| Probe DNA (B) | TTTGGTGCAATGGATTTTACTACATTACAAGCTA-SH | 231 |

3'-terminal modified with thiol

A probe DNA solution including 3 μM of each of probe DNA (A) and probe DNA (B) was prepared, and 100 nL of the solution was spotted onto the working electrode. The working electrode was dried at 40° C., and washed with ultrapure water, and ultrapure water remaining on the surface of the working electrode was then removed to fix the probe DNA to the working electrode of the chip material.

Next, a primer DNA to be used as a primer set was provided. The primer DNA to be used is a primer set for amplification by the loop-mediated isothermal amplification (LAMP). Nucleotide sequences of primer DNAs used are shown in Table 31.

TABLE 31

List of primer sets

| Primer set | Primer type | Nucleotide sequence (5' → 3') | SEQ ID NO. |
|---|---|---|---|
| A | FIP | GTGGCCCTGTGCTCGTTGTCTATGGTTACCTCTGATGCC | 232 |
| | BIP | CACGCAGTACAAATATGTCACCCCATGTCGTAGGTACTCC | 233 |
| | F3 | CAAATTATTTTCCTACACCTAGTGG | 234 |
| | B3 | GTCATAACGTCTGCAGTTAAGG | 235 |
| | LP | GCTGCCATATCTACTTCAGAAACTACA | 236 |
| B | FIP | GTTTAGTAACTCCAAAGGAGGACAAAGGCACACCTTGTAATGC | 237 |
| | BIP | GGGACATGGTAGACACAGGACATATATCTAGGGGAACATCAC | 238 |
| | F3 | CCTATAGGTGAACATTGGG | 239 |
| | B3 | GGATATTTGCAAATGGAACTG | 240 |
| | LP | CATTCTCCTGCTTTTACCTGGT | 241 |

For the primer DNA (set A), FIP, BIP, F3, B3 and LPF each in an amount of 200 μM were provided, and 0.275 μL of solutions including 0.1 μL of FIP, 0.1 μL of BIP, 0.0125 μL of F3, 0.00125 μL of B3 and 0.05 μL of LPF, respectively, were used to fix the primer DNA to a working electrode as a primer fixing region in the vicinity of the corresponding probe DNA (A). Specifically, the provided solutions each in an amount of 0.275 μL were each spotted on a working electrode in the vicinity of an area on which the probe DNA (A) was fixed, and the solutions were dried at 63° C. for 5 minutes. In this way, an array-type primer probe chip was obtained.

(3) Preparation of LAMP Reaction Solution

The composition of a LAMP reaction solution is shown in Table 32.

TABLE 32

Composition of LAMP solution

| | (μL) |
|---|---|
| Composition (1) | |
| Reaction Mixture | 14.0 |
| Bst DNA Polymerase | 2.0 |
| DW | 33.0 |
| Template B (1.0E+03copies/μL) | 1.0 |
| Total | 50.0 |
| Composition (2) | |
| Reaction Mixture | 14.0 |
| Bst DNA Polymerase | 2.0 |
| DW | 34.0 |
| Total | 50.0 |
| Composition (3) | |
| Reaction Mixture | 14.0 |
| Bst DNA Polymerase | 2.0 |
| DW | 33.0 |
| Template A (1.0E+03copies/μL) | 1.0 |
| Total | 50.0 |
| Composition (4) | |
| Reaction Mixture | 14.0 |
| Bst DNA Polymerase | 2.0 |
| DW | 32.0 |
| Template A (1.0E+03copies/μL) | 1.0 |
| Template B (1.0E+03copies/μL) | 1.0 |
| Total | 50.0 |

For compositions (1) to (4), reaction solutions, which included Bst DNA polymerase and a reaction mix in common and to which distilled water (i.e. DW) was added so that the total amount was 50 μL including the template solution, were used. The composition (1) includes a template B which is detected as an amplification reaction by the LAMP method caused by the primer DNA (set B) and hybridization with the probe DNA (B) occurs. The composition (2) does not include a template, and the composition (3) includes a template A which is detected as an amplification reaction by the LAMP method caused by the primer DNA (set A) and hybridization with the probe DNA (A) occurs. For the composition (1), one including both templates A and B was used. Templates A and B are synthetic oligo DNAs having nucleotide sequences shown in Table 33.

TABLE 33

List of templates

| | | SEQ ID NO. |
|---|---|---|
| Template A | CAAATTATTTTCCTACACCTAGTGGTTCTATGGTTACCTCTGATGCCCAAATATTCAATAAACCTTATTGGTTACAACGAGCACAGGGCCACAATAATGGCATTTGTTGGGGTAACCAACTATTTGTTACTGTTGTTGATACTACACGCAGTACAAATATGTCATTATGTGCTGCCATATCTACTTCAGAAACTACATATAAAAATACTAACTTTAAGGAGTACCTACGACATGGGGAGGAATATGATTTACAGTTTATTTTTCAACTGTGCAAAATAACCTTAACTGCAGACGTTATGAC | 242 |

TABLE 33 -continued

List of templates

| | | SEQ ID NO. |
|---|---|---|
| Template B | CCTATAGGTGAACATTGGGGAAAAGGCACACCTT GTAATGCTAACCAGGTAAAAGCAGGAGAATGTCC TCCTTTGGAGTTACTAAACACTGTACTACAAGAC GGGGACATGGTAGACACAGGATTTGGTGCAATG GATTTTACTACATTACAAGCTAATAAAAGTGATG TTCCCCTAGATATATGCAGTTCCATTTGCAAATA TCC | 243 |

(4) LAMP Amplification Reaction on Array-Type Primer Probe Chip and Detection of Object Nucleic Acid by Probe DNA As schematically illustrated in FIG. 52, a silicon rubber molded as a cover for forming a reaction container was mounted on an array-type primer probe chip so as to include an electrode as a probe fixing region and a primer DNA fixing region, and a LAMP reaction solution was injected into the reaction container through a hole provided in the silicon rubber beforehand, followed by covering the reaction container with a lid. This was installed on a plate set at 63° C. to carry out a LAMP reaction for 60 minutes. As schematically illustrated in FIG. 53, when for a specific primer, a template, which the primer can bound with and which includes a target sequence to be amplified by the primer, is included in a LAMP reaction solution, a LAMP reaction locally proceeds at a site where the primer is fixed, and the resulting LAMP product is hybridized with a probe DNA existing in the vicinity thereof.

After the LAMP reaction for 60 minutes, a hybridization reaction was carried out at 45° C. for 10 minutes, and washing was performed at 45° C. for 10 minutes. Thereafter, the washing solution was removed, and 75 μM of a Hoechst 33258 solution was injected. An electrical potential was swept through each probe nucleic acid fixing working electrode to measure an oxidation current of a Hoechst 33258 specifically bound with a double strand formed by the probe DNA and the LAMP product. The series of reactions described above were carried out in the DNA automatic examination apparatus described in the document (SICE Journal of Control, Measurement and System Integration, Vol. 1, No. 3, pp. 266-270, 2008).

(5) Detection Results

Detection results are shown in Table 34.

TABLE 34

Results of DNA chip detection

| | | | LAMP reaction solution | |
|---|---|---|---|---|
| Working electrode | Probe DNA | Primer DNA | Composition (1) Template B | Composition (2) No template |
| 1 | A | Set A | 0 nA | 0 nA |
| 2 | B | Set B | 70 nA | 0 nA |

Unit: nA

When the LAMP reaction solution composition (1) including a template B was added, a LAMP reaction by a primer DAN (set B) fixed in the vicinity of a second working electrode 121b proceeded, so that the resulting LAMP product reacted with a probe DNA (B), and as a result, a current of 70 nA was obtained.

On the other hand, for a primer DNA (set A) fixed in the vicinity of the first working electrode 121a, the LAMP reaction did not proceed, and a current value was not obtained.

From these two values, it could be determined that the LAMP reaction solution included template B.

When the LAMP reaction solution composition (2) which did not include a template was added, LAMP amplification reactions by the primer DNA (set A) and the primer DNA (set B) in the vicinity of the first and the second working electrodes 121a and 121b, respectively, did not proceed, and a current value was not obtained.

From the above results, it has been shown that when the array-type primer probe chip described in this Example was used, templates included in the LAMP reaction solution could be detected, and the sequences thereof could be identified.

7. DEVICE SUITABLE FOR FULL-AUTOMATIC TREATMENT

As a further embodiment, there are provided a nucleic acid detection cassette and a nucleic acid detector which are suitable for full-automatically performing detection of target nucleic acid subsequent to a pretreatment step.

As systems to detect nucleic acids, systems in which devices such as a nucleic acid extractor, a nucleic acid amplifier, a hybridization device, a nucleic acid detector and a data analyzer are separately used have been heretofore known. In these systems, operations other than those achieved in the above-mentioned devices, that is, adjustment of a sample or transportation of a sample between devices require a manual aid.

In amplification of nucleic acid, there is the problem that if even a very small amount of a different nucleic acid enters a sample before amplification, the nucleic acid is amplified in a large amount, thus causing false detection. It is known that nucleic acid molecules are stable even in a dried state and are adsorbed to various substances, and may float in the air. Therefore, for preventing false detection, strict control systems including prohibition on bringing an amplified sample into a site where the extraction the extraction of nucleic acid is performed, and so on are required.

In recent years, full-automatic nucleic acid detectors that automatically perform steps of from nucleic acid extraction and amplification through to hybridization to detection to data analysis have been developed. However, existing full-automatic nucleic acid detectors are not given reliable measures against the aforementioned ingress of nucleic acid molecules other than objects of detection, and often have a large size, and are therefore used for research purposes. Those given measures the aforementioned problems by employing a closed structure, but a cassette or the like has a large number of components and has a complicated structure, so that downsizing is difficult, and detection costs are increased because these consumption articles are expensive.

When a closed structure is employed in a general full-automatic nucleic acid detector, a plurality of channels for feeding a nucleic acid sample and chemical liquids are each provided with a channel, and each channel is provided with a valve to perform control, so that a cassette or the like has a large number of components and has a complicated structure, and therefore the cassette becomes expensive. The nucleic acid detector also has a complicated structure, is difficult to downsize and becomes expensive because complicated control is required along with the structure of the cassette.

According to a further embodiment, there is provided a small-size sealed nucleic acid detection cassette and nucleic acid detector suitable for automatically performing both amplification of nucleic acid and detection of target nucleic acid consistently.

Twenty-Third Embodiment

FIG. 54 is an exploded perspective view illustrating as an example an outlined configuration of a nucleic acid detection (nucleic acid extraction) cassette 7022 according to this embodiment. The nucleic acid detection cassette 7022 principally includes three components: a channel packing 7001, an upper plate 7002 and a lower plate 7003. FIG. 55 is an exploded perspective view illustrating as an example an outlined configuration of the nucleic acid detection cassette 7022 when the channel packing 7001, the upper plate 7002 and the lower plate 7003 illustrated in FIG. 54 are combined. FIG. 55(*a*) is a perspective view of the nucleic acid detection cassette 7022 viewed from the surface side. In this embodiment, the outer surface of the upper plate 7002 in a direction along which the channel packing 7001, the upper plate 7002 and the lower plate 7003 are stacked is defined as the surface of the nucleic acid detection cassette 7022. FIG. 55(*b*) is a perspective view of the nucleic acid detection cassette 7022 viewed from the back surface side. In this embodiment, the outer surface of the lower plate 7003 in a direction along which the channel packing 7001, the upper plate 7002 and the lower plate 7003 are stacked is defined as the back surface of the nucleic acid detection cassette 7022.

The channel packing 7001 includes an analyte syringe 7004, a washing syringe 7005, an intercalating agent syringe 7006, a channel 7007, a nucleic acid detection channel 7008, a waste liquid channel 7009 and a waste liquid syringe 7010. The channel packing 7001 is in the form of a thin plate having a surface (first surface) and a back surface (second surface) opposite to the surface. The channel packing 7001 has a structure in which the analyte syringe 7004, the washing syringe 7005, the intercalating agent syringe 7006, the channel 7007, the nucleic acid detection channel 7008, the waste liquid channel 7009 and the waste liquid syringe 7010 are formed integrally (molded integrally) as one component. Accordingly, the channel packing 7001 can reduce the number of components. The channel packing 7001 is formed of, for example, a soft material such as silicone or elastomer. The elastomer is a material that is denser than silicone, so that evaporation of a liquid can be more reliably prevented.

The analyte syringe 7004 is in the shape of a container having on the surface an opening for feeding (injecting) a liquid analyte (nucleic acid to be detected, also referred to as an analyte sample or a nucleic acid sample) and having on the back surface a thin film portion that can be easily deformed. Thus, the analyte syringe 7004 can be easily deformed and collapsed by application of pressure from the outside to the thin film portion side. On the other hand, the analyte syringe 7004 is expanded at the thin film portion side when filled with a liquid, for example, in a collapsed state. The analyte syringe 7004 can store an analyte.

The washing syringe 7005 is in the shape of a container having on the surface an opening for feeding a washing liquid and having on the back surface a thin film portion that can be easily deformed. Thus, like the analyte syringe 7004, the washing syringe 7005 can be easily deformed and collapsed by application of pressure from the outside to the thin film portion side. On the other hand, the washing syringe 7005 is expanded at the thin film portion side when filled with a liquid, for example, in a collapsed state. The washing syringe 7005 can store a washing liquid for performing washing after hybridization.

The intercalating agent syringe 7006 is in the shape of a container having on the surface an opening for feeding a liquid intercalating agent (chemical liquid used for detection of nucleic acid) for oxidation/reduction reaction during current detection and having on the back surface a thin film portion that can be easily deformed. Thus, like the analyte syringe 7004, the intercalating agent syringe 7006 can be easily deformed and collapsed by application of pressure from the outside to the thin film portion side. On the other hand, the intercalating agent syringe 7006 is expanded at the thin film portion side when filled with a liquid, for example, in a collapsed state. The intercalating agent syringe 7006 can store an intercalating agent.

The channel 7007 connects the analyte syringe 7004, the washing syringe 7005 and the intercalating syringe 7006 and the nucleic acid detection channel 7008. The channel 7007 further includes independently branched channels 7071, 7072 and 7073. The channel 7007 is connected to the analyte syringe 7004, the washing syringe 7005 and the intercalating syringe 7006 through channels 7071, 7072 and 7073. The channel 7007 is also connected to the nucleic acid detection channel 7008. Therefore, the channel 7007 is a channel for delivering (pouring) a liquid stored by the analyte syringe 7004, the washing syringe 7005 and the intercalating agent syringe 7006 into the nucleic acid detection channel 7008. At connection parts between the analyte syringe 7004, washing syringe 7005 and intercalating syringe 7006 and the channel 7007, check valves 7011*a*, 7011*b* and 7011*c* are provided, respectively. Check valves 7011*a*, 7011*b* and 7011*c* have a function to prevent a liquid from flowing into the analyte syringe 7004, the washing syringe 7005 and the intercalating syringe 7006, respectively, from the channel 7007. Further, check valves 7011*a*, 7011*b* and 7011*c* also have a function to prevent each liquid from accidentally flowing out from the analyte syringe 7004, the washing syringe 7005 and the intercalating syringe 7006, respectively, at a time other than during liquid delivery.

The nucleic acid detection channel 7008 is, for example, a groove provided on the back surface of the channel packing 7001. The nucleic acid detection channel 7008 is connected at the liquid inflow side to the channel 7007 and connected at the outflow side to the waste liquid channel 7009. The nucleic acid detection channel 7008 is a channel (region) for performing extraction of nucleic acid, amplification of nucleic acid, hybridization and detection of nucleic acid.

The waste liquid channel 7009 connects the nucleic acid detection channel 7008 and the waste liquid syringe 7010. The waste liquid channel 7009 is a channel for delivering to the waste liquid syringe 7010 a liquid (waste liquid) flowing out from the nucleic acid detection channel 7008.

The waste liquid syringe 7010 is in the form of a bag having on the back surface of the channel packing 7001, a thin film portion that can be easily deformed. Thus, the waste liquid syringe 7010 can be easily deformed and collapsed by application of pressure from the outside to the thin film side. At a normal time (before inflow of waste liquid), the waste liquid syringe 7010 is in a collapsed (contracted) state with the thin film folded beforehand. The waste liquid syringe 7010 is expanded at the thin film side from the collapsed state when a waste liquid flows into the waste liquid syringe 7010. Therefore, the waste liquid syringe 7010 can store a liquid flowing out from the nucleic acid detection channel 7008.

According to the configuration of the channel packing 7001 described above, the analyte syringe 7004, the washing syringe 7005 and the intercalating agent syringe 7006 are connected to the waste liquid syringe 7010 via the channel 7007, the nucleic acid detection channel 7008 and the waste liquid channel 7009.

The upper plate 7002 includes injection ports 7012a, 7012b and 7012c, a nucleic acid detection port 7014 and a positioning hole 7015. The upper plate 7002 is formed of a hard material such as plastic, glass or metal. The upper plate 7002 is in the shape of a thin plate. The upper plate 7002 faces (is opposite to) the surface of the channel packing 7001, and is in close contact with the surface of the channel packing 7001. That is, the upper plate 7002 is used for sealing (closing) the channel packing 7001.

Injection ports 7012a, 7012b and 7012c are provided at positions facing the analyte syringe 7004 (opening thereof), the washing syringe 7005 (opening thereof) and the intercalating syringe 7006 (opening thereof), respectively. Injection ports 7012a, 7012b and 7012c are openings for filling the analyte syringe 7004, the washing syringe 7005 and the intercalating syringe 7006, respectively, with a liquid after the nucleic acid detection cassette 7022 is assembled. Injection ports 7012a, 7012b and 7012c are sealed using a cap seal 7013 after the analyte syringe 7004, the washing syringe 7005 and the intercalating syringe 7006 are filled with a liquid.

The nucleic acid detection port 7014 is provided at a position in which it does not face the channel packing 7001, but faces a base plate 7020a provided on the lower plate 7003 after the nucleic acid detection cassette 7022 is assembled. The base plate 7020a is connected to a later-described nucleic acid detection portion 7020, and used for transmitting a signal detected by the nucleic acid detection portion 7020 to a nucleic acid detection base plate 7024. The nucleic acid detection port 7014 is an opening for inserting the nucleic acid detection base plate 7024 at the time of detecting a nucleic acid.

The positioning hole 7015 is an opening that is used for positioning (registering) the nucleic acid detection cassette 7022 as described later.

The lower plate 7003 includes an analyte liquid delivery hole 7016, a washing liquid delivery hole 7017, an intercalating agent liquid delivery hole 7018, a depression for waste liquid 7019, a nucleic acid detection portion 7020 and a temperature control hole 7021. The lower plate 7003 is formed of a hard material such as plastic, glass or metal like the upper plate 7002. The lower plate 7003 faces the back surface of the channel packing 7001, and is in close contact with the back surface of the channel packing 7001. That is, the lower plate 7003 is in the shape of a thin plate. The lower plate 7003 is used for sealing the channel packing 7001 along with the upper plate 7002.

The analyte liquid delivery hole 7016 is provided at a position facing the analyte syringe 7004 in the lower plate 7003. The analyte liquid delivery hole 7016 is an open provided so that expansion of the analyte syringe 7004 toward the lower plate 7003 side is not prevented even when an analyte is stored in the analyte syringe 7004 in a full state. Thus, on the back surface side of the nucleic acid detection cassette 7022, the bottom part (thin film portion side) of the analyte syringe 7004 is exposed from the inside of the lower plate 7003 through the analyte liquid delivery hole 7016 as illustrated in FIG. 55.

The washing liquid delivery hole 7017 is provided at a position facing the washing syringe 7005 in the lower plate 7003. The washing liquid delivery hole 7017 is an open provided so that expansion of the washing syringe 7005 toward the lower plate 7003 side is not prevented even when an analyte is stored in the washing syringe 7005 in a full state. Thus, on the back surface side of the nucleic acid detection cassette 7022, the bottom part (thin film portion side) of the washing syringe 7005 is exposed from the inside of the lower plate 7003 through the washing liquid delivery hole 7017 as illustrated in FIG. 55.

The intercalating agent liquid delivery hole 7018 is provided at a position facing the intercalating agent syringe 7006 in the lower plate 7003. The intercalating agent liquid delivery hole 7018 is an open provided so that expansion of the intercalating agent syringe 7006 toward the lower plate 7003 side is not prevented even when an analyte is stored in intercalating agent syringe 7006 in a full state. Thus, on the back surface side of the nucleic acid detection cassette 7022, the bottom part (thin film side) of the intercalating agent syringe 7006 is exposed from the inside of the lower plate 7003 through the intercalating agent liquid delivery hole 7018 as illustrated in FIG. 55.

The depression for waste liquid 7019 is provided on a surface of the lower plate 7003, which faces the surface of the channel packing 7001, and at a position facing the waste liquid syringe 7010. The depression for waste liquid 7019 is a depression (gap) provided so that expansion of the waste liquid syringe 7010 toward the lower plate 7003 side is not prevented even when an analyte is stored in the waste liquid syringe 7010 in a full state.

The nucleic acid detection portion 7020 is provided on a surface of the lower plate 7003, which faces the back surface of the channel packing 7001, and at a position facing the nucleic acid detection channel 7009. The nucleic acid detection portion 7020 performs detects a target nucleic acid. The nucleic acid detection portion 7020 is a sensor region on which a nucleic acid probe is fixed.

The temperature control hole 7021 is provided on a surface corresponding to the back surface of the nucleic acid detection cassette 7022 and at a position facing the nucleic acid detection portion 7020. That is, the nucleic acid detection portion 7020 is exposed from the inside of the lower plate 7003 through the temperature control hole 7021. The temperature control hole 7021 is an opening for directly heating and cooling the nucleic acid detection portion 7020 with high accuracy during detection of nucleic acid.

As described above, three components, that is, the channel packing 7001, the upper plate 7002 and the lower plate 7003 are combined such that the channel packing 7001 is held between the upper plate 7002 and the lower plate 7003. The channel packing 7001 is pressurized by the upper plate 7002 and the lower plate 7003, and therefore maintains sealing performance. That is, the nucleic acid detection cassette 7022 is a sealing container to ensure sealing performance of the channel packing 7001. The nucleic acid detection cassette 7022 can prevent a nucleic acid from leaking to the outside owing to sealing performance of the channel packing 7001. The method for joining the upper plate 7002 and the lower plate 7003 is not limited, and various methods such as bonding, welding and screw clamping can be employed.

FIG. 56 is a perspective view illustrating as an example an outlined configuration of a nucleic acid detector 7100 using the nucleic acid detection cassette 7022 according to this embodiment. In this embodiment, the nucleic acid detection cassette 7022 and the nucleic acid detector 7100 are described as separate configurations, but the nucleic acid detector 7100 may include the nucleic acid detection cassette 7022.

The nucleic acid detector 7100 includes a cassette stand 7023, a nucleic acid detection base plate 7024, a positioning pin 7025, a nucleic acid detection base plate front/rear mechanism 7026, a heating and cooling device 7027, heating and cooling device front/rear mechanism 7028, an analyte liquid delivery rod 7029, a washing liquid delivery rod 7030, an intercalating agent liquid delivery rod 7031, a rod front/rear mechanism (movement mechanism) 7032 and springs 7033*a*, 7033*b* and 7033*c*.

The cassette stand 7023 is provided in the vicinity of the center of the nucleic acid detector 7100. The cassette stand 7023 holds the nucleic acid detection cassette 7022. The cassette stand 7023 is, for example, a slot into which the nucleic acid detection cassette 7022 is removably insertable.

The nucleic acid detection base plate 7024 is provided at a position in which it faces the nucleic acid detection port 7014 when the nucleic acid detection cassette 7022 is inserted into the cassette stand 7023. The nucleic acid detection base plate 7024 has a size such that it is removably insertable to the nucleic acid detection port 7014. The nucleic acid detection base plate 7024 is a base plate configured to acquire a signal detected by the nucleic acid detection portion 7020 to perform detection of nucleic acid, thereby determining the existence of a targeted nucleic acid.

The positioning pin 7025 is provided at a position in which it faces the positioning hole 7015 when the nucleic acid detection cassette 7022 is inserted into the cassette stand 7023. The positioning pin 7025 positions the nucleic acid detection cassette 7022 with respect to the nucleic acid detector 7100.

The nucleic acid detection base plate front/rear mechanism 7026 has the nucleic acid detection base plate 7024 and the positioning pin 7025 mounted thereon. The nucleic acid detection base plate front/rear mechanism 7026 can cause the nucleic acid detection base plate 7024 and the positioning pin 7025 to move as one united body at the same time in a front-rear direction. In this embodiment, a direction of going toward or away from the nucleic acid detection cassette 7022 (or cassette stand 7023) is the front-rear direction. The nucleic acid detection base plate front/rear mechanism 7026 fits the nucleic acid detection base plate 7024 and the positioning pin 7025 to the back surface of the nucleic acid detection cassette 7022. The nucleic acid detection base plate 7024 comes into contact with the base plate of the lower plate 7003 through the nucleic acid detection port 7014. The positioning pin 7025 is inserted into the positioning hole 7015 to position the nucleic acid detection cassette 7022 with respect to the nucleic acid detector 7100.

The heating and cooling device 7027 is provided at a position in which it faces the temperature control hole 7021 when the nucleic acid detection cassette 7022 is inserted into the cassette stand 7023. The heating and cooling device 7027 has a size such that it is removably insertable to the temperature control hole 7021. The heating and cooling device 7027 controls the nucleic acid detection portion 7020 (nucleic acid detection channel 7008 facing the nucleic acid detection portion 7020) to have an optimum temperature.

The heating and cooling device front/rear mechanism 7028 has the heating and cooling device 7027 mounted thereon. That is, the heating and cooling device 7027 and the heating and cooling device front/rear mechanism 7028 are provided on a side opposite to the nucleic acid detection base plate front/rear mechanism 7026 with respect to the cassette stand 7023. The heating and cooling device front/rear mechanism 7028 can cause the heating and cooling device 7027 to move in a front-rear direction. The nucleic acid detection base plate front/rear mechanism 7026 fits the heating and cooling device 7027 to the back surface of the nucleic acid detection cassette 7022. The heating and cooling device 7027 is fitted into the temperature control hole 7021 to come into contact with the nucleic acid detection portion 7020.

The analyte liquid delivery rod 7029 is provided at a position in which it faces the analyte liquid delivery hole 7016 when the nucleic acid detection cassette 7022 is inserted into the cassette stand 7023. The analyte liquid delivery rod 7029 has a function to pressurize the thin film portion of the analyte syringe 7004 through the analyte liquid delivery hole 7016, thereby delivering an analyte in the analyte syringe 7004 to the channel 7007. The analyte liquid delivery rod 7029 has a surface orthogonal to the front-rear direction at a tip portion facing the nucleic acid detection cassette 7022. The surface of the tip portion of the analyte liquid delivery rod 7029 has substantially the same shape of the analyte liquid delivery hole 7016. The width of the tip portion of the analyte liquid delivery rod 7029 in the front-rear direction is substantially the same as a distance between the back surface of the nucleic acid detection cassette 7022 and the opening of the analyte syringe 7004 (a surface of the upper plate 7002 in contact therewith) in the front-back direction of the nucleic acid detection cassette 7022. Therefore, the analyte liquid delivery rod 7029 can completely collapse the thin film portion of the analyte syringe 7004, so that an analyte in the analyte syringe 7004 can be entirely delivered to the channel 7007.

The washing liquid delivery rod 7030 is provided at a position in which it faces the washing liquid delivery hole 7017 when the nucleic acid detection cassette 7022 is inserted into the cassette stand 7023. The washing liquid delivery rod 7030 has a function to pressurize the thin film portion of the washing syringe 7005 through the washing liquid delivery hole 7017, thereby delivering an analyte in the washing syringe 7005 to the channel 7007. The washing liquid delivery rod 7030 has a surface orthogonal to the front-rear direction at a tip portion facing the nucleic acid detection cassette 7022. The surface of the tip portion of the washing liquid delivery rod 7030 has substantially the same shape of the washing liquid delivery hole 7017. The width of the tip portion of the washing liquid delivery rod 7030 in the front-rear direction is substantially the same as a distance between the back surface of the nucleic acid detection cassette 7022 and the opening of the washing syringe 7005 (a surface of the upper plate 7002 in contact therewith) in the front-back direction of the nucleic acid detection cassette 7022. Therefore, the washing liquid delivery rod 7030 can completely collapse the thin film portion of the washing syringe 7005, so that an analyte in the washing syringe 7005 can be entirely delivered to the channel 7007.

The intercalating agent liquid delivery rod 7031 is provided at a position in which it faces the intercalating agent liquid delivery hole 7018 when the nucleic acid detection cassette 7022 is inserted into the cassette stand 7023. The intercalating agent liquid delivery rod 7031 has a function to pressurize the thin film portion of the intercalating agent syringe 7006 through the intercalating agent liquid delivery hole 7018, thereby delivering an analyte in the intercalating agent syringe 7006 to the channel 7007. The intercalating agent liquid delivery rod 7031 has a surface orthogonal to the front-rear direction at a tip portion facing the nucleic acid detection cassette 7022. The surface of the tip portion of the intercalating agent liquid delivery rod 7031 has substantially the same shape of the washing liquid delivery hole 7017. The width of the tip portion of the intercalating agent liquid delivery rod 7031 in the front-rear direction is substantially the same as a distance between the back surface of the nucleic acid detection cassette 7022 and the opening of the intercalating agent syringe 7006 (a surface of the upper plate 7002 in contact therewith) in the front-back direction of the nucleic acid detection cassette 7022. Therefore, the intercalating agent liquid delivery rod 7031 can completely collapse the thin film portion of the intercalating agent syringe 7006, so that an analyte in the intercalating agent syringe 7006 can be entirely delivered to the channel 7007.

The rod front/rear mechanism 7032 has the analyte liquid delivery rod 7029, the washing liquid delivery rod 7030 and the intercalating agent liquid delivery rod 7031 mounted thereon. That is, the analyte liquid delivery rod 7029, the washing liquid delivery rod 7030, the intercalating agent liquid delivery rod 7031 and the rod front/rear mechanism 7032 are provided on a side opposite to the nucleic acid detection base plate front/rear mechanism 7026 with respect to the cassette stand 7023. The rod front/rear mechanism 7032 can cause the analyte liquid delivery rod 7029, the washing liquid delivery rod 7030 and the intercalating agent liquid delivery rod 7031 to move as one united body at the same time in a front-rear direction with respect to the nucleic acid detection cassette 7022. The rod front/rear mechanism 7032 abuts the analyte liquid delivery rod 7029, the washing liquid delivery rod 7030 and the intercalating agent liquid delivery rod 7031 against the back surface of the nucleic acid detection cassette 7022. The analyte liquid delivery rod 7029 comes into contact with the thin film portion of the analyte syringe 7004 through the analyte liquid delivery hole 7016, and pressurizes the thin film portion. Similarly, the washing liquid delivery rod 7030 comes into contact with the thin film portion of the washing syringe 7005 through the washing liquid delivery hole 7017, and pressurizes the thin film portion. The intercalating agent liquid delivery rod 7031 comes into contact with the thin film portion of the intercalating agent syringe 7006 through the intercalating agent liquid delivery hole 7018, and pressurizes the thin film portion.

A mounting position relationship of the analyte liquid delivery rod 7029, the washing liquid delivery rod 7030 and the intercalating agent liquid delivery rod 7031 in the rod front/rear mechanism 7032 will now be described. A mounting position relationship for the analyte liquid delivery rod 7029 and the washing liquid delivery rod 7030 is as follows. Before all of the analyte liquid delivery rod 7029, the washing liquid delivery rod 7030 and the intercalating agent liquid delivery rod 7031 come into contact with the nucleic acid detection cassette 7022, the tip portion of the analyte liquid delivery rod 7029 is situated closer by a predetermined distance in a front-rear direction to the nucleic acid detection cassette 7022 than the tip portion of the washing liquid delivery rod 7030. Here, the predetermined distance is, for example, a distance greater than or equal to the width of the tip portion of the analyte liquid delivery rod 7029. That is, when the analyte liquid delivery rod 7029, the washing liquid delivery rod 7030 and the intercalating agent liquid delivery rod 7031 move toward the nucleic acid detection cassette 7022, the washing liquid delivery rod 7030 does not start delivering a washing agent in the washing syringe 7005 to the channel 7007 by coming into contact with the thin film portion of the washing syringe 7005 before the analyte liquid delivery rod 7029 completely collapses the thin film portion of the analyte syringe 7004 to deliver an analyte in the analyte syringe 7004 entirely to the channel 7007.

A mounting position relationship for the washing liquid delivery rod 7030 and the intercalating agent liquid delivery rod 7031 is as follows. Under the same conditions as those described above, the tip portion of the washing liquid delivery rod 7030 is situated closer by a predetermined distance in a front-rear direction to the nucleic acid detection cassette 7022 than the tip portion of the intercalating agent liquid delivery rod 7031. Here, the predetermined distance is, for example, a distance greater than or equal to the width of the tip portion of the washing liquid delivery rod 7030. That is, when the analyte liquid delivery rod 7029, the washing liquid delivery rod 7030 and the intercalating agent liquid delivery rod 7031 move toward the nucleic acid detection cassette 7022, the intercalating agent liquid delivery rod 7031 does not start delivering an intercalating agent in the intercalating agent syringe 7006 to the channel 7007 by coming into contact with the thin film portion of the intercalating agent syringe 7006 before the washing liquid delivery rod 7030 completely collapses the thin film portion of the washing syringe 7005 to deliver a washing agent in the washing syringe 7005 entirely to the channel 7007.

In view of the relationships described above, a mounting position relationship for the analyte liquid delivery rod 7029 and the intercalating agent liquid delivery rod 7031 is as follows. Under the same conditions as those described above, the tip portion of the analyte liquid delivery rod 7029 is situated closer by a predetermined distance in a front-rear direction to the nucleic acid detection cassette 7022 than the tip portion of the intercalating agent liquid delivery rod 7031.

Springs 7033*a*, 7033*b* and 7033*c* are provided between the analyte liquid delivery rod 7029, washing liquid delivery rod 7030 and intercalating agent liquid delivery rod 7031 and the rod front/rear mechanism 7032, respectively. Springs 7033*a*, 7033*b* and 7033*c* have elasticity such that they are extensible and contractible in a front-rear direction (traveling direction of rod front/rear mechanism 7032).

Springs 7033*a*, 7033*b* and 7033*c* contracts in a front-rear direction, respectively, when the analyte liquid delivery rod 7029, the washing liquid delivery rod 7030 and the intercalating agent liquid delivery rod 7031 come into contact with the nucleic acid detection cassette 7022. Other elastic bodies may be used in place of springs 7033. A mechanical structure, which contracts in a front-rear direction when the analyte liquid delivery rod 7029, the washing liquid delivery rod 7030 and the intercalating agent liquid delivery rod 7031 come into contact with the nucleic acid detection cassette 7022, may be used in place of springs 7033*a*, 7033*b* and 7033*c*.

Next, an example of a process (method) for using the nucleic acid detection cassette 7022 and the nucleic acid detector 7100 according to this embodiment and a process for detection of nucleic acid using the same will be described. The process described below is an example, and can be appropriately replaced.

First, an example of a process for providing the nucleic acid detection cassette 7022 will be described. The analyte syringe 7004 and the washing syringe 7005 and the intercalating agent syringe 7006 of the nucleic acid detection cassette 7022 sealed as illustrated in FIG. 55 are filled with an analyte, a washing liquid and an intercalating agent through injection ports 7012*a*, 7012*b* and 7012*c*, respectively. Injection ports 7012 are sealed using a cap seal 7013. The nucleic acid detection cassette 7022 is inserted into the cassette stand 7023 such that a portion provided with the analyte syringe 7004, the washing syringe 7005 and the intercalating agent syringe 7006 is situated on the upper side and the upper plate 7002 faces the nucleic acid detection base plate 7024.

Next, a process for using the nucleic acid detector 7100 with the nucleic acid detection cassette 7022 inserted in the cassette stand 7023 will be described.

First, the nucleic acid detection base plate front/rear mechanism 7026 is actuated. The nucleic acid detection base plate front/rear mechanism 7026 causes the nucleic acid detection base plate 7024 and the positioning pin 7025 to move forward to the nucleic acid detection cassette 7022. The nucleic acid detection base plate front/rear mechanism 7026 causes the nucleic acid detection base plate 7024 to move to a detection position (contact position with the base plate 7020*a* of the lower plate 7003). At the same time, the nucleic acid detection base plate front/rear mechanism 7026 causes the positioning pin 7025 to move to the positioning hole 7015 of the nucleic acid detection cassette 7022 to be inserted into the positioning hole 7015. The nucleic acid detection cassette 7022 is positioned with respect to the nucleic acid detector 7100 as the positioning pin 7025 is inserted into the positioning hole 7015.

Next, the heating and cooling device front/rear mechanism 7028 is actuated. The heating and cooling device front/rear mechanism 7028 causes the heating and cooling device 7027 to move forward to the nucleic acid detection cassette 7022. The heating and cooling device front/rear mechanism 7028 causes the heating and cooling device 7027 to move through the temperature control hole 7021 to a position in which the heating and cooling device 7027 comes into contact with the nucleic acid detection portion 7020.

Next, the rod front/rear mechanism 7032 is actuated. The rod front/rear mechanism 7032 causes the analyte liquid delivery rod 7029, the washing liquid delivery rod 7030 and the intercalating agent liquid delivery rod 7031 to move forward to the nucleic acid detection cassette 7022. The rod front/rear mechanism 7032 abuts the analyte liquid delivery rod 7029 against the analyte syringe 7004 through the analyte liquid delivery hole 7016. The analyte syringe 7004 has a thin film structure and is easily deformed as described above. Thus, an analyte is pressurized by the analyte liquid delivery rod 7029 to be delivered via the channel 7007 to the nucleic acid detection channel 7008. The rod front/rear mechanism 7032 causes the analyte liquid delivery rod 7029 to move forward until the analyte syringe 7004 is completely collapsed to deliver every analyte to the channel 7007. The tip portion of the washing liquid delivery rod 7030 and the tip portion of the intercalating agent liquid delivery rod 7031 are not in contact with the washing syringe 7005 and the intercalating agent syringe 7006, respectively, due to the position relationship with the analyte liquid delivery rod 7029 as described above.

At this time, air in the nucleic acid detection channel 7008 is pushed out by the analyte and flows into the waste liquid syringe 7010 via the waste liquid channel 7009. The waste liquid syringe 7010 is slightly expanded as the internal pressure is increased by air flowing therein. The waste liquid syringe 7010 secures a capacity to accommodate inflow of a waste liquid as a result of expansion. The capacity of the analyte syringe 7004 is substantially equal to a volume to fill the channel 7007, the nucleic acid detection channel 7008 and the waste liquid channel 7009. Therefore, every analyte delivered from the analyte syringe 7004 to the channel 7007 fills the channel 7007, the nucleic acid detection channel 7008 and the waste liquid channel 7009, but does not flow out to the waste liquid syringe 7010.

Next, the heating and cooling device front/rear mechanism 7028 is actuated. The heating and cooling device front/rear mechanism 7028 causes the heating and cooling device 7027 to move forward to the nucleic acid detection cassette 7022. The heating and cooling device front/rear mechanism 7028 causes the heating and cooling device 7027 to come into contact with the nucleic acid detection portion 7020 through the temperature control hole 7021. Next, the heating and cooling device 7027 is actuated to heat an analyte. Since a primer for amplification is fixed on the inner wall of the nucleic acid detection channel 7008 beforehand, the primer is eluted into the analyte. In the nucleic acid detection channel 7008, amplification of nucleic acid is performed, and simultaneously hybridization with a probe electrode fixed on the nucleic acid detection portion 7020 is performed.

Next, the rod front/rear mechanism 7032 is actuated again. The rod front/rear mechanism 7032 causes the analyte liquid delivery rod 7029, the washing liquid delivery rod 7030 and the intercalating agent rod 7031 to move forward to the nucleic acid detection cassette 7022. The rod front/rear mechanism 7032 abuts the washing liquid delivery rod 7030 against the washing syringe 7005 through the washing liquid delivery hole 7017. The analyte liquid delivery rod 7029 configured to be extensible and contractible with the spring 7033$a$ as described above. Therefore, even when the rod front/rear mechanism 7032 causes the analyte liquid delivery rod 7029 to further move to the nucleic acid detection cassette 7022 side, the analyte liquid delivery rod 7029 does not collapse the nucleic acid detection cassette 7022 because the spring 7033 contracts.

The washing syringe 7005 has a thin film structure and is easily deformed as described above. Thus, a washing liquid is pressurized by the washing liquid delivery rod 7030 to be delivered via the channel 7007 to the nucleic acid detection channel 7008. The washing liquid washes the nucleic acid detection channel 7008. The rod front/rear mechanism 7032 causes the washing liquid delivery rod 7030 to move forward until the washing syringe 7005 is completely collapsed to deliver every analyte to the channel 7007. The tip portion of the intercalating agent liquid delivery rod 7031 is not in contact with the intercalating agent syringe 7006 due to the position relationship with the washing liquid delivery rod 7030 as described above.

The capacity of the washing syringe 7005 is substantially equal to a volume to fill the channel 7007, the nucleic acid detection channel 7008 and the waste liquid channel 7009. Therefore, every washing liquid delivered from the washing syringe 7005 to the channel 7007 pushes out the analyte, which has filled the channel 7007, the nucleic acid detection channel 7008 and the waste liquid channel 7009, to the waste liquid syringe 7010, and fills the channel 7007, the nucleic acid detection channel 7008 and the waste liquid channel 7009 in place of the analyte. That is, the analyte in the nucleic acid detection channel 7008 entirely flows into the waste liquid syringe 7010 through the waste liquid channel 7009. The washing liquid fills the channel 7007, the nucleic acid detection channel 7008 and the waste liquid channel 7009, but does not flow out to the waste liquid syringe 7010. The waste liquid syringe 7010 is easily expanded, and is therefore further swollen by the analyte flowing therein.

Next, the rod front/rear mechanism 7032 is actuated again. The rod front/rear mechanism 7032 causes the analyte liquid delivery rod 7029, the washing liquid delivery rod 7030 and the intercalating agent rod 7031 to move forward to the nucleic acid detection cassette 7022. The rod front/rear mechanism 7032 abuts the intercalating agent liquid delivery rod 7031 against the intercalating agent syringe 7006 through the intercalating agent liquid delivery hole 7018. The washing liquid delivery rod 7030 configured to be extensible and contractible with the spring 7033$b$ as described above. Therefore, even when the rod front/rear mechanism 7032 causes the washing liquid delivery rod 7030 to further move to the nucleic acid detection cassette 7022 side again, the washing liquid delivery rod 7030 does not collapse the nucleic acid detection cassette 7022 because the spring 7033$b$ contracts.

The intercalating agent syringe 7006 has a thin film structure and is easily deformed as described above. Thus, an intercalating agent is pressurized by the intercalating agent liquid delivery rod 7031 to be delivered via the channel 7007 to the nucleic acid detection channel 7008. In the nucleic acid detection channel 7008, a nucleic acid detection reaction is carried out by the intercalating agent. The rod front/rear mechanism 7032 causes the intercalating agent liquid delivery rod 7031 to move forward until the intercalating agent syringe 7006 is completely collapsed to deliver every analyte to the channel 7007.

The capacity of the intercalating agent syringe 7006 is substantially equal to a volume to fill the channel 7007, the nucleic acid detection channel 7008 and the waste liquid channel 7009. Therefore, every intercalating agent delivered from the intercalating agent syringe 7006 to the channel 7007 pushes out the washing liquid, which has filled the channel 7007, the nucleic acid detection channel 7008 and the waste liquid channel 7009, to the waste liquid syringe 7010, and fills the channel 7007, the nucleic acid detection channel 7008 and the waste liquid channel 7009 in place of the washing liquid. That is, the washing liquid in the nucleic acid detection channel 7008 entirely flows into the waste liquid syringe 7010 through the waste liquid channel 7009. The intercalating agent fills the channel 7007, the nucleic acid detection channel 7008 and the waste liquid channel 7009, but does not flow out to the waste liquid syringe 7010. The waste liquid syringe 7010 is easily expanded, and is therefore further swollen by the washing liquid flowing therein.

As described above, the rod front/rear mechanism 7032 sequentially collapses the analyte syringe 7004, washing syringe 7005 and intercalating agent syringe 7006 with the analyte liquid delivery rod 7029, the washing liquid delivery rod 7030 and the intercalating agent rod 7031, which are provided side by side, to sequentially deliver the liquid to the nucleic acid detection channel 7008. The waste liquid discharged from the nucleic acid detection channel 7008 is delivered to the syringe for waste liquid 7010 as the syringe for waste liquid 7010 is naturally expanded due to an increase in pressure.

It is needless to say that the nucleic acid detection portion 7020 is controlled to have an optimum temperature by using the heating and cooling device 7027 when the above-described series of operations of from amplification of nucleic acid to the nucleic acid detection reaction are performed. After completion of the nucleic acid detection reaction, detection of nucleic acid is performed using the nucleic acid detection base plate 7024 to determine the existence of a targeted nucleic acid.

In this embodiment, an example is described in which the spring 7033c is provided between the intercalating agent liquid delivery rod 7031 and the rod front/rear mechanism 7032, but the spring 7033c does not have to be provided. This is because the rod front/rear mechanism 7032 does not cause the intercalating agent liquid delivery rod 7031 to further move to the nucleic acid detection cassette 7022 side after the intercalating agent liquid delivery rod 7031 delivers the intercalating agent in the intercalating agent syringe 7006 entirely to the channel 7007. In this embodiment, an example is described in which the nucleic acid detection cassette 7022 includes the washing syringe 7005, but the nucleic acid detection cassette 7022 does not have to include the washing syringe 7005. This is because the washing liquid is used for improving accuracy of detection of targeted nucleic acid, and therefore is not essential for processes of from amplification of nucleic acid to the nucleic acid detection reaction. In this case, the nucleic acid detection cassette 7022 does not need to include the check valve 7011b, the injection port 7012b and the washing liquid delivery hole 7017, and the nucleic acid detector 7100 does not need to include the washing liquid delivery rod 7030 and the spring 7033c.

According to this embodiment, both amplification of nucleic acid and detection of target nucleic acid can be automatically performed consistently by the small-size sealing-type nucleic acid detection cassette 7022 which has an extremely simple structure and is inexpensive, and the nucleic acid detector 7100 using the same.

Some embodiments of the present invention have been described, but these embodiments are presented as examples, and are not intended to limit the scope of the invention. These novel embodiments can be carried out in various other forms, and can be omitted, replaced and changed in a variety of ways without departing from the spirit of the invention. These embodiments and modifications thereof are included in the claims and spirit of the invention, and also included in the inventions described in the claims and their equivalents.

The following embodiments are also encompassed.

[1] A multi-nucleic-acid amplification reaction tool including: a support configured to support a reaction field of a liquid phase; and a plurality of types of primer sets configured to amplify a plurality of types of target sequences, respectively, the primer sets being releasably fixed, for each type, on a plurality of mutually independent fixing regions of at least a surface of the support, the surface being in contact with the reaction field when the liquid phase forms the reaction field.

[2] The multi-nucleic-acid amplification reaction tool according to [1], wherein the support has a container shape or a channel shape.

[3] A multi-nucleic-acid amplification reaction carrier including: a base body; and a plurality of types of primer sets configured to amplify a plurality of types target sequences, respectively, the primer sets being releasably fixed, for each type, on a plurality of mutually independent fixing regions of at least a surface of the base body.

[4] A multi-nucleic-acid amplification method including: releasably fixing a plurality of types of primer sets configured to amplify a plurality of types of target nucleic acids, respectively for each type, on a plurality of mutually independent fixing regions of at least a surface of a support configured to support a reaction field of a liquid phase, the surface being in contact with the reaction field when the liquid phase forms the reaction field; adding a reaction solution configured to perform amplification of nucleic acid to the support to form a reaction field; and carrying out an amplification reaction for each of a plurality of types target nucleic acids in the reaction field.

[5] A multi-nucleic-acid reaction tool including: a support configured to support a reaction field of a liquid phase; a plurality of primer fixing regions independently arranged on at least a surface of the support, the surface being in contact with the reaction field when the liquid phase forms the reaction field; a plurality of types of primer sets releasably fixed independently, for each type, on the plurality of primer fixing regions and configured to amplify a plurality of types of target sequences, respectively; and a thickener releasably fixed on the primer fixing region.

[6] The multi-nucleic-acid amplification reaction tool according to [5], further including a cover attached on a surface of the support which supports the reaction field, wherein the cover includes: a groove portion formed on at least an area of the support, the area corresponding to a region including all primer fixing regions; and through-holes opened at an end and the other end, respectively, of the groove portion, and a reaction portion is formed by the groove portion of the cover and a surface of the support which supports the reaction field.

[7] The multi-nucleic-acid reaction tool according to [1] or [2], further including: a plurality of probe fixing regions arranged in the vicinity of the plurality of primer fixing regions; and a plurality of probe nucleic acids fixed on the plurality of probe fixing regions.

[8] The multi-nucleic-acid reaction tool according to any one of [5] to [7], wherein the thickener is agar or gelatin.

[9] The multi-nucleic-acid reaction tool according to any one of [1] to [8], wherein the thickener is fixed so as to cover the primer.

[10] The multi-nucleic-acid reaction tool according to any one of [5] to [9], wherein the thickener is fixed on the primer fixing region together with the primer.

[11] A multi-nucleic-acid reaction carrier including: a support; a plurality of types of primer sets configured to amplify a plurality of types target sequences, respectively, the primer sets being releasably fixed, for each type, on a plurality of mutually independent primer fixing regions of at least a surface of the support; and a thickener releasably fixed on the primer fixing region.

[12] The multi-nucleic-acid reaction carrier according to [11], further including: a plurality of probe fixing regions arranged in the vicinity of the plurality of primer fixing regions; and a plurality of probe nucleic acids fixed on the plurality of probe fixing regions.

[13] The multi-nucleic-acid reaction carrier according to [11] or [12], wherein the thickener is agar or gelatin.

[14] The multi-nucleic-acid reaction carrier according to any one of [11] to [13], wherein the thickener is fixed so as to cover the primer.

[15] The multi-nucleic-acid reaction carrier according to any one of [11] to [13], wherein the thickener is fixed on the primer fixing region together with the primer.

[16] A multi-nucleic-acid reaction tool including: a plate-shaped support; a cover which is fixed on a surface of the support and in which a groove portion extending in an axial direction is opened at a surface facing to the support; a channel formed by the groove portion of the cover and the surface of the support; a first through-hole opened at an end of the channel; a second through-hole opened at the other end of the channel; a plurality of primer sets each releasably fixed on a primer fixing region of the inner wall of the channel; and a thickener releasably fixed on the primer fixing region, wherein the plurality of primer sets are fixed independently, for each type, on the primer fixing region, and a primer set includes a plurality of primers to amplify a target nucleic acid.

[17] The multi-nucleic-acid reaction tool according to [16], further including: a plurality of probe fixing regions arranged in the vicinity of the plurality of primer fixing regions; and a plurality of probe nucleic acids fixed on the plurality of probe fixing regions.

[18] A multi-nucleic-acid reaction method including:

(a) providing a multi-nucleic-acid reaction tool including: a plate-shaped support; a cover which is fixed on a surface of the support and in which a groove portion extending in an axial direction is opened at a surface facing to the support; a channel formed by the groove portion of the cover and the surface of the support; a first through-hole opened at an end of the channel; a second through-hole opened at the other end of the channel; a plurality of primer fixing regions mutually independently arranged on the inner wall of the channel; a plurality of primer sets releasably fixed, respectively, on the plurality of primer fixing regions; and a thickener releasably fixed on the primer fixing region, wherein the plurality of primer sets are fixed independently, for each type, on the primer fixing region, and a primer set includes a plurality of primers to amplify a target nucleic acid;

(b) adding a reaction solution including a target nucleic acid to the channel through the first opening; and (c) amplifying the target nucleic acid.

[19] A multi-nucleic-acid reaction method including: (a) providing a multi-nucleic-acid reaction tool including: a plate-shaped support; a cover which is fixed on a surface of the support and in which a groove portion extending in an axial direction is opened at a surface facing to the support; a channel formed by the groove portion of the cover and the surface of the support; a first through-hole opened at an end of the channel; a second through-hole opened at the other end of the channel; a plurality of primer fixing regions mutually independently arranged on the inner wall of the channel; and a plurality of primer sets releasably fixed, respectively, on the plurality of primer fixing regions, wherein the plurality of primer sets are fixed independently, for each type, on the primer fixing region, and a primer set includes a plurality of primers to amplify a target nucleic acid;

(b) adding a reaction solution including a target nucleic acid and a thickener to the channel through the first opening; and (c) amplifying the target nucleic acid.

[20] The multi-nucleic-acid reaction method according to [18] or [19], wherein the multi-nucleic-acid reaction tool further includes: a plurality of probe fixing regions arranged in the vicinity of the plurality of primer fixing regions, respectively; and probe nucleic acids fixed on the plurality of probe fixing regions, and the method further includes (d) detecting a hybridization signal of an amplification product obtained in (c) and the probe nucleic acid.

[21] The multi-nucleic-acid reaction method according to [18] to [20], wherein after the primer set is fixed to the primer fixing region, the thickener is fixed to the primer fixing region.

[22] The multi-nucleic-acid reaction method according to [18] to [21], wherein a mixture of the primer set and the thickener is fixed to the primer fixing region.

[23] The multi-nucleic-acid reaction method according to any one of [18] to [22], wherein the reaction solution is added at a flow rate of 10 mm/s or more.

[24] A nucleic acid detecting device including a first member including a groove portion at a first surface of the first member, wherein the groove portion includes a channel-type chamber for a nucleic acid sample to react, and the cross section of the channel-type chamber is larger than the cross section of a region other than the channel-type chamber in the groove portion.

[25] The nucleic acid detecting device according to [24], wherein the depth of the channel-type chamber is greater than that of a region other than the channel-type chamber in the groove portion.

[26] The nucleic acid detecting device according to [24], wherein the width of the channel-type chamber is greater than that of a region other than the channel-type chamber in the groove portion.

[27] The nucleic acid detecting device according to [24], wherein the cross section of the channel-type chamber and the cross section of a region of the groove portion other than the channel-type chamber are cross sections based on a surface orthogonal to the first surface.

[28] The nucleic acid detecting device according to [24], wherein the plurality of channel-type chambers hold a plurality of types of primer sets configured to amplify a plurality of types of target sequences, respectively.

[29] The nucleic acid detecting device according to [24], wherein the channel-type chamber holds the primer set on a wall surface.

[30] The nucleic acid detecting device according to any one of [24] to [29], wherein the nucleic acid detecting device includes a second member including an electrode for detection of nucleic acid at a position facing the first surface of the first member and facing the groove portion.

[31] A nucleic acid detector using the nucleic acid detecting device according to any one of [24] to [30], wherein a nucleic acid is detected based on a current value from the electrode.

[32] A nucleic acid detecting device including:
a base plate;
a sensor portion for detection of nucleic acid which is formed on the base plate;
a wire formed on the base plate and connected to the sensor; and
a protective film formed on the base plate,
the nucleic acid detecting device detecting a nucleic acid amplification product by the sensor portion after carrying out a nucleic acid amplification reaction in a chamber for the sensor portion and a nucleic acid sample to react with each other,
wherein the protective film includes at least an opening to expose a lower layer portion including a part of the base plate in a liquid contact region for the nucleic acid sample on the base plate.

[33] The nucleic acid detecting device according to [32], wherein the sensor portion is an electrode.

[34] The nucleic acid detecting device according to [32], wherein the protective film covers the wire in the liquid contact region.

[35] The nucleic acid detecting device according to [34], wherein the protective film covers the outer peripheral area of the sensor portion.

[36] The nucleic acid detecting device according to [32], wherein the protective film covers the base plate so as to separate an opening provided in the vicinity of the sensor portion and an opening provided in the vicinity of another sensor portion adjacent to the sensor portion in the liquid contact region.

[37] The nucleic acid detecting device according to [32], wherein the sensor portion includes at least a sensor.

[38] A nucleic acid reaction tool including: a base body; a plurality of first electrodes mutually independently arranged on at least a surface of the base body; probe nucleic acids fixed, respectively, on the plurality of first electrodes; a plurality of detection signal extraction portions in correspondence with the plurality of first electrodes; a lead which connects the plurality of first electrodes and the detection signal extraction portions corresponding thereto; and a protective film which covers the surface of the lead and an exposed area of the at least one surface of the base body, wherein the protective film is formed of at least one selected from the group consisting of polyethylene, ethylene, polypropylene, polyisobutylene, polyethylene terephthalate, unsaturated polyester, a fluorine-containing resin, polyvinyl chloride, polyvinyliden chloride, polyvinyl acetate, polyvinyl alcohol, polyvinyl acetal, an acrylic resin, polyacrylonitrile, polystyrene, an acetal resin, polycarbonate, polyamide, a phenol resin, a urea resin, an epoxy resin, a melamine resin, a styrene-acrylonitrile copolymer, an acrylonitrile-butadiene-styrene copolymer, a silicon resin, polyphenylene oxide and polysulfone, and glass, quartz glass, alumina, sapphire, forsterite, silicon carbide and a metal oxide.

[39] The nucleic acid reaction tool according to [38], further including: a plurality of primer fixing regions arranged at the same positions as the plurality of first electrodes on the at least one surface of the base body, or in the vicinity the plurality of first electrodes on the at least one surface of the base body; and a plurality of primer sets releasably fixed, for each type, on the primer fixing regions.

[40] The nucleic acid reaction tool according to [38] or [39], wherein the base body has a plate-like shape.

[41] The nucleic acid reaction tool according to [40], wherein the second electrodes are mutually independently arranged on a region of the at least one surface of the base body, which is different from the region on which the first electrodes are arranged.

[42] The nucleic acid reaction tool according to any one of [38] to [40], wherein further including a cover attached on the base body so as to cover a region including the probe nucleic acid fixing region and the primer fixing region.

[43] A nucleic acid reaction tool including: a base body; a protective film which covers an exposed area of at least a surface of the base body; and a plurality of primer sets mutually independently arranged on the protective film, wherein the protective film is formed of at least one selected from the group consisting of polyethylene, ethylene, polypropylene, polyisobutylene, polyethylene terephthalate, unsaturated polyester, a fluorine-containing resin, polyvinyl chloride, polyvinyliden chloride, polyvinyl acetate, polyvinyl alcohol, polyvinyl acetal, an acrylic resin, polyacrylonitrile, polystyrene, an acetal resin, polycarbonate, polyamide, a phenol resin, a urea resin, an epoxy resin, a melamine resin, a styrene-acrylonitrile copolymer, an acrylonitrile-butadiene-styrene copolymer, a silicon resin, polyphenylene oxide and polysulfone, and glass, quartz glass, alumina, sapphire, forsterite, silicon carbide and a metal oxide.

[44] The nucleic acid reaction tool according to any one of [38] to [43], wherein the protective film includes a novolak resin, an epoxy resin, a polyolefin resin and a silicon resin.

[45] A nucleic acid detection cassette including a channel packing, a first plate and a second plate,
the channel packing including: a nucleic acid detection channel; a first syringe to store a nucleic acid sample; a second syringe to store a chemical liquid that is used for detection of nucleic acid; a third syringe to store a liquid flowing out from the nucleic acid detection channel; a first channel that connects the first syringe and the second syringe and the nucleic acid detection channel; and a second channel that connects the nucleic acid detection channel and the third syringe and which is integrally formed of a soft material;
the first plate formed of a hard material and facing a first surface of the channel packing; and
the second plate formed of a hard material, facing a second surface opposite to the first surface, and sealing the channel packing with the first plate.

[46] The nucleic acid detection cassette according to [45], wherein the first syringe and the second syringe includes on the second surface a thin film portion which can be easily deformed.

[47] The nucleic acid detection cassette according to [46], wherein the lower plate includes a first opening at a position facing the first syringe, includes a second opening at a position facing the second syringe, and includes a nucleic acid detection portion at a position facing the nucleic acid detection channel, the nucleic acid detection portion detecting a nucleic acid as a target.

[48] The nucleic acid detection cassette according to [47], wherein the capacity of the first syringe and the capacity of the second syringe are substantially equal to a volume to fill the nucleic acid detection channel, the first channel and the second channel.

[49] The nucleic acid detection cassette according to [48], wherein the first channel includes: a first check valve that prevents inflow of a liquid into the first syringe; and a second check valve that prevents inflow of a liquid into the second syringe.

[50] A nucleic acid detector using the nucleic acid detection cassette according to any one of [47] to [49], the nucleic acid detector including:
  a stand that holds the nucleic acid detection cassette;
  a first rod that pressurizes the first syringe through the first opening;
  a second rod that pressurizes the second syringe through the second opening; and
  a movement mechanism that can cause the first rod and the second rod to move with respect to the nucleic acid detection cassette with the first rod and the second rod mounted such that the tip portion of the first rod is situated closer by a predetermined distance to the nucleic acid detection cassette than the tip portion of the second rod.

[51] The nucleic acid detector according to [50], including an elastic body having elasticity in a traveling direction of the movement mechanism between the first rod and the second rod and the movement mechanism.

According to a multi-nucleic-acid reaction tool of at least one embodiment described above, it is achieved to amplify a plurality of types of target sequence in parallel in a mutually independent manner by comprising: a support configured to support a reaction field of a liquid phase; a plurality of primer fixing regions mutually independently arranged on at least a surface of the support, the surface being in contact with the reaction field when the liquid phase forms the reaction field; and a plurality of types of primer sets releasably fixed, for each type, on the plurality of primer fixing regions and configured to amplify a plurality of types of target sequences, respectively.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A multi-nucleic-acid reaction tool comprising:
a support configured to support a reaction field of a liquid phase;
a plurality of primer fixing regions mutually independently arranged on at least a surface of the support, the surface being in contact with the reaction field when the liquid phase forms the reaction field; and
a plurality of types of primer sets releasably fixed, for each type, on the plurality of primer fixing regions and configured to amplify a plurality of types of target sequences, respectively,
wherein the primer sets are releasably fixed on the primer fixing regions by adding dropwise to each fixing region a solution comprising a primer set in water, in a buffer solution, or in an organic solvent, and drying the solution, such that the releasably fixed primer sets release from the primer fixing regions when contacted by the liquid phase that forms the reaction field.

2. The multi-nucleic-acid amplification reaction tool according to claim 1, wherein the support has a container shape or a channel shape.

3. The multi-nucleic-acid amplification reaction tool according to claim 1, further comprising a thickener releasably fixed on the primer fixing region.

4. The multi-nucleic-acid amplification reaction tool according to claim 1, further comprising a cover attached on the support and forming a chamber to retain a reaction solution together with the support.

5. The multi-nucleic-acid amplification reaction tool according to claim 1, wherein the support comprises a base plate.

6. The multi-nucleic-acid amplification reaction tool according to claim 5, which is a nucleic acid detecting device, wherein the support comprises a groove portion at a first surface thereof, the groove portion comprises a channel-type chamber for a nucleic acid sample to react, and a cross section of the channel-type chamber is larger than a cross section of a region other than the channel-type chamber in the groove portion.

7. The multi-nucleic-acid amplification reaction tool according to claim 5, further comprising:
a sensor portion configured to detect a nucleic acid which is formed on the support;
a wire formed on the support and connected to the sensor; and
a protective film formed on the support,
wherein the multi-nucleic-acid amplification reaction tool is a nucleic acid detecting device that detects a nucleic acid amplification product by the sensor portion after carrying out a nucleic acid amplification reaction in a chamber for the sensor portion and a nucleic acid sample to react with each other, and
the protective film comprises at least an opening to expose a lower layer portion including a part of the support in a liquid contact region for the nucleic acid sample on the support.

8. The multi-nucleic-acid amplification reaction tool according to claim 7, wherein the sensor portion is an electrode.

9. The multi-nucleic-acid amplification reaction tool according to claim 8, wherein the protective film covers the wire in the liquid contact region.

10. The multi-nucleic-acid amplification reaction tool according to claim 7, wherein the protective film is formed of at least one selected from the group consisting of polyethylene, ethylene, polypropylene, polyisobutylene, polyethylene terephthalate, unsaturated polyester, a fluorine-containing resin, polyvinyl chloride, polyvinylidene chloride, polyvinyl acetate, polyvinyl alcohol, polyvinyl acetal, an acrylic resin, polyacrylonitrile, polystyrene, an acetal resin, polycarbonate, polyamide, a phenol resin, a urea resin, an epoxy resin, a melamine resin, a styrene-acrylonitrile copolymer, an acrylonitrilebutadiene-styrene copolymer, a silicon resin, polyphenylene oxide, polysulfone, glass, quartz glass, alumina, sapphire, forsterite, silicon carbide and a metal oxide.

11. The multi-nucleic-acid amplification reaction tool according to claim 7, wherein the protective film comprises at least one resin selected from the group consisting of a novolak resin, an epoxy resin, a polyolefin resin and a silicon resin.

12. The multi-nucleic-acid amplification reaction tool according to claim 1, the support comprising a first plate formed of a hard material;
the multi-nucleic-acid amplification reaction tool further comprising: a channel packing and a second plate;
wherein the channel packing comprises: a nucleic acid reaction channel; a first syringe configured to store a nucleic acid sample; a second syringe configured to store a chemical liquid that is used for nucleic acid reaction; a third syringe configured to store a liquid flowing out from the nucleic acid detection channel; a first channel that connects the first syringe and the second syringe and the nucleic acid detection channel; and a second channel that connects the nucleic acid detection channel and the third syringe; and the channel packing is integrally formed of a soft material; and the second plate is formed of a hard material, and
the multi-nucleic-acid amplification reaction tool being a nucleic acid reaction cassette,
wherein the first plate faces a first surface of the channel packing, and the second plate faces a second surface opposite to the first surface, and the first plate and the second plate seal the channel packing together.

13. A multi-nucleic-acid amplification reaction carrier comprising: a base body; a plurality of primer fixing regions mutually independently arranged on at least a surface of the base body; and a plurality of types of primer sets releasably fixed, for each type, on the plurality of primer fixing regions and configured to amplify a plurality of types target sequences, respectively,
wherein the primer sets are releasably fixed on the primer fixing regions by adding dropwise to each fixing region a solution comprising a primer set in water, in a buffer solution, or in an organic solvent, and drying the solution.

14. A multi-nucleic-acid amplification method comprising:
releasably fixing, for each type, a plurality of types primer sets for amplification of a plurality of types of target nucleic acids, respectively, onto a plurality of mutually independent primer fixing regions of at least one surface of a support, by adding dropwise to each fixing region a solution comprising a primer set in water, in a buffer solution, or in an organic solvent, and drying the solution;
the support configured to support a reaction field of a liquid phase, and the surface being in contact with the reaction field, when the liquid phase forms the reaction field;
adding a reaction solution for performing an amplification of nucleic acid onto the support, such that the releasably fixed primer sets release from the primer fixing regions when contacted by the reaction solution, to form a reaction field; and carrying out an amplification reaction for each of the plurality of types target nucleic acids in the reaction field.

15. The multi-nucleic acid amplification reaction tool according to claim 1, wherein a distance between adjacent primer fixing regions is in a range of 100 µm to 10 mm.

16. The multi-nucleic acid amplification reaction carrier according to claim 13, wherein a distance between adjacent primer fixing regions is in a range of 100 µm to 10 mm.

17. The multi-nucleic acid amplification method according to claim 14, wherein a distance between adjacent primer fixing regions is in a range of 100 µm to 10 mm.

\* \* \* \* \*

```
                        SEQUENCE LISTING

<160> NUMBER OF SEQ ID NOS: 243

<210> SEQ ID NO 1
<211> LENGTH: 46
<212> TYPE: DNA
<213> ORGANISM: Artificial Sequence
<220> FEATURE:
<223> OTHER INFORMATION: FIP primer

<400> SEQUENCE: 1
aacatatacc attgttgtgg cccttccatg gtaacctctg attccc                    46

<210> SEQ ID NO 2
<211> LENGTH: 42
<212> TYPE: DNA
<213> ORGANISM: Artificial Sequence
<220> FEATURE:
<223> OTHER INFORMATION: BIP primer

<400> SEQUENCE: 2
ctacccgtag taccaacttt acccacgtgc ctggtatatt cc                        42

<210> SEQ ID NO 3
<211> LENGTH: 21
<212> TYPE: DNA
<213> ORGANISM: Artificial Sequence
<220> FEATURE:
<223> OTHER INFORMATION: F3 primer

<400> SEQUENCE: 3
gttctgtata ctgcccctct c                                               21

<210> SEQ ID NO 4
<211> LENGTH: 26
<212> TYPE: DNA
<213> ORGANISM: Artificial Sequence
<220> FEATURE:
<223> OTHER INFORMATION: B3 primer

<400> SEQUENCE: 4
gacataacat cagttgttaa tgtgac                                          26
```

```
<210> SEQ ID NO 5
<211> LENGTH: 20
<212> TYPE: DNA
<213> ORGANISM: Artificial Sequence
<220> FEATURE:
<223> OTHER INFORMATION: LP primer

<400> SEQUENCE: 5
ccttatgtag ccaataaggc                                                    20

<210> SEQ ID NO 6
<211> LENGTH: 40
<212> TYPE: DNA
<213> ORGANISM: Artificial Sequence
<220> FEATURE:
<223> OTHER INFORMATION: FIP primer

<400> SEQUENCE: 6
gctatgcgtg aattttctgt gcccttggtg ttggccttag                              40

<210> SEQ ID NO 7
<211> LENGTH: 42
<212> TYPE: DNA
<213> ORGANISM: Artificial Sequence
<220> FEATURE:
<223> OTHER INFORMATION: BIP primer

<400> SEQUENCE: 7
gcacaacaag atgttagaga taacaatagg tggagcacag cc                           42

<210> SEQ ID NO 8
<211> LENGTH: 19
<212> TYPE: DNA
<213> ORGANISM: Artificial Sequence
<220> FEATURE:
<223> OTHER INFORMATION: F3 primer

<400> SEQUENCE: 8
gttgaggtgg gcagaggac                                                     19

<210> SEQ ID NO 9
<211> LENGTH: 21
<212> TYPE: DNA
<213> ORGANISM: Artificial Sequence
<220> FEATURE:
<223> OTHER INFORMATION: B3 primer

<400> SEQUENCE: 9
ttgcatgtag tgccaatacc c                                                  21

<210> SEQ ID NO 10
<211> LENGTH: 27
<212> TYPE: DNA
<213> ORGANISM: Artificial Sequence
<220> FEATURE:
<223> OTHER INFORMATION: LP primer

<400> SEQUENCE: 10
catatttatt aaataaggga tgaccac                                            27

<210> SEQ ID NO 11
<211> LENGTH: 44
<212> TYPE: DNA
<213> ORGANISM: Artificial Sequence
<220> FEATURE:
<223> OTHER INFORMATION: FIP primer
```

-continued

<400> SEQUENCE: 11
attattgtgg ccctgcgcac gttctatggt aacctcagaa tccc         44

<210> SEQ ID NO 12
<211> LENGTH: 45
<212> TYPE: DNA
<213> ORGANISM: Artificial Sequence
<220> FEATURE:
<223> OTHER INFORMATION: BIP primer

<400> SEQUENCE: 12
accactcgta gcactaacat gactcgccat gacgaaggta ttcct        45

<210> SEQ ID NO 13
<211> LENGTH: 20
<212> TYPE: DNA
<213> ORGANISM: Artificial Sequence
<220> FEATURE:
<223> OTHER INFORMATION: F3 primer

<400> SEQUENCE: 13
gccactgtac aaagcagtgc                                    20

<210> SEQ ID NO 14
<211> LENGTH: 25
<212> TYPE: DNA
<213> ORGANISM: Artificial Sequence
<220> FEATURE:
<223> OTHER INFORMATION: B3 primer

<400> SEQUENCE: 14
tgaatgtatg tcataacatc agctg                              25

<210> SEQ ID NO 15
<211> LENGTH: 24
<212> TYPE: DNA
<213> ORGANISM: Artificial Sequence
<220> FEATURE:
<223> OTHER INFORMATION: LP primer

<400> SEQUENCE: 15
gctgaggtta aaaaggaaag caca                               24

<210> SEQ ID NO 16
<211> LENGTH: 42
<212> TYPE: DNA
<213> ORGANISM: Artificial Sequence
<220> FEATURE:
<223> OTHER INFORMATION: FIP primer

<400> SEQUENCE: 16
agtgtcccct accatgcccc acgtagggaa cagttatttg ct           42

<210> SEQ ID NO 17
<211> LENGTH: 44
<212> TYPE: DNA
<213> ORGANISM: Artificial Sequence
<220> FEATURE:
<223> OTHER INFORMATION: BIP primer

<400> SEQUENCE: 17
taagggcact gacatacgtg acagccatag acccactagg cgag         44

<210> SEQ ID NO 18

```
<211> LENGTH: 24
<212> TYPE: DNA
<213> ORGANISM: Artificial Sequence
<220> FEATURE:
<223> OTHER INFORMATION: F3 primer

<400> SEQUENCE: 18
ctgcagatgt atatggagac agta                                          24

<210> SEQ ID NO 19
<211> LENGTH: 25
<212> TYPE: DNA
<213> ORGANISM: Artificial Sequence
<220> FEATURE:
<223> OTHER INFORMATION: B3 primer

<400> SEQUENCE: 19
gttaaataac tgggagtctg aggat                                         25

<210> SEQ ID NO 20
<211> LENGTH: 23
<212> TYPE: DNA
<213> ORGANISM: Artificial Sequence
<220> FEATURE:
<223> OTHER INFORMATION: LP primer

<400> SEQUENCE: 20
ctctattcca aaatgccta gca                                            23

<210> SEQ ID NO 21
<211> LENGTH: 39
<212> TYPE: DNA
<213> ORGANISM: Artificial Sequence
<220> FEATURE:
<223> OTHER INFORMATION: FIP primer

<400> SEQUENCE: 21
gtggccctgt gctcgttgtc tatggttacc tctgatgcc                          39

<210> SEQ ID NO 22
<211> LENGTH: 40
<212> TYPE: DNA
<213> ORGANISM: Artificial Sequence
<220> FEATURE:
<223> OTHER INFORMATION: BIP primer

<400> SEQUENCE: 22
cacgcagtac aaatatgtca ccccatgtcg taggtactcc                         40

<210> SEQ ID NO 23
<211> LENGTH: 25
<212> TYPE: DNA
<213> ORGANISM: Artificial Sequence
<220> FEATURE:
<223> OTHER INFORMATION: F3 primer

<400> SEQUENCE: 23
caaattattt tcctacacct agtgg                                         25

<210> SEQ ID NO 24
<211> LENGTH: 22
<212> TYPE: DNA
<213> ORGANISM: Artificial Sequence
<220> FEATURE:
<223> OTHER INFORMATION: B3 primer

<400> SEQUENCE: 24
```
gtcataacgt ctgcagttaa gg                                              22

<210> SEQ ID NO 25
<211> LENGTH: 27
<212> TYPE: DNA
<213> ORGANISM: Artificial Sequence
<220> FEATURE:
<223> OTHER INFORMATION: LP primer

<400> SEQUENCE: 25
gctgccatat ctacttcaga aactaca                                         27

<210> SEQ ID NO 26
<211> LENGTH: 43
<212> TYPE: DNA
<213> ORGANISM: Artificial Sequence
<220> FEATURE:
<223> OTHER INFORMATION: FIP primer

<400> SEQUENCE: 26
gccagcaaac accattgtta ctctattgtt acctctgact ccc                       43

<210> SEQ ID NO 27
<211> LENGTH: 46
<212> TYPE: DNA
<213> ORGANISM: Artificial Sequence
<220> FEATURE:
<223> OTHER INFORMATION: BIP primer

<400> SEQUENCE: 27
accactcgca gtaccaattt aaccctcaac atgtctgcta tactgc                    46

<210> SEQ ID NO 28
<211> LENGTH: 21
<212> TYPE: DNA
<213> ORGANISM: Artificial Sequence
<220> FEATURE:
<223> OTHER INFORMATION: F3 primer

<400> SEQUENCE: 28
tgtattctcc ctctccaagt g                                               21

<210> SEQ ID NO 29
<211> LENGTH: 24
<212> TYPE: DNA
<213> ORGANISM: Artificial Sequence
<220> FEATURE:
<223> OTHER INFORMATION: B3 primer

<400> SEQUENCE: 29
gaatatagga cataacatct gcag                                            24

<210> SEQ ID NO 30
<211> LENGTH: 20
<212> TYPE: DNA
<213> ORGANISM: Artificial Sequence
<220> FEATURE:
<223> OTHER INFORMATION: LP primer

<400> SEQUENCE: 30
accctgtgcc ttatgtaacc                                                 20

<210> SEQ ID NO 31
<211> LENGTH: 43
<212> TYPE: DNA

```
<213> ORGANISM: Artificial Sequence
<220> FEATURE:
<223> OTHER INFORMATION: FIP primer

<400> SEQUENCE: 31
gtttagtaac tccaaaggag gacaaaggca caccttgtaa tgc                    43

<210> SEQ ID NO 32
<211> LENGTH: 42
<212> TYPE: DNA
<213> ORGANISM: Artificial Sequence
<220> FEATURE:
<223> OTHER INFORMATION: BIP primer

<400> SEQUENCE: 32
gggacatggt agacacagga catatatcta ggggaacatc ac                     42

<210> SEQ ID NO 33
<211> LENGTH: 19
<212> TYPE: DNA
<213> ORGANISM: Artificial Sequence
<220> FEATURE:
<223> OTHER INFORMATION: F3 primer

<400> SEQUENCE: 33
cctataggtg aacattggg                                               19

<210> SEQ ID NO 34
<211> LENGTH: 21
<212> TYPE: DNA
<213> ORGANISM: Artificial Sequence
<220> FEATURE:
<223> OTHER INFORMATION: B3 primer

<400> SEQUENCE: 34
ggatatttgc aaatggaact g                                            21

<210> SEQ ID NO 35
<211> LENGTH: 22
<212> TYPE: DNA
<213> ORGANISM: Artificial Sequence
<220> FEATURE:
<223> OTHER INFORMATION: LP primer

<400> SEQUENCE: 35
cattctcctg cttttacctg gt                                           22

<210> SEQ ID NO 36
<211> LENGTH: 46
<212> TYPE: DNA
<213> ORGANISM: Artificial Sequence
<220> FEATURE:
<223> OTHER INFORMATION: FIP primer

<400> SEQUENCE: 36
aattgattac cccagcaaat gccgtctatg attacgtctg aggcac                 46

<210> SEQ ID NO 37
<211> LENGTH: 47
<212> TYPE: DNA
<213> ORGANISM: Artificial Sequence
<220> FEATURE:
<223> OTHER INFORMATION: BIP primer

<400> SEQUENCE: 37
atactactag aagtactaac atgaccctcc acatgtctaa ggtactg                47
```

<210> SEQ ID NO 38
<211> LENGTH: 22
<212> TYPE: DNA
<213> ORGANISM: Artificial Sequence
<220> FEATURE:
<223> OTHER INFORMATION: F3 primer

<400> SEQUENCE: 38
gtatatgttg ctacgcctag tg                                           22

<210> SEQ ID NO 39
<211> LENGTH: 22
<212> TYPE: DNA
<213> ORGANISM: Artificial Sequence
<220> FEATURE:
<223> OTHER INFORMATION: B3 primer

<400> SEQUENCE: 39
gccataacct ctgcagacaa ag                                           22

<210> SEQ ID NO 40
<211> LENGTH: 20
<212> TYPE: DNA
<213> ORGANISM: Artificial Sequence
<220> FEATURE:
<223> OTHER INFORMATION: LP primer

<400> SEQUENCE: 40
gcacgttgca accaataagg                                              20

<210> SEQ ID NO 41
<211> LENGTH: 42
<212> TYPE: DNA
<213> ORGANISM: Artificial Sequence
<220> FEATURE:
<223> OTHER INFORMATION: FIP primer

<400> SEQUENCE: 41
ggataactgc agtattaccg gacctagggc tggaaaactt gg                     42

<210> SEQ ID NO 42
<211> LENGTH: 41
<212> TYPE: DNA
<213> ORGANISM: Artificial Sequence
<220> FEATURE:
<223> OTHER INFORMATION: BIP primer

<400> SEQUENCE: 42
tccaactcct agtggctcta tagcgctgta gccaataagg c                      41

<210> SEQ ID NO 43
<211> LENGTH: 19
<212> TYPE: DNA
<213> ORGANISM: Artificial Sequence
<220> FEATURE:
<223> OTHER INFORMATION: F3 primer

<400> SEQUENCE: 43
gacgtgagca gatgtttgt                                               19

<210> SEQ ID NO 44
<211> LENGTH: 20
<212> TYPE: DNA
<213> ORGANISM: Artificial Sequence
<220> FEATURE:

<223> OTHER INFORMATION: B3 primer

<400> SEQUENCE: 44
ccattgttat gaccttgtgc                                           20

<210> SEQ ID NO 45
<211> LENGTH: 28
<212> TYPE: DNA
<213> ORGANISM: Artificial Sequence
<220> FEATURE:
<223> OTHER INFORMATION: LP primer

<400> SEQUENCE: 45
cctcagaatc acaattattt aataagcc                                  28

<210> SEQ ID NO 46
<211> LENGTH: 45
<212> TYPE: DNA
<213> ORGANISM: Artificial Sequence
<220> FEATURE:
<223> OTHER INFORMATION: FIP primer

<400> SEQUENCE: 46
tgaggtctaa gtgatgacag ccgcaactcc taagccagtg ccaga               45

<210> SEQ ID NO 47
<211> LENGTH: 44
<212> TYPE: DNA
<213> ORGANISM: Artificial Sequence
<220> FEATURE:
<223> OTHER INFORMATION: BIP primer

<400> SEQUENCE: 47
ctagggttgg ccaatctact cccaatagat ggctctgccc tgac                44

<210> SEQ ID NO 48
<211> LENGTH: 20
<212> TYPE: DNA
<213> ORGANISM: Artificial Sequence
<220> FEATURE:
<223> OTHER INFORMATION: F3 primer

<400> SEQUENCE: 48
agggctgagg gtttgaagtc                                           20

<210> SEQ ID NO 49
<211> LENGTH: 22
<212> TYPE: DNA
<213> ORGANISM: Artificial Sequence
<220> FEATURE:
<223> OTHER INFORMATION: B3 primer

<400> SEQUENCE: 49
tgaacacagt tgtgtcagaa gc                                        22

<210> SEQ ID NO 50
<211> LENGTH: 307
<212> TYPE: DNA
<213> ORGANISM: Artificial Sequence
<220> FEATURE:
<223> OTHER INFORMATION: template

<400> SEQUENCE: 50
gttctgtata ctgcccctct cccagcggtt ccatggtaac ctctgattcc cagttattta    60
ataagcctta ttggctacat aaggcccagg gccacaacaa tggtatatgt tggcataatc   120

```
aattatttct tactgttgtg gacactaccc gtagtaccaa ctttacatta tctacctcta      180
tagagtcttc cataccttct acatatgatc cttctaagtt taaggaatat accaggcacg      240
tggaggagta tgatttacaa tttatatttc aactgtgtac tgtcacatta caactgatg      300 ttatgtc                                                                307

<210> SEQ ID NO 51
<211> LENGTH: 215
<212> TYPE: DNA
<213> ORGANISM: Artificial Sequence
<220> FEATURE:
<223> OTHER INFORMATION: template

<400> SEQUENCE: 51
gttgaggtgg gcagaggaca gccccttggt gttggcctta gtggtcatcc cttatttaat       60
aaatatgatg acacagaaaa ttcacgcata gcaaatggca atgcacaaca agatgttaga      120
gataacacat ctgttgacaa caaacagact cagttatgta taataggctg tgctccacct      180
attggggaac actggggtat tggcactaca tgcaa                                 215

<210> SEQ ID NO 52
<211> LENGTH: 323
<212> TYPE: DNA
<213> ORGANISM: Artificial Sequence
<220> FEATURE:
<223> OTHER INFORMATION: template

<400> SEQUENCE: 52
gccactgtac aaagcagtgc ttttttttcct actcctagtg gttctatggt aacctcagaa       60
tcccaattat ttaataaacc gtactggtta caacgtgcgc agggccacaa taatggcata      120
tgttggggca atcagttgtt tgtcacagtt gtggatacca ctcgtagcac taacatgact      180
ttatgtgctg aggttaaaaa ggaaagcaca tataaaaatg aaaattttaa ggaataccct      240
cgtcatggcg aggaatttga tttacaattt attttttcaat tgtgcaaaat tacattaaca      300
gctgatgtta tgacatacat tca                                              323

<210> SEQ ID NO 53
<211> LENGTH: 212
<212> TYPE: DNA
<213> ORGANISM: Artificial Sequence
<220> FEATURE:
<223> OTHER INFORMATION: template

<400> SEQUENCE: 53
ctgcagatgt atatggagac agtatgttct tttgtttacg tagggaacag ttatttgcta       60
ggcatttttg gaatagaggg ggcatggtag gggacactat acctactgaa ttgtatatta      120
agggcactga catacgtgac agtcctagta gttatgtata tgcccccctcg cctagtgggt      180 ctatggtatc ctcagactcc cagttattta ac                                    212

<210> SEQ ID NO 54
<211> LENGTH: 301
<212> TYPE: DNA
<213> ORGANISM: Artificial Sequence
<220> FEATURE:
<223> OTHER INFORMATION: template

<400> SEQUENCE: 54
caaattattt tcctacacct agtggttcta tggttacctc tgatgcccaa atattcaata       60
```

```
aaccttattg gttacaacga gcacagggcc acaataatgg catttgttgg ggtaaccaac      120
tatttgttac tgttgttgat actacacgca gtacaaatat gtcattatgt gctgccatat      180
ctacttcaga aactacatat aaaaatacta actttaagga gtacctacga catggggagg      240
aatatgattt acagtttatt tttcaactgt gcaaataac cttaactgca gacgttatga       300
c                                                                      301

<210> SEQ ID NO 55
<211> LENGTH: 309
<212> TYPE: DNA
<213> ORGANISM: Artificial Sequence
<220> FEATURE:
<223> OTHER INFORMATION: template

<400> SEQUENCE: 55
tgtattctcc ctctccaagt ggctctattg ttacctctga ctcccagttg tttaataaac      60
catattggtt acataaggca cagggtcata acaatggtgt tgctggcat aatcaattat       120 ttgttactgt ggtagatacc actcgcagta ccaatttaac aatatgtgct tctacacagt      180
ctcctgtacc tgggcaatat gatgctacca aatttaagca gtatagcaga catgttgagg      240
aatatgattt gcagtttatt tttcagttgt gtactattac tttaactgca gatgttatgt      300
cctatattc                                                              309

<210> SEQ ID NO 56
<211> LENGTH: 206
<212> TYPE: DNA
<213> ORGANISM: Artificial Sequence
<220> FEATURE:
<223> OTHER INFORMATION: template

<400> SEQUENCE: 56
cctataggtg aacattgggg aaaaggcaca ccttgtaatg ctaaccaggt aaaagcagga      60
gaatgtcctc ctttggagtt actaaacact gtactacaag acggggacat ggtagacaca     120
ggatttggtg caatggattt tactacatta caagctaata aaagtgatgt tccctagat       180 atatgcagtt ccatttgcaa atatcc                                           206

<210> SEQ ID NO 57
<211> LENGTH: 296
<212> TYPE: DNA
<213> ORGANISM: Artificial Sequence
<220> FEATURE:
<223> OTHER INFORMATION: template

<400> SEQUENCE: 57
gtatatgttg ctacgcctag tgggtctatg attacgtctg aggcacagtt atttaataaa      60
ccttattggt tgcaacgtgc ccaaggccat aataatggca tttgctgggg taatcaatta     120
tttgttactg tagtagatac tactagaagt actaacatga ctattagtac tgctacagaa      180
cagttaagta aatatgatgc acgaaaaatt aatcagtacc ttagacatgt ggaggaatat     240
gaattacaat tgttttttca attatgcaaa attactttgt ctgcagaggt tatggc         296

<210> SEQ ID NO 58
<211> LENGTH: 212
<212> TYPE: DNA
<213> ORGANISM: Artificial Sequence
<220> FEATURE:
<223> OTHER INFORMATION: template

<400> SEQUENCE: 58
```

```
gacgtgagca gatgtttgtt agacactttt ttaatagggc tggaaaactt ggcgaggctg      60
tcccggatga cctttatatt aaagggtccg gtaatactgc agttatccaa agtagtgcat     120
tttttccaac tcctagtggc tctatagtta cctcagaatc acaattattt aataagcctt    180
attggctaca gcgtgcacaa ggtcataaca at                                   212
```

```
<210> SEQ ID NO 59
<211> LENGTH: 183
<212> TYPE: DNA
<213> ORGANISM: Homo sapiens

<400> SEQUENCE: 59
```

```
agggctgagg gtttgaagtc caactcctaa gccagtgcca gaagagccaa ggacaggtac      60
ggctgtcatc acttagacct caccctgtgg agccacaccc tagggttggc caatctactc    120
ccaggagcag ggagggcagg agccagggct gggcataaaa gtcagggcag acaactgtgt    180
tca                                                                   183
```

```
<210> SEQ ID NO 60
<211> LENGTH: 33
<212> TYPE: DNA
<213> ORGANISM: Artificial Sequence
<220> FEATURE:
<223> OTHER INFORMATION: probe

<400> SEQUENCE: 60
```

```
ataccttcta catatgatcc ttctaagttt aag                                   33
```

```
<210> SEQ ID NO 61
<211> LENGTH: 38
<212> TYPE: DNA
<213> ORGANISM: Artificial Sequence
<220> FEATURE:
<223> OTHER INFORMATION: probe

<400> SEQUENCE: 61
```

```
gacaacaaac agactcagtt atgtataata ggctgtgc                              38
```

```
<210> SEQ ID NO 62
<211> LENGTH: 33
<212> TYPE: DNA
<213> ORGANISM: Artificial Sequence
<220> FEATURE:
<223> OTHER INFORMATION: probe

<400> SEQUENCE: 62
```

```
ttgtaaccag tacggtttat taaataattg gga                                   33
```

```
<210> SEQ ID NO 63
<211> LENGTH: 30
<212> TYPE: DNA
<213> ORGANISM: Artificial Sequence
<220> FEATURE:
<223> OTHER INFORMATION: probe

<400> SEQUENCE: 63
```

```
agtagttatg tatatgcccc ctcgcctagt                                       30
```

```
<210> SEQ ID NO 64
<211> LENGTH: 34
<212> TYPE: DNA
<213> ORGANISM: Artificial Sequence
<220> FEATURE:
```

-continued

```
<223> OTHER INFORMATION: probe

<400> SEQUENCE: 64
accaataagg tttattgaat atttgggcat caga                              34

<210> SEQ ID NO 65
<211> LENGTH: 30
<212> TYPE: DNA
<213> ORGANISM: Artificial Sequence
<220> FEATURE:
<223> OTHER INFORMATION: probe

<400> SEQUENCE: 65
tgcttctaca cagtctcctg tacctgggca                                   30

<210> SEQ ID NO 66
<211> LENGTH: 34
<212> TYPE: DNA
<213> ORGANISM: Artificial Sequence
<220> FEATURE:
<223> OTHER INFORMATION: probe

<400> SEQUENCE: 66
tttggtgcaa tggatttac tacattacaa gcta                               34

<210> SEQ ID NO 67
<211> LENGTH: 40
<212> TYPE: DNA
<213> ORGANISM: Artificial Sequence
<220> FEATURE:
<223> OTHER INFORMATION: probe

<400> SEQUENCE: 67
agaacagtta agtaaatatg atgcacgaaa aattaatcag                        40

<210> SEQ ID NO 68
<211> LENGTH: 30
<212> TYPE: DNA
<213> ORGANISM: Artificial Sequence
<220> FEATURE:
<223> OTHER INFORMATION: probe

<400> SEQUENCE: 68
aggtcatccg ggacagcctc gccaagtttt                                   30

<210> SEQ ID NO 69
<211> LENGTH: 27
<212> TYPE: DNA
<213> ORGANISM: Artificial Sequence
<220> FEATURE:
<223> OTHER INFORMATION: probe

<400> SEQUENCE: 69
caggagcagg gagggcagga gccaggg                                      27

<210> SEQ ID NO 70
<211> LENGTH: 35
<212> TYPE: DNA
<213> ORGANISM: Artificial Sequence
<220> FEATURE:
<223> OTHER INFORMATION: Probe

<400> SEQUENCE: 70
acaaggtcat aataatggta tttgttgggg caatc                             35
```

```
<210> SEQ ID NO 71
<211> LENGTH: 55
<212> TYPE: DNA
<213> ORGANISM: Artificial Sequence
<220> FEATURE:
<223> OTHER INFORMATION: Probe

<400> SEQUENCE: 71
tggtcctggc actgataata gggaatgtat atcaatggat tataaacaaa cacaa       55

<210> SEQ ID NO 72
<211> LENGTH: 41
<212> TYPE: DNA
<213> ORGANISM: Artificial Sequence
<220> FEATURE:
<223> OTHER INFORMATION: Probe

<400> SEQUENCE: 72
ttgtaaccag tacggtttat taaataattg ggattctgag g                      41

<210> SEQ ID NO 73
<211> LENGTH: 55
<212> TYPE: DNA
<213> ORGANISM: Artificial Sequence
<220> FEATURE:
<223> OTHER INFORMATION: Probe

<400> SEQUENCE: 73
agtactgcta cagaacagtt aagtaaatat gatgcacgaa aaattaatca gtacc       55

<210> SEQ ID NO 74
<211> LENGTH: 43
<212> TYPE: DNA
<213> ORGANISM: Artificial Sequence
<220> FEATURE:
<223> OTHER INFORMATION: Probe

<400> SEQUENCE: 74
gccccgaccg atttcaacac ctacacaggc ccagaccaag cgt                    43

<210> SEQ ID NO 75
<211> LENGTH: 55
<212> TYPE: DNA
<213> ORGANISM: Artificial Sequence
<220> FEATURE:
<223> OTHER INFORMATION: Probe

<400> SEQUENCE: 75
agctacagct gttattacgc aggatgttag ggataatgtg tcagttgatt ataag       55

<210> SEQ ID NO 76
<211> LENGTH: 34
<212> TYPE: DNA
<213> ORGANISM: Artificial Sequence
<220> FEATURE:
<223> OTHER INFORMATION: Probe

<400> SEQUENCE: 76
accaataagg tttattgaat atttgggcat caga                              34

<210> SEQ ID NO 77
<211> LENGTH: 55
<212> TYPE: DNA
<213> ORGANISM: Artificial Sequence
<220> FEATURE:
<223> OTHER INFORMATION: Probe
```

<400> SEQUENCE: 77
attatctacc tctatagagt cttccatacc ttctacatat gatccttcta agttt    55

<210> SEQ ID NO 78
<211> LENGTH: 41
<212> TYPE: DNA
<213> ORGANISM: Artificial Sequence
<220> FEATURE:
<223> OTHER INFORMATION: Probe

<400> SEQUENCE: 78
ctttaatata aaggtcatcc gggacagcct cgccaagttt t    41

<210> SEQ ID NO 79
<211> LENGTH: 38
<212> TYPE: DNA
<213> ORGANISM: Artificial Sequence
<220> FEATURE:
<223> OTHER INFORMATION: Probe

<400> SEQUENCE: 79
tcctagtagt tatgtatatg cccccctcgcc tagtgggt    38

<210> SEQ ID NO 80
<211> LENGTH: 55
<212> TYPE: DNA
<213> ORGANISM: Artificial Sequence
<220> FEATURE:
<223> OTHER INFORMATION: Probe

<400> SEQUENCE: 80
ctacacagtc tcctgtacct gggcaatatg atgctaccaa atttaagcag tatag    55

<210> SEQ ID NO 81
<211> LENGTH: 46
<212> TYPE: DNA
<213> ORGANISM: Artificial Sequence
<220> FEATURE:
<223> OTHER INFORMATION: Probe

<400> SEQUENCE: 81
acatctgttg acaacaaaca gactcagtta tgtataatag gctgtg    46

<210> SEQ ID NO 82
<211> LENGTH: 51
<212> TYPE: DNA
<213> ORGANISM: Artificial Sequence
<220> FEATURE:
<223> OTHER INFORMATION: Probe

<400> SEQUENCE: 82
tttggtgcaa tggattttac tacattacaa gctaataaaa gtgatgttcc c    51

<210> SEQ ID NO 83
<211> LENGTH: 38
<212> TYPE: DNA
<213> ORGANISM: Artificial Sequence
<220> FEATURE:
<223> OTHER INFORMATION: Primer

<400> SEQUENCE: 83
gcactgcttt gaatagaggc actgttcccg atgacctg    38

<210> SEQ ID NO 84
<211> LENGTH: 38

<212> TYPE: DNA
<213> ORGANISM: Artificial Sequence
<220> FEATURE:
<223> OTHER INFORMATION: Primer

<400> SEQUENCE: 84
ccatattggc tacaacgtgc tacctgattg ccccaaca                               38

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
agggctggta cattaggaga                                                   20

<210> SEQ ID NO 86
<211> LENGTH: 22
<212> TYPE: DNA
<213> ORGANISM: Artificial Sequence
<220> FEATURE:
<223> OTHER INFORMATION: Primer

<400> SEQUENCE: 86
gtcatattag tactgcgagt gg                                                22

<210> SEQ ID NO 87
<211> LENGTH: 27
<212> TYPE: DNA
<213> ORGANISM: Artificial Sequence
<220> FEATURE:
<223> OTHER INFORMATION: Primer

<400> SEQUENCE: 87
cagtagttcc tgaaccttta atgtaca                                           27

<210> SEQ ID NO 88
<211> LENGTH: 46
<212> TYPE: DNA
<213> ORGANISM: Artificial Sequence
<220> FEATURE:
<223> OTHER INFORMATION: Primer

<400> SEQUENCE: 88
ggatgaccac taatacctac accctgtgtt ggtttagagg taggtc                      46

<210> SEQ ID NO 89
<211> LENGTH: 51
<212> TYPE: DNA
<213> ORGANISM: Artificial Sequence
<220> FEATURE:
<223> OTHER INFORMATION: Primer

<400> SEQUENCE: 89
cactgaaaac tctaatagat atgccggtgc aaccaagtaa acacagttgt g                51

<210> SEQ ID NO 90
<211> LENGTH: 21
<212> TYPE: DNA
<213> ORGANISM: Artificial Sequence
<220> FEATURE:
<223> OTHER INFORMATION: Primer

<400> SEQUENCE: 90
aactcaacgc ttagtttggg c                                                    21

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
cctttacccc aatgctctcc                                                      20

<210> SEQ ID NO 92
<211> LENGTH: 16
<212> TYPE: DNA
<213> ORGANISM: Artificial Sequence
<220> FEATURE:
<223> OTHER INFORMATION: Primer

<400> SEQUENCE: 92
taatggctgc ccgcga                                                          16

<210> SEQ ID NO 93
<211> LENGTH: 44
<212> TYPE: DNA
<213> ORGANISM: Artificial Sequence
<220> FEATURE:
<223> OTHER INFORMATION: Primer

<400> SEQUENCE: 93
attattgtgg ccctgcgcac gttctatggt aacctcagaa tccc                           44

<210> SEQ ID NO 94
<211> LENGTH: 45
<212> TYPE: DNA
<213> ORGANISM: Artificial Sequence
<220> FEATURE:
<223> OTHER INFORMATION: Primer

<400> SEQUENCE: 94
accactcgta gcactaacat gactcgccat gacgaaggta ttcct                          45

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
gccactgtac aaagcagtgc                                                      20

<210> SEQ ID NO 96
<211> LENGTH: 25
<212> TYPE: DNA
<213> ORGANISM: Artificial Sequence
<220> FEATURE:
<223> OTHER INFORMATION: Primer

<400> SEQUENCE: 96
tgaatgtatg tcataacatc agctg                                                25

<210> SEQ ID NO 97
<211> LENGTH: 24
<212> TYPE: DNA
<213> ORGANISM: Artificial Sequence

```
<220> FEATURE:
<223> OTHER INFORMATION: Primer

<400> SEQUENCE: 97
gctgaggtta aaaaggaaag caca                                              24

<210> SEQ ID NO 98
<211> LENGTH: 46
<212> TYPE: DNA
<213> ORGANISM: Artificial Sequence
<220> FEATURE:
<223> OTHER INFORMATION: Primer

<400> SEQUENCE: 98
aattgattac cccagcaaat gccgtctatg attacgtctg aggcac                      46

<210> SEQ ID NO 99
<211> LENGTH: 47
<212> TYPE: DNA
<213> ORGANISM: Artificial Sequence
<220> FEATURE:
<223> OTHER INFORMATION: Primer

<400> SEQUENCE: 99
atactactag aagtactaac atgaccctcc acatgtctaa ggtactg                     47

<210> SEQ ID NO 100
<211> LENGTH: 22
<212> TYPE: DNA
<213> ORGANISM: Artificial Sequence
<220> FEATURE:
<223> OTHER INFORMATION: Primer

<400> SEQUENCE: 100
gtatatgttg ctacgcctag tg                                                22

<210> SEQ ID NO 101
<211> LENGTH: 22
<212> TYPE: DNA
<213> ORGANISM: Artificial Sequence
<220> FEATURE:
<223> OTHER INFORMATION: Primer

<400> SEQUENCE: 101
gccataacct ctgcagacaa ag                                                22

<210> SEQ ID NO 102
<211> LENGTH: 20
<212> TYPE: DNA
<213> ORGANISM: Artificial Sequence
<220> FEATURE:
<223> OTHER INFORMATION: Primer

<400> SEQUENCE: 102
gcacgttgca accaataagg                                                   20

<210> SEQ ID NO 103
<211> LENGTH: 43
<212> TYPE: DNA
<213> ORGANISM: Artificial Sequence
<220> FEATURE:
<223> OTHER INFORMATION: Primer

<400> SEQUENCE: 103
cactgagtcc taccccctaaa ggttgtctca acgcttggtc tgg                        43
```

<210> SEQ ID NO 104
<211> LENGTH: 50
<212> TYPE: DNA
<213> ORGANISM: Artificial Sequence
<220> FEATURE:
<223> OTHER INFORMATION: Primer

<400> SEQUENCE: 104
gatgacactg aaaactctca tgtagcgctg agtttgttta taatccacag    50

<210> SEQ ID NO 105
<211> LENGTH: 27
<212> TYPE: DNA
<213> ORGANISM: Artificial Sequence
<220> FEATURE:
<223> OTHER INFORMATION: Primer

<400> SEQUENCE: 105
ccagataaca cagtatatga tcctaac    27

<210> SEQ ID NO 106
<211> LENGTH: 24
<212> TYPE: DNA
<213> ORGANISM: Artificial Sequence
<220> FEATURE:
<223> OTHER INFORMATION: Primer

<400> SEQUENCE: 106
gcaggtacac agccaataat acac    24

<210> SEQ ID NO 107
<211> LENGTH: 25
<212> TYPE: DNA
<213> ORGANISM: Artificial Sequence
<220> FEATURE:
<223> OTHER INFORMATION: Primer

<400> SEQUENCE: 107
gctgttgata ccaaagatac acgtg    25

<210> SEQ ID NO 108
<211> LENGTH: 45
<212> TYPE: DNA
<213> ORGANISM: Artificial Sequence
<220> FEATURE:
<223> OTHER INFORMATION: Primer

<400> SEQUENCE: 108
taaaatggat ggccacttag gccggtatgg aaattggtcg tgggc    45

<210> SEQ ID NO 109
<211> LENGTH: 41
<212> TYPE: DNA
<213> ORGANISM: Artificial Sequence
<220> FEATURE:
<223> OTHER INFORMATION: Primer

<400> SEQUENCE: 109
ggatgataca gaaagtgctc aaaatacaca gctgtgtttg c    41

<210> SEQ ID NO 110
<211> LENGTH: 23
<212> TYPE: DNA
<213> ORGANISM: Artificial Sequence
<220> FEATURE:
<223> OTHER INFORMATION: Primer

<400> SEQUENCE: 110
gaaacacaac gtttggtttg ggc                                              23

<210> SEQ ID NO 111
<211> LENGTH: 21
<212> TYPE: DNA
<213> ORGANISM: Artificial Sequence
<220> FEATURE:
<223> OTHER INFORMATION: Primer

<400> SEQUENCE: 111
gtgctcacca atagcaggta c                                                21

<210> SEQ ID NO 112
<211> LENGTH: 18
<212> TYPE: DNA
<213> ORGANISM: Artificial Sequence
<220> FEATURE:
<223> OTHER INFORMATION: Primer

<400> SEQUENCE: 112
caatacctaa aggctgcc                                                    18

<210> SEQ ID NO 113
<211> LENGTH: 39
<212> TYPE: DNA
<213> ORGANISM: Artificial Sequence
<220> FEATURE:
<223> OTHER INFORMATION: Primer

<400> SEQUENCE: 113
gtggccctgt gctcgttgtc tatggttacc tctgatgcc                             39

<210> SEQ ID NO 114
<211> LENGTH: 40
<212> TYPE: DNA
<213> ORGANISM: Artificial Sequence
<220> FEATURE:
<223> OTHER INFORMATION: Primer

<400> SEQUENCE: 114
cacgcagtac aaatatgtca ccccatgtcg taggtactcc                            40

<210> SEQ ID NO 115
<211> LENGTH: 25
<212> TYPE: DNA
<213> ORGANISM: Artificial Sequence
<220> FEATURE:
<223> OTHER INFORMATION: Primer

<400> SEQUENCE: 115
caaattattt tcctacacct agtgg                                            25

<210> SEQ ID NO 116
<211> LENGTH: 22
<212> TYPE: DNA
<213> ORGANISM: Artificial Sequence
<220> FEATURE:
<223> OTHER INFORMATION: Primer

<400> SEQUENCE: 116
gtcataacgt ctgcagttaa gg                                               22

<210> SEQ ID NO 117

```
<211> LENGTH: 27
<212> TYPE: DNA
<213> ORGANISM: Artificial Sequence
<220> FEATURE:
<223> OTHER INFORMATION: Primer

<400> SEQUENCE: 117
gctgccatat ctacttcaga aactaca                                            27

<210> SEQ ID NO 118
<211> LENGTH: 46
<212> TYPE: DNA
<213> ORGANISM: Artificial Sequence
<220> FEATURE:
<223> OTHER INFORMATION: Primer

<400> SEQUENCE: 118
aacatatacc attgttgtgg cccttccatg gtaacctctg attccc                       46

<210> SEQ ID NO 119
<211> LENGTH: 42
<212> TYPE: DNA
<213> ORGANISM: Artificial Sequence
<220> FEATURE:
<223> OTHER INFORMATION: Primer

<400> SEQUENCE: 119
ctacccgtag taccaacttt acccacgtgc ctggtatatt cc                           42

<210> SEQ ID NO 120
<211> LENGTH: 21
<212> TYPE: DNA
<213> ORGANISM: Artificial Sequence
<220> FEATURE:
<223> OTHER INFORMATION: Primer

<400> SEQUENCE: 120
gttctgtata ctgcccctct c                                                  21

<210> SEQ ID NO 121
<211> LENGTH: 26
<212> TYPE: DNA
<213> ORGANISM: Artificial Sequence
<220> FEATURE:
<223> OTHER INFORMATION: Primer

<400> SEQUENCE: 121
gacataacat cagttgttaa tgtgac                                             26

<210> SEQ ID NO 122
<211> LENGTH: 20
<212> TYPE: DNA
<213> ORGANISM: Artificial Sequence
<220> FEATURE:
<223> OTHER INFORMATION: Primer

<400> SEQUENCE: 122
ccttatgtag ccaataaggc                                                    20

<210> SEQ ID NO 123
<211> LENGTH: 42
<212> TYPE: DNA
<213> ORGANISM: Artificial Sequence
<220> FEATURE:
<223> OTHER INFORMATION: Primer

<400> SEQUENCE: 123
```
ggataactgc agtattaccg gacctagggc tggaaaactt gg         42

<210> SEQ ID NO 124
<211> LENGTH: 41
<212> TYPE: DNA
<213> ORGANISM: Artificial Sequence
<220> FEATURE:
<223> OTHER INFORMATION: Primer

<400> SEQUENCE: 124
tccaactcct agtggctcta tagcgctgta gccaataagg c         41

<210> SEQ ID NO 125
<211> LENGTH: 19
<212> TYPE: DNA
<213> ORGANISM: Artificial Sequence
<220> FEATURE:
<223> OTHER INFORMATION: Primer

<400> SEQUENCE: 125
gacgtgagca gatgtttgt         19

<210> SEQ ID NO 126
<211> LENGTH: 20
<212> TYPE: DNA
<213> ORGANISM: Artificial Sequence
<220> FEATURE:
<223> OTHER INFORMATION: Primer

<400> SEQUENCE: 126
ccattgttat gaccttgtgc         20

<210> SEQ ID NO 127
<211> LENGTH: 28
<212> TYPE: DNA
<213> ORGANISM: Artificial Sequence
<220> FEATURE:
<223> OTHER INFORMATION: Primer

<400> SEQUENCE: 127
cctcagaatc acaattattt aataagcc         28

<210> SEQ ID NO 128
<211> LENGTH: 42
<212> TYPE: DNA
<213> ORGANISM: Artificial Sequence
<220> FEATURE:
<223> OTHER INFORMATION: Primer

<400> SEQUENCE: 128
agtgtcccct accatgcccc acgtagggaa cagttatttg ct         42

<210> SEQ ID NO 129
<211> LENGTH: 44
<212> TYPE: DNA
<213> ORGANISM: Artificial Sequence
<220> FEATURE:
<223> OTHER INFORMATION: Primer

<400> SEQUENCE: 129
taagggcact gacatacgtg acagccatag acccactagg cgag         44

<210> SEQ ID NO 130
<211> LENGTH: 24
<212> TYPE: DNA

```
<213> ORGANISM: Artificial Sequence
<220> FEATURE:
<223> OTHER INFORMATION: Primer

<400> SEQUENCE: 130
ctgcagatgt atatggagac agta                                          24

<210> SEQ ID NO 131
<211> LENGTH: 25
<212> TYPE: DNA
<213> ORGANISM: Artificial Sequence
<220> FEATURE:
<223> OTHER INFORMATION: Primer

<400> SEQUENCE: 131
gttaaataac tgggagtctg aggat                                         25

<210> SEQ ID NO 132
<211> LENGTH: 23
<212> TYPE: DNA
<213> ORGANISM: Artificial Sequence
<220> FEATURE:
<223> OTHER INFORMATION: Primer

<400> SEQUENCE: 132
ctctattcca aaaatgccta gca                                           23

<210> SEQ ID NO 133
<211> LENGTH: 43
<212> TYPE: DNA
<213> ORGANISM: Artificial Sequence
<220> FEATURE:
<223> OTHER INFORMATION: Primer

<400> SEQUENCE: 133
gccagcaaac accattgtta ctctattgtt acctctgact ccc                     43

<210> SEQ ID NO 134
<211> LENGTH: 46
<212> TYPE: DNA
<213> ORGANISM: Artificial Sequence
<220> FEATURE:
<223> OTHER INFORMATION: Primer

<400> SEQUENCE: 134
accactcgca gtaccaattt aaccctcaac atgtctgcta tactgc                  46

<210> SEQ ID NO 135
<211> LENGTH: 21
<212> TYPE: DNA
<213> ORGANISM: Artificial Sequence
<220> FEATURE:
<223> OTHER INFORMATION: Primer

<400> SEQUENCE: 135
tgtattctcc ctctccaagt g                                             21

<210> SEQ ID NO 136
<211> LENGTH: 24
<212> TYPE: DNA
<213> ORGANISM: Artificial Sequence
<220> FEATURE:
<223> OTHER INFORMATION: Primer

<400> SEQUENCE: 136
gaatatagga cataacatct gcag                                          24
```

<210> SEQ ID NO 137
<211> LENGTH: 20
<212> TYPE: DNA
<213> ORGANISM: Artificial Sequence
<220> FEATURE:
<223> OTHER INFORMATION: Primer

<400> SEQUENCE: 137
accctgtgcc ttatgtaacc                                              20

<210> SEQ ID NO 138
<211> LENGTH: 40
<212> TYPE: DNA
<213> ORGANISM: Artificial Sequence
<220> FEATURE:
<223> OTHER INFORMATION: Primer

<400> SEQUENCE: 138
gctatgcgtg aattttctgt gcccttggtg ttggccttag                        40

<210> SEQ ID NO 139
<211> LENGTH: 42
<212> TYPE: DNA
<213> ORGANISM: Artificial Sequence
<220> FEATURE:
<223> OTHER INFORMATION: Primer

<400> SEQUENCE: 139
gcacaacaag atgttagaga taacaatagg tggagcacag cc                     42

<210> SEQ ID NO 140
<211> LENGTH: 19
<212> TYPE: DNA
<213> ORGANISM: Artificial Sequence
<220> FEATURE:
<223> OTHER INFORMATION: Primer

<400> SEQUENCE: 140
gttgaggtgg gcagaggac                                               19

<210> SEQ ID NO 141
<211> LENGTH: 21
<212> TYPE: DNA
<213> ORGANISM: Artificial Sequence
<220> FEATURE:
<223> OTHER INFORMATION: Primer

<400> SEQUENCE: 141
ttgcatgtag tgccaatacc c                                            21

<210> SEQ ID NO 142
<211> LENGTH: 27
<212> TYPE: DNA
<213> ORGANISM: Artificial Sequence
<220> FEATURE:
<223> OTHER INFORMATION: Primer

<400> SEQUENCE: 142
catatttatt aaataaggga tgaccac                                      27

<210> SEQ ID NO 143
<211> LENGTH: 43
<212> TYPE: DNA
<213> ORGANISM: Artificial Sequence
<220> FEATURE:

<223> OTHER INFORMATION: Primer

<400> SEQUENCE: 143
gtttagtaac tccaaaggag gacaaaggca caccttgtaa tgc    43

<210> SEQ ID NO 144
<211> LENGTH: 42
<212> TYPE: DNA
<213> ORGANISM: Artificial Sequence
<220> FEATURE:
<223> OTHER INFORMATION: Primer

<400> SEQUENCE: 144
gggacatggt agacacagga catatatcta ggggaacatc ac    42

<210> SEQ ID NO 145
<211> LENGTH: 19
<212> TYPE: DNA
<213> ORGANISM: Artificial Sequence
<220> FEATURE:
<223> OTHER INFORMATION: Primer

<400> SEQUENCE: 145
cctataggtg aacattggg    19

<210> SEQ ID NO 146
<211> LENGTH: 21
<212> TYPE: DNA
<213> ORGANISM: Artificial Sequence
<220> FEATURE:
<223> OTHER INFORMATION: Primer

<400> SEQUENCE: 146
ggatatttgc aaatggaact g    21

<210> SEQ ID NO 147
<211> LENGTH: 22
<212> TYPE: DNA
<213> ORGANISM: Artificial Sequence
<220> FEATURE:
<223> OTHER INFORMATION: Primer

<400> SEQUENCE: 147
cattctcctg cttttacctg gt    22

<210> SEQ ID NO 148
<211> LENGTH: 242
<212> TYPE: DNA
<213> ORGANISM: HPV

<400> SEQUENCE: 148
agggctggta cattaggaga ggctgttccc gatgacctgt acattaaagg ttcaggaact    60
actgcctcta ttcaaagcag tgctttttt cccactccta gtggatcaat ggttacttcc    120
gaatctcagt tatttaataa gccatattgg ctacaacgtg cacaaggtca taataatggt    180
atttgttggg gcaatcaggt atttgttact gtggtagata ccactcgcag tactaatatg    240
ac    242

<210> SEQ ID NO 149
<211> LENGTH: 234
<212> TYPE: DNA
<213> ORGANISM: HPV

<400> SEQUENCE: 149

```
aactcaacgc ttagtttggg cctgtgttgg tttagaggta ggtcgcgggc agccattagg      60
tgtaggtatt agtggtcatc cattattaaa taaatttgat gacactgaaa actctaatag     120
atatgccggt ggtcctggca ctgataatag ggaatgtata tcaatggatt ataaacaaac     180
acaactgtgt ttacttggtt gcaaaccacc tattggagag cattggggta aagg           234
```

<210> SEQ ID NO 150
<211> LENGTH: 323
<212> TYPE: DNA
<213> ORGANISM: HPV

<400> SEQUENCE: 150

```
gccactgtac aaagcagtgc ttttttttcct actcctagtg gttctatggt aacctcagaa     60
tcccaattat ttaataaacc gtactggtta caacgtgcgc agggccacaa taatggcata    120
tgttggggca atcagttgtt tgtcacagtt gtggatacca ctcgtagcac taacatgact    180
ttatgtgctg aggttaaaaa ggaaagcaca tataaaaatg aaaattttaa ggaatacctt    240
cgtcatggcg aggaatttga tttacaattt attttttcaat tgtgcaaaat tacattaaca    300
gctgatgtta tgacatacat tca                                             323
```

<210> SEQ ID NO 151
<211> LENGTH: 296
<212> TYPE: DNA
<213> ORGANISM: HPV

<400> SEQUENCE: 151

```
gtatatgttg ctacgcctag tgggtctatg attacgtctg aggcacagtt atttaataaa     60
ccttattggt tgcaacgtgc ccaaggccat aataatggca tttgctgggg taatcaatta    120
tttgttactg tagtagatac tactagaagt actaacatga ctattagtac tgctacagaa    180
cagttaagta aatatgatgc acgaaaaatt aatcagtacc ttagacatgt ggaggaatat    240
gaattacaat ttgttttttca attatgcaaa attactttgt ctgcagaggt tatggc        296
```

<210> SEQ ID NO 152
<211> LENGTH: 236
<212> TYPE: DNA
<213> ORGANISM: HPV

<400> SEQUENCE: 152

```
ccagataaca cagtatatga tcctaactct caacgcttgg tctgggcctg tgtaggtgtt     60
gaaatcggtc ggggccaacc tttaggggta ggactcagtg gtcatccatt atataataaa    120
ttggatgaca ctgaaaactc tcatgtagca tctgctgttg ataccaaaga tacacgtgat    180
aatgtatctg tggattataa acaaactcag ctgtgtatta ttggctgtgt acctgc        236
```

<210> SEQ ID NO 153
<211> LENGTH: 225
<212> TYPE: DNA
<213> ORGANISM: HPV

<400> SEQUENCE: 153

```
gaaacacaac gtttggtttg gcatgtgta ggtatggaaa ttggtcgtgg gcagccttta      60
ggtattggcc taagtggcca tccattttat aataaattgg atgatacaga aagtgctcat    120
gcagctacag ctgttattac gcaggatgtt agggataatg tgtcagttga ttataagcaa    180
acacagctgt gtattttagg ttgtgtacct gctattggtg agcac                     225
```

<210> SEQ ID NO 154
<211> LENGTH: 301
<212> TYPE: DNA
<213> ORGANISM: HPV

<400> SEQUENCE: 154

```
caaattattt tcctacacct agtggttcta tggttacctc tgatgcccaa atattcaata        60
aaccttattg gttacaacga gcacagggcc acaataatgg catttgttgg ggtaaccaac       120
tatttgttac tgttgttgat actacacgca gtacaaatat gtcattatgt gctgccatat      180
ctacttcaga aactacatat aaaaatacta actttaagga gtacctacga catggggagg      240
aatatgattt acagtttatt tttcaactgt gcaaataac cttaactgca gacgttatga       300
c                                                                     301
```

<210> SEQ ID NO 155
<211> LENGTH: 307
<212> TYPE: DNA
<213> ORGANISM: HPV

<400> SEQUENCE: 155

```
gttctgtata ctgcccctct cccagcggtt ccatggtaac tctgattcc cagttattta       60
ataagcctta ttggctacat aaggcccagg ccacaacaa tggtatatgt tggcataatc      120
aattatttct tactgttgtg gacactaccc gtagtaccaa cttttacatta tctacctcta   180
tagagtcttc cataccttct acatatgatc cttctaagtt taaggaatat accaggcacg      240
tggaggagta tgattttacaa tttatatttc aactgtgtac tgtcacatta acaactgatg    300
ttatgtc                                                              307
```

<210> SEQ ID NO 156
<211> LENGTH: 214
<212> TYPE: DNA
<213> ORGANISM: HPV

<400> SEQUENCE: 156

```
gacgtgagca gatgtttgtt agacactttt ttaatagggc tggaaaactt ggcgaggctg       60
tcccggatga cctttatatt aaagggtccg gtaatactgc agttatccaa agtagtgcat     120
ttttccaac tcctagtggc tctatagtta cctcagaatc acaattattt aataagcctt     180
attggctaca gcgtgcacaa ggtcataaca atgg                                 214
```

<210> SEQ ID NO 157
<211> LENGTH: 212
<212> TYPE: DNA
<213> ORGANISM: HPV

<400> SEQUENCE: 157

```
ctgcagatgt atatggagac agtatgttct tttgtttacg tagggaacag ttatttgcta       60
ggcatttttg gaatagaggg ggcatggtag gggacactat acctactgaa ttgtatatta     120
agggcactga catacgtgac agtcctagta gttatgtata tgcccctcg cctagtgggt      180
ctatggtatc ctcagactcc cagttattta ac                                    212
```

<210> SEQ ID NO 158
<211> LENGTH: 292
<212> TYPE: DNA
<213> ORGANISM: HPV

<400> SEQUENCE: 158

```
tgtattctcc ctctccaagt ggctctattg ttacctctga ctcccagttg tttaataaac    60
catattggtt acataaggca cagggtcata acaatggtgt tgctggcat aatcaattat    120 ttgttactgt ggtagatacc actcgcagtt gcttctacac agtctcctgt acctgggcaa   180
tatgatgcta ccaaatttaa gcagtatagc agacatgttg aggaatatga tttgcagttt   240 attttcagt tgtgtactat tactttaact gcagatgtta tgtcctatat tc           292
```

<210> SEQ ID NO 159
<211> LENGTH: 215
<212> TYPE: DNA
<213> ORGANISM: HPV

<400> SEQUENCE: 159

```
gttgaggtgg gcagaggaca gccccttggt gttggcctta gtggtcatcc cttatttaat    60
aaatatgatg acacagaaaa ttcacgcata gcaaatggca atgcacaaca agatgttaga   120
gataacacat ctgttgacaa caaacagact cagttatgta aataggctg tgctccacct   180 attggggaac actggggtat tggcactaca tgcaa                              215
```

<210> SEQ ID NO 160
<211> LENGTH: 207
<212> TYPE: DNA
<213> ORGANISM: HPV

<400> SEQUENCE: 160

```
tcctataggt gaacattggg gaaaaggcac accttgtaat gctaaccagg taaaagcagg    60
agaatgtcct cctttggagt tactaaacac tgtactacaa gacggggaca tggtagacac   120
aggatttggt gcaatggatt ttactacatt acaagctaat aaaagtgatg ttccccctaga  180 tatatgcagt tccatttgca aatatcc                                       207
```

<210> SEQ ID NO 161
<211> LENGTH: 35
<212> TYPE: DNA
<213> ORGANISM: Artificial Sequence
<220> FEATURE:
<223> OTHER INFORMATION: Probe

<400> SEQUENCE: 161

```
acaaggtcat aataatggta tttgttgggg caatc                              35
```

<210> SEQ ID NO 162
<211> LENGTH: 55
<212> TYPE: DNA
<213> ORGANISM: Artificial Sequence
<220> FEATURE:
<223> OTHER INFORMATION: Probe

<400> SEQUENCE: 162

```
tggtcctggc actgataata gggaatgtat atcaatggat tataaacaaa cacaa        55
```

<210> SEQ ID NO 163
<211> LENGTH: 41
<212> TYPE: DNA
<213> ORGANISM: Artificial Sequence
<220> FEATURE:
<223> OTHER INFORMATION: Probe

<400> SEQUENCE: 163

```
ttgtaaccag tacggtttat taaataattg ggattctgag g                       41
```

<210> SEQ ID NO 164
<211> LENGTH: 55
<212> TYPE: DNA
<213> ORGANISM: Artificial Sequence
<220> FEATURE:
<223> OTHER INFORMATION: Probe

<400> SEQUENCE: 164
agtactgcta cagaacagtt aagtaaatat gatgcacgaa aaattaatca gtacc      55

<210> SEQ ID NO 165
<211> LENGTH: 43
<212> TYPE: DNA
<213> ORGANISM: Artificial Sequence
<220> FEATURE:
<223> OTHER INFORMATION: Probe

<400> SEQUENCE: 165
gccccgaccg atttcaacac ctacacaggc ccagaccaag cgt                   43

<210> SEQ ID NO 166
<211> LENGTH: 55
<212> TYPE: DNA
<213> ORGANISM: Artificial Sequence
<220> FEATURE:
<223> OTHER INFORMATION: Probe

<400> SEQUENCE: 166
agctacagct gttattacgc aggatgttag ggataatgtg tcagttgatt ataag      55

<210> SEQ ID NO 167
<211> LENGTH: 38
<212> TYPE: DNA
<213> ORGANISM: Artificial Sequence
<220> FEATURE:
<223> OTHER INFORMATION: Primer

<400> SEQUENCE: 167
gcactgcttt gaatagaggc actgttcccg atgacctg                         38

<210> SEQ ID NO 168
<211> LENGTH: 38
<212> TYPE: DNA
<213> ORGANISM: Artificial Sequence
<220> FEATURE:
<223> OTHER INFORMATION: Primer

<400> SEQUENCE: 168
ccatattggc tacaacgtgc tacctgattg ccccaaca                         38

<210> SEQ ID NO 169
<211> LENGTH: 20
<212> TYPE: DNA
<213> ORGANISM: Artificial Sequence
<220> FEATURE:
<223> OTHER INFORMATION: Primer

<400> SEQUENCE: 169
agggctggta cattaggaga                                             20

<210> SEQ ID NO 170
<211> LENGTH: 22
<212> TYPE: DNA
<213> ORGANISM: Artificial Sequence
<220> FEATURE:
<223> OTHER INFORMATION: Primer

```
<400> SEQUENCE: 170
gtcatattag tactgcgagt gg                                              22

<210> SEQ ID NO 171
<211> LENGTH: 27
<212> TYPE: DNA
<213> ORGANISM: Artificial Sequence
<220> FEATURE:
<223> OTHER INFORMATION: Primer

<400> SEQUENCE: 171
cagtagttcc tgaacctttta atgtaca                                        27

<210> SEQ ID NO 172
<211> LENGTH: 46
<212> TYPE: DNA
<213> ORGANISM: Artificial Sequence
<220> FEATURE:
<223> OTHER INFORMATION: Primer

<400> SEQUENCE: 172
ggatgaccac taatacctac accctgtgtt ggtttagagg taggtc                    46

<210> SEQ ID NO 173
<211> LENGTH: 51
<212> TYPE: DNA
<213> ORGANISM: Artificial Sequence
<220> FEATURE:
<223> OTHER INFORMATION: Primer

<400> SEQUENCE: 173
cactgaaaac tctaatagat atgccggtgc aaccaagtaa acacagttgt g              51

<210> SEQ ID NO 174
<211> LENGTH: 21
<212> TYPE: DNA
<213> ORGANISM: Artificial Sequence
<220> FEATURE:
<223> OTHER INFORMATION: Primer

<400> SEQUENCE: 174
aactcaacgc ttagtttggg c                                               21

<210> SEQ ID NO 175
<211> LENGTH: 20
<212> TYPE: DNA
<213> ORGANISM: Artificial Sequence
<220> FEATURE:
<223> OTHER INFORMATION: Primer

<400> SEQUENCE: 175
cctttacccc aatgctctcc                                                 20

<210> SEQ ID NO 176
<211> LENGTH: 16
<212> TYPE: DNA
<213> ORGANISM: Artificial Sequence
<220> FEATURE:
<223> OTHER INFORMATION: Primer

<400> SEQUENCE: 176
taatggctgc ccgcga                                                     16

<210> SEQ ID NO 177
```

```
<211> LENGTH: 44
<212> TYPE: DNA
<213> ORGANISM: Artificial Sequence
<220> FEATURE:
<223> OTHER INFORMATION: Primer

<400> SEQUENCE: 177
attattgtgg ccctgcgcac gttctatggt aacctcagaa tccc                44

<210> SEQ ID NO 178
<211> LENGTH: 45
<212> TYPE: DNA
<213> ORGANISM: Artificial Sequence
<220> FEATURE:
<223> OTHER INFORMATION: Primer

<400> SEQUENCE: 178
accactcgta gcactaacat gactcgccat gacgaaggta ttcct              45

<210> SEQ ID NO 179
<211> LENGTH: 20
<212> TYPE: DNA
<213> ORGANISM: Artificial Sequence
<220> FEATURE:
<223> OTHER INFORMATION: Primer

<400> SEQUENCE: 179
gccactgtac aaagcagtgc                                          20

<210> SEQ ID NO 180
<211> LENGTH: 25
<212> TYPE: DNA
<213> ORGANISM: Artificial Sequence
<220> FEATURE:
<223> OTHER INFORMATION: Primer

<400> SEQUENCE: 180
tgaatgtatg tcataacatc agctg                                    25

<210> SEQ ID NO 181
<211> LENGTH: 24
<212> TYPE: DNA
<213> ORGANISM: Artificial Sequence
<220> FEATURE:
<223> OTHER INFORMATION: Primer

<400> SEQUENCE: 181
gctgaggtta aaaggaaag caca                                      24

<210> SEQ ID NO 182
<211> LENGTH: 46
<212> TYPE: DNA
<213> ORGANISM: Artificial Sequence
<220> FEATURE:
<223> OTHER INFORMATION: Primer

<400> SEQUENCE: 182
aattgattac cccagcaaat gccgtctatg attacgtctg aggcac             46

<210> SEQ ID NO 183
<211> LENGTH: 47
<212> TYPE: DNA
<213> ORGANISM: Artificial Sequence
<220> FEATURE:
<223> OTHER INFORMATION: Primer

<400> SEQUENCE: 183
```

```
atactactag aagtactaac atgaccctcc acatgtctaa ggtactg        47
```

<210> SEQ ID NO 184
<211> LENGTH: 22
<212> TYPE: DNA
<213> ORGANISM: Artificial Sequence
<220> FEATURE:
<223> OTHER INFORMATION: Primer

<400> SEQUENCE: 184

```
gtatatgttg ctacgcctag tg                                   22
```

<210> SEQ ID NO 185
<211> LENGTH: 22
<212> TYPE: DNA
<213> ORGANISM: Artificial Sequence
<220> FEATURE:
<223> OTHER INFORMATION: Primer

<400> SEQUENCE: 185

```
gccataacct ctgcagacaa ag                                   22
```

<210> SEQ ID NO 186
<211> LENGTH: 20
<212> TYPE: DNA
<213> ORGANISM: Artificial Sequence
<220> FEATURE:
<223> OTHER INFORMATION: Primer

<400> SEQUENCE: 186

```
gcacgttgca accaataagg                                      20
```

<210> SEQ ID NO 187
<211> LENGTH: 43
<212> TYPE: DNA
<213> ORGANISM: Artificial Sequence
<220> FEATURE:
<223> OTHER INFORMATION: Primer

<400> SEQUENCE: 187

```
cactgagtcc taccoctaaa ggttgtctca acgcttggtc tgg            43
```

<210> SEQ ID NO 188
<211> LENGTH: 50
<212> TYPE: DNA
<213> ORGANISM: Artificial Sequence
<220> FEATURE:
<223> OTHER INFORMATION: Primer

<400> SEQUENCE: 188

```
gatgacactg aaaactctca tgtagcgctg agtttgttta taatccacag     50
```

<210> SEQ ID NO 189
<211> LENGTH: 27
<212> TYPE: DNA
<213> ORGANISM: Artificial Sequence
<220> FEATURE:
<223> OTHER INFORMATION: Primer

<400> SEQUENCE: 189

```
ccagataaca cagtatatga tcctaac                              27
```

<210> SEQ ID NO 190
<211> LENGTH: 24
<212> TYPE: DNA

```
<213> ORGANISM: Artificial Sequence
<220> FEATURE:
<223> OTHER INFORMATION: Primer

<400> SEQUENCE: 190
gcaggtacac agccaataat acac                                           24

<210> SEQ ID NO 191
<211> LENGTH: 25
<212> TYPE: DNA
<213> ORGANISM: Artificial Sequence
<220> FEATURE:
<223> OTHER INFORMATION: Primer

<400> SEQUENCE: 191
gctgttgata ccaaagatac acgtg                                          25

<210> SEQ ID NO 192
<211> LENGTH: 242
<212> TYPE: DNA
<213> ORGANISM: HPV

<400> SEQUENCE: 192
agggctggta cattaggaga ggctgttccc gatgacctgt acattaaagg ttcaggaact    60
actgcctcta ttcaaagcag tgctttttttt cccactccta gtggatcaat ggttacttcc  120
gaatctcagt tatttaataa gccatattgg ctacaacgtg cacaaggtca taataatggg   180
atttgttggg gcaatcaggt atttgttact gtggtagata ccactcgcag tactaatatg   240
ac                                                                  242

<210> SEQ ID NO 193
<211> LENGTH: 234
<212> TYPE: DNA
<213> ORGANISM: HPV

<400> SEQUENCE: 193
aactcaacgc ttagtttggg cctgtgttgg tttagaggta ggtcgcgggc agccattagg    60
tgtaggtatt agtggtcatc cattattaaa taaatttgat gacactgaaa actctaatag   120
atatgccggt ggtcctggca ctgataatag ggaatgtata tcaatggatt ataaacaaac   180
acaactgtgt ttacttggtt gcaaaccacc tattggagag cattggggta aagg         234

<210> SEQ ID NO 194
<211> LENGTH: 296
<212> TYPE: DNA
<213> ORGANISM: HPV

<400> SEQUENCE: 194
gtatatgttg ctacgcctag tgggtctatg attacgtctg aggcacagtt atttaataaa    60
ccttattggt tgcaacgtgc ccaaggccat aataatggca tttgctgggg taatcaatta   120
tttgttactg tagtagatac tactagaagt actaacatga ctattagtac tgctacagaa   180
cagttaagta aatatgatgc acgaaaaatt aatcagtacc ttagacatgt ggaggaatat   240
gaattacaat tgtttttca attatgcaaa attactttgt ctgcagaggt tatggc        296

<210> SEQ ID NO 195
<211> LENGTH: 51
<212> TYPE: DNA
<213> ORGANISM: Artificial Sequence
<220> FEATURE:
<223> OTHER INFORMATION: Probe
```

-continued

<400> SEQUENCE: 195
tttggtgcaa tggattttac tacattacaa gctaataaaa gtgatgttcc c　　　　51

<210> SEQ ID NO 196
<211> LENGTH: 35
<212> TYPE: DNA
<213> ORGANISM: Artificial Sequence
<220> FEATURE:
<223> OTHER INFORMATION: Probe

<400> SEQUENCE: 196
acaaggtcat aataatggta tttgttgggg caatc　　　　35

<210> SEQ ID NO 197
<211> LENGTH: 55
<212> TYPE: DNA
<213> ORGANISM: Artificial Sequence
<220> FEATURE:
<223> OTHER INFORMATION: Probe

<400> SEQUENCE: 197
tggtcctggc actgataata gggaatgtat atcaatggat tataaacaaa cacaa　　　　55

<210> SEQ ID NO 198
<211> LENGTH: 41
<212> TYPE: DNA
<213> ORGANISM: Artificial Sequence
<220> FEATURE:
<223> OTHER INFORMATION: Probe

<400> SEQUENCE: 198
ttgtaaccag tacggtttat taaataattg ggattctgag g　　　　41

<210> SEQ ID NO 199
<211> LENGTH: 55
<212> TYPE: DNA
<213> ORGANISM: Artificial Sequence
<220> FEATURE:
<223> OTHER INFORMATION: Probe

<400> SEQUENCE: 199
agtactgcta cagaacagtt aagtaaatat gatgcacgaa aaattaatca gtacc　　　　55

<210> SEQ ID NO 200
<211> LENGTH: 38
<212> TYPE: DNA
<213> ORGANISM: Artificial Sequence
<220> FEATURE:
<223> OTHER INFORMATION: Primer

<400> SEQUENCE: 200
gcactgcttt gaatagaggc actgttcccg atgacctg　　　　38

<210> SEQ ID NO 201
<211> LENGTH: 38
<212> TYPE: DNA
<213> ORGANISM: Artificial Sequence
<220> FEATURE:
<223> OTHER INFORMATION: Primer

<400> SEQUENCE: 201
ccatattggc tacaacgtgc tacctgattg ccccaaca　　　　38

<210> SEQ ID NO 202

```
<211> LENGTH: 20
<212> TYPE: DNA
<213> ORGANISM: Artificial Sequence
<220> FEATURE:
<223> OTHER INFORMATION: Primer

<400> SEQUENCE: 202
agggctggta cattaggaga                                              20

<210> SEQ ID NO 203
<211> LENGTH: 22
<212> TYPE: DNA
<213> ORGANISM: Artificial Sequence
<220> FEATURE:
<223> OTHER INFORMATION: Primer

<400> SEQUENCE: 203
gtcatattag tactgcgagt gg                                           22

<210> SEQ ID NO 204
<211> LENGTH: 27
<212> TYPE: DNA
<213> ORGANISM: Artificial Sequence
<220> FEATURE:
<223> OTHER INFORMATION: Primer

<400> SEQUENCE: 204
cagtagttcc tgaacctttta atgtaca                                     27

<210> SEQ ID NO 205
<211> LENGTH: 46
<212> TYPE: DNA
<213> ORGANISM: Artificial Sequence
<220> FEATURE:
<223> OTHER INFORMATION: Primer

<400> SEQUENCE: 205
ggatgaccac taatacctac accctgtgtt ggtttagagg taggtc                 46

<210> SEQ ID NO 206
<211> LENGTH: 51
<212> TYPE: DNA
<213> ORGANISM: Artificial Sequence
<220> FEATURE:
<223> OTHER INFORMATION: Primer

<400> SEQUENCE: 206
cactgaaaac tctaatagat atgccggtgc aaccaagtaa acacagttgt g           51

<210> SEQ ID NO 207
<211> LENGTH: 21
<212> TYPE: DNA
<213> ORGANISM: Artificial Sequence
<220> FEATURE:
<223> OTHER INFORMATION: Primer

<400> SEQUENCE: 207
aactcaacgc ttagtttggg c                                            21

<210> SEQ ID NO 208
<211> LENGTH: 20
<212> TYPE: DNA
<213> ORGANISM: Artificial Sequence
<220> FEATURE:
<223> OTHER INFORMATION: Primer

<400> SEQUENCE: 208
```

```
cctttacccc aatgctctcc                                                    20

<210> SEQ ID NO 209
<211> LENGTH: 16
<212> TYPE: DNA
<213> ORGANISM: Artificial Sequence
<220> FEATURE:
<223> OTHER INFORMATION: Primer

<400> SEQUENCE: 209
taatggctgc ccgcga                                                        16

<210> SEQ ID NO 210
<211> LENGTH: 44
<212> TYPE: DNA
<213> ORGANISM: Artificial Sequence
<220> FEATURE:
<223> OTHER INFORMATION: Primer

<400> SEQUENCE: 210
attattgtgg ccctgcgcac gttctatggt aacctcagaa tccc                         44

<210> SEQ ID NO 211
<211> LENGTH: 45
<212> TYPE: DNA
<213> ORGANISM: Artificial Sequence
<220> FEATURE:
<223> OTHER INFORMATION: Primer

<400> SEQUENCE: 211
accactcgta gcactaacat gactcgccat gacgaaggta ttcct                        45

<210> SEQ ID NO 212
<211> LENGTH: 20
<212> TYPE: DNA
<213> ORGANISM: Artificial Sequence
<220> FEATURE:
<223> OTHER INFORMATION: Primer

<400> SEQUENCE: 212
gccactgtac aaagcagtgc                                                    20

<210> SEQ ID NO 213
<211> LENGTH: 25
<212> TYPE: DNA
<213> ORGANISM: Artificial Sequence
<220> FEATURE:
<223> OTHER INFORMATION: Primer

<400> SEQUENCE: 213
tgaatgtatg tcataacatc agctg                                              25

<210> SEQ ID NO 214
<211> LENGTH: 24
<212> TYPE: DNA
<213> ORGANISM: Artificial Sequence
<220> FEATURE:
<223> OTHER INFORMATION: Primer

<400> SEQUENCE: 214
gctgaggtta aaaggaaag caca                                                24

<210> SEQ ID NO 215
<211> LENGTH: 46
<212> TYPE: DNA
```

```
<213> ORGANISM: Artificial Sequence
<220> FEATURE:
<223> OTHER INFORMATION: Primer

<400> SEQUENCE: 215
aattgattac cccagcaaat gccgtctatg attacgtctg aggcac                46

<210> SEQ ID NO 216
<211> LENGTH: 47
<212> TYPE: DNA
<213> ORGANISM: Artificial Sequence
<220> FEATURE:
<223> OTHER INFORMATION: Primer

<400> SEQUENCE: 216
atactactag aagtactaac atgaccctcc acatgtctaa ggtactg               47

<210> SEQ ID NO 217
<211> LENGTH: 22
<212> TYPE: DNA
<213> ORGANISM: Artificial Sequence
<220> FEATURE:
<223> OTHER INFORMATION: Primer

<400> SEQUENCE: 217
gtatatgttg ctacgcctag tg                                          22

<210> SEQ ID NO 218
<211> LENGTH: 22
<212> TYPE: DNA
<213> ORGANISM: Artificial Sequence
<220> FEATURE:
<223> OTHER INFORMATION: Primer

<400> SEQUENCE: 218
gccataacct ctgcagacaa ag                                          22

<210> SEQ ID NO 219
<211> LENGTH: 20
<212> TYPE: DNA
<213> ORGANISM: Artificial Sequence
<220> FEATURE:
<223> OTHER INFORMATION: Primer

<400> SEQUENCE: 219
gcacgttgca accaataagg                                             20

<210> SEQ ID NO 220
<211> LENGTH: 242
<212> TYPE: DNA
<213> ORGANISM: HPV

<400> SEQUENCE: 220
agggctggta cattaggaga ggctgttccc gatgacctgt acattaaagg ttcaggaact    60
actgcctcta ttcaaagcag tgctttttt cccactccta gtggatcaat ggttacttcc   120
gaatctcagt tatttaataa gccatattgg ctacaacgtg cacaaggtca taataatggt   180
atttgttggg gcaatcaggt atttgttact gtggtagata ccactcgcag tactaatatg   240
ac                                                                 242

<210> SEQ ID NO 221
<211> LENGTH: 234
<212> TYPE: DNA
<213> ORGANISM: HPV
```

<400> SEQUENCE: 221
aactcaacgc ttagtttggg cctgtgttgg tttagaggta ggtcgcgggc agccattagg    60
tgtaggtatt agtggtcatc cattattaaa taaatttgat gacactgaaa actctaatag   120
atatgccggt ggtcctggca ctgataatag ggaatgtata tcaatggatt ataaacaaac   180
acaactgtgt ttacttggtt gcaaaccacc tattggagag cattggggta aagg          234

<210> SEQ ID NO 222
<211> LENGTH: 296
<212> TYPE: DNA
<213> ORGANISM: HPV

<400> SEQUENCE: 222
gtatatgttg ctacgcctag tgggtctatg attacgtctg aggcacagtt atttaataaa    60
ccttattggt tgcaacgtgc ccaaggccat aataatggca tttgctgggg taatcaatta   120
tttgttactg tagtagatac tactagaagt actaacatga ctattagtac tgctacagaa   180
cagttaagta aatatgatgc acgaaaaatt aatcagtacc ttagacatgt ggaggaatat   240
gaattacaat tgttttttca attatgcaaa attactttgt ctgcagaggt tatggc        296

<210> SEQ ID NO 223
<211> LENGTH: 43
<212> TYPE: DNA
<213> ORGANISM: Artificial Sequence
<220> FEATURE:
<223> OTHER INFORMATION: Primer

<400> SEQUENCE: 223
gtttagtaac tccaaaggag gacaaaggca caccttgtaa tgc                       43

<210> SEQ ID NO 224
<211> LENGTH: 42
<212> TYPE: DNA
<213> ORGANISM: Artificial Sequence
<220> FEATURE:
<223> OTHER INFORMATION: Primer

<400> SEQUENCE: 224
gggacatggt agacacagga catatatcta ggggaacatc ac                        42

<210> SEQ ID NO 225
<211> LENGTH: 19
<212> TYPE: DNA
<213> ORGANISM: Artificial Sequence
<220> FEATURE:
<223> OTHER INFORMATION: Primer

<400> SEQUENCE: 225
cctataggtg aacattggg                                                  19

<210> SEQ ID NO 226
<211> LENGTH: 21
<212> TYPE: DNA
<213> ORGANISM: Artificial Sequence
<220> FEATURE:
<223> OTHER INFORMATION: Primer

<400> SEQUENCE: 226
ggatatttgc aaatggaact g                                               21

<210> SEQ ID NO 227

```
<211> LENGTH: 22
<212> TYPE: DNA
<213> ORGANISM: Artificial Sequence
<220> FEATURE:
<223> OTHER INFORMATION: Primer

<400> SEQUENCE: 227
cattctcctg cttttacctg gt                                              22

<210> SEQ ID NO 228
<211> LENGTH: 207
<212> TYPE: DNA
<213> ORGANISM: Artificial Sequence
<220> FEATURE:
<223> OTHER INFORMATION: Template

<400> SEQUENCE: 228
tcctataggt gaacattggg gaaaaggcac accttgtaat gctaaccagg taaaagcagg      60
agaatgtcct cctttggagt tactaaacac tgtactacaa gacggggaca tggtagacac     120
aggatttggt gcaatggatt ttactacatt acaagctaat aaaagtgatg ttcccctaga     180
tatatgcagt tccatttgca aatatcc                                         207

<210> SEQ ID NO 229
<211> LENGTH: 34
<212> TYPE: DNA
<213> ORGANISM: Artificial Sequence
<220> FEATURE:
<223> OTHER INFORMATION: Probe

<400> SEQUENCE: 229
tttggtgcaa tggattttac tacattacaa gcta                                 34

<210> SEQ ID NO 230
<211> LENGTH: 34
<212> TYPE: DNA
<213> ORGANISM: Artificial Sequence
<220> FEATURE:
<223> OTHER INFORMATION: Probe

<400> SEQUENCE: 230
accaataagg tttattgaat atttgggcat caga                                 34

<210> SEQ ID NO 231
<211> LENGTH: 34
<212> TYPE: DNA
<213> ORGANISM: Artificial Sequence
<220> FEATURE:
<223> OTHER INFORMATION: Probe

<400> SEQUENCE: 231
tttggtgcaa tggattttac tacattacaa gcta                                 34

<210> SEQ ID NO 232
<211> LENGTH: 39
<212> TYPE: DNA
<213> ORGANISM: Artificial Sequence
<220> FEATURE:
<223> OTHER INFORMATION: Primer

<400> SEQUENCE: 232
gtggccctgt gctcgttgtc tatggttacc tctgatgcc                            39

<210> SEQ ID NO 233
<211> LENGTH: 40
```

```
<212> TYPE: DNA
<213> ORGANISM: Artificial Sequence
<220> FEATURE:
<223> OTHER INFORMATION: Primer

<400> SEQUENCE: 233
cacgcagtac aaatatgtca ccccatgtcg taggtactcc                          40

<210> SEQ ID NO 234
<211> LENGTH: 25
<212> TYPE: DNA
<213> ORGANISM: Artificial Sequence
<220> FEATURE:
<223> OTHER INFORMATION: Primer

<400> SEQUENCE: 234
caaattattt tcctacacct agtgg                                          25

<210> SEQ ID NO 235
<211> LENGTH: 22
<212> TYPE: DNA
<213> ORGANISM: Artificial Sequence
<220> FEATURE:
<223> OTHER INFORMATION: Primer

<400> SEQUENCE: 235
gtcataacgt ctgcagttaa gg                                             22

<210> SEQ ID NO 236
<211> LENGTH: 27
<212> TYPE: DNA
<213> ORGANISM: Artificial Sequence
<220> FEATURE:
<223> OTHER INFORMATION: Primer

<400> SEQUENCE: 236
gctgccatat ctacttcaga aactaca                                        27

<210> SEQ ID NO 237
<211> LENGTH: 43
<212> TYPE: DNA
<213> ORGANISM: Artificial Sequence
<220> FEATURE:
<223> OTHER INFORMATION: Primer

<400> SEQUENCE: 237
gtttagtaac tccaaaggag gacaaaggca caccttgtaa tgc                      43

<210> SEQ ID NO 238
<211> LENGTH: 42
<212> TYPE: DNA
<213> ORGANISM: Artificial Sequence
<220> FEATURE:
<223> OTHER INFORMATION: Primer

<400> SEQUENCE: 238
gggacatggt agacacagga catatatcta ggggaacatc ac                       42

<210> SEQ ID NO 239
<211> LENGTH: 19
<212> TYPE: DNA
<213> ORGANISM: Artificial Sequence
<220> FEATURE:
<223> OTHER INFORMATION: Primer

<400> SEQUENCE: 239
```

```
cctataggtg aacattggg                                                    19

<210> SEQ ID NO 240
<211> LENGTH: 21
<212> TYPE: DNA
<213> ORGANISM: Artificial Sequence
<220> FEATURE:
<223> OTHER INFORMATION: Primer

<400> SEQUENCE: 240
ggatatttgc aaatggaact g                                                 21

<210> SEQ ID NO 241
<211> LENGTH: 22
<212> TYPE: DNA
<213> ORGANISM: Artificial Sequence
<220> FEATURE:
<223> OTHER INFORMATION: Primer

<400> SEQUENCE: 241
cattctcctg cttttacctg gt                                                22

<210> SEQ ID NO 242
<211> LENGTH: 301
<212> TYPE: DNA
<213> ORGANISM: Artificial Sequence
<220> FEATURE:
<223> OTHER INFORMATION: Template

<400> SEQUENCE: 242
caaattattt tcctacacct agtggttcta tggttacctc tgatgcccaa atattcaata        60
aaccttattg gttacaacga gcacagggcc acaataatgg catttgttgg ggtaaccaac       120
tatttgttac tgttgttgat actacacgca gtacaaatat gtcattatgt gctgccatat       180
ctacttcaga aactacatat aaaaatacta actttaagga gtacctacga catggggagg       240
aatatgattt acagtttatt tttcaactgt gcaaaataac cttaactgca gacgttatga       300
c                                                                      301

<210> SEQ ID NO 243
<211> LENGTH: 206
<212> TYPE: DNA
<213> ORGANISM: Artificial Sequence
<220> FEATURE:
<223> OTHER INFORMATION: Template

<400> SEQUENCE: 243
cctataggtg aacattgggg aaaaggcaca ccttgtaatg ctaaccaggt aaaagcagga        60
gaatgtcctc ctttggagtt actaaacact gtactacaag acggggacat ggtagacaca       120
ggatttggtg caatggattt tactacatta caagctaata aaagtgatgt tcccctagat       180
atatgcagtt ccatttgcaa atatcc                                           206
```